(12) United States Patent
Buick et al.

(10) Patent No.: US 12,378,696 B2
(45) Date of Patent: Aug. 5, 2025

(54) ANTIBODY LIBRARY AND METHOD

(71) Applicant: Fusion Antibodies PLC, Belfast Antrim (GB)

(72) Inventors: Richard Buick, Belfast Antrim (GB); Christopher Scott, Belfast Antrim (GB); Darragh MacCann, Belfast Antrim (GB); Leona McGirr, Belfast Antrim (GB); Hugh Morgan, Belfast Antrim (GB); Natasha Campbell, Belfast Antrim (GB); James McClory, Belfast Antrim (GB); Anthony O'Kane, Belfast Antrim (GB)

(73) Assignee: Fusion Antibodies PLC, Belfast Antrim (GB)

( * ) Notice: Subject to any disclaimer, the term of this patent is extended or adjusted under 35 U.S.C. 154(b) by 873 days.

(21) Appl. No.: 17/287,441

(22) PCT Filed: Oct. 22, 2019

(86) PCT No.: PCT/GB2019/053010
§ 371 (c)(1),
(2) Date: Apr. 21, 2021

(87) PCT Pub. No.: WO2020/084298
PCT Pub. Date: Apr. 30, 2020

(65) Prior Publication Data
US 2021/0388063 A1 Dec. 16, 2021

(30) Foreign Application Priority Data

| Oct. 22, 2018 | (GB) | 1817188 |
| Apr. 4, 2019 | (GB) | 1904754 |
| Apr. 9, 2019 | (GB) | 1905032 |

(51) Int. Cl.
*C40B 50/06* (2006.01)
*C07K 16/00* (2006.01)
(Continued)

(52) U.S. Cl.
CPC ............ *C40B 50/06* (2013.01); *C07K 16/005* (2013.01); *C07K 16/32* (2013.01); *C07K 16/40* (2013.01);
(Continued)

(58) Field of Classification Search
None
See application file for complete search history.

(56) References Cited

FOREIGN PATENT DOCUMENTS

WO 00/73346 A1 12/2000

OTHER PUBLICATIONS

Muller et al., "In Vitro Affinity Maturation of an Anti-PSA Antibody for Prostate Cancer Diagnostic Assay", Journal of Molecular Biology, 2011, 414(4), 545-562.
Su et al., "Mimicking the germinal center reaction in hybridoma cells to isolate temperature-selective anti-PEG antibodies", mAbs, 2014, 6(4), 1069-1083.
(Continued)

*Primary Examiner* — Christian C Boesen
(74) *Attorney, Agent, or Firm* — McDonnell Boehnen Hulbert & Berghoff LLP

(57) ABSTRACT

This disclosure relates to methods of generating antibody libraries, antibody libraries produced using such methods, and variant antibodies. Presently, methods of improving antibody binding (affinity maturation assays) require the screening of vast libraries of antibody variants (often $>10^{10}$) to identify a small fraction of variants with improved characteristics. The present invention involves taking the nucleotide sequence of the framework and complementarity determining region of a target antibody and identifying motifs which would be recognised by deamination somatic hypermutation enzymes. A small library of variants is then created which incorporate one or more of these mutations. It (Continued)

was found that a relatively high proportion of the variants have an increased affinity. The technique of the present invention was demonstrated on the trastuzumab and Cathepsin S antibodies, and the variants produced are also claimed.

8 Claims, 115 Drawing Sheets

Specification includes a Sequence Listing.

(51) Int. Cl.
    *C07K 16/32* (2006.01)
    *C07K 16/40* (2006.01)
    *C12N 15/10* (2006.01)

(52) U.S. Cl.
    CPC ...... *C12N 15/1089* (2013.01); *C07K 2317/10* (2013.01); *C07K 2317/565* (2013.01)

(56) References Cited

OTHER PUBLICATIONS

Bostrom et al., "Variants of the antibody herceptin that interact with HER2 and VEGF at the antigen binding site", Science, 2009, 323(5921), 1610-1614.

Kalani Halemano, et al. (2014) "Immunoglobulin somatic hypermutation by APOBEC3/Rfv3 during retroviral infection", PNAS, vol. 111, No. 21, pp. 7759-7764.

Kwok et al., "Antibody targeting of Cathepsin S induces antibody-dependent cellular cytotoxicity," Molecular Cancer, 2011, 10:147.

Julian MC, Li L, Garde S, Wilen R, Tessier PM., "Efficient affinity maturation of antibody variable domains requires co-selection of compensatory mutations to maintain thermodynamic stability", Sci Rep. Mar. 28, 2017;7:45259. doi: 10.1038/srep45259. Publication date: Mar. 28, 2017.

Lombana TN, Dillon M, Bevers J 3rd, Spiess C. "Optimizing antibody expression by using the naturally occurring diversity framework in a live bacterial antibody display system", Sci Rep. Dec. 3, 2015;5:17488. doi:10.1038/srep17488. Published: Mar. 12, 2015.

Light Chain

SEQ ID NO: 1  D V V M T Q S P L S L P V T L G Q P A S I S C R S S Q S L V H S N G N T Y L H W
              1 2 3 4 5 6 7 8 9 10 11 12 13 14 15 16 17 18 19 20 21 22 23 24 25 26 27 28 29 30 31 32 33 34 35 36 37 38 39 40

(position 4: T/S/A; position 10: T/S/A; positions 18-20: T/S/A, D/V/G; position 27: R; position 29: D/V/A; position 33: N/T; position 40: C)

Y L Q K P G Q S P Q L L I Y K V S N R F S G V P D R F S G S G S G T D F T L K I
41 42 43 44 45 46 47 48 49 50 51 52 53 54 55 56 57 58 59 60 61 62 63 64 65 66 67 68 69 70 71 72 73 74 75 76 77 78 79 80

(position 41: *; positions 46-48: T/S/A, HV; positions 51-53: I/F/L; position 66: S)

S R V E A E D V G V Y Y C S Q T T H V P P T F G Q G T K L E I K
81 82 83 84 85 86 87 88 89 90 91 92 93 94 95 96 97 98 99 100 101 102 103 104 105 106 107 108 109 110 111 112

(positions 81-83: N/I/T, T/S, P; position 92: *W; position 94: L; position 96: S; position 107: N)

| One Mutation | | | | |
|---|---|---|---|---|
| Residue: | Original: | Mutation: | ΔAffinity: | ΔStability: |
| H:31 | SER | ARG | -12.49 | -1 |
| H:31 | SER | ASN | -4.87 | 5.17 |
| H:31 | SER | ILE | -4.46 | -0.93 |
| L:96 | THR | ILE | -3.16 | 4.48 |
| H:30 | SER | ILE | -2.32 | 1.12 |
| H:31 | SER | THR | -1.76 | 1.18 |

| Two Mutations | | | | |
|---|---|---|---|---|
| Residue: | Original: | Mutation: | ΔAffinity: | ΔStability: |
| L:19 | ALA | VAL | -10.68 | 4.62 |
| H:31 | SER | ARG | | |

| Three Mutations | | | | |
|---|---|---|---|---|
| Residue: | Original: | Mutation: | ΔAffinity: | ΔStability: |
| L:12 | PRO | SER | | |
| H:31 | SER | ARG | -9.72 | 0.93 |
| H:92 | ALA | GLY | | |
| L:12 | PRO | THR | | |
| H:31 | SER | ARG | -9.72 | -2.61 |
| H:92 | ALA | GLY | | |
| L:12 | PRO | ALA | | |
| H:31 | SER | ARG | -9.72 | 0.84 |
| H:92 | ALA | GLY | | |
| L:12 | PRO | THR | | |
| H:31 | SER | ASN | -4.6 | 2.33 |
| H:92 | ALA | GLY | | |
| L:12 | PRO | SER | | |
| H:31 | SER | ASN | -4.48 | 4.5 |
| H:92 | ALA | GLY | | |
| L:12 | PRO | ALA | | |
| H:31 | SER | ASN | -4.48 | 4.41 |
| H:92 | ALA | GLY | | |

| Four Mutations | | | | |
|---|---|---|---|---|
| Residue: | Original: | Mutation: | ΔAffinity: | ΔStability: |
| L:12 | PRO | SER | | |
| L:96 | THR | ILE | -16.92 | -1.71 |
| H:31 | SER | ARG | | |
| H:52 | THR | ILE | | |
| L:12 | PRO | ALA | | |
| L:96 | THR | ILE | -15.33 | -1.8 |
| H:31 | SER | ARG | | |
| H:52 | THR | ILE | | |
| L:12 | PRO | THR | | |
| L:96 | THR | ILE | -15.33 | -3.9 |
| H:31 | SER | ARG | | |
| H:52 | THR | ILE | | |
| L:12 | PRO | SER | | |
| L:96 | THR | ILE | -15.27 | -12.76 |
| H:30 | SER | ILE | | |
| H:31 | SER | ARG | | |
| L:12 | PRO | THR | | |
| L:96 | THR | ILE | -15.26 | -15 |
| H:30 | SER | ILE | | |
| H:31 | SER | ARG | | |

Figure 3 (Continued)

| Three Mutations | | | | | Four Mutations | | | | |
|---|---|---|---|---|---|---|---|---|---|
| Residue: | Original: | Mutation: | ΔAffinity: | ΔStability: | Residue: | Original: | Mutation: | ΔAffinity: | ΔStability: |
| | | | | | L:12 | PRO | SER | | |
| L:12 | PRO | SER | | | L:96 | THR | ASN | -15.23 | 3.57 |
| H:31 | SER | ILE | -3.68 | 4.85 | H:30 | SER | ILE | | |
| H:92 | ALA | GLY | | | H:31 | SER | ARG | | |
| | | | | | | | | | |
| L:12 | PRO | THR | | | L:12 | PRO | ALA | | |
| H:31 | SER | ILE | -3.08 | 1.25 | L:96 | THR | ASN | -15.23 | 3.48 |
| H:92 | ALA | GLY | | | H:30 | SER | ILE | | |
| | | | | | H:31 | SER | ARG | | |
| L:12 | PRO | ALA | | | | | | | |
| H:31 | SER | ILE | -3.08 | 4.75 | L:12 | PRO | THR | | |
| H:92 | ALA | GLY | | | L:96 | THR | ASN | -15.23 | 1.38 |
| | | | | | H:30 | SER | ILE | | |
| | | | | | H:31 | SER | ARG | | |
| L:12 | PRO | THR | | | | | | | |
| L:96 | THR | ILE | -13.77 | -8.03 | L:12 | PRO | ALA | | |
| H:31 | SER | ARG | | | L:96 | THR | ASN | -14.18 | 3.42 |
| | | | | | H:30 | SER | THR | | |
| L:12 | PRO | SER | | | H:31 | SER | ARG | | |
| H:31 | THR | ARG | -13.76 | -6.2 | | | | | |
| H:52 | SER | ILE | | | | | | | |
| | | | | | L:12 | PRO | THR | | |
| | | | | | L:42 | LEU | ILE | -14.04 | 5.11 |
| L:12 | PRO | THR | | | L:96 | THR | ASN | | |
| H:31 | SER | ARG | -13.76 | -8.43 | H:31 | SER | ARG | | |
| H:52 | THR | ILE | | | | | | | |
| | | | | | L:12 | PRO | THR | | |
| L:12 | PRO | SER | | | L:96 | THR | SER | -14 | -4.06 |
| L:96 | THR | ASN | -13.67 | 2.78 | H:31 | SER | ARG | | |
| H:31 | SER | ARG | | | H:52 | THR | ILE | | |
| | | | | | | | | | |
| L:12 | PRO | THR | | | L:12 | PRO | ALA | | |
| L:96 | THR | ASN | -13.67 | 1.98 | L:50 | GLN | HID | -13.83 | -6.97 |
| H:31 | SER | ARG | | | L:96 | THR | ILE | | |
| | | | | | H:31 | SER | ARG | | |
| L:12 | PRO | ALA | | | | | | | |
| H:31 | SER | ARG | -13.36 | 4.76 | L:12 | PRO | ALA | | |
| H:52 | THR | ILE | | | L:81 | SER | ILE | -13.78 | -12.11 |
| | | | | | L:96 | THR | ILE | | |
| L:12 | PRO | SER | | | H:31 | SER | ARG | | |
| H:30 | SER | ILE | -12.93 | -16.98 | | | | | |
| H:31 | SER | ARG | | | L:12 | PRO | THR | | |
| | | | | | H:31 | SER | ARG | -13.76 | -5.98 |
| | | | | | H:37 | VAL | LEU | | |
| | | | | | H:52 | THR | ILE | | |

Figure 3 (Continued)

| Three Mutations | | | | Four Mutations | | | | |
|---|---|---|---|---|---|---|---|---|
| Residue: | Original: | Mutation: | ΔAffinity: | ΔStability: | Residue: | Original: | Mutation: | ΔAffinity: | ΔStability: |
| L:12 | PRO | THR | -12.9 | -16.3 | L:12 | PRO | ALA | | |
| H:30 | SER | ILE | | | H:31 | SER | ARG | -13.76 | -2.46 |
| H:31 | SER | ARG | | | H:37 | VAL | LEU | | |
| | | | | | H:52 | THR | ILE | | |
| L:12 | PRO | ALA | -12.9 | -14.14 | | | | | |
| H:30 | SER | ILE | | | L:12 | PRO | SER | | |
| H:31 | SER | ARG | | | H:14 | PRO | SER | -13.76 | -3.52 |
| | | | | | H:31 | SER | ARG | | |
| | | | | | H:52 | THR | ILE | | |
| | | | | | | | | | |
| | | | | | L:12 | PRO | THR | | |
| | | | | | H:14 | PRO | SER | -13.75 | -5.71 |
| | | | | | H:31 | SER | ARG | | |
| | | | | | H:52 | THR | ILE | | |
| | | | | | | | | | |
| | | | | | L:12 | PRO | SER | | |
| | | | | | H:10 | GLY | VAL | -13.73 | -4.32 |
| | | | | | H:31 | SER | ARG | | |
| | | | | | H:52 | THR | ILE | | |
| | | | | | | | | | |
| | | | | | L:12 | PRO | SER | | |
| | | | | | H:10 | GLY | ALA | -13.73 | 1.16 |
| | | | | | H:31 | SER | ARG | | |
| | | | | | H:52 | THR | ILE | | |
| | | | | | | | | | |
| | | | | | L:12 | PRO | ALA | | |
| | | | | | L:96 | THR | ILE | -13.68 | -12.9 |
| | | | | | H:30 | SER | ILE | | |
| | | | | | H:31 | SER | ARG | | |
| | | | | | | | | | |
| | | | | | L:12 | PRO | THR | | |
| | | | | | L:85 | ALA | SER | -13.67 | 2.35 |
| | | | | | L:96 | THR | ASN | | |
| | | | | | H:31 | SER | ARG | | |
| | | | | | | | | | |
| | | | | | L:12 | PRO | THR | | |
| | | | | | L:96 | THR | ASN | -13.67 | -6.16 |
| | | | | | H:31 | SER | ARG | | |
| | | | | | H:40 | ALA | THR | | |
| | | | | | | | | | |
| | | | | | L:12 | PRO | SER | | |
| | | | | | L:81 | SER | THR | -13.67 | 3.31 |
| | | | | | L:96 | THR | ASN | | |
| | | | | | H:31 | SER | ARG | | |

Figure 3 (Continued)

| Three Mutations | | | | | Four Mutations | | | | |
|---|---|---|---|---|---|---|---|---|---|
| Residue: | Original: | Mutation: | ΔAffinity: | ΔStability: | Residue: | Original: | Mutation: | ΔAffinity: | ΔStability: |
| | | | | | L:12 | PRO | THR | | |
| | | | | | L:81 | SER | THR | -13.67 | 1.13 |
| | | | | | L:96 | THR | ASN | | |
| | | | | | H:31 | SER | ARG | | |
| | | | | | | | | | |
| | | | | | L:12 | PRO | SER | | |
| | | | | | L:96 | THR | ASN | -13.62 | 2.18 |
| | | | | | H:30 | SER | ASN | | |
| | | | | | H:31 | SER | ARG | | |
| | | | | | | | | | |
| | | | | | L:12 | PRO | ALA | | |
| | | | | | L:96 | THR | ASN | -13.62 | 2.1 |
| | | | | | H:30 | SER | ASN | | |
| | | | | | H:31 | SER | ARG | | |
| | | | | | | | | | |
| | | | | | L:12 | PRO | THR | | |
| | | | | | H:31 | SER | ARG | -13.59 | -2.06 |
| | | | | | H:52 | VAL | ILE | | |
| | | | | | H:83 | THR | ILE | | |
| | | | | | | | | | |
| | | | | | L:12 | PRO | THR | | |
| | | | | | L:45 | PRO | SER | -13.51 | 5.12 |
| | | | | | L:96 | THR | ASN | | |
| | | | | | H:31 | SER | ARG | | |
| | | | | | | | | | |
| | | | | | L:12 | PRO | SER | | |
| | | | | | L:96 | THR | ASN | -13.49 | 1.81 |
| | | | | | H:30 | SER | THR | | |
| | | | | | H:31 | SER | ARG | | |
| | | | | | | | | | |
| | | | | | L:12 | PRO | THR | | |
| | | | | | L:96 | THR | ASN | -13.46 | -0.37 |
| | | | | | H:30 | SER | THR | | |
| | | | | | H:31 | SER | ARG | | |
| | | | | | | | | | |
| | | | | | L:12 | PRO | THR | | |
| | | | | | L:96 | THR | ILE | -13.42 | -1.36 |
| | | | | | H:31 | SER | ARG | | |
| | | | | | H:92 | ALA | GLY | | |
| | | | | | | | | | |
| | | | | | L:12 | PRO | SER | | |
| | | | | | L:51 | LEU | ILE | -13.41 | -9.7 |
| | | | | | H:30 | SER | ILE | | |
| | | | | | H:31 | SER | ARG | | |

Figure 3 (Continued)

| Three Mutations | | | | Four Mutations | | | | |
|---|---|---|---|---|---|---|---|---|
| Residue: | Original: | Mutation: | ΔAffinity: | ΔStability: | Residue: | Original: | Mutation: | ΔAffinity: | ΔStability: |
| | | | | | L:12 | PRO | THR | | |
| | | | | | L:51 | LEU | ILE | -13.41 | -13.29 |
| | | | | | H:30 | SER | ILE | | |
| | | | | | H:31 | SER | ARG | | |
| | | | | | | | | | |
| | | | | | L:12 | PRO | ALA | | |
| | | | | | L:51 | LEU | ILE | -13.41 | -9.79 |
| | | | | | H:30 | SER | ILE | | |
| | | | | | H:31 | SER | ARG | | |
| | | | | | | | | | |
| | | | | | L:27 | GLN | ILE | | |
| | | | | | H:31 | SER | ARG | -13.26 | -2.56 |
| | | | | | H:37 | VAL | ILE | | |
| | | | | | H:52 | THR | ILE | | |
| | | | | | | | | | |
| | | | | | L:27 | GLN | THR | | |
| | | | | | H:31 | SER | ARG | -13.22 | 3.55 |
| | | | | | H:37 | VAL | ILE | | |
| | | | | | H:52 | THR | ILE | | |
| | | | | | | | | | |
| | | | | | L:12 | PRO | THR | | |
| | | | | | L:51 | LEU | VAL | -13.06 | 1.69 |
| | | | | | L:96 | THR | ILE | | |
| | | | | | H:31 | SER | ARG | | |
| | | | | | | | | | |
| | | | | | L:12 | PRO | SER | | |
| | | | | | L:50 | GLN | HID | -13.01 | -15.3 |
| | | | | | H:30 | SER | ILE | | |
| | | | | | H:31 | SER | ARG | | |
| | | | | | | | | | |
| | | | | | L:12 | PRO | ALA | | |
| | | | | | L:50 | GLN | HID | -13 | -15.39 |
| | | | | | H:30 | SER | ILE | | |
| | | | | | H:31 | SER | ARG | | |
| | | | | | | | | | |
| | | | | | L:12 | PRO | THR | | |
| | | | | | L:50 | GLN | HID | -12.97 | -17.51 |
| | | | | | H:30 | SER | ILE | | |
| | | | | | H:31 | SER | ARG | | |
| | | | | | | | | | |
| | | | | | L:12 | PRO | THR | | |
| | | | | | L:51 | LEU | VAL | -12.95 | -9.77 |
| | | | | | H:30 | SER | ILE | | |
| | | | | | H:31 | SER | ARG | | |

Figure 3 (Continued)

| Three Mutations | | | | | Four Mutations | | | | |
|---|---|---|---|---|---|---|---|---|---|
| Residue: | Original: | Mutation: | ΔAffinity: | ΔStability: | Residue: | Original: | Mutation: | ΔAffinity: | ΔStability: |
| | | | | | L:27 | GLN | ARG | | |
| | | | | | H:31 | SER | ARG | -12.93 | -2.78 |
| | | | | | H:37 | VAL | PHE | | |
| | | | | | H:52 | THR | ILE | | |
| | | | | | | | | | |
| | | | | | L:12 | PRO | SER | | |
| | | | | | H:30 | SER | ILE | -12.91 | -17.22 |
| | | | | | H:31 | SER | ARG | | |
| | | | | | H:40 | ALA | SER | | |
| | | | | | | | | | |
| | | | | | L:12 | PRO | THR | | |
| | | | | | H:30 | SER | ILE | -12.91 | -19.41 |
| | | | | | H:31 | SER | ARG | | |
| | | | | | H:40 | ALA | SER | | |
| | | | | | | | | | |
| | | | | | L:12 | PRO | THR | | |
| | | | | | H:30 | SER | ILE | -12.9 | -24.43 |
| | | | | | H:31 | SER | ARG | | |
| | | | | | H:40 | ALA | THR | | |
| | | | | | | | | | |
| | | | | | L:12 | PRO | THR | | |
| | | | | | L:96 | THR | ASN | -12.82 | -1.56 |
| | | | | | H:30 | SER | ASN | | |
| | | | | | H:31 | SER | ARG | | |
| | | | | | | | | | |
| | | | | | L:12 | PRO | SER | | |
| | | | | | L:19 | ALA | VAL | -12.8 | -4.5 |
| | | | | | H:30 | SER | ILE | | |
| | | | | | H:31 | SER | ARG | | |
| | | | | | | | | | |
| | | | | | L:12 | PRO | ALA | | |
| | | | | | H:14 | PRO | THR | -12.8 | -12.04 |
| | | | | | H:30 | SER | ILE | | |
| | | | | | H:31 | SER | ARG | | |
| | | | | | | | | | |
| | | | | | L:12 | PRO | THR | | |
| | | | | | H:14 | PRO | SER | -12.79 | -16.44 |
| | | | | | H:30 | SER | ILE | | |
| | | | | | H:31 | SER | ARG | | |
| | | | | | | | | | |
| | | | | | L:12 | PRO | SER | | |
| | | | | | H:14 | PRO | SER | -12.79 | -12.83 |
| | | | | | H:30 | SER | ILE | | |
| | | | | | H:31 | SER | ARG | | |

Figure 3 (Continued)

| Three Mutations | | | | Four Mutations | | | | |
|---|---|---|---|---|---|---|---|---|
| Residue: | Original: | Mutation: | ΔAffinity: | ΔStability: | Residue: | Original: | Mutation: | ΔAffinity: | ΔStability: |
| | | | | | L:12 | PRO | THR | | |
| | | | | | H:14 | PRO | THR | -12.79 | -14.14 |
| | | | | | H:30 | SER | ILE | | |
| | | | | | H:31 | SER | ARG | | |
| | | | | | | | | | |
| | | | | | L:12 | PRO | ALA | | |
| | | | | | H:14 | PRO | SER | -12.79 | -12.93 |
| | | | | | H:30 | SER | ILE | | |
| | | | | | H:31 | SER | ARG | | |
| | | | | | | | | | |
| | | | | | L:12 | PRO | SER | | |
| | | | | | H:14 | PRO | SER | -12.79 | -11.2 |
| | | | | | H:30 | SER | ILE | | |
| | | | | | H:31 | SER | ARG | | |
| | | | | | | | | | |
| | | | | | L:12 | PRO | THR | | |
| | | | | | L:45 | PRO | SER | -12.78 | -13.38 |
| | | | | | H:30 | SER | ILE | | |
| | | | | | H:31 | SER | ARG | | |
| | | | | | | | | | |
| | | | | | L:12 | PRO | THR | | |
| | | | | | L:45 | PRO | THR | -12.78 | -15.1 |
| | | | | | H:30 | SER | ILE | | |
| | | | | | H:31 | SER | ARG | | |
| | | | | | | | | | |
| | | | | | L:12 | PRO | THR | | |
| | | | | | L:108 | LYS | ASN | -12.76 | -15.47 |
| | | | | | H:30 | SER | ARG | | |
| | | | | | H:31 | SER | ASP | | |
| | | | | | | | | | |
| | | | | | L:12 | PRO | THR | | |
| | | | | | L:56 | VAL | ILE | -12.74 | -15.73 |
| | | | | | H:30 | SER | ILE | | |
| | | | | | H:31 | SER | ARG | | |
| | | | | | | | | | |
| | | | | | L:12 | PRO | ALA | | |
| | | | | | L:45 | PRO | SER | -12.69 | -7.41 |
| | | | | | L:96 | THR | ILE | | |
| | | | | | H:31 | SER | ARG | | |
| | | | | | | | | | |
| | | | | | L:12 | PRO | SER | | |
| | | | | | L:108 | LYS | ASN | -12.69 | -15.77 |
| | | | | | H:30 | SER | ILE | | |
| | | | | | H:31 | SER | ARG | | |

Figure 3 (Continued)

| Five Mutations | | | | | Six Mutations | | | | |
|---|---|---|---|---|---|---|---|---|---|
| Residue | Original | Mutation | ΔAffinity | ΔStability | Residue | Original | Mutation | ΔAffinity | ΔStability |
| L:12 | PRO | SER | | | L:12 | PRO | SER | | |
| H:30 | SER | ASN | | | L:96 | THR | ASN | | |
| H:31 | SER | ARG | -16.07 | 4.91 | H:30 | SER | ILE | -17.69 | 5.29 |
| H:52 | THR | ILE | | | H:31 | SER | ARG | | |
| H:92 | ALA | GLY | | | H:40 | ALA | THR | | |
| | | | | | H:52 | THR | ILE | | |
| L:12 | PRO | THR | | | | | | | |
| L:27 | GLN | THR | | | L:12 | PRO | THR | | |
| H:31 | SER | ARG | -13.9 | 2.53 | L:96 | THR | ASN | | |
| H:52 | THR | ILE | | | H:30 | SER | ILE | -17.69 | 3.1 |
| H:92 | ALA | GLY | | | H:31 | SER | ARG | | |
| | | | | | H:40 | ALA | THR | | |
| L:12 | PRO | SER | | | H:52 | THR | ILE | | |
| L:81 | SER | THR | | | | | | | |
| H:31 | SER | ARG | -13.8 | 2.46 | L:12 | PRO | ALA | | |
| H:52 | THR | ILE | | | L:51 | LEU | VAL | | |
| H:92 | ALA | GLY | | | H:30 | SER | ILE | -16.11 | 0.88 |
| | | | | | H:31 | SER | ARG | | |
| L:12 | PRO | SER | | | H:40 | ALA | SER | | |
| L:45 | PRO | THR | | | H:52 | THR | ILE | | |
| H:31 | SER | ARG | -13.8 | 4.36 | | | | | |
| H:52 | THR | ILE | | | L:23 | PRO | THR | | |
| H:92 | ALA | GLY | | | L:51 | LEU | VAL | | |
| | | | | | H:30 | SER | ILE | -16.1 | -1.19 |
| L:12 | PRO | SER | | | H:31 | SER | ARG | | |
| L:96 | THR | ILE | | | H:40 | ALA | SER | | |
| H:30 | SER | ILE | -13.52 | -6.31 | H:52 | THR | ILE | | |
| H:31 | SER | ARG | | | | | | | |
| H:92 | ALA | GLY | | | L:12 | PRO | SER | | |
| | | | | | L:96 | THR | ASN | | |
| L:12 | PRO | ALA | | | H:30 | SER | ASN | -16.05 | 4.11 |
| L:96 | THR | ILE | | | H:31 | SER | ARG | | |
| H:30 | SER | ILE | -13.52 | -6.4 | H:40 | ALA | THR | | |
| H:31 | SER | ARG | | | H:52 | THR | ILE | | |
| H:92 | ALA | GLY | | | | | | | |
| | | | | | L:12 | PRO | ALA | | |
| L:12 | PRO | SER | | | H:10 | GLY | ALA | | |
| H:30 | SER | ILE | | | H:30 | SER | ILE | -15.37 | -7.41 |
| H:31 | SER | ARG | -15.44 | -8.88 | H:31 | SER | ARG | | |
| H:40 | ALA | SER | | | H:40 | ALA | SER | | |
| H:52 | THR | ILE | | | H:52 | THR | ILE | | |

Figure 3 (Continued)

| Five Mutations | | | | | Six Mutations | | | | |
|---|---|---|---|---|---|---|---|---|---|
| Residue | Original | Mutation | ΔAffinity | ΔStability | Residue | Original | Mutation | ΔAffinity | ΔStability |
| L:12 | PRO | THR | | | L:12 | PRO | SER | | |
| H:30 | SER | ILE | | | H:30 | SER | ILE | | |
| H:31 | SER | ARG | -15.28 | -16.01 | H:31 | SER | ARG | -15.36 | 2.08 |
| H:40 | ALA | THR | | | H:40 | ALA | SER | | |
| H:52 | THR | ILE | | | H:52 | THR | ILE | | |
| | | | | | H:83 | MET | ILE | | |
| L:12 | PRO | SER | | | | | | | |
| L:96 | THR | ILE | | | L:12 | PRO | THR | | |
| H:31 | SER | ARG | -15.27 | -10.16 | H:30 | SER | ILE | | |
| H:40 | ALA | THR | | | H:31 | SER | ARG | -15.36 | -0.1 |
| H:52 | THR | ILE | | | H:40 | ALA | SER | | |
| | | | | | H:52 | THR | ILE | | |
| L:12 | PRO | SER | | | H:83 | MET | ILE | | |
| H:30 | SER | ILE | | | | | | | |
| H:31 | SER | ARG | -15.26 | -13.79 | L:12 | PRO | ALA | | |
| H:40 | ALA | THR | | | H:10 | GLY | ALA | | |
| H:52 | THR | ILE | | | H:30 | SER | ILE | -15.36 | -12.36 |
| | | | | | H:31 | SER | ARG | | |
| L:12 | PRO | ALA | | | H:40 | ALA | THR | | |
| H:30 | SER | ILE | | | H:52 | THR | ILE | | |
| H:31 | SER | ARG | -15.25 | -8.79 | | | | | |
| H:40 | ALA | PRO | | | L:12 | PRO | SER | | |
| H:52 | THR | ILE | | | H:10 | GLY | ALA | | |
| | | | | | H:30 | SER | ILE | -15.36 | -7.31 |
| | | | | | H:31 | SER | ARG | | |
| | | | | | H:40 | ALA | SER | | |
| | | | | | H:52 | THR | ILE | | |
| | | | | | L:12 | PRO | SER | | |
| | | | | | H:10 | GLY | VAL | | |
| | | | | | H:30 | SER | ILE | -15.36 | -7.14 |
| | | | | | H:31 | SER | ARG | | |
| | | | | | H:40 | ALA | SER | | |
| | | | | | H:52 | THR | ILE | | |
| | | | | | L:12 | PRO | SER | | |
| | | | | | L:45 | PRO | ALA | | |
| | | | | | H:30 | SER | ILE | -15.35 | -5.15 |
| | | | | | H:31 | SER | ARG | | |
| | | | | | H:40 | ALA | SER | | |
| | | | | | H:52 | THR | ILE | | |

Figure 3 (Continued)

| Five Mutations | | | | | Six Mutations | | | | |
|---|---|---|---|---|---|---|---|---|---|
| Residue | Original | Mutation | ΔAffinity | ΔStability | Residue | Original | Mutation | ΔAffinity | ΔStability |
| | | | | | L:12 | PRO | SER | | |
| | | | | | H:10 | GLY | ALA | | |
| | | | | | H:30 | SER | ILE | -15.35 | -12.26 |
| | | | | | H:31 | SER | ARG | | |
| | | | | | H:40 | ALA | THR | | |
| | | | | | H:52 | THR | ILE | | |
| | | | | | | | | | |
| | | | | | L:12 | PRO | ALA | | |
| | | | | | H:30 | SER | ILE | | |
| | | | | | H:31 | SER | ARG | -15.34 | 2.01 |
| | | | | | H:40 | ALA | SER | | |
| | | | | | H:52 | THR | ILE | | |
| | | | | | H:83 | MET | ILE | | |
| | | | | | | | | | |
| | | | | | L:12 | PRO | SER | | |
| | | | | | H:30 | SER | ILE | | |
| | | | | | H:31 | SER | ARG | -15.32 | -2.58 |
| | | | | | H:40 | ALA | SER | | |
| | | | | | H:52 | THR | ILE | | |
| | | | | | H:92 | ALA | GLY | | |
| | | | | | | | | | |
| | | | | | L:12 | PRO | THR | | |
| | | | | | L:27 | GLN | ILE | | |
| | | | | | H:30 | SE5R | ILE | -15.31 | -12.88 |
| | | | | | H:31 | SER | ARG | | |
| | | | | | H:40 | ALA | SER | | |
| | | | | | H:52 | THR | ILE | | |
| | | | | | | | | | |
| | | | | | L:12 | PRO | THR | | |
| | | | | | L:27 | GLN | ILE | | |
| | | | | | H:30 | SER | ILE | -15.31 | 4.6 |
| | | | | | H:31 | SER | ARG | | |
| | | | | | H:40 | ALA | PRO | | |
| | | | | | H:52 | THR | ILE | | |
| | | | | | | | | | |
| | | | | | L:12 | PRO | THR | | |
| | | | | | L:27 | GLN | ILE | | |
| | | | | | H:30 | SER | ILE | -15.3 | -17.85 |
| | | | | | H:31 | SER | ARG | | |
| | | | | | H:40 | ALA | THR | | |
| | | | | | H:52 | THR | ILE | | |

Figure 3 (Continued)

| Five Mutations | | | | | Six Mutations | | | | |
|---|---|---|---|---|---|---|---|---|---|
| Residue | Original | Mutation | ΔAffinity | ΔStability | Residue | Original | Mutation | ΔAffinity | ΔStability |
| | | | | | L:12 | PRO | SER | | |
| | | | | | L:96 | THR | ILE | | |
| | | | | | H:10 | GLY | VAL | -15.27 | -3.35 |
| | | | | | H:31 | SER | ARG | | |
| | | | | | H:40 | ALA | SER | | |
| | | | | | H:52 | THR | ILE | | |
| | | | | | | | | | |
| | | | | | L:12 | PRO | SER | | |
| | | | | | L:96 | SER | ILE | | |
| | | | | | H:10 | THR | ILE | -15.26 | -15.43 |
| | | | | | H:31 | SER | ARG | | |
| | | | | | H:40 | ALA | THR | | |
| | | | | | H:52 | THR | ILE | | |
| | | | | | | | | | |
| | | | | | L:12 | PRO | SER | | |
| | | | | | L:96 | THR | ILE | | |
| | | | | | H:10 | GLY | VAL | -15.26 | -8.31 |
| | | | | | H:31 | SER | ARG | | |
| | | | | | H:40 | ALA | THR | | |
| | | | | | H:52 | THR | ILE | | |
| | | | | | | | | | |
| | | | | | L:12 | PRO | ALA | | |
| | | | | | H:10 | GLY | VAL | | |
| | | | | | H:30 | SER | ILE | -15.25 | -7 |
| | | | | | H:31 | SER | ARG | | |
| | | | | | H:40 | ALA | SER | | |
| | | | | | H:52 | THR | ILE | | |
| | | | | | | | | | |
| | | | | | L:12 | PRO | THR | | |
| | | | | | L:81 | SER | THR | | |
| | | | | | H:30 | SER | ILE | -15.25 | -10.28 |
| | | | | | H:31 | SER | ARG | | |
| | | | | | H:40 | ALA | SER | | |
| | | | | | H:52 | THR | ILE | | |
| | | | | | | | | | |
| | | | | | L:12 | PRO | THR | | |
| | | | | | L:108 | LYS | ASN | | |
| | | | | | H:30 | SER | ILE | -15.14 | -11.18 |
| | | | | | H:31 | SER | ARG | | |
| | | | | | H:40 | ALA | SER | | |
| | | | | | H:52 | THR | ILE | | |

Figure 3 (Continued)

| Five Mutations | | | | | Six Mutations | | | | |
|---|---|---|---|---|---|---|---|---|---|
| Residue | Original | Mutation | ΔAffinity | ΔStability | Residue | Original | Mutation | ΔAffinity | ΔStability |
| | | | | | L:12 | PRO | SER | | |
| | | | | | L:51 | LEU | VAL | | |
| | | | | | H:30 | SER | THR | -15.07 | 1.04 |
| | | | | | H:31 | SER | ARG | | |
| | | | | | H:40 | ALA | SER | | |
| | | | | | H:52 | THR | ILE | | |
| | | | | | | | | | |
| | | | | | L:12 | PRO | THR | | |
| | | | | | L:51 | LEU | VAL | | |
| | | | | | H:30 | SER | THR | -15.07 | -1.15 |
| | | | | | H:31 | SER | ARG | | |
| | | | | | H:40 | ALA | SER | | |
| | | | | | H:52 | THR | ILE | | |

Figure 5

Run 1

| Sample ID | KD (M) | kon (1/Ms) | kdis (1/s) |
|---|---|---|---|
| Fsn0503h | 3.05E-09 | 3.96E+04 | 1.21E-04 |
| *WT* | *<1.0E-12* | *4.51E+04* | *<1.0E-07* |
| Mut 1 | 3.63E-09 | 3.77E+04 | 1.37E-04 |
| *Mut 2* | *<1.0E-12* | *2.02E+05* | *<1.0E-07* |
| *Mut 3* | *<1.0E-12* | *8.72E+04* | *<1.0E-07* |
| *Mut 4* | *<1.0E-12* | *2.96E+04* | *<1.0E-07* |
| Mut 5 | 1.40E-09 | 2.84E+04 | 3.99E-05 |
| Mut 6 | 1.75E-08 | 4.17E+04 | 7.31E-04 |
| Mut 7 | 4.88E-09 | 3.70E+04 | 1.80E-04 |
| Mut 8 | 7.69E-09 | 3.13E+04 | 2.41E-04 |
| Mut 9 | 5.66E-09 | 5.73E+04 | 2.11E-04 |
| Mut 10 | 8.01E-09 | 1.68E+04 | 1.34E-04 |
| *Mut 11* | *<1.0E-12* | *4.28E+04* | *<1.0E-07* |
| Mut 12 | 8.42E-09 | 2.71E+04 | 2.28E-04 |
| Mut 13 | 7.31E-09 | 3.96E+04 | 2.89E-04 |
| Mut 14 | 7.28E-09 | 3.75E+04 | 2.73E-04 |
| Mut 15 | 6.04E-09 | 2.99E+04 | 1.80E-04 |
| Mut 16 | 6.24E-09 | 3.77E+04 | 2.35E-04 |
| Mut 17 | 3.10E-09 | 3.06E+04 | 1.13E-04 |
| Mut 18 | 5.03E-09 | 2.07E+04 | 1.04E-04 |
| *Mut 19* | *<1.0E-12* | *1.78E+04* | *<1.0E-07* |

| Sample ID | KD (M) | kon (1/Ms) | kdis (1/s) |
|---|---|---|---|
| Mut 20 | 3.54E-10 | 3.67E+04 | 1.30E-05 |
| Mut 21 | 3.10E-09 | 3.16E+04 | 9.80E-05 |
| Mut 22 | 4.55E-09 | 4.28E+04 | 1.95E-04 |
| Mut 23 | 1.20E-08 | 2.53E+04 | 3.04E-04 |
| Mut 24 | 1.48E-09 | 3.68E+04 | 5.44E-05 |
| Mut 25 | 2.81E-09 | 3.83E+04 | 1.07E-04 |
| *Mut 26* | *<1.0E-12* | *1.17E+05* | *<1.0E-07* |
| *Mut 27* | *<1.0E-12* | *8.78E+04* | *<1.0E-07* |
| Mut 29 | 4.78E-09 | 3.35E+04 | 1.60E-04 |
| Mut 30 | 2.80E-09 | 3.80E+04 | 1.06E-04 |
| Mut 31 | 5.33E-09 | 2.98E+04 | 1.59E-04 |
| Mut 32 | 4.48E-09 | 4.27E+04 | 1.91E-04 |
| Mut 33 | 3.13E-09 | 3.79E+04 | 1.18E-04 |
| Mut 34 | 7.39E-09 | 3.99E+04 | 2.95E-04 |
| Mut 35 | 6.82E-09 | 2.64E+04 | 1.80E-04 |
| *Mut 36* | *<1.0E-12* | *2.04E+05* | *<1.0E-07* |
| Mut 37 | 5.53E-09 | 3.40E+04 | 1.88E-04 |
| Mut 38 | 3.10E-09 | 4.34E+04 | 1.34E-04 |
| Mut 39 | 3.92E-09 | 3.89E+04 | 1.52E-04 |
| Mut 40 | 3.03E-09 | 3.81E+04 | 1.15E-04 |

Run 1

| Sample ID | KD (M) | kon (1/Ms) | kdis (1/s) |
|---|---|---|---|
| Mut 41 | 3.34E-09 | 2.72E+04 | 9.07E-05 |
| Mut 42 | 4.40E-09 | 4.11E+04 | 1.81E-04 |
| Mut 43 | 6.31E-09 | 1.93E+04 | 1.22E-04 |
| *Mut 44* | *<1.0E-12* | *1.82E+05* | *<1.0E-07* |
| Mut 45 | 1.56E-09 | 1.74E+04 | 2.72E-05 |
| Mut 46 | 6.33E-09 | 1.84E+04 | 1.17E-04 |
| Mut 47 | 2.55E-09 | 1.22E+04 | 3.12E-05 |
| Mut 48 | 3.14E-09 | 2.09E+04 | 6.56E-05 |
| Mut 49 | 1.77E-08 | 2.38E+04 | 4.21E-04 |
| Mut 50 | 6.59E-09 | 1.96E+04 | 1.29E-04 |
| Mut 51 | 9.01E-09 | 3.73E+04 | 3.36E-04 |
| Mut 52 | 1.80E-08 | 2.21E+04 | 3.99E-04 |
| Fsn0503h | 5.47E-09 | 2.62E+04 | 1.44E-04 |
| *No hIgG* | *<1.0E-12* | *2.52E+05* | *<1.0E-07* |

Run 2

| Sample ID | KD (M) | kon (1/Ms) | kdis (1/s) |
|---|---|---|---|
| Fsn0503h | 4.39E-09 | 4.28E+04 | 1.88E-04 |
| Mut 53 | 4.04E-09 | 3.83E+04 | 1.55E-04 |
| *Mut 54* | *<1.0E-12* | *1.08E+05* | *<1.0E-07* |
| *Mut 55* | *<1.0E-12* | *1.10E+05* | *<1.0E-07* |
| Mut 56 | 5.14E-09 | 4.02E+04 | 2.07E-04 |
| Mut 57 | 4.49E-10 | 3.79E+04 | 1.70E-05 |
| Mut 58 | 5.37E-09 | 1.69E+04 | 9.07E-05 |
| Mut 59 | 9.21E-09 | 1.87E+04 | 1.72E-04 |
| Mut 60 | 2.89E-09 | 2.33E+04 | 6.72E-05 |
| Mut 61 | 4.12E-08 | 3.15E+04 | 1.30E-03 |
| Mut 62 | 2.63E-08 | 1.16E+04 | 3.05E-04 |
| Mut 63 | 1.24E-08 | 1.27E+04 | 1.58E-04 |
| Mut 64 | 2.78E-09 | 3.57E+04 | 9.94E-05 |
| Mut 65 | 2.63E-09 | 1.50E+04 | 3.96E-05 |
| Mut 66 | 2.31E-09 | 3.44E+04 | 7.94E-05 |
| Fsn0503h | 5.11E-09 | 4.73E+04 | 2.42E-04 |
| No hIgG | 1.91E-08 | 1.81E+05 | 3.45E-03 |
| *No hIgG* | *<1.0E-12* | *1.00E+05* | *<1.0E-07* |

Bold = Affinity higher than best reading for Fsn0503h
Underline = Fsn0503h control
*Italic* = Affinity to be determined

Figure 7

| # | Region | AA | | | | | | | | | |
|---|---|---|---|---|---|---|---|---|---|---|---|
| 1 | FR1 | D | | | | | | | | | |
| 2 | | I | | | | | | | | | |
| 3 | | Q | | | | | | | | | |
| 4 | | M | | | | | | | | | |
| 5 | | T | | | | | | | | | |
| 6 | | Q | | | | | | | | | |
| 7 | | S | | | | | | | | | |
| 8 | | P | | | | | | | | | |
| 9 | | S | S | N | T | I | R | K | | | |
| 10 | | S | | | | | | | | | |
| 11 | | L | | | | | | | | | |
| 12 | | S | | | | | | | | | |
| 13 | | A | | | | | | | | | |
| 14 | | S | | | | | | | | | |
| 15 | | V | | | | | | | | | |
| 16 | | G | | | | | | | | | |
| 17 | | D | | | | | | | | | |
| 18 | | R | | | | | | | | | |
| 19 | | V | | | | | | | | | |
| 20 | | T | | | | | | | | | |
| 21 | | I | | | | | | | | | |
| 22 | | T | | | | | | | | | |
| 23 | | C | C | W | * | | | | | | |
| 24 | CDR1 | R | | | | | | | | | |
| 25 | | A | G | A | V | D | | | | | |
| 26 | | S | | | | | | | | | |
| 27 | | Q | | | | | | | | | |
| 28 | | D | | | | | | | | | |
| 29 | | V | | | | | | | | | |
| 30 | | N | | | | | | | | | |
| 31 | | T | S | N | T | I | | | | | |
| 32 | | A | A | D | G | V | T | N | S | I | P | L | F |
| 33 | | V | L | I | V | | | | | | |
| 34 | | A | G | A | V | D | | | | | |
| 35 | FR2 | W | C | W | STOP | | | | | | |
| 36 | | Y | | | | | | | | | |
| 37 | | Q | | | | | | | | | |
| 38 | | Q | E | STOP | Q | K | | | | | |
| 39 | | K | | | | | | | | | |
| 40 | | P | A | S | P | T | | | | | |
| 41 | | G | | | | | | | | | |
| 42 | | K | | | | | | | | | |
| 43 | | A | A | D | G | V | T | N | S | I | P | L | F |
| 44 | | P | | | | | | | | | |
| 45 | | K | | | | | | | | | |
| 46 | | L | V | L | I | | | | | | |
| 47 | | L | V | L | M | | | | | | |

SEQ ID NO: 3

Figure 7
(Continued)

| # | Region | AA | | | | | |
|---|---|---|---|---|---|---|---|
| 48 | FR2 | I | | | | | |
| 49 | | Y | Y | STOP | | | |
| 50 | | S | | | | | |
| 51 | | A | A | S | P | T | |
| 52 | | S | | | | | |
| 53 | | F | | | | | |
| 54 | | L | | | | | |
| 55 | CDR 2 | Y | | | | | |
| 56 | | S | | | | | |
| 57 | | G | | | | | |
| 58 | | V | | | | | |
| 59 | | P | | | | | |
| 60 | | S | | | | | |
| 61 | | R | | | | | |
| 62 | | F | | | | | |
| 63 | | S | | | | | |
| 64 | | G | | | | | |
| 65 | | S | | | | | |
| 66 | | R | | | | | |
| 67 | | S | | | | | |
| 68 | | G | | | | | |
| 69 | | T | | | | | |
| 70 | | D | | | | | |
| 71 | | F | | | | | |
| 72 | | T | | | | | |
| 73 | | L | | | | | |
| 74 | | T | | | | | |
| 75 | FR3 | I | | | | | |
| 76 | | S | R | S | N | T | K | I |
| 77 | | S | | | | | |
| 78 | | L | | | | | |
| 79 | | Q | K | E | Q | STOP | |
| 80 | | P | T | S | P | A | |
| 81 | | E | | | | | |
| 82 | | D | | | | | |
| 83 | | F | | | | | |
| 84 | | A | | | | | |
| 85 | | T | S | N | T | I | |
| 86 | | Y | | | | | |
| 87 | | Y | Y | STOP | | | |
| 88 | | C | | | | | |
| 89 | | Q | Q | H | | | |
| 90 | | Q | E | STOP | Q | A | |
| 91 | CDR3 | H | N | D | Y | H | |
| 92 | | Y | | | | | |
| 93 | | T | S | N | T | I | |
| 94 | | T | S | N | T | I | |

| 95 | | P | | | | |
|---|---|---|---|---|---|---|
| 96 | | P | | | | |
| 97 | CDR3 | T | | | | |
| 98 | | F | | | | |
| 99 | | G | | | | |
| 100 | | Q | | | | |
| 101 | | G | G | A | V | D |
| 102 | FR4 | T | S | N | T | I |
| 103 | | K | | | | |
| 104 | | V | | | | |
| 105 | | E | | | | |
| 106 | | I | | | | |
| 107 | | K | | | | |

| # | Region | AA | | | | | | | | | | | |
|---|---|---|---|---|---|---|---|---|---|---|---|---|---|
| | | SEQ ID NO: 4 | | | | | | | | | | | |
| 1 | | E | | | | | | | | | | | |
| 2 | | V | V | L | I | F | | | | | | | |
| 3 | | Q | Q | H | | | | | | | | | |
| 4 | | L | M | V | L | | | | | | | | |
| 5 | | V | | | | | | | | | | | |
| 6 | | E | | | | | | | | | | | |
| 7 | | S | | | | | | | | | | | |
| 8 | | G | | | | | | | | | | | |
| 9 | | G | | | | | | | | | | | |
| 10 | | G | | | | | | | | | | | |
| 11 | | L | | | | | | | | | | | |
| 12 | | V | | | | | | | | | | | |
| 13 | | Q | K | E | Q | STOP | | | | | | | |
| 14 | | P | P | A | T | S | | | | | | | |
| 15 | FR1 | G | | | | | | | | | | | |
| 16 | | G | G | A | V | D | | | | | | | |
| 17 | | S | | | | | | | | | | | |
| 18 | | L | | | | | | | | | | | |
| 19 | | R | | | | | | | | | | | |
| 20 | | L | | | | | | | | | | | |
| 21 | | S | | | | | | | | | | | |
| 22 | | C | | | | | | | | | | | |
| 23 | | A | A | E | G | V | T | K | R | I | P | L | S |
| 24 | | A | A | D | G | V | T | N | S | I | P | L | F |
| 25 | | S | | | | | | | | | | | |
| 26 | | G | G | A | V | D | | | | | | | |
| 27 | | F | | | | | | | | | | | |
| 28 | | N | K | N | | | | | | | | | |
| 29 | | I | | | | | | | | | | | |
| 30 | | K | | | | | | | | | | | |
| 31 | | D | | | | | | | | | | | |
| 32 | | T | | | | | | | | | | | |
| 33 | CDR1 | Y | | | | | | | | | | | |
| 34 | | I | | | | | | | | | | | |
| 35 | | H | H | N | D | Y | | | | | | | |
| 36 | | W | | | | | | | | | | | |
| 37 | | V | | | | | | | | | | | |
| 38 | | R | | | | | | | | | | | |
| 39 | | Q | | | | | | | | | | | |
| 40 | | A | | | | | | | | | | | |
| 41 | | P | | | | | | | | | | | |
| 42 | FR2 | G | G | A | V | D | | | | | | | |
| 43 | | K | | | | | | | | | | | |
| 44 | | G | | | | | | | | | | | |
| 45 | | L | | | | | | | | | | | |
| 46 | | E | | | | | | | | | | | |
| 47 | | W | | | | | | | | | | | |

Figure 8 (Continued)

| # | Region | AA | | | | | | | | | | |
|---|---|---|---|---|---|---|---|---|---|---|---|---|
| 48 | FR2 | V | F | L | V | I | | | | | | |
| 49 | FR2 | A | A | E | G | V | T | K | R | I | P | L | S |
| 50 | | R | | | | | | | | | | |
| 51 | | I | | | | | | | | | | |
| 52 | | Y | | | | | | | | | | |
| 53 | | P | | | | | | | | | | |
| 54 | | T | | | | | | | | | | |
| 55 | | N | | | | | | | | | | |
| 56 | | G | G | A | V | D | | | | | | |
| 57 | | Y | | | | | | | | | | |
| 58 | CDR2 | T | S | N | T | I | | | | | | |
| 59 | | R | | | | | | | | | | |
| 60 | | Y | | | | | | | | | | |
| 61 | | A | G | A | V | D | | | | | | |
| 62 | | D | | | | | | | | | | |
| 63 | | S | | | | | | | | | | |
| 64 | | V | | | | | | | | | | |
| 65 | | K | | | | | | | | | | |
| 66 | | G | | | | | | | | | | |
| 67 | | R | | | | | | | | | | |
| 68 | | F | | | | | | | | | | |
| 69 | | T | | | | | | | | | | |
| 70 | | I | | | | | | | | | | |
| 71 | | S | | | | | | | | | | |
| 72 | | A | | | | | | | | | | |
| 73 | | D | | | | | | | | | | |
| 74 | | T | | | | | | | | | | |
| 75 | | S | | | | | | | | | | |
| 76 | | K | | | | | | | | | | |
| 77 | | N | K | N | | | | | | | | |
| 78 | | T | | | | | | | | | | |
| 79 | | A | G | A | V | D | | | | | | |
| 80 | | Y | Y | STOP | | | | | | | | |
| 81 | FR3 | L | | | | | | | | | | |
| 82 | | Q | E | K | Q | STOP | | | | | | |
| 83 | | M | | | | | | | | | | |
| 84 | | N | K | N | | | | | | | | |
| 85 | | S | R | S | | | | | | | | |
| 86 | | L | | | | | | | | | | |
| 87 | | R | | | | | | | | | | |
| 88 | | A | A | D | G | V | T | N | S | I | P | L | F |
| 89 | | E | | | | | | | | | | |
| 90 | | D | | | | | | | | | | |
| 91 | | T | | | | | | | | | | |
| 92 | | A | G | A | V | D | | | | | | |
| 93 | | V | | | | | | | | | | |
| 94 | | Y | | | | | | | | | | |
| 95 | | Y | | | | | | | | | | |

| | | | | | | | | | | | | |
|---|---|---|---|---|---|---|---|---|---|---|---|---|
| 96 | FR3 | C | F | S | Y | C | | | | | | |
| 97 | | S | | | | | | | | | | |
| 98 | | R | | | | | | | | | | |
| 99 | | W | | | | | | | | | | |
| 100 | CDR3 | G | | | | | | | | | | |
| 101 | | G | | | | | | | | | | |
| 102 | | D | | | | | | | | | | |
| 103 | | G | G | A | V | D | | | | | | |
| 104 | | F | | | | | | | | | | |
| 105 | | Y | | | | | | | | | | |
| 106 | | A | A | D | G | V | T | N | S | I | P | L | F |
| 107 | | M | | | | | | | | | | |
| 108 | | D | | | | | | | | | | |
| 109 | | Y | | | | | | | | | | |
| 110 | FR4 | W | | | | | | | | | | |
| 111 | | G | | | | | | | | | | |
| 112 | | Q | | | | | | | | | | |
| 113 | | G | | | | | | | | | | |
| 114 | | T | S | N | T | I | | | | | | |
| 115 | | L | | | | | | | | | | |
| 116 | | V | | | | | | | | | | |
| 117 | | T | | | | | | | | | | |
| 118 | | V | | | | | | | | | | |
| 119 | | S | | | | | | | | | | |
| 120 | | S | | | | | | | | | | |

| 1 Mutation | | | | | |
|---|---|---|---|---|---|
| Variant Number | Residue | Original | Mutated | Δ Affinity | Δ Stability |
| 1 | L:51 | ALA | THR | -4.33 | 7.33 |
| 2 | H:103 | GLY | VAL | -3.99 | 19.62 |
| 3 | L:31 | THR | SER | -3.56 | 7.03 |
| 4 | H:103 | GLY | ALA | -3.01 | 1.12 |
| 5 | L:25 | ALA | VAL | -1.74 | 45.76 |
| 6 | L:32 | ALA | VAL | -1.42 | 37.08 |
| 7 | L:93 | THR | ILE | -0.91 | *-6.9* |
| 8 | L:9 | SER | LYS | -0.77 | 4.2 |
| 9 | L:9 | SER | ARG | -0.71 | *-9.36* |
| 10 | L:93 | THR | ASN | -0.49 | 6.78 |
| 11 | L:9 | SER | ILE | -0.34 | *-5.4* |
| 12 | L:46 | LEU | ILE | -0.28 | 11.43 |
| 13 | H:85 | SER | ARG | -0.25 | *-10.35* |
| 14 | L:31 | THR | ILE | -0.18 | 1.53 |
| 15 | L:34 | ALA | GLY | -0.17 | 5.6 |
| 16 | H:114 | THR | ILE | -0.17 | *-9.08* |
| 17 | H:61 | ALA | GLY | -0.16 | 4.56 |
| 18 | L:51 | ALA | PRO | -0.15 | 57.67 |
| 19 | H:56 | GLY | ALA | -0.15 | 0.43 |
| 20 | H:79 | ALA | GLY | -0.15 | 8.7 |
| 21 | L:25 | ALA | GLY | -0.11 | 8.48 |
| 22 | L:46 | LEU | VAL | -0.1 | 16.58 |
| 23 | H:24 | ALA | GLY | -0.1 | 6.2 |
| 24 | H:79 | ALA | VAL | -0.1 | *-10.71* |
| 25 | H:114 | THR | ASN | -0.07 | -1.79 |
| 26 | H:114 | THR | SER | -0.06 | 0.82 |
| 27 | L:47 | LEU | VAL | -0.05 | 8.2 |
| 28 | H:48 | VAL | LEU | -0.05 | 10.23 |
| 29 | L:101 | GLY | VAL | -0.03 | 1.3 |
| 30 | H:48 | VAL | ILE | -0.02 | 0.64 |
| 31 | L:43 | ALA | GLY | -0.01 | 4.12 |
| 32 | L:9 | SER | THR | 0 | *-4.63* |
| 33 | L:51 | ALA | SER | 0 | 2.2 |
| 34 | L:76 | SER | THR | 0 | *-6.43* |
| 35 | L:80 | PRO | THR | 0 | *-4.29* |
| 36 | L:80 | PRO | SER | 0 | 0.3 |
| 37 | H:4 | LEU | VAL | 0 | 15.82 |
| 38 | H:14 | PRO | THR | 0 | 1.28 |
| 39 | H:14 | PRO | ALA | 0 | 6.03 |
| 40 | H:14 | PRO | SER | 0 | 6.35 |
| 41 | H:88 | ALA | VAL | 0 | *-3.97* |
| 42 | H:88 | ALA | GLY | 0 | 2.56 |
| 43 | L:40 | PRO | THR | 0.01 | 8.27 |
| 44 | L:40 | PRO | SER | 0.01 | 6.92 |
| 45 | L:80 | PRO | ALA | 0.01 | 2.89 |
| 46 | L:101 | GLY | ALA | 0.01 | 3.6 |
| 47 | H:16 | GLY | ALA | 0.01 | 1.65 |
| 48 | L:40 | PRO | ALA | 0.02 | 6.79 |
| 49 | L:43 | ALA | PRO | 0.03 | *-2.02* |
| 50 | L:85 | THR | SER | 0.03 | 5.27 |
| 51 | H:2 | VAL | LEU | 0.03 | 12.41 |
| 52 | H:16 | GLY | VAL | 0.03 | 4.11 |
| 53 | H:58 | THR | SER | 0.03 | 6.62 |
| 54 | H:92 | ALA | GLY | 0.03 | 6.24 |
| 55 | L:43 | ALA | ASN | 0.04 | *-7.99* |
| 56 | H:2 | VAL | ILE | 0.04 | *-2.26* |
| 57 | H:61 | ALA | VAL | 0.04 | -1.73 |
| 58 | L:102 | THR | ILE | 0.05 | *-2.42* |
| 59 | L:43 | ALA | PHE | 0.06 | 0.82 |
| 60 | H:3 | GLN | HID | 0.07 | 6.94 |
| 61 | H:56 | GLY | VAL | 0.07 | -1.4 |
| 62 | L:76 | SER | ILE | 0.08 | *-10.69* |

| | | | | | |
|---|---|---|---|---|---|
| 63 | L:93 | THR | SER | 0.08 | 2.35 |
| 64 | L:102 | THR | ASN | 0.08 | 6.08 |
| 65 | H:48 | VAL | PHE | 0.08 | 119.92 |
| 66 | L:85 | THR | ILE | 0.09 | -5.15 |
| 67 | L:89 | GLN | HID | 0.09 | 13.16 |
| 68 | H:24 | ALA | PRO | 0.09 | 32.5 |
| 69 | H:4 | LEU | MET | 0.1 | -5.89 |
| 70 | L:34 | ALA | VAL | 0.11 | 9.25 |
| 71 | H:26 | GLY | ALA | 0.11 | -7.27 |
| 72 | H:92 | ALA | VAL | 0.11 | 47.33 |
| 73 | L:85 | THR | ASN | 0.14 | 3.85 |
| 74 | H:106 | ALA | GLY | 0.15 | 7.17 |
| 75 | L:102 | THR | SER | 0.16 | 0.32 |
| 76 | L:76 | SER | ASN | 0.19 | -3.06 |
| 77 | H:26 | GLY | VAL | 0.21 | -7.3 |
| 78 | H:88 | ALA | ASP | 0.3 | -0.16 |
| 79 | H:58 | THR | ASN | 0.36 | 1.07 |
| 80 | H:24 | ALA | PHE | 0.39 | 78.02 |
| 81 | H:58 | THR | ILE | 0.49 | 2.2 |
| 82 | H:24 | ALA | ASN | 0.5 | 17.06 |
| 83 | H:26 | GLY | ASP | 0.53 | -7.85 |
| 84 | H:92 | ALA | ASP | 0.62 | 28.05 |
| 85 | H:106 | ALA | VAL | 0.68 | 8.45 |
| 86 | L:101 | GLY | ASP | 0.69 | 11.64 |
| 87 | H:61 | ALA | ASP | 0.9 | 6.52 |
| 88 | H:56 | GLY | ASP | 1.26 | 3.08 |
| 89 | L:32 | ALA | GLY | 1.75 | 11.73 |
| 90 | H:79 | ALA | ASP | 1.84 | 21.41 |
| 91 | L:31 | THR | ASN | 1.91 | 0.6 |
| 92 | L:25 | ALA | ASP | 2.84 | 86.7 |
| 93 | H:106 | ALA | ASP | 3.94 | 28.94 |
| 94 | L:34 | ALA | ASP | 4.24 | 36.04 |
| 95 | L:32 | ALA | ASP | 11.37 | 16.31 |
| 96 | H:103 | GLY | ASP | 12.53 | 16.85 |

2 Mutations

| Number | Residue | Original | Mutated | Δ Affinity | Δ Stability |
|---|---|---|---|---|---|
| 1 | L:9<br>L:43 | SER<br>ALA | LYS<br>PHE | -26.91 | 66.79 |
| 2 | L:9<br>L:43 | SER<br>ALA | THR<br>PHE | -26.08 | 62.78 |
| 3 | L:9<br>H:103 | SER<br>GLY | ARG<br>VAL | -24.17 | 33.13 |
| 4 | L:9<br>H:103 | SER<br>GLY | LYS<br>VAL | -23.96 | 43.24 |
| 5 | L:9<br>H:103 | SER<br>GLY | THR<br>VAL | -23.23 | 35.33 |
| 6 | L:9<br>H:103 | SER<br>GLY | ILE<br>VAL | -23.21 | 35.04 |
| 7 | L:9<br>H:103 | SER<br>GLY | LYS<br>ALA | -20.26 | 1.22 |
| 8 | L:9<br>H:103 | SER<br>GLY | ARG<br>ALA | -20.01 | -11.42 |
| 9 | L:9<br>L:102 | SER<br>THR | THR<br>ASN | -18.24 | 37.61 |
| 10 | L:9<br>L:40 | SER<br>PRO | ARG<br>ALA | -18.91 | 25.27 |
| 11 | L:9<br>H:103 | SER<br>GLY | THR<br>ALA | -18.59 | -5.37 |
| 12 | L:9<br>H:103 | SER<br>GLY | ILE<br>ALA | -18.57 | -6.91 |
| 13 | L:9<br>L:32 | SER<br>ALA | THR<br>VAL | -18.32 | 48.63 |
| 14 | L:9<br>L:102 | SER<br>THR | THR<br>ASN | -18.24 | 37.61 |
| 15 | L:9<br>L:102 | SER<br>THR | ILE<br>ASN | -18.22 | 37.32 |
| 16 | L:9 | SER | THR | -18.2 | 23.83 |
| 17 | L:9 | SER | ILE | -18.19 | 23.47 |
| 18 | L:9<br>L:40 | SER<br>PRO | ILE<br>ALA | -18.18 | 30.15 |
| 19 | L:9<br>H:2 | SER<br>VAL | THR<br>LEU | -18.1 | 27.69 |
| 20 | L:9<br>L:93 | SER<br>THR | ARG<br>ASN | -17.86 | 23.9 |
| 21 | L:9<br>L:32 | SER<br>ALA | LYS<br>VAL | -17.51 | -30.41 |
| 22 | L:9<br>L:32 | SER<br>ALA | ARG<br>VAL | -17.46 | -42.8 |
| 23 | L:9<br>L:80 | SER<br>PRO | ARG<br>ALA | -16.83 | -74.92 |
| 24 | L:9<br>L:51 | SER<br>ALA | ARG<br>SER | -16.81 | 56.69 |
| 25 | L:9<br>L:51 | SER<br>ALA | LYS<br>PRO | -16.7 | 55.02 |
| 26 | L:9<br>H:92 | SER<br>ALA | LYS<br>VAL | -16.64 | -43.9 |
| 27 | L:9<br>H:14 | SER<br>PRO | LYS<br>SER | -16.6 | -51.7 |
| 28 | L:9<br>H:79 | SER<br>ALA | ARG<br>GLY | -16.58 | -60.45 |
| 29 | L:9<br>L:43 | SER<br>ALA | ARG<br>ASN | -16.58 | -84.28 |
| 30 | L:9<br>L:25 | SER<br>ALA | ARG<br>GLY | -16.56 | 69.73 |

Figure 11B (Continued)

| | | | | | |
|---|---|---|---|---|---|
| 31 | L:9<br>L:93 | SER<br>THR | ARG<br>SER | -16.55 | -69.14 |
| 32 | L:9<br>H:16 | SER<br>GLY | LYS<br>ALA | -16.55 | -58.01 |
| 33 | L:9<br>L:93 | SER<br>THR | ARG<br>ILE | -16.55 | -21.78 |
| 34 | L:9<br>H:58 | SER<br>THR | ILE<br>SER | -16.54 | -63.79 |
| 35 | L:9<br>L:93 | SER<br>THR | THR<br>ILE | -16.53 | -73.77 |
| 36 | L:9<br>L:102 | SER<br>THR | ARG<br>ASN | -16.53 | -54.45 |
| 37 | L:9<br>H:48 | SER<br>VAL | LYS<br>ILE | -16.52 | -54.76 |
| 38 | L:9<br>H:56 | SER<br>GLY | LYS<br>ALA | -16.51 | -64.22 |
| 39 | L:9<br>L:47 | SER<br>LEU | LYS<br>VAL | -16.5 | -51.96 |
| 40 | L:9<br>L:76 | SER<br>SER | ARG<br>THR | -16.5 | -79.57 |
| 41 | L:9<br>L:101 | SER<br>GLY | ARG<br>ALA | -16.5 | -71.42 |
| 42 | L:9<br>H:56 | SER<br>GLY | ILE<br>ALA | -16.49 | -69.38 |
| 43 | L:9<br>H:2 | SER<br>VAL | ARG<br>ILE | -16.45 | -75.03 |
| 44 | L:9<br>H:114 | SER<br>THR | ARG<br>SER | -16.44 | -66.76 |
| 45 | L:9<br>H:14 | SER<br>PRO | ARG<br>ALA | -16.44 | -71.28 |
| 46 | L:9<br>L:43 | SER<br>ALA | ARG<br>PRO | -16.43 | -76.51 |
| 47 | L:9<br>H:61 | SER<br>ALA | LYS<br>VAL | -16.39 | -60.92 |
| 48 | L:9<br>H:61 | SER<br>ALA | ARG<br>VAL | -16.38 | -74.21 |
| 49 | L:9<br>L:43 | SER<br>ALA | ARG<br>PHE | -16.33 | 60.52 |
| 50 | L:9<br>H:58 | SER<br>THR | ARG<br>ILE | -16.32 | -72.44 |
| 51 | L:9<br>L:31 | SER<br>THR | LYS<br>SER | -16.31 | -54.16 |
| 52 | L:9<br>L:31 | SER<br>THR | ARG<br>SER | -16.29 | -67.24 |
| 53 | L:9<br>H:88 | SER<br>ALA | LYS<br>ASP | -16.28 | -61.14 |
| 54 | L:9<br>H:24 | SER<br>ALA | LYS<br>ASN | -16.25 | -57.56 |
| 55 | L:9<br>H:58 | SER<br>THR | ARG<br>SER | -16.23 | 1.68 |
| 56 | L:9<br>L:46 | SER<br>LEU | ARG<br>VAL | -16.21 | 12.27 |
| 57 | L:9<br>H:24 | SER<br>ALA | ARG<br>ASN | -16.19 | -69.82 |
| 58 | L:9<br>L:51 | SER<br>ALA | LYS<br>THR | -16.19 | -9.02 |
| 59 | L:9<br>H:106 | SER<br>ALA | LYS<br>VAL | -16.16 | -54.48 |
| 60 | L:9<br>H:114 | SER<br>THR | LYS<br>ILE | -16.16 | -12.53 |
| 61 | L:9<br>L:93 | SER<br>THR | ILE<br>ILE | -16.16 | -76.44 |

Figure 11B (Continued)

| | | | | | |
|---|---|---|---|---|---|
| 62 | L:9 H:88 | SER ALA | THR VAL | -16.14 | -76.29 |
| 63 | L:9 L:51 | SER ALA | ARG THR | -16.12 | -21.44 |
| 64 | L:9 L:101 | SER GLY | THR ALA | -16.12 | -70.99 |
| 65 | L:9 L:34 | SER ALA | ARG VAL | -16.09 | 6.58 |
| 66 | L:9 L:51 | SER ALA | THR PRO | -16.09 | 48.2 |
| 67 | L:9 H:61 | SER ALA | ARG GLY | -16.08 | 0.92 |
| 68 | L:9 H:61 | SER ALA | LYS GLY | -16.06 | 12.12 |
| 69 | L:9 H:79 | SER ALA | ARG VAL | -16.06 | -19.38 |
| 70 | L:9 L:85 | SER THR | THR ILE | -16.05 | -78.22 |
| 71 | L:9 H:106 | SER ALA | LYS GLY | -16.05 | 19.57 |
| 72 | L:9 H:114 | SER THR | LYS ASN | -16.04 | -5.16 |
| 73 | L:9 H:114 | SER THR | ARG ASN | -16.02 | -17.55 |
| 74 | L:9 L:93 | SER THR | LYS ILE | -16.02 | -13.85 |
| 75 | L:9 L:43 | SER ALA | LYS GLY | -16.01 | 1.02 |
| 76 | L:9 L:76 | SER SER | LYS THR | -16 | -9.72 |
| 77 | L:9 | SER | LYS | -16 | -3.24 |
| 78 | L:9 L:25 | SER ALA | LYS VAL | -16 | 62.99 |
| 79 | L:9 H:58 | SER THR | LYS SER | -15.99 | 2.62 |
| 80 | L:9 L:85 | SER THR | LYS SER | -15.98 | -4.34 |
| 81 | L:9 L:85 | SER THR | ARG SER | -15.97 | -16.83 |
| 82 | L:9 H:14 | SER PRO | LYS THR | -15.96 | -3.27 |
| 83 | L:9 L:46 | SER LEU | ILE ILE | -15.96 | -60.4 |
| 84 | L:9 L:80 | SER PRO | ARG THR | -15.96 | -27.85 |
| 85 | L:9 L:43 | SER ALA | ARG GLY | -15.95 | -11.52 |
| 86 | L:9 H:26 | SER GLY | ARG VAL | -15.94 | 4.91 |
| 87 | L:9 H:48 | SER VAL | LYS LEU | -15.93 | 13.32 |
| 88 | L:9 H:79 | SER ALA | LYS VAL | -15.93 | -4.21 |
| 89 | L:9 H:48 | SER VAL | ARG ILE | -15.93 | -17.62 |
| 90 | L:9 L:85 | SER THR | ARG ILE | -15.92 | -8.89 |
| 91 | L:9 H:58 | SER THR | THR SER | -15.9 | -61.71 |
| 92 | L:9 H:48 | SER VAL | ARG PHE | -15.89 | 133.57 |
| 93 | L:9 L:25 | SER ALA | THR GLY | -15.89 | -54.93 |

Figure 11B (Continued)

| 94  | L:9 H:4   | SER LEU | ARG MET | -15.88 | -4.6   |
|-----|-----------|---------|---------|--------|--------|
| 95  | L:9 L:85  | SER THR | LYS ILE | -15.88 | -9.08  |
| 96  | L:9 H:56  | SER GLY | THR ALA | -15.86 | -67.29 |
| 97  | L:9 L:76  | SER SER | ILE THR | -15.86 | -18.81 |
| 98  | L:9 L:93  | SER THR | THR SER | -15.86 | -64.34 |
| 99  | L:9 H:14  | SER PRO | THR SER | -15.84 | -58.59 |
| 100 | L:9 L:80  | SER PRO | ILE SER | -15.81 | -69.43 |
| 101 | L:9 L:89  | SER GLN | LYS HID | -15.81 | 3.09   |
| 102 | L:9 H:48  | SER VAL | THR LEU | -15.81 | -51.33 |
| 103 | L:9 H:16  | SER GLY | THR ALA | -15.79 | -64.81 |
| 104 | L:9 L:43  | SER ALA | THR PRO | -15.79 | -73.51 |
| 105 | L:9 H:3   | SER GLN | LYS HID | -15.78 | 75.97  |
| 106 | L:9 H:92  | SER ALA | ILE VAL | -15.78 | -52.87 |
| 107 | L:9 L:80  | SER PRO | THR ALA | -15.78 | -64.55 |
| 108 | L:9 L:93  | SER THR | ILE SER | -15.76 | -63.25 |
| 109 | L:9 H:88  | SER ALA | ILE VAL | -15.76 | -73.28 |
| 110 | L:9 L:43  | SER ALA | ILE PRO | -15.76 | -75.35 |
| 111 | L:9 H:58  | SER THR | LYS ILE | -15.76 | -1.84  |
| 112 | L:9 L:46  | SER LEU | LYS VAL | -15.75 | 83.94  |
| 113 | L:9 L:40  | SER PRO | ILE SER | -15.74 | -62.95 |
| 114 | L:9 H:79  | SER ALA | LYS GLY | -15.72 | 74.64  |
| 115 | L:9 H:3   | SER GLN | ARG HID | -15.72 | 64     |
| 116 | L:9 L:25  | SER ALA | ARG VAL | -15.7  | 42.01  |
| 117 | L:9 L:25  | SER ALA | LYS GLY | -15.69 | 75.85  |
| 118 | L:9 H:4   | SER LEU | LYS MET | -15.68 | 64.29  |
| 119 | L:9 L:43  | SER ALA | LYS ASN | -15.67 | 59.33  |
| 120 | L:9 L:40  | SER PRO | LYS THR | -15.64 | 75.96  |
| 121 | L:9 H:24  | SER ALA | LYS GLY | -15.63 | 73.96  |
| 122 | L:9 H:56  | SER GLY | ARG ALA | -15.63 | 63.88  |
| 123 | L:9 L:46  | SER LEU | ARG ILE | -15.62 | 69.38  |
| 124 | L:9 H:24  | SER ALA | ARG GLY | -15.62 | 61.59  |

Figure 11B (Continued)

| | | | | | |
|---|---|---|---|---|---|
| 125 | L:9 H:14 | SER PRO | ARG SER | -15.61 | 63.52 |
| 126 | L:9 H:88 | SER ALA | ARG GLY | -15.61 | 57.74 |
| 127 | L:9 L:80 | SER PRO | LYS SER | -15.6 | 67.39 |
| 128 | L:9 H:56 | SER GLY | LYS VAL | -15.59 | -4.12 |
| 129 | L:9 L:80 | SER PRO | LYS THR | -15.58 | -6.83 |
| 130 | L:9 H:16 | SER GLY | ARG ALA | -15.58 | 52.51 |
| 131 | L:9 L:76 | SER SER | ARG ILE | -15.58 | 44.51 |
| 132 | L:9 L:102 | SER THR | LYS ILE | -15.58 | 81.18 |
| 133 | L:9 H:48 | SER VAL | ARG LEU | -15.58 | 63.85 |
| 134 | L:9 L:34 | SER ALA | LYS GLY | -15.58 | 4.93 |
| 135 | L:9 H:92 | SER ALA | LYS GLY | -15.57 | 77.1 |
| 136 | L:9 H:16 | SER GLY | ARG VAL | -15.57 | 51.75 |
| 137 | L:9 L:102 | SER THR | ARG ILE | -15.57 | 68.15 |
| 138 | L:9 L:34 | SER ALA | ARG GLY | -15.57 | -7.48 |
| 139 | L:9 H:2 | SER VAL | ARG LEU | -15.56 | 69.54 |
| 140 | L:9 L:47 | SER LEU | ARG VAL | -15.56 | 63.8 |
| 141 | L:9 L:40 | SER PRO | LYS SER | -15.56 | 77.58 |
| 142 | L:9 L:80 | SER PRO | ARG SER | -15.56 | -14.69 |
| 143 | L:9 H:26 | SER GLY | LYS VAL | -15.56 | 68.81 |
| 144 | L:9 H:85 | SER SER | LYS ARG | -15.55 | -2.09 |
| 145 | L:9 L:76 | SER SER | LYS ASN | -15.55 | 64.54 |
| 146 | L:9 L:40 | SER PRO | ARG SER | -15.55 | 65.26 |
| 147 | L:9 L:89 | SER GLN | ILE HID | -15.55 | 0.8 |
| 148 | L:9 H:4 | SER LEU | ARG VAL | -15.55 | 73.02 |
| 149 | L:9 L:85 | SER THR | LYS ASN | -15.55 | 73.89 |
| 150 | L:9 H:16 | SER GLY | LYS VAL | -15.55 | -5.53 |
| 151 | L:9 H:24 | SER ALA | ARG PRO | -15.54 | 6.7 |
| 152 | L:9 L:40 | SER PRO | LYS ALA | -15.53 | 74.11 |
| 153 | L:9 L:85 | SER THR | ARG ASN | -15.53 | -11.09 |

Figure 11C

3 Mutations

| Number | Residue | Original | Mutated | Δ Affinity | Δ Stability |
|---|---|---|---|---|---|
| 1 | L:9 | SER | ARG | -31.23 | -36.46 |
|   | L:43 | ALA | PHE |  |  |
|   | H:114 | THR | SER |  |  |
| 2 | L:9 | SER | THR | -30.47 | -78.74 |
|   | L:43 | ALA | PHE |  |  |
|   | H:114 | THR | ASN |  |  |
| 3 | L:9 | SER | THR | -29.97 | -76.82 |
|   | L:43 | ALA | PHE |  |  |
|   | H:114 | THR | ILE |  |  |
| 4 | L:9 | SER | LYS | -28.37 | -45.98 |
|   | L:43 | ALA | PHE |  |  |
|   | H:106 | ALA | VAL |  |  |
| 5 | L:9 | SER | LYS | -27.14 | -21.57 |
|   | L:43 | ALA | PHE |  |  |
|   | H:114 | THR | SER |  |  |
| 6 | L:9 | SER | THR | -26.36 | -37.27 |
|   | L:43 | ALA | PHE |  |  |
|   | H:114 | THR | SER |  |  |
| 7 | L:9 | SER | LYS | -25.73 | -25.84 |
|   | L:43 | ALA | PHE |  |  |
|   | H:106 | ALA | GLY |  |  |
| 8 | L:9 | SER | LYS | -24.74 | -62.52 |
|   | H:103 | GLY | ALA |  |  |
|   | H:114 | THR | ASN |  |  |
| 9 | L:9 | SER | LYS | -24.69 | -56.48 |
|   | H:103 | GLY | ALA |  |  |
|   | H:114 | THR | SER |  |  |
| 10 | L:9 | SER | LYS | -24.39 | -31.96 |
|   | H:103 | GLY | ALA |  |  |
|   | H:106 | ALA | GLY |  |  |
| 11 | L:9 | SER | ARG | -24.23 | -44.64 |
|   | H:103 | GLY | ALA |  |  |
|   | H:106 | ALA | VAL |  |  |
| 12 | L:9 | SER | ARG | -23.91 | -67.4 |
|   | H:103 | GLY | ALA |  |  |
|   | H:114 | THR | SER |  |  |
| 13 | L:9 | SER | ARG | -23.83 | -77.36 |
|   | H:103 | GLY | ALA |  |  |
|   | H:114 | THR | ILE |  |  |
| 14 | L:9 | SER | ARG | -23.61 | -73.47 |
|   | H:103 | GLY | ALA |  |  |
|   | H:114 | THR | ASN |  |  |
| 15 | L:9 | SER | ARG | -23.51 | -43.94 |
|   | H:103 | GLY | ALA |  |  |
|   | H:106 | ALA | GLY |  |  |
| 16 | L:9 | SER | ILE | -23.44 | -41.02 |
|   | H:103 | GLY | ALA |  |  |
|   | H:106 | ALA | GLY |  |  |
| 17 | L:9 | SER | LYS | -23.39 | -67.34 |
|   | H:103 | GLY | ALA |  |  |
|   | H:114 | THR | ILE |  |  |
| 18 | L:9 | SER | LYS | -23.27 | -35.88 |
|   | H:103 | GLY | ALA |  |  |
|   | H:106 | ALA | VAL |  |  |
| 19 | L:9 | SER | ILE | -23.14 | -44.47 |
|   | H:103 | GLY | ALA |  |  |
|   | H:106 | ALA | VAL |  |  |
| 20 | L:9 | SER | ILE | -23.13 | -69.27 |
|   | H:103 | GLY | ALA |  |  |
|   | H:114 | THR | ASN |  |  |

Figure 11C (Continued)

| | | | | | |
|---|---|---|---|---|---|
| 21 | L:9<br>L:51<br>H:114 | SER<br>ALA<br>THR | ARG<br>THR<br>SER | -22.85 | -32.94 |
| 22 | L:9<br>H:103<br>H:106 | SER<br>GLY<br>ALA | THR<br>ALA<br>GLY | -22.81 | -38.94 |
| 23 | L:9<br>H:103<br>H:114 | SER<br>GLY<br>THR | THR<br>ALA<br>ILE | -22.68 | -74.57 |
| 24 | L:9<br>H:103<br>H:114 | SER<br>GLY<br>THR | ILE<br>ALA<br>ILE | -22.54 | -78.31 |
| 25 | L:9<br>H:103<br>H:114 | SER<br>GLY<br>THR | THR<br>ALA<br>ASN | -22.53 | -67.13 |
| 26 | L:9<br>H:103<br>H:114 | SER<br>GLY<br>THR | THR<br>ALA<br>SER | -22.52 | -64.56 |
| 27 | L:9<br>H:103<br>H:106 | SER<br>GLY<br>ALA | THR<br>ALA<br>VAL | -22.51 | -42.54 |
| 28 | L:9<br>H:103<br>H:114 | SER<br>GLY<br>THR | ILE<br>ALA<br>SER | -22.49 | -66.44 |
| 29 | L:9<br>H:114 | SER<br>THR | LYS<br>ASN | -22.18 | -19.52 |
| 30 | L:9<br>H:24<br>H:114 | SER<br>ALA<br>THR | ARG<br>PRO<br>ASN | -22.16 | -17.48 |
| 31 | L:9<br>L:76<br>H:114 | SER<br>SER<br>THR | LYS<br>ASN<br>ASN | -22.13 | -35.83 |
| 32 | L:9<br>L:51<br>H:114 | SER<br>ALA<br>THR | ARG<br>THR<br>ASN | -22.09 | -67.18 |
| 33 | L:9<br>H:92<br>H:114 | SER<br>ALA<br>THR | ARG<br>VAL<br>SER | -21.9 | -21.63 |
| 34 | L:9<br>H:114 | SER<br>THR | ARG<br>ASN | -21.83 | -42.75 |
| 35 | L:9<br>H:92<br>H:114 | SER<br>ALA<br>THR | LYS<br>ASP<br>SER | -21.81 | -3.58 |
| 36 | L:9<br>L:46<br>H:114 | SER<br>LEU<br>THR | ARG<br>VAL<br>ASN | -21.75 | -54.78 |
| 37 | L:9<br>H:2<br>H:114 | SER<br>VAL<br>THR | LYS<br>ILE<br>ASN | -21.74 | -34.8 |
| 38 | L:9<br>L:47<br>H:114 | SER<br>LEU<br>THR | ARG<br>VAL<br>ILE | -21.68 | -43.52 |
| 39 | L:9<br>H:24<br>H:114 | SER<br>ALA<br>THR | LYS<br>GLY<br>ILE | -21.64 | -34.99 |
| 40 | L:9<br>L:51<br>H:114 | SER<br>ALA<br>THR | LYS<br>THR<br>ASN | -21.6 | -59.8 |
| 41 | L:9<br>L:102<br>H:114 | SER<br>THR<br>THR | LYS<br>ASN<br>ILE | -21.58 | -56.69 |

Figure 11C (Continued)

| # | Pos | Res1 | Res2 | V1 | V2 |
|---|---|---|---|---|---|
| 42 | L:9<br>L:32<br>H:114 | SER<br>ALA<br>THR | LYS<br>VAL<br>ASN | -21.57 | -37.67 |
| 43 | L:9<br>L:34<br>H:114 | SER<br>ALA<br>THR | LYS<br>VAL<br>SER | -21.53 | -18.63 |
| 44 | L:9<br>H:24<br>H:114 | SER<br>ALA<br>THR | LYS<br>GLY<br>ASN | -21.49 | -27.52 |
| 45 | L:9<br>L:34<br>H:114 | SER<br>ALA<br>THR | LYS<br>VAL<br>ASN | -21.47 | -9.63 |
| 46 | L:9<br>L:34<br>H:114 | SER<br>ALA<br>THR | ARG<br>VAL<br>ILE | -21.47 | -46.2 |
| 47 | L:9<br>H:48<br>H:114 | SER<br>VAL<br>THR | ARG<br>PHE<br>ILE | -21.46 | -18.79 |
| 48 | L:9<br>L:25<br>H:114 | SER<br>ALA<br>THR | LYS<br>GLY<br>ILE | -21.45 | -32.92 |
| 49 | L:9<br>H:114 | SER<br>THR | LYS<br>SER | -21.43 | -30.02 |
| 50 | L:9<br>H:24<br>H:114 | SER<br>ALA<br>THR | LYS<br>GLY<br>SER | -21.42 | -23.34 |
| 51 | L:9<br>H:3<br>H:114 | SER<br>GLN<br>THR | ARG<br>HID<br>ASN | -21.42 | -40.42 |
| 52 | L:9<br>L:34<br>H:114 | SER<br>ALA<br>THR | ARG<br>GLY<br>ILE | -21.36 | -49.09 |
| 53 | L:9<br>L:43<br>H:114 | SER<br>ALA<br>THR | LYS<br>PRO<br>ASN | -21.34 | -36.84 |
| 54 | L:9<br>H:114 | SER<br>THR | LYS<br>ILE | -21.33 | -41.62 |
| 55 | L:9<br>H:85<br>H:114 | SER<br>SER<br>THR | LYS<br>ARG<br>ILE | -21.33 | -33.57 |
| 56 | L:9<br>L:47<br>H:114 | SER<br>LEU<br>THR | LYS<br>VAL<br>SER | -21.33 | -19.04 |
| 57 | L:9<br>L:47<br>H:114 | SER<br>LEU<br>THR | ARG<br>VAL<br>ASN | -21.32 | -35.6 |
| 58 | L:9<br>L:80<br>H:114 | SER<br>PRO<br>THR | ARG<br>THR<br>ASN | -21.32 | -50.76 |
| 59 | L:9<br>L:47<br>H:114 | SER<br>LEU<br>THR | ARG<br>VAL<br>SER | -21.31 | -33.05 |
| 60 | L:9<br>L:46<br>H:114 | SER<br>LEU<br>THR | LYS<br>VAL<br>ILE | -21.31 | -23.06 |
| 61 | L:9<br>L:40<br>H:114 | SER<br>PRO<br>THR | LYS<br>SER<br>SER | -21.31 | -23.36 |
| 62 | L:9<br>L:47<br>H:114 | SER<br>LEU<br>THR | LYS<br>VAL<br>ILE | -21.31 | -30.61 |

Figure 11C (Continued)

| | | | | | |
|---|---|---|---|---|---|
| 63 | L:9<br>H:4<br>H:114 | SER<br>LEU<br>THR | LYS<br>VAL<br>SER | -21.31 | -16.24 |
| 64 | L:9<br>H:48<br>H:114 | SER<br>VAL<br>THR | LYS<br>PHE<br>SER | -21.31 | 5.13 |
| 65 | L:9<br>H:56<br>H:114 | SER<br>GLY<br>THR | ARG<br>ALA<br>ILE | -21.3 | -78.22 |
| 66 | L:9<br>H:48<br>H:114 | SER<br>VAL<br>THR | LYS<br>PHE<br>ILE | -21.29 | 5.19 |
| 67 | L:9<br>L:102<br>H:114 | SER<br>THR<br>THR | LYS<br>ILE<br>ILE | -21.29 | -14.8 |
| 68 | L:9<br>H:48<br>H:114 | SER<br>VAL<br>THR | LYS<br>LEU<br>SER | -21.29 | -28.52 |
| 69 | L:9<br>H:92<br>H:114 | SER<br>ALA<br>THR | LYS<br>GLY<br>SER | -21.29 | -17.89 |
| 70 | L:9<br>H:2<br>H:114 | SER<br>VAL<br>THR | LYS<br>ILE<br>SER | -21.28 | -29.52 |
| 71 | L:9<br>H:48<br>H:114 | SER<br>VAL<br>THR | ARG<br>LEU<br>SER | -21.28 | -40.34 |
| 72 | L:9<br>L:51<br>H:114 | SER<br>ALA<br>THR | ILE<br>SER<br>SER | -21.28 | -43.45 |
| 73 | L:9<br>H:48<br>H:114 | SER<br>VAL<br>THR | LYS<br>LEU<br>ILE | -21.27 | -40.08 |
| 74 | L:9<br>H:92<br>H:114 | SER<br>ALA<br>THR | LYS<br>GLY<br>ILE | -21.27 | -29.49 |
| 75 | L:9<br>H:88<br>H:114 | SER<br>ALA<br>THR | LYS<br>GLY<br>ASN | -21.26 | -16.12 |
| 76 | L:9<br>H:48<br>H:114 | SER<br>VAL<br>THR | ARG<br>PHE<br>SER | -21.24 | -7.2 |
| 77 | L:9<br>H:114 | SER<br>THR | ARG<br>SER | -21.24 | -39.89 |
| 78 | L:9<br>L:51<br>H:114 | SER<br>ALA<br>THR | LYS<br>THR<br>ILE | -21.23 | -65.88 |
| 79 | L:9<br>H:114 | SER<br>THR | ARG<br>ILE | -21.22 | -51.47 |
| 80 | L:9<br>H:92<br>H:114 | SER<br>ALA<br>THR | ARG<br>GLY<br>SER | -21.22 | -30.22 |
| 81 | L:9<br>L:85<br>H:114 | SER<br>THR<br>THR | ARG<br>ASN<br>ASN | -21.22 | -42.91 |
| 82 | L:9<br>H:2<br>H:114 | SER<br>VAL<br>THR | ARG<br>ILE<br>SER | -21.21 | -41.86 |
| 83 | L:9<br>H:92<br>H:114 | SER<br>ALA<br>THR | ARG<br>GLY<br>ILE | -21.21 | -41.81 |

Figure 11C (Continued)

| # | | | | | |
|---|---|---|---|---|---|
| 84 | L:9<br>L:76<br>H:114 | SER<br>SER<br>THR | LYS<br>THR<br>ASN | -21.21 | -25.66 |
| 85 | L:9<br>L:51<br>H:114 | SER<br>ALA<br>THR | ARG<br>PRO<br>ILE | -21.17 | -1.63 |
| 86 | L:9<br>H:16<br>H:114 | SER<br>GLY<br>THR | LYS<br>ALA<br>SER | -21.16 | -18.68 |
| 87 | L:9<br>H:3<br>H:114 | SER<br>GLN<br>THR | LYS<br>HID<br>ILE | -21.15 | -34.4 |
| 88 | L:9<br>H:24<br>H:114 | SER<br>ALA<br>THR | THR<br>GLY<br>ILE | -21.14 | -42.13 |
| 89 | L:9<br>L:47<br>H:114 | SER<br>LEU<br>THR | LYS<br>VAL<br>ASN | -21.12 | -57.41 |
| 90 | L:9<br>L:51<br>H:114 | SER<br>ALA<br>THR | LYS<br>THR<br>SER | -21.11 | -54.3 |
| 91 | L:9<br>H:3<br>H:114 | SER<br>GLN<br>THR | LYS<br>HID<br>ASN | -21.11 | -27.04 |
| 92 | L:9<br>L:43<br>H:114 | SER<br>ALA<br>THR | ARG<br>PHE<br>ASN | -21.1 | -75.76 |
| 93 | L:9<br>L:40<br>H:114 | SER<br>PRO<br>THR | LYS<br>SER<br>ASN | -21.09 | -59.52 |
| 94 | L:9<br>L:25<br>H:114 | SER<br>ALA<br>THR | LYS<br>GLY<br>SER | -21.09 | -22.45 |
| 95 | L:9<br>L:31<br>H:114 | SER<br>THR<br>THR | LYS<br>SER<br>SER | -21.09 | -24.73 |
| 96 | L:9<br>H:79<br>H:114 | SER<br>ALA<br>THR | LYS<br>GLY<br>SER | -21.07 | -23.51 |
| 97 | L:9<br>L:31<br>H:114 | SER<br>THR<br>THR | ARG<br>SER<br>ILE | -21.06 | -51.18 |
| 98 | L:9<br>L:51<br>H:114 | SER<br>ALA<br>THR | ARG<br>THR<br>ILE | -21.06 | -77.98 |
| 99 | L:9<br>H:16<br>H:114 | SER<br>GLY<br>THR | LYS<br>ALA<br>ILE | -21.06 | -72.79 |
| 100 | L:9<br>L:102<br>H:114 | SER<br>THR<br>THR | LYS<br>SER<br>ASN | -21.05 | -28.72 |
| 101 | L:9<br>L:51<br>H:114 | SER<br>ALA<br>THR | ARG<br>SER<br>ASN | -21.04 | -89.85 |
| 102 | L:9<br>L:102<br>H:114 | SER<br>THR<br>THR | ARG<br>ILE<br>ILE | -21.04 | -70.46 |
| 103 | L:9<br>L:25<br>H:114 | SER<br>ALA<br>THR | LYS<br>VAL<br>ILE | -21.03 | 14.9 |

Figure 11C (Continued)

| | | | | | |
|---|---|---|---|---|---|
| 104 | L:9<br>L:51<br>H:114 | SER<br>ALA<br>THR | ARG<br>SER<br>SER | -21.03 | -87.23 |
| 105 | L:9<br>H:58<br>H:114 | SER<br>THR<br>THR | LYS<br>SER<br>ILE | -21.03 | -38.04 |
| 106 | L:9<br>L:51<br>H:114 | SER<br>ALA<br>THR | LYS<br>SER<br>ILE | -21.02 | -84.87 |
| 107 | L:9<br>L:34<br>H:114 | SER<br>ALA<br>THR | LYS<br>GLY<br>SER | -21.02 | -21.01 |
| 108 | L:9<br>L:34<br>H:114 | SER<br>ALA<br>THR | ARG<br>GLY<br>ASN | -21.01 | -41.09 |
| 109 | L:9<br>L:76<br>H:114 | SER<br>SER<br>THR | ARG<br>THR<br>SER | -21.01 | -87.7 |
| 110 | L:9<br>L:102<br>H:114 | SER<br>THR<br>THR | LYS<br>ILE<br>ASN | -21 | -20.09 |
| 111 | L:9<br>L:34<br>H:114 | SER<br>ALA<br>THR | ARG<br>GLY<br>SER | -21 | -38.62 |
| 112 | L:9<br>H:61<br>H:114 | SER<br>ALA<br>THR | LYS<br>GLY<br>ASN | -21 | -26.71 |
| 113 | L:9<br>L:40<br>H:114 | SER<br>PRO<br>THR | LYS<br>ALA<br>SER | -20.99 | -21.92 |
| 114 | L:9<br>L:102<br>H:114 | SER<br>THR<br>THR | LYS<br>ILE<br>SER | -20.99 | -17.55 |
| 115 | L:9<br>H:26<br>H:114 | SER<br>GLY<br>THR | ARG<br>VAL<br>ILE | -20.99 | -54.75 |
| 116 | L:9<br>L:85<br>H:114 | SER<br>THR<br>THR | LYS<br>SER<br>ILE | -20.98 | -37.13 |
| 117 | L:9<br>L:102<br>H:114 | SER<br>THR<br>THR | ARG<br>SER<br>ASN | -20.98 | -40.92 |
| 118 | L:9<br>L:40<br>H:114 | SER<br>PRO<br>THR | LYS<br>ALA<br>ILE | -20.98 | -33.49 |
| 119 | L:9<br>H:48<br>H:114 | SER<br>VAL<br>THR | ARG<br>PHE<br>ASN | -20.98 | -15.82 |
| 120 | L:9<br>H:58<br>H:114 | SER<br>THR<br>THR | ARG<br>ILE<br>ASN | -20.98 | -74.03 |
| 121 | L:9<br>L:80<br>H:114 | SER<br>PRO<br>THR | LYS<br>THR<br>ASN | -20.98 | -37.74 |
| 122 | L:9<br>H:3<br>H:114 | SER<br>GLN<br>THR | ARG<br>HID<br>SER | -20.98 | -35.12 |
| 123 | L:9<br>L:43<br>H:114 | SER<br>ALA<br>THR | LYS<br>PRO<br>SER | -20.98 | -30.74 |

Figure 11C (Continued)

| | | | | | |
|---|---|---|---|---|---|
| 124 | L:9<br>L:51<br>H:114 | SER<br>ALA<br>THR | ARG<br>SER<br>ILE | -20.96 | -97.11 |
| 125 | L:9<br>H:79<br>H:114 | SER<br>ALA<br>THR | LYS<br>GLY<br>ASN | -20.91 | -63.43 |
| 126 | L:9<br>L:25<br>H:114 | SER<br>ALA<br>THR | ARG<br>VAL<br>ASN | -20.85 | -62.63 |
| 127 | L:9<br>H:24<br>H:114 | SER<br>ALA<br>THR | ARG<br>GLY<br>ASN | -20.83 | -71.62 |
| 128 | L:9<br>L:43<br>H:114 | SER<br>ALA<br>THR | ARG<br>PHE<br>ILE | -20.83 | -81.93 |
| 129 | L:9<br>L:40<br>H:114 | SER<br>PRO<br>THR | ARG<br>ALA<br>SER | -20.83 | -70.96 |
| 130 | L:9<br>L:51<br>H:114 | SER<br>ALA<br>THR | ILE<br>THR<br>ASN | -20.81 | -68.13 |
| 131 | L:9<br>L:102<br>H:114 | SER<br>THR<br>THR | ARG<br>ASN<br>ASN | -20.77 | -60.94 |
| 132 | L:9<br>L:76<br>H:114 | SER<br>SER<br>THR | ARG<br>THR<br>ASN | -20.76 | -84.86 |
| 133 | L:9<br>L:43<br>H:114 | SER<br>ALA<br>THR | ARG<br>GLY<br>ASN | -20.76 | -74.39 |
| 134 | L:9<br>H:24<br>H:114 | SER<br>ALA<br>THR | ARG<br>GLY<br>ILE | -20.76 | -78.89 |
| 135 | L:9<br>L:76<br>H:114 | SER<br>SER<br>THR | ARG<br>ASN<br>ASN | -20.75 | -83.79 |
| 136 | L:9<br>L:40<br>H:114 | SER<br>PRO<br>THR | LYS<br>SER<br>ILE | -20.75 | -65.78 |
| 137 | L:9<br>H:79<br>H:114 | SER<br>ALA<br>THR | LYS<br>GLY<br>ILE | -20.74 | -65.64 |
| 138 | L:9<br>H:14<br>H:114 | SER<br>PRO<br>THR | ARG<br>ALA<br>ASN | -20.74 | -74.03 |
| 139 | L:9<br>L:51<br>H:114 | SER<br>ALA<br>THR | LYS<br>PRO<br>ILE | -20.73 | -21.43 |
| 140 | L:9<br>L:80<br>H:114 | SER<br>PRO<br>THR | ARG<br>ALA<br>SER | -20.73 | -72.9 |
| 141 | L:9<br>H:92<br>H:114 | SER<br>ALA<br>THR | ARG<br>GLY<br>ASN | -20.73 | -65.47 |
| 142 | L:9<br>H:56<br>H:114 | SER<br>GLY<br>THR | LYS<br>VAL<br>ILE | -20.73 | -71.64 |
| 143 | L:9<br>H:48<br>H:114 | SER<br>VAL<br>THR | ARG<br>LEU<br>ASN | -20.72 | -76.27 |

Figure 11C (Continued)

| | | | | | |
|---|---|---|---|---|---|
| 144 | L:9<br>H:61<br>H:114 | SER<br>ALA<br>THR | LYS<br>VAL<br>ILE | -20.71 | -74.97 |
| 145 | L:9<br>H:16<br>H:114 | SER<br>GLY<br>THR | ARG<br>ALA<br>SER | -20.71 | -70.28 |
| 146 | L:9<br>H:4<br>H:114 | SER<br>LEU<br>THR | ARG<br>VAL<br>ASN | -20.7 | -63.71 |
| 147 | L:9<br>H:16<br>H:114 | SER<br>GLY<br>THR | ARG<br>ALA<br>ILE | -20.7 | -81.88 |
| 148 | L:9<br>H:56<br>H:114 | SER<br>GLY<br>THR | ARG<br>VAL<br>ASN | -20.68 | -80.26 |
| 149 | L:9<br>H:56<br>H:114 | SER<br>GLY<br>THR | LYS<br>VAL<br>ASN | -20.68 | -64.37 |
| 150 | L:9<br>H:106<br>H:114 | SER<br>ALA<br>THR | LYS<br>GLY<br>ILE | -20.68 | -65.31 |
| 151 | L:9<br>H:106<br>H:114 | SER<br>ALA<br>THR | LYS<br>VAL<br>ASN | -20.67 | -67.65 |
| 152 | L:9<br>L:80<br>H:114 | SER<br>PRO<br>THR | ARG<br>ALA<br>ILE | -20.67 | -82.75 |
| 153 | L:9<br>H:61<br>H:114 | SER<br>ALA<br>THR | LYS<br>VAL<br>ASN | -20.67 | -67.66 |
| 154 | L:9<br>L:25<br>H:114 | SER<br>ALA<br>THR | ARG<br>VAL<br>SER | -20.66 | -57.1 |
| 155 | L:9<br>H:114 | SER<br>THR | THR<br>ILE | -20.66 | -81.4 |
| 156 | L:9<br>H:114 | SER<br>THR | ILE<br>SER | -20.65 | -68.93 |
| 157 | L:9<br>H:48<br>H:114 | SER<br>VAL<br>THR | LYS<br>ILE<br>ILE | -20.64 | -79.52 |
| 158 | L:9<br>L:101<br>H:114 | SER<br>GLY<br>THR | LYS<br>ALA<br>ILE | -20.63 | -73.89 |
| 159 | L:9<br>H:106<br>H:114 | SER<br>ALA<br>THR | ARG<br>GLY<br>ILE | -20.62 | -77.61 |
| 160 | L:9<br>H:4<br>H:114 | SER<br>LEU<br>THR | ARG<br>VAL<br>ILE | -20.62 | -70.14 |
| 161 | L:9<br>L:32<br>H:114 | SER<br>ALA<br>THR | ARG<br>VAL<br>ASN | -20.62 | -49.41 |
| 162 | L:9<br>L:43<br>H:114 | SER<br>ALA<br>THR | LYS<br>PRO<br>ILE | -20.61 | -74.45 |
| 163 | L:9<br>H:2<br>H:114 | SER<br>VAL<br>THR | LYS<br>LEU<br>ILE | -20.6 | -55.85 |
| 164 | L:9<br>L:89<br>H:114 | SER<br>GLN<br>THR | LYS<br>HID<br>ASN | -20.59 | -62.74 |

| | | | | | |
|---|---|---|---|---|---|
| 165 | L:9<br>L:40<br>H:114 | SER<br>PRO<br>THR | ARG<br>SER<br>ILE | -20.57 | -75.46 |
| 166 | L:9<br>L:76<br>H:114 | SER<br>SER<br>THR | ARG<br>ASN<br>SER | -20.57 | -81.18 |
| 167 | L:9<br>L:40<br>H:114 | SER<br>PRO<br>THR | ARG<br>THR<br>ILE | -20.57 | -73.45 |
| 168 | L:9<br>H:58<br>H:114 | SER<br>THR<br>THR | ARG<br>ILE<br>SER | -20.55 | -70.24 |
| 169 | L:9<br>H:24<br>H:114 | SER<br>ALA<br>THR | LYS<br>PRO<br>ILE | -20.55 | -44.78 |

4 Mutations

| Number | Residue | Original | Mutated | Δ Affinity | Δ Stability |
|---|---|---|---|---|---|
| 1 | L:9<br>L:43<br>H:26<br>H:58 | SER<br>ALA<br>GLY<br>THR | ARG<br>PHE<br>ALA<br>SER | -32.48 | -47.75 |
| 2 | L:9<br>L:43<br>H:26<br>H:85 | SER<br>ALA<br>GLY<br>SER | ILE<br>PHE<br>VAL<br>ARG | -31.91 | -60.15 |
| 3 | L:9<br>L:43<br>H:24<br>H:61 | SER<br>ALA<br>ALA<br>ALA | ARG<br>PHE<br>PRO<br>VAL | -31.54 | 73.47 |
| 4 | L:9<br>L:43<br>L:51<br>H:92 | SER<br>ALA<br>ALA<br>ALA | THR<br>PHE<br>PRO<br>VAL | -31.44 | 61.87 |
| 5 | L:9<br>L:43<br>L:101<br>H:79 | SER<br>ALA<br>GLY<br>ALA | ILE<br>PHE<br>ASP<br>VAL | -31.05 | -53.04 |
| 6 | L:9<br>L:31<br>L:43<br>L:102 | SER<br>THR<br>ALA<br>THR | ILE<br>SER<br>PHE<br>SER | -31.02 | -48.23 |
| 7 | L:9<br>L:43<br>L:51<br>H:14 | SER<br>ALA<br>ALA<br>PRO | LYS<br>PHE<br>SER<br>THR | -29.87 | -5.55 |
| 8 | L:9<br>L:43<br>L:46<br>L:76 | SER<br>ALA<br>LEU<br>SER | ILE<br>PHE<br>VAL<br>ASN | -29.74 | -16.58 |
| 9 | L:9<br>L:43<br>H:14<br>H:88 | SER<br>ALA<br>PRO<br>ALA | ARG<br>PHE<br>THR<br>VAL | -29.36 | -23.71 |
| 10 | L:9<br>L:43<br>L:101<br>H:79 | SER<br>ALA<br>GLY<br>ALA | THR<br>PHE<br>ALA<br>GLY | -29.26 | -4.8 |
| 11 | L:9<br>L:43<br>L:102<br>H:14 | SER<br>ALA<br>THR<br>PRO | ILE<br>PHE<br>ASN<br>THR | -28.95 | 2.85 |
| 12 | L:9<br>L:43<br>L:80<br>H:61 | SER<br>ALA<br>PRO<br>ALA | ARG<br>PHE<br>THR<br>ASP | -28.55 | -24.01 |
| 13 | L:9<br>H:56<br>H:79<br>H:103 | SER<br>GLY<br>ALA<br>GLY | ARG<br>ALA<br>VAL<br>VAL | -28.1 | -28.88 |
| 14 | L:9<br>H:92<br>H:103 | SER<br>ALA<br>GLY | THR<br>VAL<br>VAL | -26.36 | 70.21 |
| 15 | L:9<br>H:92<br>H:103 | SER<br>ALA<br>GLY | ARG<br>VAL<br>VAL | -26.27 | 68.12 |

Figure 11D (Continued)

| | | | | | |
|---|---|---|---|---|---|
| 16 | L:9<br>H:56<br>H:92<br>H:103 | SER<br>GLY<br>ALA<br>GLY | ARG<br>VAL<br>VAL<br>VAL | -26.03 | 62.68 |
| 17 | L:9<br>L:89<br>H:92<br>H:103 | SER<br>GLN<br>ALA<br>GLY | ARG<br>HID<br>VAL<br>VAL | -25.68 | 86.35 |
| 18 | L:9<br>L:89<br>H:92<br>H:103 | SER<br>GLN<br>ALA<br>GLY | ARG<br>HID<br>GLY<br>VAL | -25.67 | 82.6 |
| 19 | L:9<br>L:43<br>H:92<br>H:103 | SER<br>ALA<br>ALA<br>GLY | LYS<br>ASN<br>VAL<br>VAL | -25.48 | 66.08 |
| 20 | L:9<br>H:92<br>H:103 | SER<br>ALA<br>GLY | LYS<br>GLY<br>VAL | -25.41 | 70.24 |
| 21 | L:9<br>H:92<br>H:103 | SER<br>ALA<br>GLY | LYS<br>VAL<br>VAL | -25.41 | 73.99 |
| 22 | L:9<br>L:76<br>H:92<br>H:103 | SER<br>SER<br>ALA<br>GLY | LYS<br>ILE<br>GLY<br>VAL | -25.39 | 65.53 |
| 23 | L:9<br>L:40<br>H:92<br>H:103 | SER<br>PRO<br>ALA<br>GLY | LYS<br>SER<br>GLY<br>VAL | -25.39 | 82.76 |
| 24 | L:9<br>H:88<br>H:92<br>H:103 | SER<br>ALA<br>ALA<br>GLY | LYS<br>GLY<br>VAL<br>VAL | -25.38 | 77.03 |
| 25 | L:9<br>L:80<br>H:92<br>H:103 | SER<br>PRO<br>ALA<br>GLY | LYS<br>THR<br>VAL<br>VAL | -25.37 | 69 |
| 26 | L:9<br>H:56<br>H:92<br>H:103 | SER<br>GLY<br>ALA<br>GLY | LYS<br>VAL<br>VAL<br>VAL | -25.37 | 72.36 |
| 27 | L:9<br>H:56<br>H:92<br>H:103 | SER<br>GLY<br>ALA<br>GLY | LYS<br>VAL<br>GLY<br>VAL | -25.36 | 68.57 |
| 28 | L:9<br>L:85<br>H:92<br>H:103 | SER<br>THR<br>ALA<br>GLY | LYS<br>ILE<br>GLY<br>VAL | -25.33 | 64.14 |
| 29 | L:9<br>H:14<br>H:92<br>H:103 | SER<br>PRO<br>ALA<br>GLY | ARG<br>THR<br>GLY<br>VAL | -25.33 | 57.8 |
| 30 | L:9<br>L:85<br>H:92<br>H:103 | SER<br>THR<br>ALA<br>GLY | LYS<br>ILE<br>VAL<br>VAL | -25.33 | 70.03 |
| 31 | L:9<br>H:88<br>H:92<br>H:103 | SER<br>ALA<br>ALA<br>GLY | LYS<br>GLY<br>GLY<br>VAL | -25.32 | 73.34 |

Figure 11D (Continued)

| | | | | | |
|---|---|---|---|---|---|
| 32 | L:9<br>L:93<br>H:16<br>H:103 | SER<br>THR<br>GLY<br>GLY | LYS<br>ILE<br>VAL<br>ALA | -25.31 | -52.18 |
| 33 | L:9<br>H:88<br>H:92<br>H:103 | SER<br>ALA<br>ALA<br>GLY | ARG<br>GLY<br>GLY<br>VAL | -25.31 | 60.86 |
| 34 | L:9<br>L:43<br>H:92<br>H:103 | SER<br>ALA<br>ALA<br>GLY | ARG<br>ASN<br>GLY<br>VAL | -25.3 | 50.03 |
| 35 | L:9<br>H:56<br>H:92<br>H:103 | SER<br>GLY<br>ALA<br>GLY | ARG<br>VAL<br>GLY<br>VAL | -25.3 | 56.45 |
| 36 | L:9<br>L:85<br>H:92<br>H:103 | SER<br>THR<br>ALA<br>GLY | ARG<br>ILE<br>GLY<br>VAL | -25.27 | 51.96 |
| 37 | L:9<br>H:4<br>H:92<br>H:103 | SER<br>LEU<br>ALA<br>GLY | LYS<br>MET<br>VAL<br>VAL | -25.26 | 74.81 |
| 38 | L:9<br>H:58<br>H:92<br>H:103 | SER<br>THR<br>ALA<br>GLY | LYS<br>ILE<br>VAL<br>VAL | -25.26 | 75.35 |
| 39 | L:9<br>L:85<br>H:92<br>H:103 | SER<br>THR<br>ALA<br>GLY | ARG<br>ILE<br>VAL<br>VAL | -25.24 | 55.74 |
| 40 | L:9<br>L:76<br>H:92<br>H:103 | SER<br>SER<br>ALA<br>GLY | LYS<br>ASN<br>VAL<br>VAL | -25.22 | 70.92 |
| 41 | L:9<br>H:24<br>H:92<br>H:103 | SER<br>ALA<br>ALA<br>GLY | LYS<br>PHE<br>VAL<br>VAL | -25.01 | 95.86 |
| 42 | L:9<br>H:24<br>H:92<br>H:103 | SER<br>ALA<br>ALA<br>GLY | LYS<br>PHE<br>GLY<br>VAL | -25 | 92.16 |
| 43 | L:9<br>H:24<br>H:92<br>H:103 | SER<br>ALA<br>ALA<br>GLY | ARG<br>PHE<br>GLY<br>VAL | -24.96 | 78.74 |
| 44 | L:9<br>H:2<br>H:92<br>H:103 | SER<br>VAL<br>ALA<br>GLY | LYS<br>LEU<br>VAL<br>ALA | -24.9 | 74.08 |
| 45 | L:9<br>H:2<br>H:103 | SER<br>VAL<br>GLY | LYS<br>LEU<br>ALA | -24.89 | 59.87 |
| 46 | L:9<br>H:2<br>H:92<br>H:103 | SER<br>VAL<br>ALA<br>GLY | LYS<br>LEU<br>GLY<br>ALA | -24.86 | 69.88 |
| 47 | L:9<br>H:3<br>H:56<br>H:103 | SER<br>GLN<br>GLY<br>GLY | ARG<br>HID<br>ALA<br>VAL | -24.85 | -9.98 |

Figure 11D (Continued)

| | | | | | |
|---|---|---|---|---|---|
| 48 | L:9<br>H:103<br>H:114 | SER<br>GLY<br>THR | ARG<br>VAL<br>ASN | -24.84 | -19.23 |
| 49 | L:9<br>H:2<br>H:92<br>H:103 | SER<br>VAL<br>ALA<br>GLY | ARG<br>LEU<br>VAL<br>ALA | -24.84 | 62.12 |
| 50 | L:9<br>H:79<br>H:103 | SER<br>ALA<br>GLY | LYS<br>VAL<br>VAL | -24.84 | -18.78 |
| 51 | L:9<br>L:47<br>H:3<br>H:103 | SER<br>LEU<br>GLN<br>GLY | ARG<br>VAL<br>HID<br>VAL | -24.84 | -1.82 |
| 52 | L:9<br>H:3<br>H:103 | SER<br>GLN<br>GLY | ARG<br>HID<br>VAL | -24.82 | -10.4 |
| 53 | L:9<br>H:56<br>H:103 | SER<br>GLY<br>GLY | ARG<br>ALA<br>VAL | -24.81 | -15.76 |
| 54 | L:9<br>H:4<br>H:79<br>H:103 | SER<br>LEU<br>ALA<br>GLY | LYS<br>MET<br>GLY<br>VAL | -24.81 | 0.51 |
| 55 | L:9<br>L:101<br>H:3<br>H:103 | SER<br>GLY<br>GLN<br>GLY | ARG<br>ALA<br>HID<br>VAL | -24.79 | -12.68 |
| 56 | L:9<br>L:76<br>H:92<br>H:103 | SER<br>SER<br>ALA<br>GLY | LYS<br>ILE<br>ASP<br>VAL | -24.77 | 78.59 |
| 57 | L:9<br>H:88<br>H:92<br>H:103 | SER<br>ALA<br>ALA<br>GLY | LYS<br>GLY<br>ASP<br>VAL | -24.76 | 89.79 |
| 58 | L:9<br>H:79<br>H:103 | SER<br>ALA<br>GLY | ARG<br>VAL<br>VAL | -24.75 | -29.31 |
| 59 | L:9<br>L:101<br>H:103 | SER<br>GLY<br>GLY | ARG<br>ALA<br>VAL | -24.75 | -18.08 |
| 60 | L:9<br>L:47<br>H:92<br>H:103 | SER<br>LEU<br>ALA<br>GLY | LYS<br>VAL<br>ASP<br>VAL | -24.74 | 111.08 |
| 61 | L:9<br>L:43<br>H:92<br>H:103 | SER<br>ALA<br>ALA<br>GLY | THR<br>ASN<br>VAL<br>VAL | -24.71 | 59.03 |
| 62 | L:9<br>H:4<br>H:79<br>H:103 | SER<br>LEU<br>ALA<br>GLY | LYS<br>MET<br>VAL<br>VAL | -24.7 | -19.87 |
| 63 | L:9<br>L:85<br>H:92<br>H:103 | SER<br>THR<br>ALA<br>GLY | LYS<br>ILE<br>ASP<br>VAL | -24.7 | 83.23 |
| 64 | L:9<br>L:43<br>H:92<br>H:103 | SER<br>ALA<br>ALA<br>GLY | THR<br>ASN<br>GLY<br>VAL | -24.7 | 55.27 |

Figure 11D (Continued)

| | | | | | |
|---|---|---|---|---|---|
| 65 | L:9<br>H:24<br>H:92<br>H:103 | SER<br>ALA<br>ALA<br>GLY | THR<br>GLY<br>VAL<br>VAL | -24.69 | 76.82 |
| 66 | L:9<br>H:79<br>H:85<br>H:103 | SER<br>ALA<br>SER<br>GLY | ARG<br>GLY<br>ARG<br>ALA | -24.68 | -54.2 |
| 67 | L:9<br>L:85<br>H:92<br>H:103 | SER<br>THR<br>ALA<br>GLY | THR<br>SER<br>VAL<br>VAL | -24.67 | 73.18 |
| 68 | L:9<br>L:34<br>H:92<br>H:103 | SER<br>ALA<br>ALA<br>GLY | THR<br>GLY<br>VAL<br>VAL | -24.65 | 77.6 |
| 69 | L:9<br>L:85<br>H:92<br>H:103 | SER<br>THR<br>ALA<br>GLY | ARG<br>ILE<br>ASP<br>VAL | -24.64 | 70.96 |
| 70 | L:9<br>L:102<br>H:92<br>H:103 | SER<br>THR<br>ALA<br>GLY | THR<br>ASN<br>VAL<br>VAL | -24.64 | 83.96 |
| 71 | L:9<br>H:4<br>H:79<br>H:103 | SER<br>LEU<br>ALA<br>GLY | ARG<br>MET<br>VAL<br>VAL | -24.64 | -30.61 |
| 72 | L:9<br>H:26<br>H:92<br>H:103 | SER<br>GLY<br>ALA<br>GLY | THR<br>ALA<br>VAL<br>VAL | -24.62 | 72.5 |
| 73 | L:9<br>H:14<br>H:92<br>H:103 | SER<br>PRO<br>ALA<br>GLY | THR<br>ALA<br>VAL<br>VAL | -24.61 | 74.74 |
| 74 | L:9<br>H:92<br>H:103<br>H:114 | SER<br>ALA<br>GLY<br>THR | THR<br>VAL<br>VAL<br>ILE | -24.61 | 68.62 |
| 75 | L:9<br>H:56<br>H:92<br>H:103 | SER<br>GLY<br>ALA<br>GLY | THR<br>VAL<br>VAL<br>VAL | -24.6 | 65.31 |
| 76 | L:9<br>H:85<br>H:103 | SER<br>SER<br>GLY | ARG<br>ARG<br>ALA | -24.6 | -61.78 |
| 77 | L:9<br>H:14<br>H:92<br>H:103 | SER<br>PRO<br>ALA<br>GLY | THR<br>ALA<br>GLY<br>VAL | -24.6 | 77.36 |
| 78 | L:9<br>H:16<br>H:85<br>H:103 | SER<br>GLY<br>SER<br>GLY | LYS<br>VAL<br>ARG<br>ALA | -24.59 | -52.03 |
| 79 | L:9<br>H:16<br>H:85<br>H:103 | SER<br>GLY<br>SER<br>GLY | ARG<br>VAL<br>ARG<br>ALA | -24.58 | -64.84 |
| 80 | L:9<br>L:85<br>H:92<br>H:103 | SER<br>THR<br>ALA<br>GLY | ILE<br>ILE<br>GLY<br>VAL | -24.54 | 55.22 |

Figure 11D (Continued)

| | | | | | |
|---|---|---|---|---|---|
| 81 | L:9<br>H:3<br>H:85<br>H:103 | SER<br>GLN<br>SER<br>GLY | LYS<br>HID<br>ARG<br>ALA | -24.53 | -56.52 |
| 82 | L:9<br>H:85<br>H:103 | SER<br>SER<br>GLY | LYS<br>ARG<br>ALA | -24.5 | -62.14 |
| 83 | L:9<br>L:76<br>H:85<br>H:103 | SER<br>SER<br>SER<br>GLY | LYS<br>ILE<br>ARG<br>ALA | -24.48 | -72.72 |
| 84 | L:9<br>L:93<br>H:26<br>H:103 | SER<br>THR<br>GLY<br>GLY | LYS<br>ILE<br>ALA<br>ALA | -24.48 | 56.08 |
| 85 | L:9<br>H:85<br>H:103<br>H:114 | SER<br>SER<br>GLY<br>THR | LYS<br>ARG<br>ALA<br>SER | -24.46 | -53.1 |
| 86 | L:9<br>H:61<br>H:92<br>H:103 | SER<br>ALA<br>ALA<br>GLY | ARG<br>ASP<br>GLY<br>VAL | -24.44 | 64.17 |
| 87 | L:9<br>H:92<br>H:103<br>H:114 | SER<br>ALA<br>GLY<br>THR | THR<br>VAL<br>ALA<br>ILE | -24.42 | 51.32 |
| 88 | L:9<br>H:85<br>H:103<br>H:114 | SER<br>SER<br>GLY<br>THR | ARG<br>ARG<br>ALA<br>SER | -24.38 | -60.85 |
| 89 | L:9<br>H:16<br>H:103 | SER<br>GLY<br>GLY | LYS<br>VAL<br>ALA | -24.37 | -45.25 |
| 90 | L:9<br>H:24<br>H:92<br>H:103 | SER<br>ALA<br>ALA<br>GLY | ARG<br>PHE<br>ASP<br>VAL | -24.33 | 110.82 |
| 91 | L:9<br>H:85<br>H:103<br>H:106 | SER<br>SER<br>GLY<br>ALA | ARG<br>ARG<br>ALA<br>GLY | -24.32 | -54.91 |
| 92 | L:9<br>L:93<br>H:26<br>H:103 | SER<br>THR<br>GLY<br>GLY | THR<br>ILE<br>ALA<br>ALA | -24.29 | 48.96 |
| 93 | L:9<br>H:92<br>H:103 | SER<br>ALA<br>GLY | LYS<br>ASP<br>VAL | -24.22 | 18.85 |
| 94 | L:9<br>L:80<br>H:92<br>H:103 | SER<br>PRO<br>ALA<br>GLY | LYS<br>THR<br>ASP<br>VAL | -24.22 | 14.57 |
| 95 | L:9<br>H:24<br>H:92<br>H:103 | SER<br>ALA<br>ALA<br>GLY | ILE<br>PHE<br>VAL<br>VAL | -24.21 | 86.99 |
| 96 | L:9<br>H:103<br>H:114 | SER<br>GLY<br>THR | ARG<br>ALA<br>SER | -24.19 | -52.86 |

Figure 11D (Continued)

| | | | | | |
|---|---|---|---|---|---|
| 97 | L:9<br>H:58<br>H:85<br>H:103 | SER<br>THR<br>SER<br>GLY | ARG<br>ILE<br>ARG<br>ALA | -24.18 | -61.95 |
| 98 | L:9<br>H:79<br>H:92<br>H:103 | SER<br>ALA<br>ALA<br>GLY | LYS<br>VAL<br>ASP<br>VAL | -24.17 | 5.95 |
| 99 | L:9<br>H:92<br>H:103 | SER<br>ALA<br>GLY | THR<br>VAL<br>ALA | -24.17 | 52.92 |
| 100 | L:9<br>H:24<br>H:85<br>H:103 | SER<br>ALA<br>SER<br>GLY | LYS<br>ASN<br>ARG<br>ALA | -24.16 | -57.83 |
| 101 | L:9<br>H:79<br>H:92<br>H:103 | SER<br>ALA<br>ALA<br>GLY | THR<br>VAL<br>GLY<br>VAL | -24.15 | -47.96 |
| 102 | L:9<br>L:93<br>H:26<br>H:103 | SER<br>THR<br>GLY<br>GLY | LYS<br>ILE<br>ASP<br>ALA | -24.14 | 55.85 |
| 103 | L:9<br>H:2<br>H:92<br>H:103 | SER<br>VAL<br>ALA<br>GLY | THR<br>LEU<br>VAL<br>ALA | -24.14 | 67 |
| 104 | L:9<br>H:3<br>H:56<br>H:103 | SER<br>GLN<br>GLY<br>GLY | ILE<br>HID<br>ALA<br>VAL | -24.12 | -8.1 |
| 105 | L:9<br>L:25<br>H:92<br>H:103 | SER<br>ALA<br>ALA<br>GLY | ARG<br>VAL<br>GLY<br>ALA | -24.12 | 34.13 |
| 106 | L:9<br>H:24<br>H:85<br>H:103 | SER<br>ALA<br>SER<br>GLY | ARG<br>ASN<br>ARG<br>ALA | -24.09 | -69.73 |
| 107 | L:9<br>H:92<br>H:103<br>H:106 | SER<br>ALA<br>GLY<br>ALA | THR<br>VAL<br>VAL<br>VAL | -24.07 | 77.62 |
| 108 | L:9<br>H:3<br>H:92<br>H:103 | SER<br>GLN<br>ALA<br>GLY | THR<br>HID<br>ASP<br>VAL | -24.06 | 87.86 |
| 109 | L:9<br>H:26<br>H:92<br>H:103 | SER<br>GLY<br>ALA<br>GLY | THR<br>ALA<br>ASP<br>VAL | -24.02 | 84.67 |
| 110 | L:9<br>H:92<br>H:103 | SER<br>ALA<br>GLY | THR<br>ASP<br>VAL | -24.02 | 82.33 |
| 111 | L:9<br>H:14<br>H:92<br>H:103 | SER<br>PRO<br>ALA<br>GLY | THR<br>ALA<br>ASP<br>VAL | -23.99 | 87.75 |
| 112 | L:9<br>L:76<br>H:92<br>H:103 | SER<br>SER<br>ALA<br>GLY | THR<br>ILE<br>ASP<br>VAL | -23.96 | 71.75 |

Figure 11D (Continued)

| | | | | | |
|---|---|---|---|---|---|
| 113 | L:9<br>L:85<br>H:92<br>H:103 | SER<br>THR<br>ALA<br>GLY | THR<br>ILE<br>ASP<br>VAL | -23.94 | 76.39 |
| 114 | L:9<br>L:85<br>H:92<br>H:103 | SER<br>THR<br>ALA<br>GLY | ILE<br>ILE<br>ASP<br>VAL | -23.91 | 74.55 |
| 115 | L:9<br>H:4<br>H:79<br>H:103 | SER<br>LEU<br>ALA<br>GLY | ILE<br>MET<br>VAL<br>VAL | -23.91 | -28.76 |
| 116 | L:9<br>L:31<br>H:103<br>H:114 | SER<br>THR<br>GLY<br>THR | ARG<br>ASN<br>VAL<br>ASN | -23.89 | -13.7 |
| 117 | L:9<br>H:3<br>H:14<br>H:103 | SER<br>GLN<br>PRO<br>GLY | LYS<br>HID<br>THR<br>VAL | -23.87 | 78.54 |
| 118 | L:9<br>H:14<br>H:103 | SER<br>PRO<br>GLY | LYS<br>THR<br>VAL | -23.83 | 73 |
| 119 | L:9<br>L:31<br>H:103 | SER<br>THR<br>GLY | ARG<br>ASN<br>VAL | -23.82 | -11.93 |
| 120 | L:9<br>L:34<br>H:14<br>H:103 | SER<br>ALA<br>PRO<br>GLY | LYS<br>VAL<br>THR<br>VAL | -23.81 | 90.99 |
| 121 | L:9<br>L:31<br>L:101<br>H:103 | SER<br>THR<br>GLY<br>GLY | ARG<br>ASN<br>ALA<br>VAL | -23.81 | -12.59 |
| 122 | L:9<br>H:3<br>H:85<br>H:103 | SER<br>GLN<br>SER<br>GLY | THR<br>HID<br>ARG<br>ALA | -23.76 | -63.67 |
| 123 | L:9<br>L:46<br>H:26<br>H:103 | SER<br>LEU<br>GLY<br>GLY | THR<br>ILE<br>ALA<br>ALA | -23.74 | 69 |
| 124 | L:9<br>H:61<br>H:92<br>H:103 | SER<br>ALA<br>ALA<br>GLY | THR<br>ASP<br>VAL<br>VAL | -23.73 | 76.6 |
| 125 | L:9<br>H:26<br>H:103 | SER<br>GLY<br>GLY | THR<br>ALA<br>ALA | -23.72 | 54.88 |
| 126 | L:9<br>H:88<br>H:92<br>H:103 | SER<br>ALA<br>ALA<br>GLY | THR<br>ASP<br>ASP<br>VAL | -23.7 | 86.85 |
| 127 | L:9<br>L:93<br>H:26<br>H:103 | SER<br>THR<br>GLY<br>GLY | ILE<br>ILE<br>ALA<br>ALA | -23.69 | 47.1 |
| 128 | L:9<br>L:93<br>H:26<br>H:103 | SER<br>THR<br>GLY<br>GLY | THR<br>ILE<br>VAL<br>ALA | -23.68 | 48.26 |

| | | | | | |
|---|---|---|---|---|---|
| 129 | L:9<br>H:85<br>H:103<br>H:114 | SER<br>SER<br>GLY<br>THR | ILE<br>ARG<br>ALA<br>SER | -23.67 | -62.25 |
| 130 | L:9<br>H:3<br>H:88<br>H:103 | SER<br>GLN<br>ALA<br>GLY | ARG<br>HID<br>VAL<br>ALA | -23.67 | -52.39 |
| 131 | L:9<br>L:34<br>H:92<br>H:103 | SER<br>ALA<br>ALA<br>GLY | ARG<br>VAL<br>VAL<br>ALA | -23.65 | -1.63 |
| 132 | L:9<br>L:31<br>H:103<br>H:106 | SER<br>THR<br>GLY<br>ALA | ARG<br>ASN<br>VAL<br>VAL | -23.62 | -4.47 |
| 133 | L:9<br>L:101<br>H:16<br>H:103 | SER<br>GLY<br>GLY<br>GLY | LYS<br>ASP<br>ALA<br>ALA | -23.6 | -40.42 |
| 134 | L:9<br>L:101<br>H:16<br>H:103 | SER<br>GLY<br>GLY<br>GLY | LYS<br>ASP<br>VAL<br>ALA | -23.6 | -42.56 |
| 135 | L:9<br>H:3<br>H:92<br>H:103 | SER<br>GLN<br>ALA<br>GLY | ARG<br>HID<br>GLY<br>ALA | -23.56 | -14.7 |
| 136 | L:9<br>H:26<br>H:92<br>H:103 | SER<br>GLY<br>ALA<br>GLY | ARG<br>ALA<br>VAL<br>ALA | -23.55 | -14.96 |
| 137 | L:9<br>H:92<br>H:103 | SER<br>ALA<br>GLY | ARG<br>VAL<br>ALA | -23.55 | -17.14 |
| 138 | L:9<br>L:93<br>H:92<br>H:103 | SER<br>THR<br>ALA<br>GLY | LYS<br>ILE<br>VAL<br>ALA | -23.53 | -44.07 |
| 139 | L:9<br>H:92<br>H:103 | SER<br>ALA<br>GLY | ARG<br>GLY<br>ALA | -23.52 | -20.47 |
| 140 | L:9<br>H:2<br>H:92<br>H:103 | SER<br>VAL<br>ALA<br>GLY | THR<br>LEU<br>ASP<br>ALA | -23.51 | 80.07 |
| 141 | L:9<br>L:93<br>H:2<br>H:103 | SER<br>THR<br>VAL<br>GLY | LYS<br>ASN<br>LEU<br>ALA | -23.51 | 66.19 |
| 142 | L:9<br>L:85<br>H:92<br>H:103 | SER<br>THR<br>ALA<br>GLY | ARG<br>ILE<br>VAL<br>ALA | -23.48 | -23.63 |
| 143 | L:9<br>L:80<br>H:88<br>H:103 | SER<br>PRO<br>ALA<br>GLY | LYS<br>ALA<br>GLY<br>ALA | -23.47 | -10.36 |
| 144 | L:9<br>H:79<br>H:92<br>H:103 | SER<br>ALA<br>ALA<br>GLY | ILE<br>VAL<br>ASP<br>VAL | -23.47 | -26.24 |

| # | Pos | From | To | Val1 | Val2 |
|---|---|---|---|---|---|
| 145 | L:9 | SER | ARG | -23.46 | -15.99 |
| | H:48 | VAL | LEU | | |
| | H:92 | ALA | GLY | | |
| | H:103 | GLY | ALA | | |
| 146 | L:9 | SER | THR | -23.41 | -0.55 |
| | H:79 | ALA | VAL | | |
| | H:92 | ALA | ASP | | |
| | H:103 | GLY | VAL | | |
| 147 | L:9 | SER | LYS | -23.38 | -0.82 |
| | H:58 | THR | ILE | | |
| | H:92 | ALA | VAL | | |
| | H:103 | GLY | ALA | | |
| 148 | L:9 | SER | ARG | -23.37 | -20.12 |
| | L:76 | SER | ASN | | |
| | H:92 | ALA | VAL | | |
| | H:103 | GLY | ALA | | |
| 149 | L:9 | SER | THR | -23.37 | 48.84 |
| | L:93 | THR | ILE | | |
| | H:26 | GLY | ASP | | |
| | H:103 | GLY | ALA | | |
| 150 | L:9 | SER | ARG | -23.35 | -7.22 |
| | H:3 | GLN | HID | | |
| | H:56 | GLY | ASP | | |
| | H:103 | GLY | VAL | | |
| 151 | L:9 | SER | ARG | -23.33 | -12.31 |
| | H:58 | THR | ILE | | |
| | H:92 | ALA | VAL | | |
| | H:103 | GLY | ALA | | |
| 152 | L:9 | SER | THR | -23.3 | 72.99 |
| | H:56 | GLY | ASP | | |
| | H:92 | ALA | VAL | | |
| | H:103 | GLY | VAL | | |
| 153 | L:9 | SER | ARG | -23.22 | -12.64 |
| | H:24 | ALA | ASN | | |
| | H:92 | ALA | VAL | | |
| | H:103 | GLY | ALA | | |
| 154 | L:9 | SER | ILE | -23.08 | -8.89 |
| | L:31 | THR | ASN | | |
| | L:101 | GLY | ALA | | |
| | H:103 | GLY | VAL | | |
| 155 | L:9 | SER | ARG | -23.07 | -14.2 |
| | H:61 | ALA | VAL | | |
| | H:92 | ALA | ASP | | |
| | H:103 | GLY | VAL | | |
| 156 | L:9 | SER | LYS | -23.05 | 18.98 |
| | H:58 | THR | SER | | |
| | H:92 | ALA | ASP | | |
| | H:103 | GLY | ALA | | |
| 157 | L:9 | SER | LYS | -22.98 | 13.03 |
| | H:92 | ALA | ASP | | |
| | H:103 | GLY | ALA | | |
| 158 | L:9 | SER | ARG | -22.97 | -19.38 |
| | H:24 | ALA | ASN | | |
| | H:92 | ALA | GLY | | |
| | H:103 | GLY | ALA | | |
| 159 | L:9 | SER | ARG | -22.97 | -29.82 |
| | H:92 | ALA | GLY | | |
| | H:103 | GLY | VAL | | |
| 160 | L:9 | SER | ARG | -22.95 | 19.39 |
| | H:3 | GLN | HID | | |
| | H:92 | ALA | ASP | | |
| | H:103 | GLY | ALA | | |

Figure 11D (Continued)

| | | | | | |
|---|---|---|---|---|---|
| 161 | L:9<br>H:92<br>H:103 | SER<br>ALA<br>GLY | LYS<br>VAL<br>ALA | -22.92 | -38.05 |
| 162 | L:9<br>H:16<br>H:92<br>H:103 | SER<br>GLY<br>ALA<br>GLY | LYS<br>ALA<br>GLY<br>VAL | -22.92 | -19.26 |
| 163 | L:9<br>H:92<br>H:103 | SER<br>ALA<br>GLY | ARG<br>ASP<br>ALA | -22.91 | 13.64 |
| 164 | L:9<br>H:92<br>H:103 | SER<br>ALA<br>GLY | LYS<br>GLY<br>ALA | -22.89 | -43.34 |
| 165 | L:9<br>H:4<br>H:92<br>H:103 | SER<br>LEU<br>ALA<br>GLY | ARG<br>VAL<br>GLY<br>VAL | -22.86 | -15.65 |
| 166 | L:9<br>H:16<br>H:92<br>H:103 | SER<br>GLY<br>ALA<br>GLY | ARG<br>ALA<br>GLY<br>VAL | -22.86 | -31.55 |
| 167 | L:9<br>H:58<br>H:92<br>H:103 | SER<br>THR<br>ALA<br>GLY | ILE<br>SER<br>GLY<br>ALA | -22.85 | -3.84 |
| 168 | L:9<br>H:58<br>H:92<br>H:103 | SER<br>THR<br>ALA<br>GLY | ILE<br>SER<br>VAL<br>ALA | -22.85 | -5.21 |
| 169 | L:9<br>H:24<br>H:88<br>H:103 | SER<br>ALA<br>ALA<br>GLY | ARG<br>GLY<br>VAL<br>ALA | -22.84 | -53.51 |
| 170 | L:9<br>L:76<br>H:92<br>H:103 | SER<br>SER<br>ALA<br>GLY | THR<br>ASN<br>VAL<br>ALA | -22.84 | -14.9 |
| 171 | L:9<br>L:80<br>L:102<br>H:79 | SER<br>PRO<br>THR<br>ALA | LYS<br>THR<br>ILE<br>VAL | -22.83 | -52.04 |
| 172 | L:9<br>H:24<br>H:85 | SER<br>ALA<br>SER | ARG<br>GLY<br>ARG | -22.82 | 47.27 |
| 173 | L:9<br>L:102<br>H:88<br>H:103 | SER<br>THR<br>ALA<br>GLY | ARG<br>ASN<br>GLY<br>ALA | -22.82 | -41.36 |
| 174 | L:9<br>H:88<br>H:92<br>H:103 | SER<br>ALA<br>ALA<br>GLY | LYS<br>GLY<br>ASP<br>ALA | -22.82 | 6.45 |
| 175 | L:9<br>L:102<br>H:88<br>H:103 | SER<br>THR<br>ALA<br>GLY | ARG<br>ASN<br>VAL<br>ALA | -22.82 | -47.74 |
| 176 | L:9<br>H:79<br>H:92<br>H:103 | SER<br>ALA<br>ALA<br>GLY | ILE<br>VAL<br>GLY<br>VAL | -22.82 | -50.34 |

Figure 11D (Continued)

| | | | | | |
|---|---|---|---|---|---|
| 177 | L:9<br>H:2<br>H:48<br>H:103 | SER<br>VAL<br>VAL<br>GLY | ARG<br>LEU<br>ILE<br>VAL | -22.81 | -32.27 |
| 178 | L:9<br>H:88<br>H:92<br>H:103 | SER<br>ALA<br>ALA<br>GLY | LYS<br>GLY<br>GLY<br>ALA | -22.8 | -40.92 |
| 179 | L:9<br>H:88<br>H:103 | SER<br>ALA<br>GLY | ARG<br>GLY<br>ALA | -22.8 | -54.17 |
| 180 | L:9<br>H:58<br>H:92<br>H:103 | SER<br>THR<br>ALA<br>GLY | LYS<br>ILE<br>ASP<br>ALA | -22.79 | 14.4 |
| 181 | L:9<br>H:48<br>H:88<br>H:103 | SER<br>VAL<br>ALA<br>GLY | ARG<br>LEU<br>VAL<br>ALA | -22.79 | -63.37 |
| 182 | L:9<br>H:4<br>H:92<br>H:103 | SER<br>LEU<br>ALA<br>GLY | LYS<br>VAL<br>GLY<br>ALA | -22.79 | -29.18 |
| 183 | L:9<br>H:88<br>H:92<br>H:103 | SER<br>ALA<br>ALA<br>GLY | ARG<br>GLY<br>GLY<br>ALA | -22.79 | -53.46 |
| 184 | L:9<br>H:88<br>H:103 | SER<br>ALA<br>GLY | ARG<br>VAL<br>ALA | -22.78 | -60.38 |
| 185 | L:9<br>H:85<br>H:88<br>H:103 | SER<br>SER<br>ALA<br>GLY | ARG<br>ARG<br>GLY<br>ALA | -22.78 | -33.12 |
| 186 | L:9<br>L:34<br>H:2<br>H:103 | SER<br>ALA<br>VAL<br>GLY | ARG<br>GLY<br>ILE<br>ALA | -22.78 | -49.05 |
| 187 | L:9<br>H:92<br>H:103 | SER<br>ALA<br>GLY | ILE<br>VAL<br>ALA | -22.77 | -11.16 |
| 188 | L:9<br>L:34<br>H:2<br>H:103 | SER<br>ALA<br>VAL<br>GLY | ARG<br>GLY<br>LEU<br>ALA | -22.76 | -35.07 |
| 189 | L:9<br>L:85<br>H:92<br>H:103 | SER<br>THR<br>ALA<br>GLY | ILE<br>ILE<br>GLY<br>ALA | -22.75 | -27.49 |
| 190 | L:9<br>L:85<br>H:92<br>H:103 | SER<br>THR<br>ALA<br>GLY | ILE<br>ILE<br>VAL<br>ALA | -22.74 | -20.7 |
| 191 | L:9<br>H:2<br>H:103 | SER<br>VAL<br>GLY | ARG<br>ILE<br>ALA | -22.73 | -56.48 |
| 192 | L:9<br>L:25<br>H:92<br>H:103 | SER<br>ALA<br>ALA<br>GLY | LYS<br>ASP<br>VAL<br>VAL | -22.72 | 109.94 |

| | | | | | |
|---|---|---|---|---|---|
| 193 | L:9<br>H:56<br>H:79<br>H:103 | SER<br>GLY<br>ALA<br>GLY | LYS<br>ALA<br>VAL<br>ALA | -22.67 | -21.71 |
| 194 | L:9<br>H:88<br>H:103 | SER<br>ALA<br>GLY | LYS<br>GLY<br>ALA | -22.63 | -14.02 |
| 195 | L:9<br>H:103<br>H:114 | SER<br>GLY<br>THR | LYS<br>ALA<br>SER | -22.63 | -6.9 |
| 196 | L:9<br>H:88<br>H:103<br>H:114 | SER<br>ALA<br>GLY<br>THR | LYS<br>GLY<br>ALA<br>SER | -22.63 | -3.96 |
| 197 | L:9<br>L:80<br>H:26<br>H:103 | SER<br>PRO<br>GLY<br>GLY | LYS<br>SER<br>ALA<br>ALA | -22.62 | -15.29 |

5 Mutations

| Number | Residue | Original | Mutated | Δ Affinity | Δ Stability |
|---|---|---|---|---|---|
| 1 | L:9 | SER | ARG | -35.47 | 21.7 |
| | L:43 | ALA | PHE | | |
| | H:92 | ALA | ASP | | |
| | H:103 | GLY | VAL | | |
| | H:114 | THR | ASN | | |
| 2 | L:9 | SER | ARG | -32.78 | -75.08 |
| | L:43 | ALA | PHE | | |
| | H:88 | ALA | GLY | | |
| | H:103 | GLY | ALA | | |
| | H:114 | THR | ASN | | |
| 3 | L:9 | SER | ILE | -31.99 | -73.44 |
| | L:43 | ALA | PHE | | |
| | H:85 | SER | ARG | | |
| | H:103 | GLY | ALA | | |
| | H:114 | THR | ILE | | |
| 4 | L:9 | SER | ARG | -30.43 | 9.38 |
| | L:43 | ALA | PHE | | |
| | H:16 | GLY | VAL | | |
| | H:85 | SER | ARG | | |
| | H:114 | THR | ILE | | |
| 5 | L:9 | SER | ARG | -29.51 | -60.66 |
| | L:43 | ALA | PHE | | |
| | H:2 | VAL | LEU | | |
| | H:14 | PRO | SER | | |
| | H:114 | THR | ILE | | |
| 6 | L:9 | SER | ARG | -29.09 | -81.47 |
| | L:43 | ALA | PHE | | |
| | H:16 | GLY | ALA | | |
| | H:58 | THR | ASN | | |
| | H:114 | THR | ILE | | |
| 7 | L:9 | SER | ARG | -25.78 | -12.61 |
| | L:93 | THR | ILE | | |
| | H:92 | ALA | GLY | | |
| | H:103 | GLY | VAL | | |
| | H:114 | THR | ILE | | |
| 8 | L:9 | SER | ARG | -25.44 | 7.33 |
| | L:102 | THR | ILE | | |
| | H:92 | ALA | GLY | | |
| | H:103 | GLY | VAL | | |
| | H:114 | THR | SER | | |
| 9 | L:9 | SER | LYS | -25.4 | 7.37 |
| | L:51 | ALA | THR | | |
| | H:92 | ALA | VAL | | |
| | H:103 | GLY | VAL | | |
| | H:114 | THR | ASN | | |
| 10 | L:9 | SER | ARG | -25.31 | 114.9 |
| | H:48 | VAL | PHE | | |
| | H:92 | ALA | VAL | | |
| | H:103 | GLY | VAL | | |
| | H:114 | THR | ASN | | |
| 11 | L:9 | SER | ARG | -25.3 | 81.52 |
| | L:25 | ALA | VAL | | |
| | H:92 | ALA | ASP | | |
| | H:103 | GLY | VAL | | |
| | H:114 | THR | SER | | |
| 12 | L:9 | SER | ARG | -25.27 | 108.05 |
| | H:48 | VAL | PHE | | |
| | H:92 | ALA | VAL | | |
| | H:103 | GLY | VAL | | |
| | H:114 | THR | ILE | | |

Figure 11E (Continued)

| | | | | | |
|---|---|---|---|---|---|
| 13 | L:9<br>L:93<br>H:92<br>H:103<br>H:114 | SER<br>THR<br>ALA<br>GLY<br>THR | ARG<br>ILE<br>GLY<br>VAL<br>SER | -25.23 | -13.15 |
| 14 | L:9<br>H:85<br>H:92<br>H:103<br>H:114 | SER<br>SER<br>ALA<br>GLY<br>THR | ARG<br>ARG<br>VAL<br>VAL<br>ASN | -25.15 | -23.8 |
| 15 | L:9<br>L:80<br>H:92<br>H:103<br>H:114 | SER<br>PRO<br>ALA<br>GLY<br>THR | ARG<br>THR<br>GLY<br>VAL<br>ILE | -25.09 | -22.29 |
| 16 | L:9<br>L:101<br>H:92<br>H:103<br>H:114 | SER<br>GLY<br>ALA<br>GLY<br>THR | LYS<br>ALA<br>GLY<br>VAL<br>ASN | -25.07 | -10.03 |
| 17 | L:9<br>H:56<br>H:79<br>H:103<br>H:114 | SER<br>GLY<br>ALA<br>GLY<br>THR | ARG<br>ALA<br>VAL<br>VAL<br>ASN | -25.03 | -40.37 |
| 18 | L:9<br>H:58<br>H:92<br>H:103<br>H:114 | SER<br>THR<br>ALA<br>GLY<br>THR | ARG<br>SER<br>VAL<br>VAL<br>ASN | -25.01 | -5.57 |
| 19 | L:9<br>L:101<br>H:92<br>H:103<br>H:114 | SER<br>GLY<br>ALA<br>GLY<br>THR | ARG<br>VAL<br>VAL<br>VAL<br>ILE | -24.99 | -21.41 |
| 20 | L:9<br>L:51<br>H:92<br>H:103<br>H:114 | SER<br>ALA<br>ALA<br>GLY<br>THR | LYS<br>THR<br>VAL<br>VAL<br>SER | -24.97 | 11.01 |
| 21 | L:9<br>L:80<br>H:92<br>H:103<br>H:114 | SER<br>PRO<br>ALA<br>GLY<br>THR | ARG<br>ALA<br>VAL<br>VAL<br>ASN | -24.95 | 1.03 |
| 22 | L:9<br>H:92<br>H:103<br>H:114 | SER<br>ALA<br>GLY<br>THR | ARG<br>VAL<br>VAL<br>SER | -24.94 | -3.32 |
| 23 | L:9<br>H:92<br>H:103<br>H:114 | SER<br>ALA<br>GLY<br>THR | ARG<br>VAL<br>VAL<br>ASN | -24.93 | -11.42 |
| 24 | L:9<br>L:80<br>H:92<br>H:103<br>H:114 | SER<br>PRO<br>ALA<br>GLY<br>THR | ARG<br>THR<br>VAL<br>VAL<br>ASN | -24.93 | -14.81 |
| 25 | L:9<br>L:101<br>H:92<br>H:103<br>H:114 | SER<br>GLY<br>ALA<br>GLY<br>THR | ARG<br>VAL<br>VAL<br>VAL<br>ASN | -24.93 | -14.01 |

Figure 11E (Continued)

| | | | | | |
|---|---|---|---|---|---|
| 26 | L:9<br>L:101<br>H:92<br>H:103<br>H:114 | SER<br>GLY<br>ALA<br>GLY<br>THR | ARG<br>VAL<br>VAL<br>VAL<br>SER | -24.92 | -11.41 |
| 27 | L:9<br>L:51<br>H:92<br>H:103<br>H:114 | SER<br>ALA<br>ALA<br>GLY<br>THR | LYS<br>THR<br>GLY<br>VAL<br>SER | -24.9 | 9.21 |
| 28 | L:9<br>H:48<br>H:92<br>H:103<br>H:114 | SER<br>VAL<br>ALA<br>GLY<br>THR | ARG<br>PHE<br>VAL<br>VAL<br>SER | -24.88 | 118.53 |
| 29 | L:9<br>H:92<br>H:103<br>H:114 | SER<br>ALA<br>GLY<br>THR | ARG<br>VAL<br>VAL<br>ILE | -24.87 | -0.53 |
| 30 | L:9<br>H:61<br>H:103<br>H:114 | SER<br>ALA<br>GLY<br>THR | LYS<br>GLY<br>ALA<br>ASN | -24.86 | -42.87 |
| 31 | L:9<br>L:80<br>H:92<br>H:103<br>H:114 | SER<br>PRO<br>ALA<br>GLY<br>THR | ARG<br>THR<br>VAL<br>VAL<br>SER | -24.86 | 4.94 |
| 32 | L:9<br>H:56<br>H:92<br>H:103<br>H:114 | SER<br>GLY<br>ALA<br>GLY<br>THR | ARG<br>ALA<br>GLY<br>VAL<br>SER | -24.86 | -5.83 |
| 33 | L:9<br>H:92<br>H:103<br>H:114 | SER<br>ALA<br>GLY<br>THR | ARG<br>GLY<br>VAL<br>SER | -24.86 | -6.2 |
| 34 | L:9<br>L:80<br>H:92<br>H:103<br>H:114 | SER<br>PRO<br>ALA<br>GLY<br>THR | ARG<br>THR<br>GLY<br>VAL<br>SER | -24.86 | -10.58 |
| 35 | L:9<br>L:80<br>H:92<br>H:103<br>H:114 | SER<br>PRO<br>ALA<br>GLY<br>THR | ARG<br>THR<br>VAL<br>VAL<br>ILE | -24.85 | -6.72 |
| 36 | L:9<br>H:26<br>H:92<br>H:103<br>H:114 | SER<br>GLY<br>ALA<br>GLY<br>THR | ARG<br>ALA<br>VAL<br>VAL<br>ILE | -24.85 | 2.01 |
| 37 | L:9<br>L:40<br>H:92<br>H:103<br>H:114 | SER<br>PRO<br>ALA<br>GLY<br>THR | ARG<br>ALA<br>VAL<br>VAL<br>ILE | -24.85 | 4.58 |
| 38 | L:9<br>H:92<br>H:103<br>H:114 | SER<br>ALA<br>GLY<br>THR | ARG<br>GLY<br>VAL<br>ILE | -24.84 | -5.72 |

Figure 11E (Continued)

| | | | | | |
|---|---|---|---|---|---|
| 39 | L:9<br>L:51<br>H:79<br>H:103<br>H:114 | SER<br>ALA<br>ALA<br>GLY<br>THR | ARG<br>PRO<br>GLY<br>VAL<br>ASN | -24.8 | 3.96 |
| 40 | L:9<br>H:2<br>H:92<br>H:103<br>H:114 | SER<br>VAL<br>ALA<br>GLY<br>THR | ARG<br>ILE<br>GLY<br>VAL<br>SER | -24.8 | -8.78 |
| 41 | L:9<br>L:51<br>H:61<br>H:103<br>H:114 | SER<br>ALA<br>ALA<br>GLY<br>THR | LYS<br>PRO<br>GLY<br>ALA<br>ASN | -24.77 | -20.92 |
| 42 | L:9<br>L:51<br>H:79<br>H:103<br>H:114 | SER<br>ALA<br>ALA<br>GLY<br>THR | LYS<br>PRO<br>VAL<br>VAL<br>ASN | -24.76 | -2.89 |
| 43 | L:9<br>L:32<br>H:92<br>H:103<br>H:114 | SER<br>ALA<br>ALA<br>GLY<br>THR | ARG<br>VAL<br>GLY<br>VAL<br>SER | -24.75 | 19.22 |
| 44 | L:9<br>H:88<br>H:92<br>H:103<br>H:114 | SER<br>ALA<br>ALA<br>GLY<br>THR | ARG<br>GLY<br>VAL<br>VAL<br>ASN | -24.72 | -3.63 |
| 45 | L:9<br>H:88<br>H:92<br>H:103<br>H:114 | SER<br>ALA<br>ALA<br>GLY<br>THR | ARG<br>GLY<br>GLY<br>VAL<br>ASN | -24.71 | -19.57 |
| 46 | L:9<br>L:89<br>H:92<br>H:103<br>H:114 | SER<br>GLN<br>ALA<br>GLY<br>THR | ARG<br>HID<br>VAL<br>VAL<br>ASN | -24.71 | -6.52 |
| 47 | L:9<br>L:51<br>H:26<br>H:103<br>H:114 | SER<br>ALA<br>GLY<br>GLY<br>THR | LYS<br>SER<br>ALA<br>VAL<br>ASN | -24.7 | -11.4 |
| 48 | L:9<br>L:51<br>H:79<br>H:103<br>H:114 | SER<br>ALA<br>ALA<br>GLY<br>THR | ARG<br>PRO<br>VAL<br>VAL<br>ASN | -24.7 | -15.23 |
| 49 | L:9<br>H:92<br>H:103<br>H:114 | SER<br>ALA<br>GLY<br>THR | LYS<br>GLY<br>VAL<br>SER | -24.7 | -5.17 |
| 50 | L:9<br>H:24<br>H:61<br>H:103<br>H:114 | SER<br>ALA<br>ALA<br>GLY<br>THR | LYS<br>PRO<br>VAL<br>ALA<br>ILE | -24.7 | -44.49 |

Figure 11E (Continued)

| | | | | | |
|---|---|---|---|---|---|
| 51 | L:9 | SER | LYS | -24.68 | 24.34 |
| | H:88 | ALA | GLY | | |
| | H:92 | ALA | VAL | | |
| | H:103 | GLY | VAL | | |
| | H:114 | THR | ASN | | |
| 52 | L:9 | SER | LYS | -24.68 | 21.38 |
| | H:92 | ALA | VAL | | |
| | H:103 | GLY | VAL | | |
| | H:114 | THR | ASN | | |
| 53 | L:9 | SER | LYS | -24.67 | 75.26 |
| | H:48 | VAL | PHE | | |
| | H:92 | ALA | GLY | | |
| | H:103 | GLY | VAL | | |
| | H:114 | THR | SER | | |
| 54 | L:9 | SER | LYS | -24.67 | -6.39 |
| | L:101 | GLY | ALA | | |
| | H:92 | ALA | GLY | | |
| | H:103 | GLY | VAL | | |
| | H:114 | THR | SER | | |
| 55 | L:9 | SER | LYS | -24.66 | -36.74 |
| | H:14 | PRO | ALA | | |
| | H:61 | ALA | GLY | | |
| | H:103 | GLY | ALA | | |
| | H:114 | THR | ASN | | |
| 56 | L:9 | SER | ARG | -24.66 | -13.58 |
| | H:26 | GLY | VAL | | |
| | H:92 | ALA | GLY | | |
| | H:103 | GLY | VAL | | |
| | H:114 | THR | SER | | |
| 57 | L:9 | SER | LYS | -24.66 | 7.75 |
| | H:79 | ALA | VAL | | |
| | H:92 | ALA | VAL | | |
| | H:103 | GLY | VAL | | |
| | H:114 | THR | ASN | | |
| 58 | L:9 | SER | LYS | -24.66 | -42.3 |
| | L:46 | LEU | ILE | | |
| | H:61 | ALA | GLY | | |
| | H:103 | GLY | ALA | | |
| | H:114 | THR | ASN | | |
| 59 | L:9 | SER | LYS | -24.65 | -39.69 |
| | L:46 | LEU | ILE | | |
| | H:61 | ALA | GLY | | |
| | H:103 | GLY | ALA | | |
| | H:114 | THR | SER | | |
| 60 | L:9 | SER | ARG | -24.64 | -23.69 |
| | L:51 | ALA | SER | | |
| | H:26 | GLY | ALA | | |
| | H:103 | GLY | VAL | | |
| | H:114 | THR | ASN | | |
| 61 | L:9 | SER | LYS | -24.62 | -18.73 |
| | L:51 | ALA | SER | | |
| | H:26 | GLY | ALA | | |
| | H:103 | GLY | VAL | | |
| | H:114 | THR | ILE | | |
| 62 | L:9 | SER | ARG | -24.62 | -20.49 |
| | L:101 | GLY | ALA | | |
| | H:92 | ALA | GLY | | |
| | H:103 | GLY | VAL | | |
| | H:114 | THR | ASN | | |
| 63 | L:9 | SER | ARG | -24.61 | -9.85 |
| | L:102 | THR | ASN | | |
| | H:103 | GLY | VAL | | |
| | H:114 | THR | ASN | | |

Figure 11E (Continued)

| | | | | | |
|---|---|---|---|---|---|
| 64 | L:9<br>H:48<br>H:92<br>H:103<br>H:114 | SER<br>VAL<br>ALA<br>GLY<br>THR | ARG<br>PHE<br>GLY<br>VAL<br>SER | -24.61 | 63.22 |
| 65 | L:9<br>L:51<br>H:26<br>H:103<br>H:114 | SER<br>ALA<br>GLY<br>GLY<br>THR | LYS<br>SER<br>VAL<br>VAL<br>ILE | -24.6 | -19.64 |
| 66 | L:9<br>L:102<br>H:26<br>H:103<br>H:114 | SER<br>THR<br>GLY<br>GLY<br>THR | ARG<br>ASN<br>ALA<br>VAL<br>ASN | -24.6 | -7.84 |
| 67 | L:9<br>H:79<br>H:103<br>H:114 | SER<br>ALA<br>GLY<br>THR | ARG<br>VAL<br>VAL<br>ASN | -24.6 | -39.78 |
| 68 | L:9<br>H:79<br>H:92<br>H:103<br>H:114 | SER<br>ALA<br>ALA<br>GLY<br>THR | ARG<br>VAL<br>VAL<br>VAL<br>ASN | -24.59 | -3.99 |
| 69 | L:9<br>H:92<br>H:103<br>H:114 | SER<br>ALA<br>GLY<br>THR | ARG<br>GLY<br>VAL<br>ASN | -24.59 | -17.28 |
| 70 | L:9<br>L:85<br>H:56<br>H:103<br>H:114 | SER<br>THR<br>GLY<br>GLY<br>THR | ARG<br>SER<br>ALA<br>VAL<br>ILE | -24.58 | -27.72 |
| 71 | L:9<br>H:56<br>H:79<br>H:103<br>H:114 | SER<br>GLY<br>ALA<br>GLY<br>THR | ARG<br>ALA<br>VAL<br>VAL<br>SER | -24.58 | -35.14 |
| 72 | L:9<br>L:43<br>H:92<br>H:103<br>H:114 | SER<br>ALA<br>ALA<br>GLY<br>THR | ARG<br>ASN<br>VAL<br>VAL<br>ASN | -24.57 | 0.51 |
| 73 | L:9<br>H:26<br>H:103<br>H:114 | SER<br>GLY<br>GLY<br>THR | ARG<br>ALA<br>VAL<br>ASN | -24.57 | -22.13 |
| 74 | L:9<br>H:56<br>H:103<br>H:114 | SER<br>GLY<br>GLY<br>THR | ARG<br>ALA<br>VAL<br>ILE | -24.57 | -34.36 |
| 75 | L:9<br>H:61<br>H:103<br>H:114 | SER<br>ALA<br>GLY<br>THR | LYS<br>VAL<br>ALA<br>ASN | -24.57 | -50.23 |
| 76 | L:9<br>L:43<br>H:92<br>H:103<br>H:114 | SER<br>ALA<br>ALA<br>GLY<br>THR | ARG<br>PRO<br>VAL<br>VAL<br>ASN | -24.57 | 6.46 |

Figure 11E (Continued)

| | | | | | |
|---|---|---|---|---|---|
| 77 | L:9<br>H:56<br>H:79<br>H:103<br>H:114 | SER<br>GLY<br>ALA<br>GLY<br>THR | ARG<br>ALA<br>VAL<br>VAL<br>ILE | -24.57 | -46.74 |
| 78 | L:9<br>H:56<br>H:58<br>H:103<br>H:114 | SER<br>GLY<br>THR<br>GLY<br>THR | LYS<br>VAL<br>ILE<br>ALA<br>ILE | -24.56 | -57.89 |
| 79 | L:9<br>H:14<br>H:61<br>H:103<br>H:114 | SER<br>PRO<br>ALA<br>GLY<br>THR | LYS<br>ALA<br>VAL<br>ALA<br>ASN | -24.56 | -44.15 |
| 80 | L:9<br>L:51<br>H:26<br>H:103<br>H:114 | SER<br>ALA<br>GLY<br>GLY<br>THR | ARG<br>SER<br>ALA<br>VAL<br>ILE | -24.56 | -31.07 |
| 81 | L:9<br>H:48<br>H:92<br>H:103<br>H:114 | SER<br>VAL<br>ALA<br>GLY<br>THR | ARG<br>ILE<br>GLY<br>VAL<br>ASN | -24.55 | -24.23 |
| 82 | L:9<br>H:48<br>H:92<br>H:103<br>H:114 | SER<br>VAL<br>ALA<br>GLY<br>THR | ARG<br>ILE<br>VAL<br>VAL<br>ASN | -24.54 | -7.63 |
| 83 | L:9<br>H:26<br>H:56<br>H:103<br>H:114 | SER<br>GLY<br>GLY<br>GLY<br>THR | ARG<br>VAL<br>ALA<br>VAL<br>ILE | -24.54 | -32.83 |
| 84 | L:9<br>L:80<br>H:92<br>H:103<br>H:114 | SER<br>PRO<br>ALA<br>GLY<br>THR | ARG<br>ALA<br>VAL<br>VAL<br>SER | -24.53 | 4.65 |
| 85 | L:9<br>H:14<br>H:92<br>H:103<br>H:114 | SER<br>PRO<br>ALA<br>GLY<br>THR | ARG<br>SER<br>VAL<br>VAL<br>SER | -24.53 | 17.99 |
| 86 | L:9<br>L:43<br>H:92<br>H:103<br>H:114 | SER<br>ALA<br>ALA<br>GLY<br>THR | ARG<br>PHE<br>GLY<br>VAL<br>ASN | -24.52 | 3.89 |
| 87 | L:9<br>H:14<br>H:92<br>H:103<br>H:114 | SER<br>PRO<br>ALA<br>GLY<br>THR | ARG<br>SER<br>VAL<br>VAL<br>ILE | -24.52 | 6.38 |
| 88 | L:9<br>L:43<br>H:92<br>H:103<br>H:114 | SER<br>ALA<br>ALA<br>GLY<br>THR | ARG<br>PHE<br>VAL<br>VAL<br>ASN | -24.51 | 9.25 |

Figure 11E (Continued)

| | | | | | |
|---|---|---|---|---|---|
| 89 | L:9<br>H:26<br>H:103<br>H:114 | SER<br>GLY<br>GLY<br>THR | ARG<br>ALA<br>VAL<br>ILE | -24.51 | -32.32 |
| 90 | L:9<br>L:80<br>H:92<br>H:103<br>H:114 | SER<br>PRO<br>ALA<br>GLY<br>THR | ARG<br>THR<br>ASP<br>VAL<br>ILE | -24.5 | 7.11 |
| 91 | L:9<br>H:2<br>H:92<br>H:103<br>H:114 | SER<br>VAL<br>ALA<br>GLY<br>THR | ARG<br>ILE<br>VAL<br>VAL<br>ASN | -24.49 | -2.12 |
| 92 | L:9<br>H:26<br>H:103<br>H:114 | SER<br>GLY<br>GLY<br>THR | ARG<br>VAL<br>VAL<br>ILE | -24.49 | -33.23 |
| 93 | L:9<br>L:93<br>H:92<br>H:103<br>H:114 | SER<br>THR<br>ALA<br>GLY<br>THR | ILE<br>ILE<br>GLY<br>VAL<br>ILE | -24.48 | -11.16 |
| 94 | L:9<br>L:25<br>H:61<br>H:103<br>H:114 | SER<br>ALA<br>ALA<br>GLY<br>THR | LYS<br>VAL<br>VAL<br>ALA<br>ASN | -24.46 | -7.7 |
| 95 | L:9<br>H:26<br>H:103<br>H:114 | SER<br>GLY<br>GLY<br>THR | ARG<br>ALA<br>ALA<br>ASN | -24.45 | -57.56 |
| 96 | L:9<br>H:92<br>H:103<br>H:114 | SER<br>ALA<br>GLY<br>THR | ILE<br>VAL<br>VAL<br>SER | -24.41 | 5.45 |
| 97 | L:9<br>H:58<br>H:92<br>H:103<br>H:114 | SER<br>THR<br>ALA<br>GLY<br>THR | THR<br>SER<br>VAL<br>VAL<br>ILE | -24.36 | -7.65 |
| 98 | L:9<br>H:24<br>H:61<br>H:103<br>H:114 | SER<br>ALA<br>ALA<br>GLY<br>THR | LYS<br>PRO<br>VAL<br>ALA<br>ASN | -24.34 | -36.72 |
| 99 | L:9<br>H:56<br>H:58<br>H:103<br>H:114 | SER<br>GLY<br>THR<br>GLY<br>THR | LYS<br>VAL<br>ILE<br>ALA<br>SER | -24.34 | -46.16 |
| 100 | L:9<br>L:102<br>H:103<br>H:106<br>H:114 | SER<br>THR<br>GLY<br>ALA<br>THR | LYS<br>ASN<br>VAL<br>VAL<br>ASN | -24.34 | 10.69 |
| 101 | L:9<br>H:24<br>H:61<br>H:103<br>H:114 | SER<br>ALA<br>ALA<br>GLY<br>THR | LYS<br>PRO<br>VAL<br>ALA<br>SER | -24.33 | -34.04 |

Figure 11E (Continued)

| | | | | | |
|---|---|---|---|---|---|
| 102 | L:9<br>L:51<br>H:92<br>H:103<br>H:114 | SER<br>ALA<br>ALA<br>GLY<br>THR | LYS<br>THR<br>ASP<br>VAL<br>SER | -24.32 | 26.27 |
| 103 | L:9<br>L:102<br>H:103<br>H:106<br>H:114 | SER<br>THR<br>GLY<br>ALA<br>THR | ARG<br>ASN<br>VAL<br>VAL<br>ASN | -24.32 | -2.3 |
| 104 | L:9<br>H:24<br>H:61<br>H:103<br>H:114 | SER<br>ALA<br>ALA<br>GLY<br>THR | LYS<br>PRO<br>GLY<br>ALA<br>ILE | -24.3 | -36.39 |
| 105 | L:9<br>H:58<br>H:92<br>H:103<br>H:114 | SER<br>THR<br>ALA<br>GLY<br>THR | THR<br>SER<br>VAL<br>VAL<br>ASN | -24.3 | -0.25 |
| 106 | L:9<br>H:24<br>H:92<br>H:103<br>H:114 | SER<br>ALA<br>ALA<br>GLY<br>THR | THR<br>GLY<br>VAL<br>VAL<br>ASN | -24.29 | -0.25 |
| 107 | L:9<br>L:76<br>H:92<br>H:103<br>H:114 | SER<br>SER<br>ALA<br>GLY<br>THR | ILE<br>THR<br>VAL<br>ALA<br>SER | -24.29 | -31.39 |
| 108 | L:9<br>L:80<br>H:92<br>H:103<br>H:114 | SER<br>PRO<br>ALA<br>GLY<br>THR | ARG<br>THR<br>ASP<br>VAL<br>SER | -24.27 | 18.76 |
| 109 | L:9<br>H:24<br>H:61<br>H:103<br>H:114 | SER<br>ALA<br>ALA<br>GLY<br>THR | ARG<br>PRO<br>VAL<br>ALA<br>ILE | -24.25 | -56.18 |
| 110 | L:9<br>L:102<br>H:92<br>H:103<br>H:114 | SER<br>THR<br>ALA<br>GLY<br>THR | THR<br>ASN<br>VAL<br>VAL<br>ASN | -24.25 | 8.02 |
| 111 | L:9<br>H:92<br>H:103<br>H:114 | SER<br>ALA<br>GLY<br>THR | THR<br>VAL<br>VAL<br>ASN | -24.23 | -6.04 |
| 112 | L:9<br>L:51<br>H:92<br>H:103<br>H:114 | SER<br>ALA<br>ALA<br>GLY<br>THR | THR<br>THR<br>VAL<br>VAL<br>ASN | -24.22 | 1.46 |
| 113 | L:9<br>H:58<br>H:88<br>H:103<br>H:114 | SER<br>THR<br>ALA<br>GLY<br>THR | LYS<br>ILE<br>GLY<br>ALA<br>ILE | -24.22 | -52.96 |

Figure 11E (Continued)

| | | | | | |
|---|---|---|---|---|---|
| 114 | L:9<br>H:58<br>H:103<br>H:114 | SER<br>THR<br>GLY<br>THR | LYS<br>ILE<br>ALA<br>ILE | -24.22 | -55.9 |
| 115 | L:9<br>H:48<br>H:92<br>H:103<br>H:114 | SER<br>VAL<br>ALA<br>GLY<br>THR | THR<br>PHE<br>VAL<br>VAL<br>ILE | -24.19 | 126.02 |
| 116 | L:9<br>H:2<br>H:92<br>H:103<br>H:114 | SER<br>VAL<br>ALA<br>GLY<br>THR | THR<br>ILE<br>VAL<br>VAL<br>ASN | -24.19 | -8.39 |
| 117 | L:9<br>L:43<br>H:92<br>H:103<br>H:114 | SER<br>ALA<br>ALA<br>GLY<br>THR | THR<br>ASN<br>VAL<br>VAL<br>ASN | -24.19 | -13.87 |
| 118 | L:9<br>H:2<br>H:92<br>H:103<br>H:114 | SER<br>VAL<br>ALA<br>GLY<br>THR | THR<br>ILE<br>GLY<br>VAL<br>ASN | -24.18 | -23.62 |
| 119 | L:9<br>H:24<br>H:92<br>H:103<br>H:114 | SER<br>ALA<br>ALA<br>GLY<br>THR | ARG<br>ASN<br>VAL<br>VAL<br>SER | -24.18 | 6.15 |
| 120 | L:9<br>L:80<br>H:92<br>H:103<br>H:114 | SER<br>PRO<br>ALA<br>GLY<br>THR | THR<br>THR<br>VAL<br>VAL<br>SER | -24.16 | 8.3 |
| 121 | L:9<br>H:79<br>H:92<br>H:103<br>H:114 | SER<br>ALA<br>ALA<br>GLY<br>THR | ILE<br>GLY<br>GLY<br>VAL<br>SER | -23.98 | 0.84 |
| 122 | L:9<br>H:92<br>H:103<br>H:114 | SER<br>ALA<br>GLY<br>THR | ILE<br>GLY<br>VAL<br>SER | -23.9 | -6.97 |
| 123 | L:9<br>L:80<br>H:92<br>H:103<br>H:114 | SER<br>PRO<br>ALA<br>GLY<br>THR | ILE<br>THR<br>GLY<br>VAL<br>SER | -23.89 | -12 |
| 124 | L:9<br>H:79<br>H:88<br>H:103<br>H:114 | SER<br>ALA<br>ALA<br>GLY<br>THR | THR<br>GLY<br>GLY<br>ALA<br>ILE | -23.8 | -32.54 |
| 125 | L:9<br>H:79<br>H:92<br>H:103<br>H:114 | SER<br>ALA<br>ALA<br>GLY<br>THR | ILE<br>GLY<br>ASP<br>VAL<br>ASN | -23.77 | 25.36 |
| 126 | L:9<br>H:79<br>H:88<br>H:103<br>H:114 | SER<br>ALA<br>ALA<br>GLY<br>THR | THR<br>GLY<br>GLY<br>ALA<br>ASN | -23.76 | -25.29 |

Figure 11E (Continued)

| | | | | | |
|---|---|---|---|---|---|
| 127 | L:9<br>L:25<br>H:61<br>H:103<br>H:114 | SER<br>ALA<br>ALA<br>GLY<br>THR | THR<br>VAL<br>VAL<br>ALA<br>ASN | -23.76 | -14.8 |
| 128 | L:9<br>H:14<br>H:61<br>H:103<br>H:114 | SER<br>PRO<br>ALA<br>GLY<br>THR | LYS<br>ALA<br>ASP<br>ALA<br>ASN | -23.72 | -36.88 |
| 129 | L:9<br>L:76<br>H:92<br>H:103<br>H:114 | SER<br>SER<br>ALA<br>GLY<br>THR | THR<br>THR<br>VAL<br>ALA<br>SER | -23.69 | -29.09 |
| 130 | L:9<br>H:88<br>H:92<br>H:103<br>H:114 | SER<br>ALA<br>ALA<br>GLY<br>THR | THR<br>GLY<br>VAL<br>ALA<br>SER | -23.67 | -19.85 |
| 131 | L:9<br>H:92<br>H:103<br>H:114 | SER<br>ALA<br>GLY<br>THR | THR<br>VAL<br>ALA<br>SER | -23.67 | -22.8 |
| 132 | L:9<br>H:92<br>H:103<br>H:114 | SER<br>ALA<br>GLY<br>THR | ILE<br>VAL<br>ALA<br>SER | -23.67 | -24.63 |
| 133 | L:9<br>H:88<br>H:92<br>H:103<br>H:114 | SER<br>ALA<br>ALA<br>GLY<br>THR | THR<br>GLY<br>GLY<br>ALA<br>ASN | -23.65 | -22.83 |
| 134 | L:9<br>H:26<br>H:92<br>H:103<br>H:114 | SER<br>GLY<br>ALA<br>GLY<br>THR | ILE<br>VAL<br>VAL<br>ALA<br>SER | -23.64 | -23.01 |
| 135 | L:9<br>H:88<br>H:92<br>H:103<br>H:114 | SER<br>ALA<br>ALA<br>GLY<br>THR | THR<br>GLY<br>GLY<br>ALA<br>SER | -23.64 | -20.28 |
| 136 | L:9<br>H:88<br>H:92<br>H:103<br>H:114 | SER<br>ALA<br>ALA<br>GLY<br>THR | THR<br>GLY<br>VAL<br>ALA<br>ILE | -23.61 | -24.4 |
| 137 | L:9<br>H:26<br>H:92<br>H:103<br>H:114 | SER<br>GLY<br>ALA<br>GLY<br>THR | ILE<br>ASP<br>VAL<br>VAL<br>SER | -23.61 | -6.38 |
| 138 | L:9<br>H:14<br>H:88<br>H:103<br>H:114 | SER<br>PRO<br>ALA<br>GLY<br>THR | THR<br>THR<br>GLY<br>ALA<br>ILE | -23.6 | -34.47 |
| 139 | L:9<br>H:88<br>H:103<br>H:114 | SER<br>ALA<br>GLY<br>THR | THR<br>GLY<br>ALA<br>ILE | -23.6 | -40.38 |

Figure 11E (Continued)

| | | | | | |
|---|---|---|---|---|---|
| 140 | L:9<br>L:31<br>H:56<br>H:103<br>H:114 | SER<br>THR<br>GLY<br>GLY<br>THR | ARG<br>SER<br>VAL<br>ALA<br>ILE | -23.6 | -64.89 |
| 141 | L:9<br>H:88<br>H:92<br>H:103<br>H:114 | SER<br>ALA<br>ALA<br>GLY<br>THR | THR<br>GLY<br>GLY<br>ALA<br>ILE | -23.58 | -30.18 |
| 142 | L:9<br>H:26<br>H:92<br>H:103<br>H:114 | SER<br>GLY<br>ALA<br>GLY<br>THR | ILE<br>ASP<br>GLY<br>VAL<br>SER | -23.57 | -6.67 |
| 143 | L:9<br>H:58<br>H:88<br>H:103<br>H:114 | SER<br>THR<br>ALA<br>GLY<br>THR | ILE<br>ILE<br>GLY<br>ALA<br>ILE | -23.43 | -61.68 |
| 144 | L:9<br>L:43<br>H:92<br>H:103<br>H:114 | SER<br>ALA<br>ALA<br>GLY<br>THR | ILE<br>ASN<br>ASP<br>VAL<br>ASN | -23.41 | 10.69 |
| 145 | L:9<br>H:79<br>H:92<br>H:103<br>H:114 | SER<br>ALA<br>ALA<br>GLY<br>THR | ILE<br>GLY<br>ASP<br>VAL<br>SER | -23.38 | 29.08 |
| 146 | L:9<br>L:76<br>H:92<br>H:103<br>H:114 | SER<br>SER<br>ALA<br>GLY<br>THR | ILE<br>THR<br>ASP<br>VAL<br>ASN | -23.3 | 12.29 |
| 147 | L:9<br>H:92<br>H:103<br>H:114 | SER<br>ALA<br>GLY<br>THR | ILE<br>ASP<br>VAL<br>ASN | -23.3 | 18.73 |
| 148 | L:9<br>L:76<br>H:92<br>H:103<br>H:114 | SER<br>SER<br>ALA<br>GLY<br>THR | ILE<br>THR<br>ASP<br>VAL<br>SER | -23.29 | 14.83 |
| 149 | L:9<br>L:51<br>H:56<br>H:103<br>H:114 | SER<br>ALA<br>GLY<br>GLY<br>THR | ARG<br>PRO<br>VAL<br>ALA<br>ILE | -23.18 | -34.67 |
| 150 | L:9<br>H:58<br>H:88<br>H:103<br>H:114 | SER<br>THR<br>ALA<br>GLY<br>THR | THR<br>ILE<br>ASP<br>ALA<br>ILE | -23.14 | -59.75 |
| 151 | L:9<br>L:93<br>H:24<br>H:58<br>H:114 | SER<br>THR<br>ALA<br>THR<br>THR | LYS<br>ILE<br>PRO<br>ILE<br>ILE | -23.13 | -36.78 |

Figure 11E (Continued)

| | | | | | |
|---|---|---|---|---|---|
| 152 | L:9 | SER | ILE | -23.11 | -61.51 |
| | H:58 | THR | ILE | | |
| | H:88 | ALA | ASP | | |
| | H:103 | GLY | ALA | | |
| | H:114 | THR | ILE | | |
| 153 | L:9 | SER | THR | -23.04 | 5.79 |
| | H:88 | ALA | GLY | | |
| | H:92 | ALA | ASP | | |
| | H:103 | GLY | ALA | | |
| | H:114 | THR | ASN | | |
| 154 | L:9 | SER | LYS | -22.92 | -63.41 |
| | H:2 | VAL | ILE | | |
| | H:58 | THR | ASN | | |
| | H:103 | GLY | ALA | | |
| | H:114 | THR | ASN | | |
| 155 | L:9 | SER | ARG | -22.83 | -26.68 |
| | L:51 | ALA | PRO | | |
| | H:56 | GLY | VAL | | |
| | H:103 | GLY | ALA | | |
| | H:114 | THR | ASN | | |
| 156 | L:9 | SER | ARG | -22.82 | -24.1 |
| | L:51 | ALA | PRO | | |
| | H:56 | GLY | VAL | | |
| | H:103 | GLY | ALA | | |
| | H:114 | THR | SER | | |
| 157 | L:9 | SER | LYS | -22.79 | -62.42 |
| | L:102 | THR | ILE | | |
| | H:24 | ALA | GLY | | |
| | H:103 | GLY | ALA | | |
| | H:114 | THR | ILE | | |
| 158 | L:9 | SER | ARG | -22.69 | -31.89 |
| | L:51 | ALA | PRO | | |
| | H:56 | GLY | ALA | | |
| | H:103 | GLY | ALA | | |
| | H:114 | THR | ILE | | |
| 159 | L:9 | SER | ARG | -22.69 | -73.38 |
| | H:56 | GLY | VAL | | |
| | H:103 | GLY | ALA | | |
| | H:114 | THR | ILE | | |
| 160 | L:9 | SER | ARG | -22.64 | -64.67 |
| | L:101 | GLY | VAL | | |
| | L:102 | THR | ILE | | |
| | H:103 | GLY | ALA | | |
| | H:114 | THR | SER | | |
| 161 | L:9 | SER | LYS | -22.61 | -47.9 |
| | H:4 | LEU | VAL | | |
| | H:56 | GLY | ALA | | |
| | H:103 | GLY | ALA | | |
| | H:114 | THR | ILE | | |
| 162 | L:9 | SER | ILE | -22.61 | -65.92 |
| | L:101 | GLY | VAL | | |
| | L:102 | THR | ILE | | |
| | H:103 | GLY | ALA | | |
| | H:114 | THR | SER | | |
| 163 | L:9 | SER | LYS | -22.6 | -69.41 |
| | H:56 | GLY | ALA | | |
| | H:58 | THR | ASN | | |
| | H:103 | GLY | ALA | | |
| | H:114 | THR | ILE | | |
| 164 | L:9 | SER | ARG | -22.58 | -72.48 |
| | H:56 | GLY | ALA | | |
| | H:103 | GLY | ALA | | |
| | H:114 | THR | ILE | | |

Figure 11E (Continued)

| | | | | | |
|---|---|---|---|---|---|
| 165 | L:9<br>L:102<br>H:24<br>H:103<br>H:114 | SER<br>THR<br>ALA<br>GLY<br>THR | LYS<br>ILE<br>GLY<br>ALA<br>SER | -22.57 | -50.72 |
| 166 | L:9<br>H:56<br>H:58<br>H:103<br>H:114 | SER<br>GLY<br>THR<br>GLY<br>THR | LYS<br>ALA<br>ASN<br>ALA<br>ASN | -22.56 | -62 |
| 167 | L:9<br>H:4<br>H:56<br>H:103<br>H:114 | SER<br>LEU<br>GLY<br>GLY<br>THR | ARG<br>VAL<br>ALA<br>ALA<br>ILE | -22.54 | -59.48 |
| 168 | L:9<br>L:32<br>L:93<br>L:101<br>H:114 | SER<br>ALA<br>THR<br>GLY<br>THR | ARG<br>VAL<br>ASN<br>ALA<br>ASN | -22.53 | -53.88 |
| 169 | L:9<br>L:31<br>H:56<br>H:103<br>H:114 | SER<br>THR<br>GLY<br>GLY<br>THR | ARG<br>SER<br>ALA<br>ALA<br>ILE | -22.52 | -65.69 |
| 170 | L:9<br>H:58<br>H:103<br>H:114 | SER<br>THR<br>GLY<br>THR | LYS<br>ASN<br>ALA<br>ASN | -22.48 | -62.49 |
| 171 | L:9<br>L:102<br>H:58<br>H:103<br>H:114 | SER<br>THR<br>THR<br>GLY<br>THR | LYS<br>ASN<br>ASN<br>ALA<br>ILE | -22.4 | -55.98 |
| 172 | L:9<br>H:58<br>H:103<br>H:114 | SER<br>THR<br>GLY<br>THR | LYS<br>ASN<br>ALA<br>ILE | -22.38 | -70.02 |
| 173 | L:9<br>H:24<br>H:56<br>H:103<br>H:114 | SER<br>ALA<br>GLY<br>GLY<br>THR | ARG<br>PHE<br>VAL<br>ALA<br>ILE | -22.36 | 24.42 |
| 174 | L:9<br>L:102<br>H:24<br>H:103<br>H:114 | SER<br>THR<br>ALA<br>GLY<br>THR | LYS<br>ILE<br>PHE<br>ALA<br>SER | -22.29 | 35.91 |
| 175 | L:9<br>H:4<br>H:56<br>H:103<br>H:114 | SER<br>LEU<br>GLY<br>GLY<br>THR | THR<br>VAL<br>ALA<br>ALA<br>ILE | -22.27 | -55.67 |
| 176 | L:9<br>L:25<br>H:58<br>H:103<br>H:114 | SER<br>ALA<br>THR<br>GLY<br>THR | LYS<br>GLY<br>ASN<br>ALA<br>ILE | -22.1 | -60.35 |
| 177 | L:9<br>H:56<br>H:103<br>H:114 | SER<br>GLY<br>GLY<br>THR | THR<br>ALA<br>ALA<br>ASN | -22.06 | -58.43 |

Figure 11E (Continued)

| ID | Position | From | To | Value1 | Value2 |
|---|---|---|---|---|---|
| 178 | L:9 | SER | ARG | -22.02 | -61.28 |
| | L:34 | ALA | GLY | | |
| | L:93 | THR | ASN | | |
| | H:88 | ALA | GLY | | |
| | H:114 | THR | ILE | | |
| 179 | L:9 | SER | THR | -22.02 | -57.14 |
| | L:101 | GLY | VAL | | |
| | L:102 | THR | SER | | |
| | H:103 | GLY | ALA | | |
| | H:114 | THR | SER | | |
| 180 | L:9 | SER | LYS | -21.98 | -59.74 |
| | H:2 | VAL | ILE | | |
| | H:58 | THR | ASN | | |
| | H:103 | GLY | ALA | | |
| | H:114 | THR | SER | | |
| 181 | L:9 | SER | LYS | -21.97 | -71.38 |
| | H:2 | VAL | ILE | | |
| | H:58 | THR | ASN | | |
| | H:103 | GLY | ALA | | |
| | H:114 | THR | ILE | | |
| 182 | L:9 | SER | THR | -21.94 | -58.27 |
| | L:101 | GLY | VAL | | |
| | L:102 | THR | ILE | | |
| | H:103 | GLY | ALA | | |
| | H:114 | THR | SER | | |
| 183 | L:9 | SER | THR | -21.94 | -53.19 |
| | L:101 | GLY | VAL | | |
| | L:102 | THR | ASN | | |
| | H:103 | GLY | ALA | | |
| | H:114 | THR | SER | | |
| 184 | L:9 | SER | THR | -21.93 | -22.74 |
| | H:79 | ALA | GLY | | |
| | H:88 | ALA | GLY | | |
| | H:114 | THR | ASN | | |
| 185 | L:9 | SER | THR | -21.91 | -47.7 |
| | H:4 | LEU | VAL | | |
| | H:56 | GLY | ALA | | |
| | H:103 | GLY | ALA | | |
| | H:114 | THR | ASN | | |
| 186 | L:9 | SER | THR | -21.9 | -45.12 |
| | H:4 | LEU | VAL | | |
| | H:56 | GLY | ALA | | |
| | H:103 | GLY | ALA | | |
| | H:114 | THR | SER | | |
| 187 | L:9 | SER | THR | -21.9 | -68.29 |
| | H:56 | GLY | ALA | | |
| | H:103 | GLY | ALA | | |
| | H:114 | THR | ILE | | |
| 188 | L:9 | SER | THR | -21.88 | -65.93 |
| | L:43 | ALA | GLY | | |
| | L:102 | THR | SER | | |
| | H:103 | GLY | ALA | | |
| | H:114 | THR | ILE | | |
| 189 | L:9 | SER | THR | -21.87 | -63.44 |
| | L:31 | THR | SER | | |
| | H:56 | GLY | VAL | | |
| | H:103 | GLY | ALA | | |
| | H:114 | THR | ILE | | |
| 190 | L:9 | SER | THR | -21.87 | -56.66 |
| | H:56 | GLY | ALA | | |
| | H:103 | GLY | ALA | | |
| | H:114 | THR | SER | | |

| | | | | | |
|---|---|---|---|---|---|
| 191 | L:9<br>L:43<br>L:102<br>H:103<br>H:114 | SER<br>ALA<br>THR<br>GLY<br>THR | THR<br>GLY<br>SER<br>ALA<br>ASN | -21.85 | -58.54 |
| 192 | L:9<br>H:26<br>H:61<br>H:103<br>H:114 | SER<br>GLY<br>ALA<br>GLY<br>THR | THR<br>ALA<br>VAL<br>ALA<br>ASN | -21.83 | -66.04 |
| 193 | L:9<br>H:26<br>H:61<br>H:103<br>H:114 | SER<br>GLY<br>ALA<br>GLY<br>THR | THR<br>ALA<br>VAL<br>ALA<br>SER | -21.82 | -63.47 |
| 194 | L:9<br>H:61<br>H:103<br>H:114 | SER<br>ALA<br>GLY<br>THR | THR<br>VAL<br>ALA<br>ASN | -21.82 | -66.93 |
| 195 | L:9<br>L:102<br>H:24<br>H:103<br>H:114 | SER<br>THR<br>ALA<br>GLY<br>THR | THR<br>ILE<br>GLY<br>ALA<br>SER | -21.8 | -58.27 |
| 196 | L:9<br>L:43<br>L:102<br>H:103<br>H:114 | SER<br>ALA<br>THR<br>GLY<br>THR | THR<br>GLY<br>ASN<br>ALA<br>ASN | -21.8 | -53.97 |
| 197 | L:9<br>L:102<br>H:24<br>H:103<br>H:114 | SER<br>THR<br>ALA<br>GLY<br>THR | THR<br>ILE<br>GLY<br>ALA<br>ILE | -21.79 | -69.89 |
| 198 | L:9<br>L:102<br>H:61<br>H:103<br>H:114 | SER<br>THR<br>ALA<br>GLY<br>THR | THR<br>SER<br>VAL<br>ALA<br>ASN | -21.79 | -59.4 |
| 199 | L:9<br>H:2<br>H:58<br>H:103<br>H:114 | SER<br>VAL<br>THR<br>GLY<br>THR | THR<br>ILE<br>ASN<br>ALA<br>ASN | -21.78 | -70.94 |

6 Mutations

| Number | Residue | Original | Mutated | Δ Affinity | Δ Stability |
|---|---|---|---|---|---|
| 1 | L:9 | SER | LYS | -38.89 | 65.02 |
|  | L:25 | ALA | GLY |  |  |
|  | H:24 | ALA | ASN |  |  |
|  | H:56 | GLY | ALA |  |  |
|  | H:92 | ALA | VAL |  |  |
|  | H:106 | ALA | VAL |  |  |
| 2 | L:9 | SER | LYS | -37.52 | -1.22 |
|  | L:40 | PRO | THR |  |  |
|  | L:43 | ALA | PHE |  |  |
|  | H:16 | GLY | VAL |  |  |
|  | H:85 | SER | ARG |  |  |
|  | H:103 | GLY | VAL |  |  |
| 3 | L:9 | SER | THR | -29.14 | -29.16 |
|  | L:43 | ALA | PHE |  |  |
|  | L:46 | LEU | VAL |  |  |
|  | L:80 | PRO | ALA |  |  |
|  | L:93 | THR | SER |  |  |
|  | H:3 | GLN | HID |  |  |
| 4 | L:9 | SER | ARG | -28.58 | -15.8 |
|  | L:47 | LEU | VAL |  |  |
|  | L:51 | ALA | THR |  |  |
|  | H:48 | VAL | ILE |  |  |
|  | H:58 | THR | SER |  |  |
|  | H:103 | GLY | VAL |  |  |
| 5 | L:9 | SER | LYS | -28.22 | 39.26 |
|  | L:40 | PRO | ALA |  |  |
|  | L:43 | ALA | ASN |  |  |
|  | L:46 | LEU | VAL |  |  |
|  | H:92 | ALA | VAL |  |  |
|  | H:103 | GLY | VAL |  |  |
| 6 | L:9 | SER | LYS | -28.22 | 39.26 |
|  | L:40 | PRO | ALA |  |  |
|  | L:43 | ALA | ASN |  |  |
|  | L:46 | LEU | VAL |  |  |
|  | H:92 | ALA | VAL |  |  |
|  | H:103 | GLY | VAL |  |  |
| 7 | L:9 | SER | LYS | -28.02 | 0.05 |
|  | L:51 | ALA | THR |  |  |
|  | L:102 | THR | SER |  |  |
|  | H:16 | GLY | ALA |  |  |
|  | H:92 | ALA | VAL |  |  |
|  | H:103 | GLY | VAL |  |  |
| 8 | L:9 | SER | LYS | -27.93 | 16.17 |
|  | L:89 | GLN | HID |  |  |
|  | L:102 | THR | SER |  |  |
|  | H:16 | GLY | ALA |  |  |
|  | H:92 | ALA | GLY |  |  |
|  | H:103 | GLY | VAL |  |  |
| 9 | L:9 | SER | LYS | -27.92 | 20.59 |
|  | L:89 | GLN | HID |  |  |
|  | L:102 | THR | SER |  |  |
|  | H:16 | GLY | ALA |  |  |
|  | H:92 | ALA | VAL |  |  |
|  | H:103 | GLY | VAL |  |  |
| 10 | L:9 | SER | LYS | -27.91 | 1.39 |
|  | L:89 | GLN | HID |  |  |
|  | H:16 | GLY | ALA |  |  |
|  | H:48 | VAL | LEU |  |  |
|  | H:92 | ALA | GLY |  |  |
|  | H:103 | GLY | VAL |  |  |

Figure 11F (Continued)

| | | | | | |
|---|---|---|---|---|---|
| 11 | L:9<br>L:89<br>L:102<br>H:16<br>H:92<br>H:103 | SER<br>GLN<br>THR<br>GLY<br>ALA<br>GLY | LYS<br>HID<br>ILE<br>ALA<br>VAL<br>VAL | -27.87 | 24.48 |
| 12 | L:9<br>L:89<br>H:16<br>H:92<br>H:103 | SER<br>GLN<br>GLY<br>ALA<br>GLY | LYS<br>HID<br>ALA<br>GLY<br>VAL | -27.86 | 6.53 |
| 13 | L:9<br>L:43<br>L:76<br>H:92<br>H:103 | SER<br>ALA<br>SER<br>ALA<br>GLY | ARG<br>ASN<br>ASN<br>VAL<br>VAL | -27.69 | 1.95 |
| 14 | L:9<br>L:47<br>L:51<br>H:48<br>H:58<br>H:103 | SER<br>LEU<br>ALA<br>VAL<br>THR<br>GLY | ARG<br>VAL<br>PRO<br>LEU<br>SER<br>VAL | -27.69 | 23.87 |
| 15 | L:9<br>L:85<br>L:102<br>H:58<br>H:92<br>H:103 | SER<br>THR<br>THR<br>THR<br>ALA<br>GLY | ARG<br>SER<br>ILE<br>SER<br>GLY<br>VAL | -27.69 | -3.14 |
| 16 | L:9<br>L:102<br>H:58<br>H:92<br>H:103 | SER<br>THR<br>THR<br>ALA<br>GLY | ARG<br>ILE<br>SER<br>GLY<br>VAL | -27.68 | -10.06 |
| 17 | L:9<br>L:102<br>H:48<br>H:58<br>H:92<br>H:103 | SER<br>THR<br>VAL<br>THR<br>ALA<br>GLY | ARG<br>ILE<br>ILE<br>SER<br>GLY<br>VAL | -27.67 | -17.6 |
| 18 | L:9<br>L:32<br>L:43<br>H:92<br>H:103 | SER<br>ALA<br>ALA<br>ALA<br>GLY | ARG<br>VAL<br>ASN<br>VAL<br>VAL | -27.65 | 29.95 |
| 19 | L:9<br>L:32<br>L:43<br>H:88<br>H:92<br>H:103 | SER<br>ALA<br>ALA<br>ALA<br>ALA<br>GLY | ARG<br>VAL<br>ASN<br>VAL<br>VAL<br>VAL | -27.65 | 27.22 |
| 20 | L:9<br>L:85<br>L:102<br>H:92<br>H:103 | SER<br>THR<br>THR<br>ALA<br>GLY | ARG<br>SER<br>ILE<br>GLY<br>VAL | -27.65 | -8.58 |
| 21 | L:9<br>L:47<br>L:51<br>H:58<br>H:103 | SER<br>LEU<br>ALA<br>THR<br>GLY | ARG<br>VAL<br>PRO<br>SER<br>VAL | -27.65 | 28.9 |

Figure 11F (Continued)

| | | | | | |
|---|---|---|---|---|---|
| 22 | L:9<br>L:32<br>L:43<br>L:80<br>H:92<br>H:103 | SER<br>ALA<br>ALA<br>PRO<br>ALA<br>GLY | ARG<br>VAL<br>ASN<br>THR<br>VAL<br>VAL | -27.64 | 24.67 |
| 23 | L:9<br>L:40<br>L:85<br>L:102<br>H:92<br>H:103 | SER<br>PRO<br>THR<br>THR<br>ALA<br>GLY | ARG<br>SER<br>SER<br>ILE<br>GLY<br>VAL | -27.64 | -1.97 |
| 24 | L:9<br>L:47<br>L:51<br>H:48<br>H:58<br>H:103 | SER<br>LEU<br>ALA<br>VAL<br>THR<br>GLY | ARG<br>VAL<br>PRO<br>ILE<br>SER<br>VAL | -27.63 | 21.43 |
| 25 | L:9<br>L:102<br>H:48<br>H:92<br>H:103 | SER<br>THR<br>VAL<br>ALA<br>GLY | ARG<br>ILE<br>ILE<br>GLY<br>VAL | -27.63 | -23.04 |
| 26 | L:9<br>H:16<br>H:48<br>H:58<br>H:92<br>H:103 | SER<br>GLY<br>VAL<br>THR<br>ALA<br>GLY | LYS<br>ALA<br>LEU<br>SER<br>GLY<br>VAL | -27.62 | -13.68 |
| 27 | L:9<br>L:102<br>H:16<br>H:92<br>H:103 | SER<br>THR<br>GLY<br>ALA<br>GLY | LYS<br>SER<br>ALA<br>VAL<br>VAL | -27.61 | -0.24 |
| 28 | L:9<br>L:80<br>H:16<br>H:92<br>H:103 | SER<br>PRO<br>GLY<br>ALA<br>GLY | ARG<br>SER<br>ALA<br>VAL<br>VAL | -27.6 | 12.84 |
| 29 | L:9<br>L:31<br>L:32<br>H:85<br>H:103 | SER<br>THR<br>ALA<br>SER<br>GLY | ARG<br>ASN<br>VAL<br>ARG<br>VAL | -27.6 | 8.08 |
| 30 | L:9<br>L:40<br>L:102<br>H:92<br>H:103 | SER<br>PRO<br>THR<br>ALA<br>GLY | ARG<br>SER<br>ILE<br>GLY<br>VAL | -27.6 | -3.99 |
| 31 | L:9<br>L:51<br>H:48<br>H:58<br>H:103 | SER<br>ALA<br>VAL<br>THR<br>GLY | ARG<br>PRO<br>LEU<br>SER<br>VAL | -27.59 | 7.25 |
| 32 | L:9<br>H:16<br>H:26<br>H:92<br>H:103 | SER<br>GLY<br>GLY<br>ALA<br>GLY | ARG<br>ALA<br>ALA<br>VAL<br>VAL | -27.59 | 14.15 |

Figure 11F (Continued)

| | | | | | |
|---|---|---|---|---|---|
| 33 | L:9<br>L:80<br>H:16<br>H:26<br>H:92<br>H:103 | SER<br>PRO<br>GLY<br>GLY<br>ALA<br>GLY | ARG<br>SER<br>ALA<br>ALA<br>VAL<br>VAL | -27.59 | 12.87 |
| 34 | L:9<br>L:102<br>H:48<br>H:61<br>H:92<br>H:103 | SER<br>THR<br>VAL<br>ALA<br>ALA<br>GLY | ARG<br>ILE<br>ILE<br>VAL<br>GLY<br>VAL | -27.59 | -25.3 |
| 35 | L:9<br>L:51<br>H:48<br>H:58<br>H:92<br>H:103 | SER<br>ALA<br>VAL<br>THR<br>ALA<br>GLY | ARG<br>PRO<br>LEU<br>SER<br>GLY<br>VAL | -27.59 | 9 |
| 36 | L:9<br>H:16<br>H:48<br>H:92<br>H:103 | SER<br>GLY<br>VAL<br>ALA<br>GLY | LYS<br>ALA<br>LEU<br>GLY<br>VAL | -27.58 | -19.13 |
| 37 | L:9<br>H:48<br>H:58<br>H:92<br>H:103 | SER<br>VAL<br>THR<br>ALA<br>GLY | ARG<br>LEU<br>SER<br>GLY<br>VAL | -27.58 | -23.11 |
| 38 | L:9<br>L:40<br>L:43<br>L:46<br>H:92<br>H:103 | SER<br>PRO<br>ALA<br>LEU<br>ALA<br>GLY | LYS<br>ALA<br>ASN<br>VAL<br>ASP<br>VAL | -27.58 | 52.88 |
| 39 | L:9<br>L:43<br>L:101<br>H:92<br>H:103 | SER<br>ALA<br>GLY<br>ALA<br>GLY | LYS<br>PHE<br>VAL<br>GLY<br>VAL | -27.58 | -15.08 |
| 40 | L:9<br>H:48<br>H:58<br>H:92<br>H:103 | SER<br>VAL<br>THR<br>ALA<br>GLY | LYS<br>ILE<br>ASN<br>VAL<br>VAL | -27.57 | -19.84 |
| 41 | L:9<br>H:48<br>H:61<br>H:92<br>H:103 | SER<br>VAL<br>ALA<br>ALA<br>GLY | ARG<br>ILE<br>VAL<br>GLY<br>VAL | -27.57 | -38.17 |
| 42 | L:9<br>L:25<br>L:43<br>L:76<br>H:92<br>H:103 | SER<br>ALA<br>ALA<br>SER<br>ALA<br>GLY | ARG<br>VAL<br>ASN<br>ASN<br>VAL<br>VAL | -27.57 | 33.37 |
| 43 | L:9<br>H:16<br>H:48<br>H:58<br>H:92<br>H:103 | SER<br>GLY<br>VAL<br>THR<br>ALA<br>GLY | ARG<br>ALA<br>LEU<br>SER<br>GLY<br>VAL | -27.57 | -25.7 |

Figure 11F (Continued)

| | | | | | |
|---|---|---|---|---|---|
| 44 | L:9<br>L:80<br>H:48<br>H:58<br>H:92<br>H:103 | SER<br>PRO<br>VAL<br>THR<br>ALA<br>GLY | LYS<br>ALA<br>ILE<br>ASN<br>VAL<br>VAL | -27.56 | -16.79 |
| 45 | L:9<br>L:40<br>L:85<br>L:102<br>H:92<br>H:103 | SER<br>PRO<br>THR<br>THR<br>ALA<br>GLY | ARG<br>SER<br>ILE<br>ILE<br>GLY<br>VAL | -27.55 | -14.5 |
| 46 | L:9<br>L:32<br>H:16<br>H:26<br>H:92<br>H:103 | SER<br>ALA<br>GLY<br>GLY<br>ALA<br>GLY | ARG<br>VAL<br>ALA<br>ALA<br>VAL<br>VAL | -27.55 | 38.96 |
| 47 | L:9<br>L:32<br>L:80<br>H:92<br>H:103 | SER<br>ALA<br>PRO<br>ALA<br>GLY | ARG<br>VAL<br>THR<br>VAL<br>VAL | -27.55 | 32.64 |
| 48 | L:9<br>L:32<br>H:16<br>H:92<br>H:103 | SER<br>ALA<br>GLY<br>ALA<br>GLY | ARG<br>VAL<br>ALA<br>VAL<br>VAL | -27.54 | 36.11 |
| 49 | L:9<br>L:40<br>L:85<br>H:48<br>H:103 | SER<br>PRO<br>THR<br>VAL<br>GLY | LYS<br>ALA<br>ILE<br>PHE<br>VAL | -27.54 | -0.62 |
| 50 | L:9<br>L:32<br>L:80<br>H:16<br>H:92<br>H:103 | SER<br>ALA<br>PRO<br>GLY<br>ALA<br>GLY | ARG<br>VAL<br>THR<br>ALA<br>VAL<br>VAL | -27.54 | 30.8 |
| 51 | L:9<br>L:43<br>L:102<br>H:92<br>H:103 | SER<br>ALA<br>THR<br>ALA<br>GLY | ARG<br>PHE<br>ASN<br>GLY<br>VAL | -27.52 | -14.35 |
| 52 | L:9<br>L:40<br>L:43<br>L:46<br>H:92<br>H:103 | SER<br>PRO<br>ALA<br>LEU<br>ALA<br>GLY | ARG<br>ALA<br>ASN<br>VAL<br>ASP<br>VAL | -27.52 | 40.44 |
| 53 | L:9<br>L:80<br>H:48<br>H:58<br>H:92<br>H:103 | SER<br>PRO<br>VAL<br>THR<br>ALA<br>GLY | ARG<br>ALA<br>ILE<br>ASN<br>VAL<br>VAL | -27.51 | -28.38 |
| 54 | L:9<br>L:43<br>L:101<br>H:4<br>H:92<br>H:103 | SER<br>ALA<br>GLY<br>LEU<br>ALA<br>GLY | LYS<br>PHE<br>VAL<br>MET<br>GLY<br>VAL | -27.48 | -10.11 |

Figure 11F (Continued)

| | | | | | |
|---|---|---|---|---|---|
| 55 | L:9 | SER | ARG | -27.46 | 26.87 |
| | L:32 | ALA | VAL | | |
| | L:43 | ALA | ASN | | |
| | L:76 | SER | ASN | | |
| | H:92 | ALA | VAL | | |
| | H:103 | GLY | VAL | | |
| 56 | L:9 | SER | LYS | -27.44 | -5.02 |
| | L:80 | PRO | SER | | |
| | H:48 | VAL | LEU | | |
| | H:61 | ALA | GLY | | |
| | H:103 | GLY | VAL | | |
| | H:114 | THR | SER | | |
| 57 | L:9 | SER | LYS | -27.44 | -11.48 |
| | L:32 | ALA | VAL | | |
| | L:43 | ALA | PRO | | |
| | L:51 | ALA | SER | | |
| | H:92 | ALA | GLY | | |
| | H:103 | GLY | VAL | | |
| 58 | L:9 | SER | ILE | -27.43 | 29.85 |
| | L:40 | PRO | ALA | | |
| | L:43 | ALA | ASN | | |
| | L:46 | LEU | VAL | | |
| | H:92 | ALA | VAL | | |
| | H:103 | GLY | VAL | | |
| 59 | L:9 | SER | ARG | -27.43 | -7.56 |
| | L:102 | THR | ASN | | |
| | H:58 | THR | ILE | | |
| | H:92 | ALA | GLY | | |
| | H:103 | GLY | VAL | | |
| 60 | L:9 | SER | LYS | -27.42 | -1.61 |
| | L:40 | PRO | ALA | | |
| | L:85 | THR | ILE | | |
| | H:4 | LEU | MET | | |
| | H:48 | VAL | PHE | | |
| | H:103 | GLY | VAL | | |
| 61 | L:9 | SER | LYS | -27.42 | -6.93 |
| | L:32 | ALA | VAL | | |
| | L:43 | ALA | PRO | | |
| | L:51 | ALA | SER | | |
| | H:92 | ALA | VAL | | |
| | H:103 | GLY | VAL | | |
| 62 | L:9 | SER | ARG | -27.42 | -0.96 |
| | L:40 | PRO | SER | | |
| | L:102 | THR | ASN | | |
| | H:58 | THR | ILE | | |
| | H:92 | ALA | GLY | | |
| | H:103 | GLY | VAL | | |
| 63 | L:9 | SER | ARG | -27.42 | -2.22 |
| | L:40 | PRO | SER | | |
| | L:102 | THR | ILE | | |
| | H:58 | THR | ILE | | |
| | H:92 | ALA | GLY | | |
| | H:103 | GLY | VAL | | |
| 64 | L:9 | SER | ARG | -27.41 | 3.47 |
| | L:40 | PRO | SER | | |
| | L:102 | THR | ASN | | |
| | H:58 | THR | ILE | | |
| | H:92 | ALA | VAL | | |
| | H:103 | GLY | VAL | | |

Figure 11F (Continued)

| | | | | | |
|---|---|---|---|---|---|
| 65 | L:9 | SER | LYS | -27.4 | -14.41 |
| | L:80 | PRO | SER | | |
| | H:48 | VAL | LEU | | |
| | H:61 | ALA | GLY | | |
| | H:103 | GLY | VAL | | |
| 66 | L:9 | SER | ARG | -27.39 | -30.88 |
| | L:31 | THR | SER | | |
| | H:48 | VAL | ILE | | |
| | H:92 | ALA | GLY | | |
| | H:103 | GLY | VAL | | |
| 67 | L:9 | SER | LYS | -27.39 | 11.61 |
| | H:48 | VAL | PHE | | |
| | H:61 | ALA | GLY | | |
| | H:103 | GLY | VAL | | |
| | H:114 | THR | SER | | |
| 68 | L:9 | SER | ARG | -27.39 | 25.61 |
| | L:80 | PRO | SER | | |
| | H:16 | GLY | ALA | | |
| | H:24 | ALA | ASN | | |
| | H:92 | ALA | VAL | | |
| | H:103 | GLY | VAL | | |
| 69 | L:9 | SER | LYS | -27.38 | 10.35 |
| | L:80 | PRO | SER | | |
| | H:48 | VAL | PHE | | |
| | H:61 | ALA | GLY | | |
| | H:103 | GLY | VAL | | |
| | H:114 | THR | SER | | |
| 70 | L:9 | SER | LYS | -27.38 | 12.2 |
| | L:34 | ALA | VAL | | |
| | L:40 | PRO | SER | | |
| | H:48 | VAL | PHE | | |
| | H:103 | GLY | VAL | | |
| 71 | L:9 | SER | LYS | -27.37 | 8.42 |
| | L:34 | ALA | VAL | | |
| | L:40 | PRO | SER | | |
| | L:43 | ALA | PRO | | |
| | H:48 | VAL | PHE | | |
| | H:103 | GLY | VAL | | |
| 72 | L:9 | SER | ARG | -27.36 | -33 |
| | L:31 | THR | SER | | |
| | H:48 | VAL | ILE | | |
| | H:61 | ALA | VAL | | |
| | H:92 | ALA | GLY | | |
| | H:103 | GLY | VAL | | |
| 73 | L:9 | SER | LYS | -27.36 | 6.78 |
| | L:34 | ALA | VAL | | |
| | L:40 | PRO | SER | | |
| | L:85 | THR | ILE | | |
| | H:48 | VAL | PHE | | |
| | H:103 | GLY | VAL | | |
| 74 | L:9 | SER | LYS | -27.36 | -17.32 |
| | L:80 | PRO | ALA | | |
| | H:48 | VAL | ILE | | |
| | H:92 | ALA | VAL | | |
| | H:103 | GLY | VAL | | |
| 75 | L:9 | SER | ARG | -27.35 | -12.66 |
| | L:43 | ALA | PHE | | |
| | L:102 | THR | ASN | | |
| | H:58 | THR | ILE | | |
| | H:92 | ALA | GLY | | |
| | H:103 | GLY | VAL | | |

Figure 11F (Continued)

| | | | | | |
|---|---|---|---|---|---|
| 76 | L:9 | SER | LYS | -27.35 | -23.57 |
| | L:76 | SER | THR | | |
| | L:80 | PRO | SER | | |
| | H:48 | VAL | LEU | | |
| | H:103 | GLY | VAL | | |
| 77 | L:9 | SER | ARG | -27.34 | 43.12 |
| | L:40 | PRO | ALA | | |
| | L:43 | ALA | PHE | | |
| | L:46 | LEU | VAL | | |
| | H:92 | ALA | ASP | | |
| | H:103 | GLY | VAL | | |
| 78 | L:9 | SER | LYS | -27.33 | -21.75 |
| | L:76 | SER | THR | | |
| | L:80 | PRO | SER | | |
| | L:85 | THR | ASN | | |
| | H:48 | VAL | LEU | | |
| | H:103 | GLY | VAL | | |
| 79 | L:9 | SER | ILE | -27.33 | 13.27 |
| | L:40 | PRO | ALA | | |
| | L:43 | ALA | ASN | | |
| | H:92 | ALA | VAL | | |
| | H:103 | GLY | VAL | | |
| 80 | L:9 | SER | LYS | -27.33 | -18.94 |
| | L:31 | THR | SER | | |
| | H:48 | VAL | ILE | | |
| | H:58 | THR | ASN | | |
| | H:92 | ALA | GLY | | |
| | H:103 | GLY | VAL | | |
| 81 | L:9 | SER | LYS | -27.33 | -8.88 |
| | L:34 | ALA | VAL | | |
| | L:40 | PRO | SER | | |
| | L:43 | ALA | PRO | | |
| | H:48 | VAL | ILE | | |
| | H:103 | GLY | VAL | | |
| 82 | L:9 | SER | LYS | -27.33 | -8.83 |
| | L:34 | ALA | VAL | | |
| | L:40 | PRO | ALA | | |
| | L:43 | ALA | PRO | | |
| | H:48 | VAL | ILE | | |
| | H:103 | GLY | VAL | | |
| 83 | L:9 | SER | LYS | -27.33 | 38.79 |
| | L:40 | PRO | ALA | | |
| | L:43 | ALA | PHE | | |
| | H:92 | ALA | ASP | | |
| | H:103 | GLY | VAL | | |
| 84 | L:9 | SER | LYS | -27.33 | -14.67 |
| | L:31 | THR | SER | | |
| | H:48 | VAL | ILE | | |
| | H:58 | THR | ASN | | |
| | H:92 | ALA | VAL | | |
| | H:103 | GLY | VAL | | |
| 85 | L:9 | SER | ILE | -27.31 | 11.37 |
| | L:40 | PRO | ALA | | |
| | L:43 | ALA | ASN | | |
| | H:2 | VAL | ILE | | |
| | H:92 | ALA | VAL | | |
| | H:103 | GLY | VAL | | |
| 86 | L:9 | SER | ARG | -27.31 | -28.91 |
| | L:80 | PRO | ALA | | |
| | H:48 | VAL | ILE | | |
| | H:92 | ALA | VAL | | |
| | H:103 | GLY | VAL | | |

Figure 11F (Continued)

| | | | | | |
|---|---|---|---|---|---|
| 87 | L:9 | SER | LYS | -27.3 | 6.82 |
| | L:34 | ALA | VAL | | |
| | L:40 | PRO | ALA | | |
| | L:85 | THR | ILE | | |
| | H:48 | VAL | PHE | | |
| | H:103 | GLY | VAL | | |
| 88 | L:9 | SER | ILE | -27.29 | 11.32 |
| | L:43 | ALA | ASN | | |
| | H:3 | GLN | HID | | |
| | H:92 | ALA | VAL | | |
| | H:103 | GLY | VAL | | |
| 89 | L:9 | SER | ARG | -27.28 | -30.63 |
| | L:31 | THR | SER | | |
| | H:48 | VAL | ILE | | |
| | H:58 | THR | ASN | | |
| | H:92 | ALA | GLY | | |
| | H:103 | GLY | VAL | | |
| 90 | L:9 | SER | ILE | -27.28 | 18.03 |
| | L:40 | PRO | ALA | | |
| | L:43 | ALA | ASN | | |
| | H:3 | GLN | HID | | |
| | H:92 | ALA | VAL | | |
| | H:103 | GLY | VAL | | |
| 91 | L:9 | SER | ARG | -27.27 | 26.34 |
| | L:40 | PRO | ALA | | |
| | L:43 | ALA | PHE | | |
| | H:92 | ALA | ASP | | |
| | H:103 | GLY | VAL | | |
| 92 | L:9 | SER | ILE | -27.26 | -10.74 |
| | L:51 | ALA | THR | | |
| | L:102 | THR | SER | | |
| | H:92 | ALA | GLY | | |
| | H:103 | GLY | VAL | | |
| 93 | L:9 | SER | ILE | -27.26 | -5.16 |
| | L:25 | ALA | GLY | | |
| | L:34 | ALA | VAL | | |
| | L:101 | GLY | ALA | | |
| | H:92 | ALA | GLY | | |
| | H:103 | GLY | VAL | | |
| 94 | L:9 | SER | ILE | -27.25 | -6.31 |
| | L:51 | ALA | THR | | |
| | L:102 | THR | SER | | |
| | H:92 | ALA | VAL | | |
| | H:103 | GLY | VAL | | |
| 95 | L:9 | SER | ILE | -27.24 | -8.9 |
| | L:51 | ALA | THR | | |
| | L:102 | THR | SER | | |
| | H:16 | GLY | ALA | | |
| | H:92 | ALA | VAL | | |
| | H:103 | GLY | VAL | | |
| 96 | L:9 | SER | ARG | -27.23 | -3.17 |
| | L:40 | PRO | SER | | |
| | L:102 | THR | ILE | | |
| | H:26 | GLY | ASP | | |
| | H:92 | ALA | GLY | | |
| | H:103 | GLY | VAL | | |
| 97 | L:9 | SER | LYS | -27.21 | 69.91 |
| | L:25 | ALA | VAL | | |
| | L:40 | PRO | ALA | | |
| | L:43 | ALA | PHE | | |
| | H:92 | ALA | ASP | | |
| | H:103 | GLY | VAL | | |

Figure 11F (Continued)

| | | | | | |
|---|---|---|---|---|---|
| 98 | L:9<br>L:46<br>H:61<br>H:79<br>H:103<br>H:114 | SER<br>LEU<br>ALA<br>ALA<br>GLY<br>THR | ARG<br>ILE<br>GLY<br>GLY<br>VAL<br>ASN | -27.17 | 2.38 |
| 99 | L:9<br>L:43<br>L:47<br>L:51<br>H:58<br>H:103 | SER<br>ALA<br>LEU<br>ALA<br>THR<br>GLY | THR<br>ASN<br>VAL<br>THR<br>SER<br>VAL | -27.17 | -14.19 |
| 100 | L:9<br>L:25<br>L:40<br>L:43<br>H:92<br>H:103 | SER<br>ALA<br>PRO<br>ALA<br>ALA<br>GLY | ARG<br>VAL<br>ALA<br>PHE<br>ASP<br>VAL | -27.15 | 57.48 |
| 101 | L:9<br>L:43<br>L:46<br>H:61<br>H:103<br>H:114 | SER<br>ALA<br>LEU<br>ALA<br>GLY<br>THR | ARG<br>ASN<br>ILE<br>VAL<br>VAL<br>ASN | -27.14 | -20.43 |
| 102 | L:9<br>L:46<br>H:61<br>H:79<br>H:103<br>H:114 | SER<br>LEU<br>ALA<br>ALA<br>GLY<br>THR | ARG<br>ILE<br>VAL<br>GLY<br>VAL<br>ASN | -27.13 | -4.64 |
| 103 | L:9<br>L:43<br>L:46<br>L:80<br>H:61<br>H:103 | SER<br>ALA<br>LEU<br>PRO<br>ALA<br>GLY | LYS<br>ASN<br>ILE<br>SER<br>VAL<br>VAL | -27.11 | -8.25 |
| 104 | L:9<br>L:80<br>H:24<br>H:61<br>H:92<br>H:103 | SER<br>PRO<br>ALA<br>ALA<br>ALA<br>GLY | ILE<br>SER<br>PHE<br>GLY<br>VAL<br>VAL | -27.11 | 190.19 |
| 105 | L:9<br>L:80<br>H:48<br>H:103<br>H:114 | SER<br>PRO<br>VAL<br>GLY<br>THR | LYS<br>SER<br>PHE<br>VAL<br>ASN | -27.09 | 0.7 |
| 106 | L:9<br>L:34<br>L:80<br>H:48<br>H:92<br>H:103 | SER<br>ALA<br>PRO<br>VAL<br>ALA<br>GLY | ARG<br>VAL<br>ALA<br>ILE<br>VAL<br>VAL | -27.09 | -19.97 |
| 107 | L:9<br>L:80<br>H:48<br>H:92<br>H:103<br>H:114 | SER<br>PRO<br>VAL<br>ALA<br>GLY<br>THR | LYS<br>SER<br>PHE<br>VAL<br>VAL<br>ASN | -27.08 | 7.67 |

Figure 11F (Continued)

| | | | | | |
|---|---|---|---|---|---|
| 108 | L:9<br>L:47<br>L:51<br>H:58<br>H:103 | SER<br>LEU<br>ALA<br>THR<br>GLY | THR<br>VAL<br>THR<br>SER<br>VAL | -27.07 | -6.22 |
| 109 | L:9<br>L:43<br>L:46<br>H:61<br>H:103 | SER<br>ALA<br>LEU<br>ALA<br>GLY | ARG<br>ASN<br>ILE<br>VAL<br>VAL | -27.06 | -18.58 |
| 110 | L:9<br>L:43<br>L:46<br>L:80<br>H:61<br>H:103 | SER<br>ALA<br>LEU<br>PRO<br>ALA<br>GLY | ARG<br>ASN<br>ILE<br>SER<br>VAL<br>VAL | -27.06 | -19.84 |
| 111 | L:9<br>L:47<br>L:51<br>H:48<br>H:58<br>H:103 | SER<br>LEU<br>ALA<br>VAL<br>THR<br>GLY | THR<br>VAL<br>THR<br>ILE<br>SER<br>VAL | -27.05 | -13.69 |
| 112 | L:9<br>L:46<br>H:61<br>H:103<br>H:114 | SER<br>LEU<br>ALA<br>GLY<br>THR | ARG<br>ILE<br>VAL<br>VAL<br>ASN | -27.04 | -12.6 |
| 113 | L:9<br>L:25<br>L:80<br>H:48<br>H:92<br>H:103 | SER<br>ALA<br>PRO<br>VAL<br>ALA<br>GLY | ARG<br>GLY<br>SER<br>PHE<br>VAL<br>VAL | -27.04 | -0.64 |
| 114 | L:9<br>L:46<br>H:61<br>H:103<br>H:114 | SER<br>LEU<br>ALA<br>GLY<br>THR | ARG<br>ILE<br>GLY<br>VAL<br>ASN | -27.03 | -5.96 |
| 115 | L:9<br>L:43<br>L:80<br>H:61<br>H:103 | SER<br>ALA<br>PRO<br>ALA<br>GLY | LYS<br>ASN<br>SER<br>VAL<br>VAL | -27.03 | -21.94 |
| 116 | L:9<br>L:80<br>H:48<br>H:92<br>H:103<br>H:114 | SER<br>PRO<br>VAL<br>ALA<br>GLY<br>THR | ARG<br>SER<br>PHE<br>VAL<br>VAL<br>ASN | -27.03 | -3.91 |
| 117 | L:9<br>L:43<br>L:47<br>H:79<br>H:103<br>H:114 | SER<br>ALA<br>LEU<br>ALA<br>GLY<br>THR | THR<br>ASN<br>VAL<br>GLY<br>VAL<br>SER | -27.02 | -2.42 |
| 118 | L:9<br>L:80<br>H:48<br>H:88<br>H:92<br>H:103 | SER<br>PRO<br>VAL<br>ALA<br>ALA<br>GLY | ARG<br>ALA<br>ILE<br>ASP<br>VAL<br>VAL | -27.01 | -29.42 |

Figure 11F (Continued)

| | | | | | |
|---|---|---|---|---|---|
| 119 | L:9 | SER | ARG | -27.01 | -15.68 |
| | L:25 | ALA | GLY | | |
| | L:80 | PRO | SER | | |
| | H:92 | ALA | VAL | | |
| | H:103 | GLY | VAL | | |
| 120 | L:9 | SER | ARG | -27.01 | -11.32 |
| | L:25 | ALA | GLY | | |
| | L:80 | PRO | ALA | | |
| | H:92 | ALA | VAL | | |
| | H:103 | GLY | VAL | | |
| 121 | L:9 | SER | ARG | -27 | 34.17 |
| | L:80 | PRO | SER | | |
| | L:89 | GLN | HID | | |
| | H:24 | ALA | ASN | | |
| | H:92 | ALA | VAL | | |
| | H:103 | GLY | VAL | | |
| 122 | L:9 | SER | LYS | -27 | 19.68 |
| | H:16 | GLY | ALA | | |
| | H:48 | VAL | LEU | | |
| | H:58 | THR | SER | | |
| | H:92 | ALA | ASP | | |
| | H:103 | GLY | VAL | | |
| 123 | L:9 | SER | THR | -26.99 | -11.87 |
| | L:43 | ALA | ASN | | |
| | L:47 | LEU | VAL | | |
| | H:79 | ALA | GLY | | |
| | H:103 | GLY | VAL | | |
| 124 | L:9 | SER | ARG | -26.98 | -6.88 |
| | L:46 | LEU | ILE | | |
| | L:101 | GLY | VAL | | |
| | H:61 | ALA | GLY | | |
| | H:103 | GLY | VAL | | |
| | H:114 | THR | ASN | | |
| 125 | L:9 | SER | ARG | -26.98 | -9.2 |
| | L:25 | ALA | GLY | | |
| | L:80 | PRO | ALA | | |
| | L:93 | THR | SER | | |
| | H:92 | ALA | VAL | | |
| | H:103 | GLY | VAL | | |
| 126 | L:9 | SER | THR | -26.97 | -4.88 |
| | L:43 | ALA | ASN | | |
| | L:47 | LEU | VAL | | |
| | H:58 | THR | SER | | |
| | H:103 | GLY | VAL | | |
| | H:114 | THR | SER | | |
| 127 | L:9 | SER | THR | -26.97 | -19.34 |
| | L:43 | ALA | ASN | | |
| | L:47 | LEU | VAL | | |
| | H:48 | VAL | ILE | | |
| | H:79 | ALA | GLY | | |
| | H:103 | GLY | VAL | | |
| 128 | L:9 | SER | ARG | -26.97 | -9.61 |
| | L:80 | PRO | SER | | |
| | H:48 | VAL | PHE | | |
| | H:92 | ALA | VAL | | |
| | H:103 | GLY | VAL | | |
| 129 | L:9 | SER | LYS | -26.97 | -9.64 |
| | L:43 | ALA | GLY | | |
| | L:80 | PRO | SER | | |
| | H:61 | ALA | VAL | | |
| | H:103 | GLY | VAL | | |

Figure 11F (Continued)

| | | | | | |
|---|---|---|---|---|---|
| 130 | L:9<br>L:51<br>L:76<br>L:80<br>L:101<br>H:103 | SER<br>ALA<br>SER<br>PRO<br>GLY<br>GLY | LYS<br>SER<br>THR<br>SER<br>ASP<br>VAL | -26.96 | -19.77 |
| 131 | L:9<br>L:25<br>L:43<br>L:76<br>H:92<br>H:103 | SER<br>ALA<br>ALA<br>SER<br>ALA<br>GLY | ARG<br>VAL<br>ASN<br>ASN<br>ASP<br>VAL | -26.96 | 46.25 |
| 132 | L:9<br>L:43<br>H:3<br>H:103<br>H:106 | SER<br>ALA<br>GLN<br>GLY<br>ALA | ILE<br>ASN<br>HID<br>VAL<br>VAL | -26.94 | 11.01 |
| 133 | L:9<br>L:43<br>H:3<br>H:24<br>H:103<br>H:106 | SER<br>ALA<br>GLN<br>ALA<br>GLY<br>ALA | ILE<br>ASN<br>HID<br>PHE<br>VAL<br>VAL | -26.94 | 7.36 |
| 134 | L:9<br>L:43<br>L:47<br>H:103<br>H:114 | SER<br>ALA<br>LEU<br>GLY<br>THR | THR<br>ASN<br>VAL<br>VAL<br>SER | -26.94 | -10.37 |
| 135 | L:9<br>L:25<br>L:43<br>L:76<br>H:92<br>H:103 | SER<br>ALA<br>ALA<br>SER<br>ALA<br>GLY | ARG<br>VAL<br>PRO<br>ASN<br>ASP<br>VAL | -26.85 | 50.46 |
| 136 | L:9<br>L:25<br>L:43<br>H:92<br>H:103 | SER<br>ALA<br>ALA<br>ALA<br>GLY | ARG<br>VAL<br>PRO<br>ASP<br>VAL | -26.84 | 53.4 |
| 137 | L:9<br>L:40<br>L:43<br>L:46<br>H:92<br>H:103 | SER<br>PRO<br>ALA<br>LEU<br>ALA<br>GLY | THR<br>ALA<br>ASN<br>VAL<br>ASP<br>VAL | -26.81 | 45.8 |
| 138 | L:9<br>L:43<br>H:3<br>H:92<br>H:103<br>H:106 | SER<br>ALA<br>GLN<br>ALA<br>GLY<br>ALA | ILE<br>ASN<br>HID<br>VAL<br>VAL<br>VAL | -26.79 | 18.85 |
| 139 | L:9<br>L:80<br>H:24<br>H:61<br>H:92<br>H:103 | SER<br>PRO<br>ALA<br>ALA<br>ALA<br>GLY | THR<br>SER<br>ASN<br>GLY<br>VAL<br>VAL | -26.77 | 39.56 |

| | | | | | |
|---|---|---|---|---|---|
| 140 | L:9 | SER | ILE | -26.74 | 37.47 |
| | L:80 | PRO | SER | | |
| | H:24 | ALA | ASN | | |
| | H:61 | ALA | GLY | | |
| | H:92 | ALA | VAL | | |
| | H:103 | GLY | VAL | | |
| 141 | L:9 | SER | ILE | -26.71 | 117.37 |
| | L:43 | ALA | ASN | | |
| | H:3 | GLN | HID | | |
| | H:48 | VAL | PHE | | |
| | H:103 | GLY | VAL | | |
| | H:106 | ALA | VAL | | |
| 142 | L:9 | SER | THR | -26.7 | 33.42 |
| | L:80 | PRO | SER | | |
| | H:24 | ALA | ASN | | |
| | H:92 | ALA | VAL | | |
| | H:103 | GLY | VAL | | |
| 143 | L:9 | SER | ARG | -26.69 | 5.9 |
| | L:51 | ALA | SER | | |
| | L:85 | THR | ILE | | |
| | H:79 | ALA | GLY | | |
| | H:103 | GLY | ALA | | |
| 144 | L:9 | SER | ARG | -26.51 | 42.72 |
| | L:102 | THR | ASN | | |
| | H:2 | VAL | ILE | | |
| | H:48 | VAL | LEU | | |
| | H:103 | GLY | VAL | | |
| | H:114 | THR | ASN | | |
| 145 | L:9 | SER | ARG | -26.48 | 33.67 |
| | L:31 | THR | ASN | | |
| | L:80 | PRO | SER | | |
| | H:24 | ALA | ASN | | |
| | H:92 | ALA | VAL | | |
| | H:103 | GLY | VAL | | |
| 146 | L:9 | SER | ARG | -26.29 | -2.22 |
| | L:43 | ALA | ASN | | |
| | L:51 | ALA | SER | | |
| | L:85 | THR | ILE | | |
| | H:79 | ALA | GLY | | |
| | H:103 | GLY | ALA | | |
| 147 | L:9 | SER | ARG | -26.25 | 22.64 |
| | L:46 | LEU | VAL | | |
| | L:51 | ALA | SER | | |
| | L:85 | THR | ILE | | |
| | H:79 | ALA | GLY | | |
| | H:103 | GLY | ALA | | |
| 148 | L:9 | SER | LYS | -26.22 | 69.47 |
| | L:25 | ALA | VAL | | |
| | L:43 | ALA | PHE | | |
| | L:93 | THR | ASN | | |
| | H:92 | ALA | ASP | | |
| | H:103 | GLY | VAL | | |
| 149 | L:9 | SER | LYS | -26.19 | 26.7 |
| | L:51 | ALA | SER | | |
| | L:85 | THR | ILE | | |
| | H:14 | PRO | SER | | |
| | H:79 | ALA | GLY | | |
| | H:103 | GLY | ALA | | |

| | | | | | |
|---|---|---|---|---|---|
| 150 | L:9<br>L:51<br>L:85<br>H:14<br>H:79<br>H:103 | SER<br>ALA<br>THR<br>PRO<br>ALA<br>GLY | ARG<br>SER<br>ILE<br>SER<br>GLY<br>ALA | -26.18 | 14.17 |
| 151 | L:9<br>L:43<br>L:85<br>H:14<br>H:103<br>H:106 | SER<br>ALA<br>THR<br>PRO<br>GLY<br>ALA | LYS<br>ASN<br>ILE<br>SER<br>VAL<br>GLY | -26.08 | 48.55 |
| 152 | L:9<br>L:43<br>L:85<br>H:103<br>H:106 | SER<br>ALA<br>THR<br>GLY<br>ALA | LYS<br>ASN<br>ILE<br>VAL<br>GLY | -26.08 | 40.27 |
| 153 | L:9<br>L:101<br>H:88<br>H:92<br>H:103<br>H:114 | SER<br>GLY<br>ALA<br>ALA<br>GLY<br>THR | LYS<br>ALA<br>VAL<br>VAL<br>VAL<br>ASN | -26 | 9.4 |
| 154 | L:9<br>L:43<br>L:85<br>H:24<br>H:103<br>H:106 | SER<br>ALA<br>THR<br>ALA<br>GLY<br>ALA | LYS<br>ASN<br>ILE<br>PRO<br>VAL<br>GLY | -25.98 | 63.87 |
| 155 | L:9<br>L:51<br>L:85<br>H:79<br>H:103 | SER<br>ALA<br>THR<br>ALA<br>GLY | ARG<br>THR<br>ILE<br>GLY<br>ALA | -25.96 | 15.38 |
| 156 | L:9<br>L:43<br>L:93<br>H:92<br>H:103 | SER<br>ALA<br>THR<br>ALA<br>GLY | LYS<br>PHE<br>ASN<br>ASP<br>VAL | -25.92 | 38.36 |
| 157 | L:9<br>H:2<br>H:48<br>H:92<br>H:103<br>H:114 | SER<br>VAL<br>VAL<br>ALA<br>GLY<br>THR | ARG<br>ILE<br>LEU<br>VAL<br>VAL<br>ASN | -25.92 | 36.49 |
| 158 | L:9<br>H:2<br>H:48<br>H:103<br>H:114 | SER<br>VAL<br>VAL<br>GLY<br>THR | ARG<br>ILE<br>LEU<br>VAL<br>ASN | -25.91 | 26.05 |
| 159 | L:9<br>L:40<br>L:43<br>L:93<br>H:92<br>H:103 | SER<br>PRO<br>ALA<br>THR<br>ALA<br>GLY | LYS<br>ALA<br>PHE<br>ASN<br>ASP<br>VAL | -25.9 | 45.1 |
| 160 | L:9<br>L:43<br>L:85<br>H:24<br>H:103<br>H:106 | SER<br>ALA<br>THR<br>ALA<br>GLY<br>ALA | LYS<br>ASN<br>ILE<br>PRO<br>ALA<br>GLY | -25.9 | 49.78 |

Figure 11F (Continued)

| | | | | |
|---|---|---|---|---|
| 161 | L:9 SER LYS<br>L:25 ALA VAL<br>L:43 ALA PRO<br>L:93 THR ASN<br>H:92 ALA ASP<br>H:103 GLY VAL | -25.86 | 71.07 |
| 162 | L:9 SER ARG<br>H:2 VAL ILE<br>H:48 VAL LEU<br>H:92 ALA VAL<br>H:103 GLY VAL | -25.85 | 37.97 |
| 163 | L:9 SER ARG<br>L:80 PRO SER<br>H:2 VAL ILE<br>H:48 VAL LEU<br>H:92 ALA VAL<br>H:103 GLY VAL | -25.85 | 36.69 |
| 164 | L:9 SER ARG<br>L:25 ALA VAL<br>L:43 ALA GLY<br>L:93 THR ASN<br>H:92 ALA ASP<br>H:103 GLY VAL | -25.84 | 66.82 |
| 165 | L:9 SER LYS<br>L:85 THR ILE<br>H:14 PRO SER<br>H:79 ALA GLY<br>H:103 GLY ALA | -25.84 | 32.49 |
| 166 | L:9 SER LYS<br>L:43 ALA ASN<br>L:85 THR ILE<br>H:14 PRO SER<br>H:103 GLY ALA<br>H:106 ALA GLY | -25.83 | 32.37 |
| 167 | L:9 SER LYS<br>L:85 THR ILE<br>H:14 PRO SER<br>H:79 ALA GLY<br>H:103 GLY ALA<br>H:106 ALA GLY | -25.81 | 40.8 |
| 168 | L:9 SER ARG<br>L:25 ALA VAL<br>L:43 ALA PRO<br>L:93 THR ASN<br>H:92 ALA ASP<br>H:103 GLY VAL | -25.8 | 58.69 |
| 169 | L:9 SER LYS<br>L:85 THR ILE<br>H:24 ALA PRO<br>H:92 ALA GLY<br>H:103 GLY ALA | -25.78 | 59.84 |
| 170 | L:9 SER LYS<br>L:85 THR ILE<br>H:24 ALA PRO<br>H:103 GLY ALA<br>H:106 ALA GLY | -25.78 | 57.94 |
| 171 | L:9 SER LYS<br>L:85 THR ILE<br>H:24 ALA PRO<br>H:92 ALA GLY<br>H:103 GLY ALA<br>H:106 ALA GLY | -25.76 | 68.1 |

| | | | | | |
|---|---|---|---|---|---|
| 172 | L:9<br>L:85<br>H:14<br>H:103<br>H:106 | SER<br>THR<br>PRO<br>GLY<br>ALA | LYS<br>ILE<br>SER<br>ALA<br>GLY | -25.73 | 32.89 |
| 173 | L:9<br>L:85<br>H:14<br>H:103<br>H:106<br>H:114 | SER<br>THR<br>PRO<br>GLY<br>ALA<br>THR | LYS<br>ILE<br>SER<br>ALA<br>GLY<br>SER | -25.72 | 42.98 |
| 174 | L:9<br>L:40<br>L:85<br>H:14<br>H:103<br>H:106 | SER<br>PRO<br>THR<br>PRO<br>GLY<br>ALA | LYS<br>SER<br>ILE<br>SER<br>ALA<br>GLY | -25.71 | 39.62 |
| 175 | L:9<br>L:76<br>L:85<br>H:14<br>H:103<br>H:106 | SER<br>SER<br>THR<br>PRO<br>GLY<br>ALA | LYS<br>ILE<br>ILE<br>SER<br>ALA<br>GLY | -25.68 | 22.3 |
| 176 | L:9<br>L:85<br>H:24<br>H:58<br>H:92<br>H:103 | SER<br>THR<br>ALA<br>THR<br>ALA<br>GLY | LYS<br>ILE<br>PRO<br>ASN<br>GLY<br>ALA | -25.6 | 61.71 |
| 177 | L:9<br>L:46<br>H:26<br>H:88<br>H:103<br>H:106 | SER<br>LEU<br>GLY<br>ALA<br>GLY<br>ALA | LYS<br>ILE<br>ASP<br>GLY<br>VAL<br>GLY | -25.59 | 22.05 |
| 178 | L:9<br>L:46<br>L:85<br>H:24<br>H:58<br>H:103 | SER<br>LEU<br>THR<br>ALA<br>THR<br>GLY | LYS<br>ILE<br>ILE<br>ASN<br>ASN<br>ALA | -25.57 | 46.88 |
| 179 | L:9<br>H:24<br>H:48<br>H:92<br>H:103 | SER<br>ALA<br>VAL<br>ALA<br>GLY | ARG<br>ASN<br>LEU<br>VAL<br>VAL | -25.56 | 41.78 |
| 180 | L:9<br>L:46<br>L:85<br>H:24<br>H:58<br>H:103 | SER<br>LEU<br>THR<br>ALA<br>THR<br>GLY | ARG<br>ILE<br>ILE<br>ASN<br>ASN<br>ALA | -25.56 | 34.36 |
| 181 | L:9<br>L:85<br>H:24<br>H:58<br>H:103 | SER<br>THR<br>ALA<br>THR<br>GLY | LYS<br>ILE<br>ASN<br>ASN<br>ALA | -25.55 | 32.65 |
| 182 | L:9<br>L:85<br>H:24<br>H:58<br>H:92<br>H:103 | SER<br>THR<br>ALA<br>THR<br>ALA<br>GLY | LYS<br>ILE<br>ASN<br>ASN<br>GLY<br>ALA | -25.55 | 39.26 |

| | | | | | |
|---|---|---|---|---|---|
| 183 | L:9<br>H:3<br>H:26<br>H:48<br>H:103 | SER<br>GLN<br>GLY<br>VAL<br>GLY | LYS<br>HID<br>ALA<br>ILE<br>ALA | -25.5 | 66.26 |
| 184 | L:9<br>H:24<br>H:48<br>H:79<br>H:92<br>H:103 | SER<br>ALA<br>VAL<br>ALA<br>ALA<br>GLY | ARG<br>ASN<br>LEU<br>VAL<br>VAL<br>VAL | -25.5 | 29.66 |
| 185 | L:9<br>L:46<br>L:85<br>H:24<br>H:103 | SER<br>LEU<br>THR<br>ALA<br>GLY | ARG<br>ILE<br>ASN<br>ASN<br>ALA | -25.48 | 45.43 |
| 186 | L:9<br>L:46<br>L:85<br>H:24<br>H:58<br>H:103 | SER<br>LEU<br>THR<br>ALA<br>THR<br>GLY | ARG<br>ILE<br>ASN<br>ASN<br>ASN<br>ALA | -25.47 | 47.52 |
| 187 | L:9<br>H:24<br>H:26<br>H:48<br>H:103 | SER<br>ALA<br>GLY<br>VAL<br>GLY | LYS<br>PRO<br>ALA<br>PHE<br>ALA | -25.44 | 144.15 |
| 188 | L:9<br>H:3<br>H:24<br>H:26<br>H:48<br>H:103 | SER<br>GLN<br>ALA<br>GLY<br>VAL<br>GLY | LYS<br>HID<br>PRO<br>ALA<br>ILE<br>ALA | -25.4 | 91.26 |
| 189 | L:9<br>H:3<br>H:24<br>H:26<br>H:48<br>H:103 | SER<br>GLN<br>ALA<br>GLY<br>VAL<br>GLY | LYS<br>HID<br>PRO<br>ALA<br>PHE<br>ALA | -25.4 | 149.66 |
| 190 | L:9<br>L:25<br>H:24<br>H:92<br>H:103<br>H:106 | SER<br>ALA<br>ALA<br>ALA<br>GLY<br>ALA | ARG<br>GLY<br>ASN<br>VAL<br>ALA<br>VAL | -25.39 | 49.6 |
| 191 | L:9<br>L:25<br>H:24<br>H:103<br>H:106 | SER<br>ALA<br>ALA<br>GLY<br>ALA | ARG<br>GLY<br>ASN<br>ALA<br>VAL | -25.37 | 42.92 |
| 192 | L:9<br>L:25<br>L:46<br>H:24<br>H:103<br>H:106 | SER<br>ALA<br>LEU<br>ALA<br>GLY<br>ALA | ARG<br>GLY<br>ILE<br>ASN<br>ALA<br>VAL | -25.36 | 56.72 |
| 193 | L:9<br>L:51<br>L:102<br>H:2<br>H:103<br>H:114 | SER<br>ALA<br>THR<br>VAL<br>GLY<br>THR | THR<br>PRO<br>ASN<br>LEU<br>VAL<br>ASN | -25.32 | 82.73 |

| | | | | | |
|---|---|---|---|---|---|
| 194 | L:9<br>L:46<br>H:24<br>H:103<br>H:106 | SER<br>LEU<br>ALA<br>GLY<br>ALA | ARG<br>ILE<br>ASN<br>ALA<br>VAL | -25.31 | 46.14 |
| 195 | L:9<br>H:2<br>H:24<br>H:48<br>H:92<br>H:103 | SER<br>VAL<br>ALA<br>VAL<br>ALA<br>GLY | ARG<br>ILE<br>ASN<br>LEU<br>VAL<br>VAL | -25.28 | 40.29 |
| 196 | L:9<br>L:43<br>L:101<br>H:92<br>H:103 | SER<br>ALA<br>GLY<br>ALA<br>GLY | ARG<br>PHE<br>VAL<br>VAL<br>VAL | -25.24 | -4.24 |
| 197 | L:9<br>L:102<br>H:2<br>H:48<br>H:103<br>H:114 | SER<br>THR<br>VAL<br>VAL<br>GLY<br>THR | THR<br>ASN<br>ILE<br>LEU<br>VAL<br>ASN | -25.22 | 45.28 |
| 198 | L:9<br>L:46<br>L:85<br>H:24<br>H:58<br>H:103 | SER<br>LEU<br>THR<br>ALA<br>THR<br>GLY | ARG<br>ILE<br>ASN<br>ASN<br>ILE<br>ALA | -25.21 | 45.46 |
| 199 | L:9<br>L:102<br>H:2<br>H:103<br>H:114 | SER<br>THR<br>VAL<br>GLY<br>THR | THR<br>ASN<br>LEU<br>VAL<br>ASN | -25.19 | 47.81 |
| 200 | L:9<br>L:102<br>H:2<br>H:48<br>H:103<br>H:114 | SER<br>THR<br>VAL<br>VAL<br>GLY<br>THR | THR<br>ASN<br>LEU<br>LEU<br>VAL<br>ASN | -25.17 | 59.94 |

| Number | Residue | Original | Mutated | Δ Affinity | Δ Stability | # Mutations |
|---|---|---|---|---|---|---|
| 1 | L:9 | SER | ARG | -32.78 | -75.08 | 5 |
| | L:43 | ALA | PHE | | | |
| | H:88 | ALA | GLY | | | |
| | H:103 | GLY | ALA | | | |
| | H:114 | THR | ASN | | | |
| 2 | L:9 | SER | ARG | -32.48 | -47.75 | 4 |
| | L:43 | ALA | PHE | | | |
| | H:26 | GLY | ALA | | | |
| | H:58 | THR | SER | | | |
| 3 | L:9 | SER | ILE | -31.99 | -73.44 | 5 |
| | L:43 | ALA | PHE | | | |
| | H:85 | SER | ARG | | | |
| | H:103 | GLY | ALA | | | |
| | H:114 | THR | ILE | | | |
| 4 | L:9 | SER | ILE | -31.91 | -60.15 | 4 |
| | L:43 | ALA | PHE | | | |
| | H:26 | GLY | VAL | | | |
| | H:85 | SER | ARG | | | |
| 5 | L:9 | SER | ARG | -31.23 | -36.46 | 3 |
| | L:43 | ALA | PHE | | | |
| | H:114 | THR | SER | | | |
| 6 | L:9 | SER | ILE | -31.05 | -53.04 | 4 |
| | L:43 | ALA | PHE | | | |
| | L:101 | GLY | ASP | | | |
| | H:79 | ALA | VAL | | | |
| 7 | L:9 | SER | ILE | -31.02 | -48.23 | 4 |
| | L:31 | THR | SER | | | |
| | L:43 | ALA | PHE | | | |
| | L:102 | THR | SER | | | |
| 8 | L:9 | SER | THR | -30.47 | -78.74 | 3 |
| | L:43 | ALA | PHE | | | |
| | H:114 | THR | ASN | | | |
| 9 | L:9 | SER | THR | -29.97 | -76.82 | 3 |
| | L:43 | ALA | PHE | | | |
| | H:114 | THR | ILE | | | |
| 10 | L:9 | SER | LYS | -29.87 | -5.55 | 4 |
| | L:43 | ALA | PHE | | | |
| | L:51 | ALA | SER | | | |
| | H:14 | PRO | THR | | | |
| 11 | L:9 | SER | ILE | -29.74 | -16.58 | 4 |
| | L:43 | ALA | PHE | | | |
| | L:46 | LEU | VAL | | | |
| | L:76 | SER | ASN | | | |
| 12 | L:9 | SER | ARG | -29.51 | -60.66 | 5 |
| | L:43 | ALA | PHE | | | |
| | H:2 | VAL | LEU | | | |
| | H:14 | PRO | SER | | | |
| | H:114 | THR | ILE | | | |
| 13 | L:9 | SER | ARG | -29.36 | -23.71 | 4 |
| | L:43 | ALA | PHE | | | |
| | H:14 | PRO | THR | | | |
| | H:88 | ALA | VAL | | | |
| 14 | L:9 | SER | THR | -29.26 | -4.8 | 4 |
| | L:43 | ALA | PHE | | | |
| | L:101 | GLY | ALA | | | |
| | H:79 | ALA | GLY | | | |

Figure 12 (Continued)

| | | | | | | |
|---|---|---|---|---|---|---|
| 15 | L:9<br>L:43<br>L:46<br>L:80<br>L:93<br>H:3 | SER<br>ALA<br>LEU<br>PRO<br>THR<br>GLN | THR<br>PHE<br>VAL<br>ALA<br>SER<br>HID | -29.14 | -29.16 | 6 |
| 16 | L:9<br>L:43<br>H:16<br>H:58<br>H:114 | SER<br>ALA<br>GLY<br>THR<br>THR | ARG<br>PHE<br>ALA<br>ASN<br>ILE | -29.09 | -81.47 | 5 |
| 17 | L:9<br>L:47<br>L:51<br>H:48<br>H:58<br>H:103 | SER<br>LEU<br>ALA<br>VAL<br>THR<br>GLY | ARG<br>VAL<br>THR<br>ILE<br>SER<br>VAL | -28.58 | -15.8 | 6 |
| 18 | L:9<br>L:43<br>L:80<br>H:61 | SER<br>ALA<br>PRO<br>ALA | ARG<br>PHE<br>THR<br>ASP | -28.55 | -24.01 | 4 |
| 19 | L:9<br>L:43<br>H:106 | SER<br>ALA<br>ALA | LYS<br>PHE<br>VAL | -28.37 | -45.98 | 3 |
| 20 | L:9<br>H:56<br>H:79<br>H:103 | SER<br>GLY<br>ALA<br>GLY | ARG<br>ALA<br>VAL<br>VAL | -28.1 | -28.88 | 4 |
| 21 | L:9<br>L:85<br>L:102<br>H:58<br>H:92<br>H:103 | SER<br>THR<br>THR<br>THR<br>ALA<br>GLY | ARG<br>SER<br>ILE<br>SER<br>GLY<br>VAL | -27.69 | -3.14 | 6 |
| 22 | L:9<br>L:102<br>H:58<br>H:92<br>H:103 | SER<br>THR<br>THR<br>ALA<br>GLY | ARG<br>ILE<br>SER<br>GLY<br>VAL | -27.68 | -10.06 | 5 |
| 23 | L:9<br>L:102<br>H:48<br>H:58<br>H:92<br>H:103 | SER<br>THR<br>VAL<br>THR<br>ALA<br>GLY | ARG<br>ILE<br>ILE<br>SER<br>GLY<br>VAL | -27.67 | -17.6 | 6 |
| 24 | L:9<br>L:85<br>L:102<br>H:92<br>H:103 | SER<br>THR<br>THR<br>ALA<br>GLY | ARG<br>SER<br>ILE<br>GLY<br>VAL | -27.65 | -8.58 | 5 |
| 25 | L:9<br>L:102<br>H:48<br>H:92<br>H:103 | SER<br>THR<br>VAL<br>ALA<br>GLY | ARG<br>ILE<br>ILE<br>GLY<br>VAL | -27.63 | -23.04 | 5 |
| 26 | L:9<br>H:16<br>H:48<br>H:58<br>H:92<br>H:103 | SER<br>GLY<br>VAL<br>THR<br>ALA<br>GLY | LYS<br>ALA<br>LEU<br>SER<br>GLY<br>VAL | -27.62 | -13.68 | 6 |

Figure 12 (Continued)

| | | | | | | |
|---|---|---|---|---|---|---|
| 27 | L:9<br>L:40<br>L:102<br>H:92<br>H:103 | SER<br>PRO<br>THR<br>ALA<br>GLY | ARG<br>SER<br>ILE<br>GLY<br>VAL | -27.6 | -3.99 | 5 |
| 28 | L:9<br>L:102<br>H:48<br>H:61<br>H:92<br>H:103 | SER<br>THR<br>VAL<br>ALA<br>ALA<br>GLY | ARG<br>ILE<br>ILE<br>VAL<br>GLY<br>VAL | -27.59 | -25.3 | 6 |
| 29 | L:9<br>H:16<br>H:48<br>H:92<br>H:103 | SER<br>GLY<br>VAL<br>ALA<br>GLY | LYS<br>ALA<br>LEU<br>GLY<br>VAL | -27.58 | -19.13 | 5 |
| 30 | L:9<br>H:48<br>H:58<br>H:92<br>H:103 | SER<br>VAL<br>THR<br>ALA<br>GLY | ARG<br>LEU<br>SER<br>GLY<br>VAL | -27.58 | -23.11 | 5 |
| 31 | L:9<br>L:43<br>L:101<br>H:92<br>H:103 | SER<br>ALA<br>GLY<br>ALA<br>GLY | LYS<br>PHE<br>VAL<br>GLY<br>VAL | -27.58 | -15.08 | 5 |
| 32 | L:9<br>H:48<br>H:58<br>H:92<br>H:103 | SER<br>VAL<br>THR<br>ALA<br>GLY | LYS<br>ILE<br>ASN<br>VAL<br>VAL | -27.57 | -19.84 | 5 |
| 33 | L:9<br>H:48<br>H:61<br>H:92<br>H:103 | SER<br>VAL<br>ALA<br>ALA<br>GLY | ARG<br>ILE<br>VAL<br>GLY<br>VAL | -27.57 | -38.17 | 5 |
| 34 | L:9<br>H:16<br>H:48<br>H:58<br>H:92<br>H:103 | SER<br>GLY<br>VAL<br>THR<br>ALA<br>GLY | ARG<br>ALA<br>LEU<br>SER<br>GLY<br>VAL | -27.57 | -25.7 | 6 |
| 35 | L:9<br>L:80<br>H:48<br>H:58<br>H:92<br>H:103 | SER<br>PRO<br>VAL<br>THR<br>ALA<br>GLY | LYS<br>ALA<br>ILE<br>ASN<br>VAL<br>VAL | -27.56 | -16.79 | 6 |
| 36 | L:9<br>L:40<br>L:85<br>L:102<br>H:92<br>H:103 | SER<br>PRO<br>THR<br>THR<br>ALA<br>GLY | ARG<br>SER<br>ILE<br>ILE<br>GLY<br>VAL | -27.55 | -14.5 | 6 |
| 37 | L:9<br>L:43<br>L:102<br>H:92<br>H:103 | SER<br>ALA<br>THR<br>ALA<br>GLY | ARG<br>PHE<br>ASN<br>GLY<br>VAL | -27.52 | -14.35 | 5 |

Figure 12 (Continued)

| # | Position | WT | Mut | Score1 | Score2 | Count |
|---|---|---|---|---|---|---|
| 38 | L:9 | SER | ARG | -27.51 | -28.38 | 6 |
| | L:80 | PRO | ALA | | | |
| | H:48 | VAL | ILE | | | |
| | H:58 | THR | ASN | | | |
| | H:92 | ALA | VAL | | | |
| | H:103 | GLY | VAL | | | |
| 39 | L:9 | SER | LYS | -27.48 | -10.11 | 6 |
| | L:43 | ALA | PHE | | | |
| | L:101 | GLY | VAL | | | |
| | H:4 | LEU | MET | | | |
| | H:92 | ALA | GLY | | | |
| | H:103 | GLY | VAL | | | |
| 40 | L:9 | SER | LYS | -27.44 | -5.02 | 6 |
| | L:80 | PRO | SER | | | |
| | H:48 | VAL | LEU | | | |
| | H:61 | ALA | GLY | | | |
| | H:103 | GLY | VAL | | | |
| | H:114 | THR | SER | | | |
| 41 | L:9 | SER | LYS | -27.44 | -11.48 | 6 |
| | L:32 | ALA | VAL | | | |
| | L:43 | ALA | PRO | | | |
| | L:51 | ALA | SER | | | |
| | H:92 | ALA | GLY | | | |
| | H:103 | GLY | VAL | | | |
| 42 | L:9 | SER | ARG | -27.43 | -7.56 | 5 |
| | L:102 | THR | ASN | | | |
| | H:58 | THR | ILE | | | |
| | H:92 | ALA | GLY | | | |
| | H:103 | GLY | VAL | | | |
| 43 | L:9 | SER | LYS | -27.42 | -6.93 | 6 |
| | L:32 | ALA | VAL | | | |
| | L:43 | ALA | PRO | | | |
| | L:51 | ALA | SER | | | |
| | H:92 | ALA | VAL | | | |
| | H:103 | GLY | VAL | | | |
| 44 | L:9 | SER | ARG | -27.42 | -2.22 | 6 |
| | L:40 | PRO | SER | | | |
| | L:102 | THR | ILE | | | |
| | H:58 | THR | ILE | | | |
| | H:92 | ALA | GLY | | | |
| | H:103 | GLY | VAL | | | |
| 45 | L:9 | SER | LYS | -27.4 | -14.41 | 5 |
| | L:80 | PRO | SER | | | |
| | H:48 | VAL | LEU | | | |
| | H:61 | ALA | GLY | | | |
| | H:103 | GLY | VAL | | | |
| 46 | L:9 | SER | ARG | -27.39 | -30.88 | 5 |
| | L:31 | THR | SER | | | |
| | H:48 | VAL | ILE | | | |
| | H:92 | ALA | GLY | | | |
| | H:103 | GLY | VAL | | | |
| 47 | L:9 | SER | LYS | -27.36 | -17.32 | 5 |
| | L:80 | PRO | ALA | | | |
| | H:48 | VAL | ILE | | | |
| | H:92 | ALA | VAL | | | |
| | H:103 | GLY | VAL | | | |
| 48 | L:9 | SER | ARG | -27.36 | -33 | 6 |
| | L:31 | THR | SER | | | |
| | H:48 | VAL | ILE | | | |
| | H:61 | ALA | VAL | | | |
| | H:92 | ALA | GLY | | | |
| | H:103 | GLY | VAL | | | |

Figure 12 (Continued)

| | | | | | | |
|---|---|---|---|---|---|---|
| 49 | L:9<br>L:76<br>L:80<br>H:48<br>H:103 | SER<br>SER<br>PRO<br>VAL<br>GLY | LYS<br>THR<br>SER<br>LEU<br>VAL | -27.35 | -23.57 | 5 |
| 50 | L:9<br>L:43<br>L:102<br>H:58<br>H:92<br>H:103 | SER<br>ALA<br>THR<br>THR<br>ALA<br>GLY | ARG<br>PHE<br>ASN<br>ILE<br>GLY<br>VAL | -27.35 | -12.66 | 6 |
| 51 | L:9<br>L:76<br>L:80<br>L:85<br>H:48<br>H:103 | SER<br>SER<br>PRO<br>THR<br>VAL<br>GLY | LYS<br>THR<br>SER<br>ASN<br>LEU<br>VAL | -27.33 | -21.75 | 6 |
| 52 | L:9<br>L:31<br>H:48<br>H:58<br>H:92<br>H:103 | SER<br>THR<br>VAL<br>THR<br>ALA<br>GLY | LYS<br>SER<br>ILE<br>ASN<br>GLY<br>VAL | -27.33 | -18.94 | 6 |
| 53 | L:9<br>L:34<br>L:40<br>L:43<br>H:48<br>H:103 | SER<br>ALA<br>PRO<br>ALA<br>VAL<br>GLY | LYS<br>VAL<br>SER<br>PRO<br>ILE<br>VAL | -27.33 | -8.88 | 6 |
| 54 | L:9<br>L:34<br>L:40<br>L:43<br>H:48<br>H:103 | SER<br>ALA<br>PRO<br>ALA<br>VAL<br>GLY | LYS<br>VAL<br>ALA<br>PRO<br>ILE<br>VAL | -27.33 | -8.83 | 6 |
| 55 | L:9<br>L:31<br>H:48<br>H:58<br>H:92<br>H:103 | SER<br>THR<br>VAL<br>THR<br>ALA<br>GLY | LYS<br>SER<br>ILE<br>ASN<br>VAL<br>VAL | -27.33 | -14.67 | 6 |
| 56 | L:9<br>L:80<br>H:48<br>H:92<br>H:103 | SER<br>PRO<br>VAL<br>ALA<br>GLY | ARG<br>ALA<br>ILE<br>VAL<br>VAL | -27.31 | -28.91 | 5 |
| 57 | L:9<br>L:31<br>H:48<br>H:58<br>H:92<br>H:103 | SER<br>THR<br>VAL<br>THR<br>ALA<br>GLY | ARG<br>SER<br>ILE<br>ASN<br>GLY<br>VAL | -27.28 | -30.63 | 6 |
| 58 | L:9<br>L:51<br>L:102<br>H:92<br>H:103 | SER<br>ALA<br>THR<br>ALA<br>GLY | ILE<br>THR<br>SER<br>GLY<br>VAL | -27.26 | -10.74 | 5 |
| 59 | L:9<br>L:25<br>L:34<br>L:101<br>H:92<br>H:103 | SER<br>ALA<br>ALA<br>GLY<br>ALA<br>GLY | ILE<br>GLY<br>VAL<br>ALA<br>GLY<br>VAL | -27.26 | -5.16 | 6 |

Figure 12 (Continued)

| | | | | | | |
|---|---|---|---|---|---|---|
| 60 | L:9<br>L:51<br>L:102<br>H:92<br>H:103 | SER<br>ALA<br>THR<br>ALA<br>GLY | ILE<br>THR<br>SER<br>VAL<br>VAL | -27.25 | -6.31 | 5 |
| 61 | L:9<br>L:51<br>L:102<br>H:16<br>H:92<br>H:103 | SER<br>ALA<br>THR<br>GLY<br>ALA<br>GLY | ILE<br>THR<br>SER<br>ALA<br>VAL<br>VAL | -27.24 | -8.9 | 6 |
| 62 | L:9<br>L:40<br>L:102<br>H:26<br>H:92<br>H:103 | SER<br>PRO<br>THR<br>GLY<br>ALA<br>GLY | ARG<br>SER<br>ILE<br>ASP<br>GLY<br>VAL | -27.23 | -3.17 | 6 |
| 63 | L:9<br>L:43<br>L:47<br>L:51<br>H:58<br>H:103 | SER<br>ALA<br>LEU<br>ALA<br>THR<br>GLY | THR<br>ASN<br>VAL<br>THR<br>SER<br>VAL | -27.17 | -14.19 | 6 |
| 64 | L:9<br>L:43<br>H:114 | SER<br>ALA<br>THR | LYS<br>PHE<br>SER | -27.14 | -21.57 | 3 |
| 65 | L:9<br>L:43<br>L:46<br>H:61<br>H:103<br>H:114 | SER<br>ALA<br>LEU<br>ALA<br>GLY<br>THR | ARG<br>ASN<br>ILE<br>VAL<br>VAL<br>ASN | -27.14 | -20.43 | 6 |
| 66 | L:9<br>L:46<br>H:61<br>H:79<br>H:103<br>H:114 | SER<br>LEU<br>ALA<br>ALA<br>GLY<br>THR | ARG<br>ILE<br>VAL<br>GLY<br>VAL<br>ASN | -27.13 | -4.64 | 6 |
| 67 | L:9<br>L:43<br>L:46<br>L:80<br>H:61<br>H:103 | SER<br>ALA<br>LEU<br>PRO<br>ALA<br>GLY | LYS<br>ASN<br>ILE<br>SER<br>VAL<br>VAL | -27.11 | -8.25 | 6 |
| 68 | L:9<br>L:34<br>L:80<br>H:48<br>H:92<br>H:103 | SER<br>ALA<br>PRO<br>VAL<br>ALA<br>GLY | ARG<br>VAL<br>ALA<br>ILE<br>VAL<br>VAL | -27.09 | -19.97 | 6 |
| 69 | L:9<br>L:47<br>L:51<br>H:58<br>H:103 | SER<br>LEU<br>ALA<br>THR<br>GLY | THR<br>VAL<br>THR<br>SER<br>VAL | -27.07 | -6.22 | 5 |
| 70 | L:9<br>L:43<br>L:46<br>H:61<br>H:103 | SER<br>ALA<br>LEU<br>ALA<br>GLY | ARG<br>ASN<br>ILE<br>VAL<br>VAL | -27.06 | -18.58 | 5 |

Figure 12 (Continued)

| | | | | | | |
|---|---|---|---|---|---|---|
| 71 | L:9<br>L:43<br>L:46<br>L:80<br>H:61<br>H:103 | SER<br>ALA<br>LEU<br>PRO<br>ALA<br>GLY | ARG<br>ASN<br>ILE<br>SER<br>VAL<br>VAL | -27.06 | -19.84 | 6 |
| 72 | L:9<br>L:47<br>L:51<br>H:48<br>H:58<br>H:103 | SER<br>LEU<br>ALA<br>VAL<br>THR<br>GLY | THR<br>VAL<br>THR<br>ILE<br>SER<br>VAL | -27.05 | -13.69 | 6 |
| 73 | L:9<br>L:46<br>H:61<br>H:103<br>H:114 | SER<br>LEU<br>ALA<br>GLY<br>THR | ARG<br>ILE<br>VAL<br>VAL<br>ASN | -27.04 | -12.6 | 5 |
| 74 | L:9<br>L:46<br>H:61<br>H:103<br>H:114 | SER<br>LEU<br>ALA<br>GLY<br>THR | ARG<br>ILE<br>GLY<br>VAL<br>ASN | -27.03 | -5.96 | 5 |
| 75 | L:9<br>L:43<br>L:80<br>H:61<br>H:103 | SER<br>ALA<br>PRO<br>ALA<br>GLY | LYS<br>ASN<br>SER<br>VAL<br>VAL | -27.03 | -21.94 | 5 |
| 76 | L:9<br>L:80<br>H:48<br>H:92<br>H:103<br>H:114 | SER<br>PRO<br>VAL<br>ALA<br>GLY<br>THR | ARG<br>SER<br>PHE<br>VAL<br>VAL<br>ASN | -27.03 | -3.91 | 6 |
| 77 | L:9<br>L:43<br>L:47<br>H:79<br>H:103<br>H:114 | SER<br>ALA<br>LEU<br>ALA<br>GLY<br>THR | THR<br>ASN<br>VAL<br>GLY<br>VAL<br>SER | -27.02 | -2.42 | 6 |
| 78 | L:9<br>L:25<br>L:80<br>H:92<br>H:103 | SER<br>ALA<br>PRO<br>ALA<br>GLY | ARG<br>GLY<br>SER<br>VAL<br>VAL | -27.01 | -15.68 | 5 |
| 79 | L:9<br>L:25<br>L:80<br>H:92<br>H:103 | SER<br>ALA<br>PRO<br>ALA<br>GLY | ARG<br>GLY<br>ALA<br>VAL<br>VAL | -27.01 | -11.32 | 5 |
| 80 | L:9<br>L:80<br>H:48<br>H:88<br>H:92<br>H:103 | SER<br>PRO<br>VAL<br>ALA<br>ALA<br>GLY | ARG<br>ALA<br>ILE<br>ASP<br>VAL<br>VAL | -27.01 | -29.42 | 6 |
| 81 | L:9<br>L:43<br>L:47<br>H:79<br>H:103 | SER<br>ALA<br>LEU<br>ALA<br>GLY | THR<br>ASN<br>VAL<br>GLY<br>VAL | -26.99 | -11.87 | 5 |

Figure 12 (Continued)

| | | | | | | |
|---|---|---|---|---|---|---|
| 82 | L:9<br>L:46<br>L:101<br>H:61<br>H:103<br>H:114 | SER<br>LEU<br>GLY<br>ALA<br>GLY<br>THR | ARG<br>ILE<br>VAL<br>GLY<br>VAL<br>ASN | -26.98 | -6.88 | 6 |
| 83 | L:9<br>L:25<br>L:80<br>L:93<br>H:92<br>H:103 | SER<br>ALA<br>PRO<br>THR<br>ALA<br>GLY | ARG<br>GLY<br>ALA<br>SER<br>VAL<br>VAL | -26.98 | -9.2 | 6 |
| 84 | L:9<br>L:80<br>H:48<br>H:92<br>H:103 | SER<br>PRO<br>VAL<br>ALA<br>GLY | ARG<br>SER<br>PHE<br>VAL<br>VAL | -26.97 | -9.61 | 5 |
| 85 | L:9<br>L:43<br>L:80<br>H:61<br>H:103 | SER<br>ALA<br>PRO<br>ALA<br>GLY | LYS<br>GLY<br>SER<br>VAL<br>VAL | -26.97 | -9.64 | 5 |
| 86 | L:9<br>L:43<br>L:47<br>H:58<br>H:103<br>H:114 | SER<br>ALA<br>LEU<br>THR<br>GLY<br>THR | THR<br>ASN<br>VAL<br>SER<br>VAL<br>SER | -26.97 | -4.88 | 6 |
| 87 | L:9<br>L:43<br>L:47<br>H:48<br>H:79<br>H:103 | SER<br>ALA<br>LEU<br>VAL<br>ALA<br>GLY | THR<br>ASN<br>VAL<br>ILE<br>GLY<br>VAL | -26.97 | -19.34 | 6 |
| 88 | L:9<br>L:51<br>L:76<br>L:80<br>L:101<br>H:103 | SER<br>ALA<br>SER<br>PRO<br>GLY<br>GLY | LYS<br>SER<br>THR<br>SER<br>ASP<br>VAL | -26.96 | -19.77 | 6 |
| 89 | L:9<br>L:43<br>L:47<br>H:103<br>H:114 | SER<br>ALA<br>LEU<br>GLY<br>THR | THR<br>ASN<br>VAL<br>VAL<br>SER | -26.94 | -10.37 | 5 |
| 90 | L:9<br>L:43<br>H:114 | SER<br>ALA<br>THR | THR<br>PHE<br>SER | -26.36 | -37.27 | 3 |
| 91 | L:9<br>L:43<br>L:51<br>L:85<br>H:79<br>H:103 | SER<br>ALA<br>ALA<br>THR<br>ALA<br>GLY | ARG<br>ASN<br>SER<br>ILE<br>GLY<br>ALA | -26.29 | -2.22 | 6 |
| 92 | L:9<br>L:93<br>H:92<br>H:103<br>H:114 | SER<br>THR<br>ALA<br>GLY<br>THR | ARG<br>ILE<br>GLY<br>VAL<br>ILE | -25.78 | -12.61 | 5 |
| 93 | L:9<br>L:43<br>H:106 | SER<br>ALA<br>ALA | LYS<br>PHE<br>GLY | -25.73 | -25.84 | 3 |

| | | | | | | |
|---|---|---|---|---|---|---|
| 94 | L:9 | SER | LYS | -25.31 | -52.18 | 4 |
| | L:93 | THR | ILE | | | |
| | H:16 | GLY | VAL | | | |
| | H:103 | GLY | ALA | | | |
| 95 | L:9 | SER | ARG | -25.24 | -4.24 | 5 |
| | L:43 | ALA | PHE | | | |
| | L:101 | GLY | VAL | | | |
| | H:92 | ALA | VAL | | | |
| | H:103 | GLY | VAL | | | |
| 96 | L:9 | SER | ARG | -25.23 | -13.15 | 5 |
| | L:93 | THR | ILE | | | |
| | H:92 | ALA | GLY | | | |
| | H:103 | GLY | VAL | | | |
| | H:114 | THR | SER | | | |
| 97 | L:9 | SER | ARG | -25.15 | -23.8 | 5 |
| | H:85 | SER | ARG | | | |
| | H:92 | ALA | VAL | | | |
| | H:103 | GLY | VAL | | | |
| | H:114 | THR | ASN | | | |
| 98 | L:9 | SER | ARG | -25.09 | -22.29 | 5 |
| | L:80 | PRO | THR | | | |
| | H:92 | ALA | GLY | | | |
| | H:103 | GLY | VAL | | | |
| | H:114 | THR | ILE | | | |
| 99 | L:9 | SER | LYS | -25.07 | -10.03 | 5 |
| | L:101 | GLY | ALA | | | |
| | H:92 | ALA | GLY | | | |
| | H:103 | GLY | VAL | | | |
| | H:114 | THR | ASN | | | |
| 100 | L:9 | SER | ARG | -25.03 | -40.37 | 5 |
| | H:56 | GLY | ALA | | | |
| | H:79 | ALA | VAL | | | |
| | H:103 | GLY | VAL | | | |
| | H:114 | THR | ASN | | | |

Figure 12 (Continued)

Figure 13A
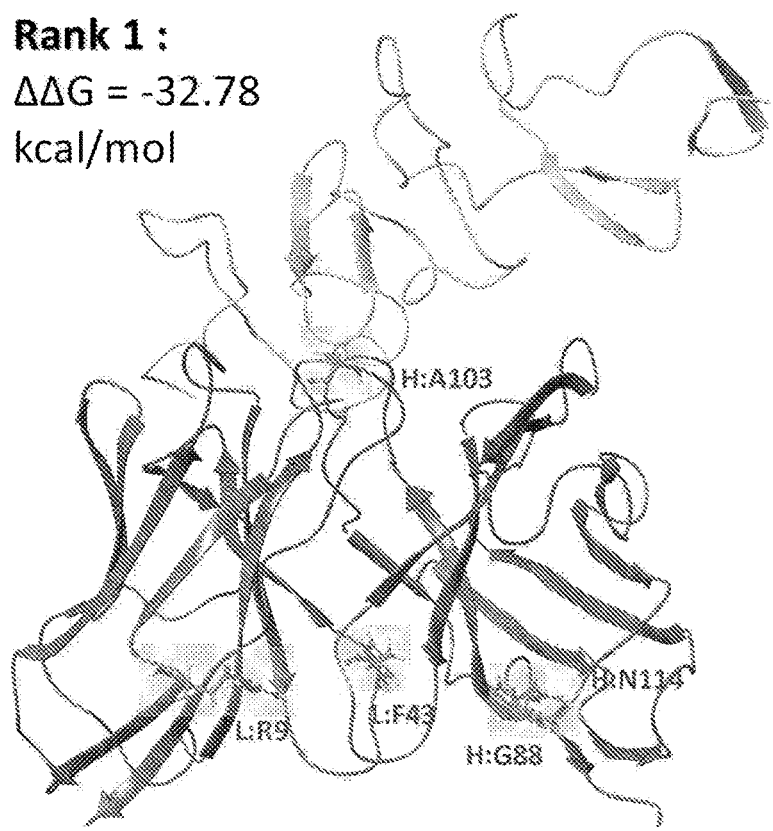
Rank 1:
ΔΔG = -32.78 kcal/mol
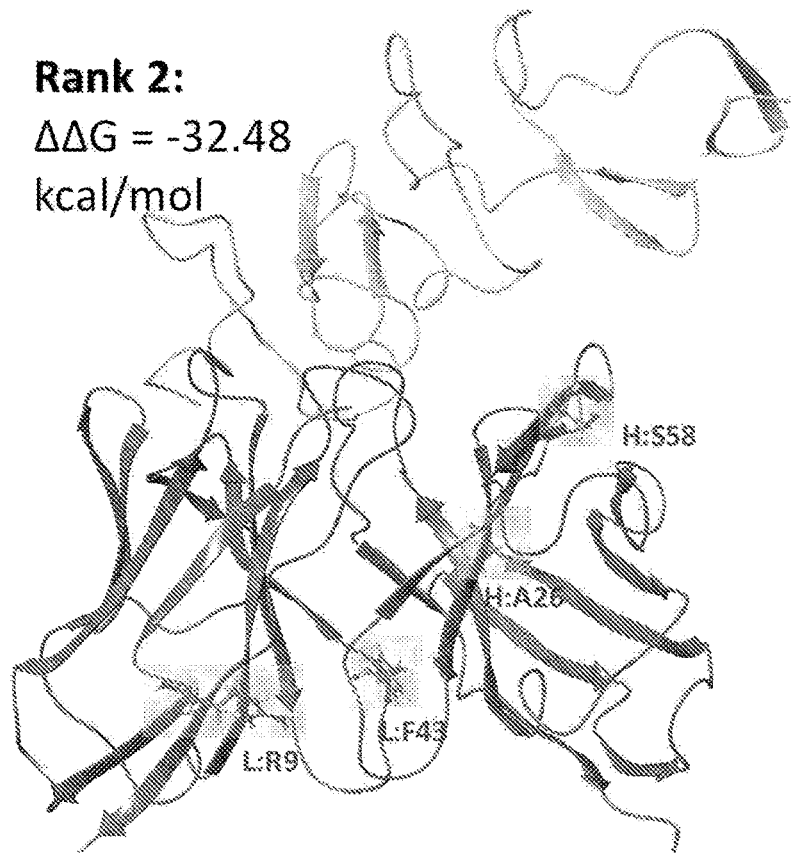
Rank 2:
ΔΔG = -32.48 kcal/mol Figure 13B
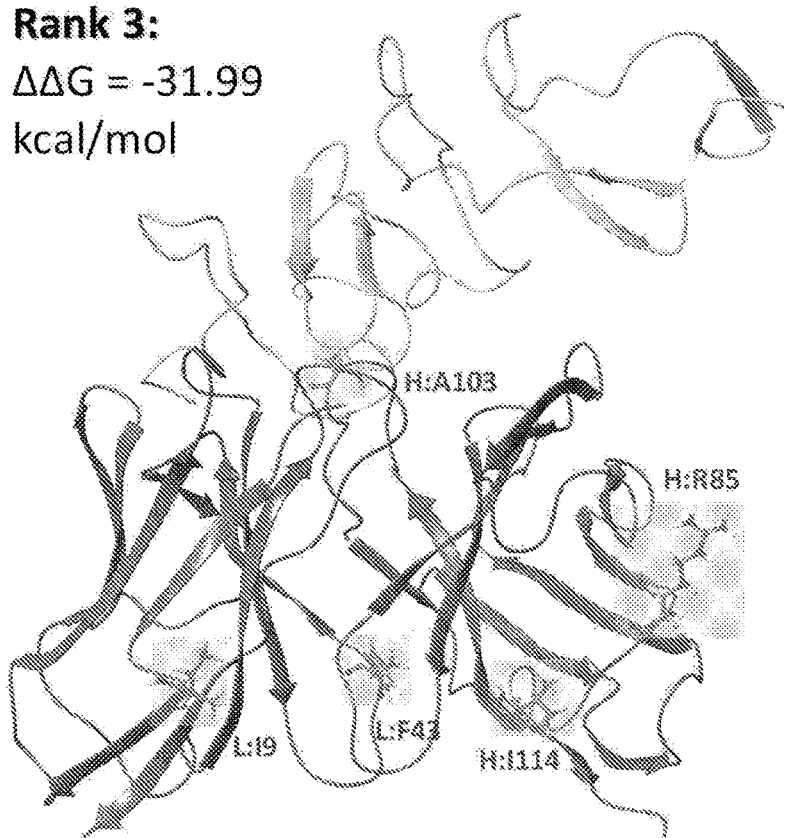
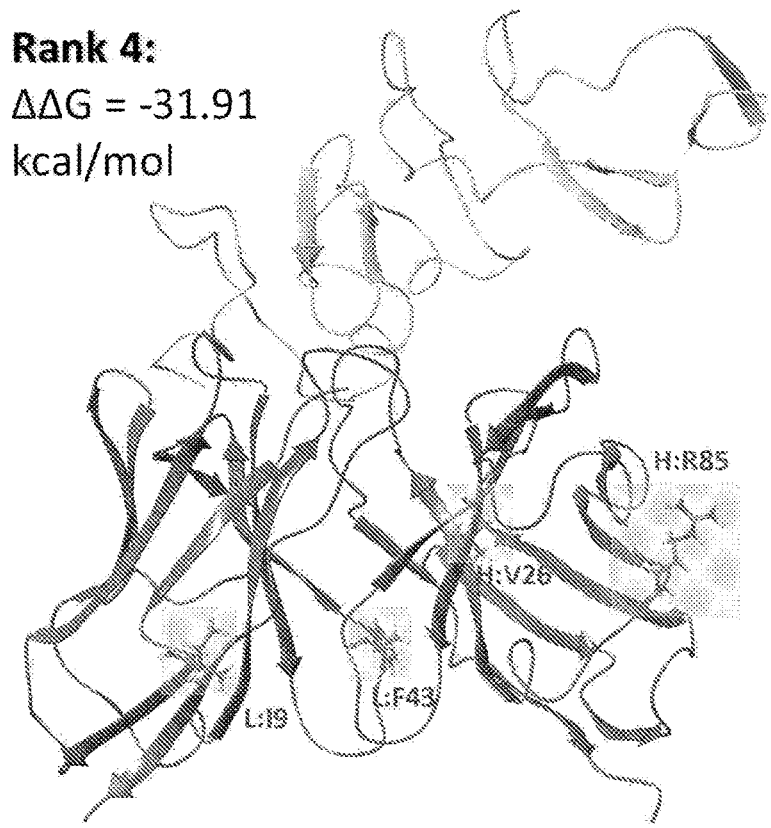

Rank 5:
$\Delta\Delta G = -31.23$ kcal/mol

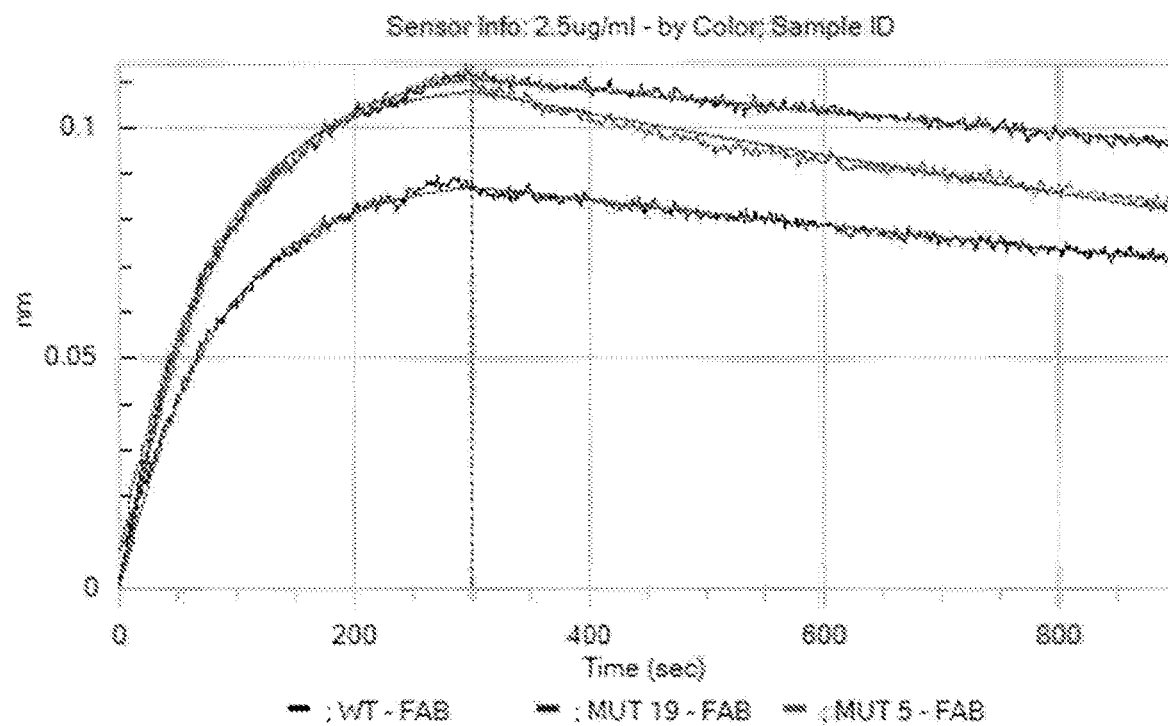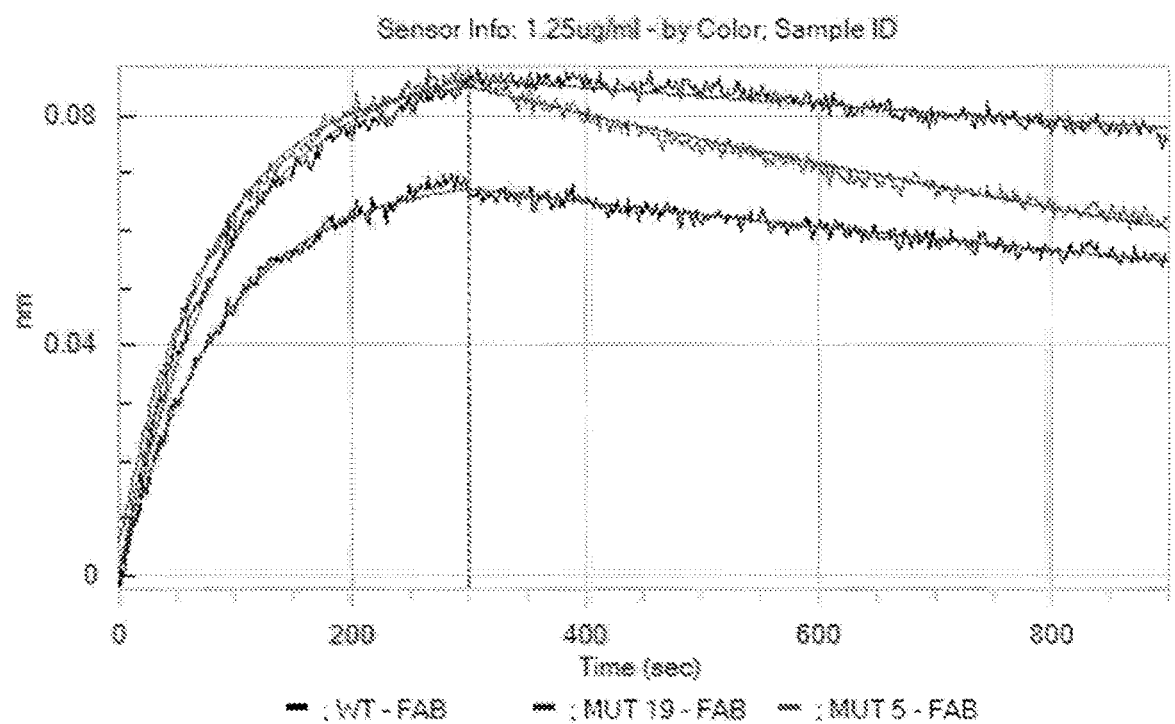
Figure 20

ANTIBODY LIBRARY AND METHOD

CROSS-REFERENCE TO RELATED APPLICATIONS

This application is the US national phase under 35 U.S.C. § 371 of International Application No. PCT/GB2019/053010, filed Oct. 22, 2019, which claims priority to GB Patent Application No. 1817188.4 filed Oct. 22, 2018, GB Patent Application No. 1904754.7 filed Apr. 4, 2019, and GB Patent Application No. 1905032.7 filed Apr. 9, 2019, the contents of each of which are hereby incorporated by reference in their entirety.

FIELD OF THE INVENTION

The present invention relates to methods of generating antibody libraries, antibody libraries produced using such methods, and variant antibodies.

BACKGROUND TO THE INVENTION

Antibody affinity is the measure of the strength of interaction between the antibody and protein that it specifically binds to, as a ratio of the association rate and dissociation rate. There are many reasons why optimisation of this ratio is desirable. Increased affinity may mean that an antibody therapeutic is more effective at a given dose, or it may mean that less of the drug is required per dose, and diagnostic tests could improve sensitivity. Reducing affinity may also be beneficial for some drugs that require tissue penetration and therefore a faster dissociation. It has also been shown that bispecific antibodies require intricate tuning of affinity of each binding site in order to maximise efficacy.

Existing affinity maturation platforms generally involve creating a large library of variants through random mutagenesis focussed within antibody complementarity determining regions (CDRs). This process has the disadvantage of screening a very large number of variants (often >$10^{10}$) to identify a small fraction of variants with improved characteristics.

SUMMARY OF THE INVENTION

The present invention addresses many of the problems of the prior art. As described in the examples, the inventors have surprisingly shown that by limiting mutations to a nucleotide sequence encoding a given antibody sequence to sites which correspond to DNA motifs which are targeted by enzymes involved in somatic hypermutation, a library of variants of a given antibody sequence may be created, the library, when compared to those prepared by many existing technologies, being relatively small but comprising a relatively high proportion of variants having increased affinity, or aggregation, or melting point, or expression level in CHO cells or combinations of the same. The inventors have exemplified the invention utilising two unrelated antibodies, an anti-CathepsinS antibody, Fsn0503h (Fusion Antibodies Ltd), and the anti-HER2 antibody trastuzumab, (Herceptin®, Roche).

Accordingly a first aspect of the present invention provides a library of antibody molecules, wherein each antibody molecule is a variant of a reference antibody, wherein the amino acid sequence of each antibody molecule differs from the amino acid sequence of the reference antibody at one or more amino acid residues, wherein each of said amino acid residues are independently encoded from a DNA segment of the DNA sequence encoding the variant, wherein said DNA segment of the variant differs from that of the corresponding DNA sequence encoding the reference antibody by a point mutation in a DNA motif susceptible to deamination by a somatic hypermutation inducing enzyme.

A second aspect of the invention provides a method of generating/producing a library of variant antibody molecules, wherein said variant antibody molecules are variants of a reference antibody, said method comprising the steps:
a) providing a nucleotide sequence encoding the reference antibody,
b) in said nucleotide sequence, identifying one or more DNA motifs susceptible to deamination by a somatic hypermutation inducing enzyme;
c) for one or more of said DNA motifs, selecting at least one variant nucleotide residue to substitute for a residue of said DNA motif, wherein said substitution will result in a variant nucleotide sequence which encodes a variant antibody molecule having, relative to the reference antibody, a change in the amino acid sequence being encoded by said DNA motif; and
d) repeating steps (b) and (c);
such that a library containing a plurality of variants of said reference antibody is generated. The reference antibody may be any antibody molecule of which variants are desired or required. In one embodiment said reference antibody is a humanised antibody molecule.

A third aspect of the invention provides a method of generating a variant antibody molecule, wherein said variant antibody molecule is a variant of a reference antibody, said method comprising the steps:
a) providing a nucleotide sequence encoding the reference antibody,
b) in said nucleotide sequence, identifying one or more DNA motifs susceptible to deamination by a somatic hypermutation inducing enzyme;
c) for one or more of said DNA motifs, selecting at least one variant nucleotide residue to substitute for a residue of said DNA motif, wherein said substitution will result in a variant nucleotide sequence which encoding a variant antibody molecule having, relative to the reference antibody, a change in the amino acid sequence being encoded by said DNA motif.

In one embodiment of the invention, said somatic hypermutation inducing enzyme is Activation-Induced Deaminase (AID).

In embodiments of the invention, said DNA motif is DGYW or WRCH, for example RGYW or WRCY, where D is adenine, guanine or thymine, R is adenine or guanine, G is guanine, C is cytosine, H is adenine or cytosine or thymine, W is adenine or thymine, and Y is cytosine or thymine.

Said DNA motif may be on either strand of the DNA. Where there are more than one of said DNA motifs, the motifs may overlap.

The inventors have shown that the antibody library of the invention or produced according to a method of the invention may be refined by further limiting the members of the library to those variants resulting from mutations at the DNA motif targeted by a somatic hypermutation inducing enzyme which do not result in either a STOP codon or indeed a other motifs in the variant antibody molecule which relative to the reference antibody would be considered to be potentially undesirable, for example in terms of stability or binding.

Accordingly, in certain embodiments of the invention, the DNA sequence of each variant does not comprise (or encode) a deamination site, isomerisation site, N-linked glycosylation site or oxidation site which originates from said point mutation in said DNA motif.

In some embodiments, one or more of said DNA motifs are in DNA sequences which encode CDRs of said antibody molecule. However, as described in the examples, the inventors have shown that using the method with some reference antibodies, the variants generated may not have any mutations in some CDRs compared to the corresponding CDRs of the reference antibody.

In one embodiment, the variants have no changes in one or more of its CDRs compared to the corresponding CDRs of the reference sequence.

In one such embodiment, the variants have no changes in Light chain CDR1 compared to the corresponding CDR of the reference sequence.

In another such embodiment, the variants have no changes in Light chain CDR2 compared to the corresponding CDR of the reference sequence.

In another such embodiment, the variants have no changes in Light chain CDR3 compared to the corresponding CDR of the reference sequence.

In another such embodiment, the variants have no changes in heavy chain CDR1 compared to the corresponding CDR of the reference sequence.

In another such embodiment, the variants have no changes in heavy chain CDR2 compared to the corresponding CDR of the reference sequence.

In another such embodiment, the variants have no changes in heavy chain CDR3 compared to the corresponding CDR of the parent sequence.

Moreover, as shown in the examples, for some variants of reference antibodies, many of the mutations characterising the variants may be in the framework regions of the variant antibody molecules.

Accordingly in particular embodiments of the library or method of the invention, one or more of said DNA motifs are in DNA sequences which encode framework regions of said antibody molecule. In some such embodiments, all of said DNA motifs are in DNA sequences which encode framework regions of said antibody molecule.

In one embodiment of the invention, greater than 20%, for example greater than 40%, greater than 50%, greater than 60%, greater than 70%, greater than 80% or greater than 90% of the nucleotide residues of each variant antibody which differ from nucleotide residues in corresponding positions in the reference antibody are residues at a DNA motif susceptible to deamination by a somatic hypermutation inducing enzyme.

In some embodiments of the invention, the nucleotide sequence encoding each of said antibody molecules does not differ from that of the reference antibody at any residue other than residues of said DNA motif.

An antibody library of the invention and/or produced using the method of the invention may be further refined to enhance the proportion of variants of high affinity and/or stability.

An antibody library of the invention and/or produced using the method of the invention may be further refined to enhance the proportion of variants with differential aggregation, i.e. less able to aggregate to each other. An antibody library of the invention and/or produced using the method of the invention may be further refined to enhance the proportion of variants with particular melting point characteristics. An antibody library of the invention and/or produced using the method of the invention may be further refined to enhance the proportion of variants which show favourable or desired expression level in CHO cells. An antibody library of the invention and/or produced using the method of the invention may be further refined to enhance the proportion of variants with high affinity, stability, desired aggregation characteristics, desired melting point characteristics, desired expression level characteristics or combinations of the same.

Thus in the invention, the method may further comprise determining the affinity and/or stability of binding of said variant antibody molecule to the binding target of the reference antibody, melting point in relation to a reference antibody, aggregation in relation to a reference antibody, expression level in relation to a reference antibody or combinations of the same. Accordingly in one embodiment of the method of the invention, said method further comprises screening said library of variants to determine binding to an epitope to which the reference antibody binds. Suitably, the method of the invention, may further comprises screening said library of variants to determine a melting point, expression level, aggregation level or stability of a variant with respect to the reference antibody. Those variants determined to bind to said epitope with an affinity and/or stability/ or have a melting characteristic or aggregation characteristic or expression characteristic less or greater than a predetermined value relative to the reference antibody may be used to generate an optimised library of variant antibody molecules. Said screening method may be via conventional in vitro techniques. Such techniques may include an affinity ELISA assay, a BIAcore assay, a kinetic method or an equilibrium/solution method. In an alternative, said screening may be via an in silico technique, using, for example computer implemented molecular docking software to model the binding of the variant to the epitope of the reference antibody.

As shown in the examples, using molecular docking software, variants can be ranked by predicted affinity and stability allowing the selection of a small library of variants for DNA synthesis and expression. The inventors have demonstrated that within such a small library a very high number of the variants have increased affinity compared to the number which would be expected to be identified in a library generated by existing technologies such as error-prone PCR and phage display.

Molecular docking software products are commercially available. Any suitable software or tool suitable for modelling antibody binding to an epitope may be used in the present invention. For example, suitable software includes Bioluminate software from Schrodinger but others are available.

Accordingly, in embodiments of the invention, the antibody library comprises greater than 1%, for example greater than 5%, 10%, 20%, 30%, 40% or 50% of variants having increased affinity to the epitope bound by the reference antibody compared to the affinity of the reference antibody to said epitope.

In one embodiment of the method of the invention, the method is a computer implemented method.

A fourth aspect of the invention provides a computer readable storage media comprising instructions to perform a method for generating a library of variant antibody molecules according to the second aspect of the invention.

In the methods of the invention, whether computer implemented or not, the method may further comprise the step of synthesising the variant antibody molecules.

In embodiments of the method of the invention, where the method comprised a computer implemented screening method by, for example, docking modelling software, the method of the invention may further comprise in vitro screening of said library of variants to determine binding to an epitope to which the reference antibody binds.

A fifth aspect of the present invention is a variant of a trastuzumab antibody, wherein said variant has (i) at least two amino acid changes in the light chain sequence when compared to the light chain amino acid sequence of a reference antibody, wherein said reference antibody is trastuzumab, (ii) at least two amino acid changes in the heavy chain sequence when compared to the heavy chain amino acid sequence of trastuzumab, or (iii) at least one amino acid change in the light chain sequence when compared to the light chain amino acid sequence of trastuzumab and at least one amino acid change in the heavy chain sequence when compared to the heavy chain amino acid sequence of trastuzumab; wherein each of said amino acid changes are at amino acid residues independently encoded from a DNA segment of the variant DNA sequence, wherein said DNA segment of the variant differs from that of the corresponding DNA sequence encoding the reference antibody by a point mutation in a DNA motif susceptible to deamination by a somatic hypermutation inducing enzyme.

In one embodiment of the fifth aspect of the invention, said amino acid changes are selected from the group consisting of lc9N, lc9T, 1c9I, lc9R, lc9K, lc25G, lc25V, lc25D, lc31N, lc31S, lc31I, lc32D, lc32G, lc32V, lc32T, lc32N, lc32S, 1c32I, lc32P, lc32L, lc32F, lc33L, lc33I, lc34G, lc34V, lc34D, lc38E, lc38K, lc40A, lc40S, lc40T, lc43G, lc43V, lc43T, lc43N, lc43S, 1c43I, lc43P, lc43L, lc43F, lc46V, 1c46I, lc47V, lc51S, lc51P, lc51T, lc76R, lc76N, lc76T, lc76K, 1c76I, lc79K, lc79E, lc80T, lc80S, lc80A, lc85N, lc85I, 1c85I, lc89H, lc90E, lc90A, lc91N, lc91D, lc91Y, lc93S, lc93N, 1c93I, lc94S, lc94N, 1c94I, lc101D, lc102S, lc102N, hc2L, hc2I, hc3H, hc4M, hc4V, hc13K, hc13E, hc14A, hc14T, hc14S, hc16A, hc16V, hc16D, hc23E, hc23G, hc23V, hc23T, hc23K, hc23R, hc23I, hc23P, hc23L, hc23S, hc24D, hc24G, hc24V, hc24T, hc24N, hc24S, hc24I, hc24P, hc24L, hc24F, hc26A, hc26V, hc26D, hc28K, hc35N, hc35D, hc35Y, hc48L, hc48I, hc49G, hc49S, hc56A, hc56V, hc56D, hc58S, hc58N, hc58I, hc61G, hc61V, hc61D, hc79G, hc79V, hc79D, hc82E, hc82K, hc85R, hc88D, hc88T, hc88S, hc88P, hc88G, hc92G, hc92V, hc92D, hc103A, hc103V, hc103D, hc106D, hc106G, hc106V, hc106T, hc106N, hc106S, hc106I, hc106P, hc106L, hc106F, hc114S, hc114N, and hc114I.

In the context of the invention, mutations are identified using the above nomenclature, where lc=light chain, hc=heavy chain, the number refers to the amino acid residue of the chain and the capital letter is the one letter amino acid code for the amino acid mutation at said site. Thus, for example, in the amino acid changes listed above for the fourth aspect, lc9N, refers to an asparagine at position 9 of the variant trastuzumab light chain.

In an embodiment of the fifth aspect of the invention, said amino acid changes are selected from the group consisting of lc9T, lc9I, lc9R, lc9K, lc43F, lc47V, lc51P, lc51T, lc101D, hc2L, hc3H, hc14S, hc16V, hc24P, hc26A, hc26V, hc48I, hc58S, hc61V, hc79V, hc85R, hc88G, hc92V, hc92D, hc103A, hc103V, hc106V, hc114S, hc114N, and hc114I.

In one embodiment of the fifth aspect, the variant light chain and heavy chain sequences do not differ from that of the reference antibody at any residue other than by the amino acid changes recited above in relation to the fifth aspect.

A sixth aspect of the invention provides a variant of a Cathepsin S antibody, wherein said variant has (i) at least two amino acid changes in the light chain sequence when compared to the light chain amino acid sequence of a reference antibody, wherein said reference antibody is Fsn503h, (ii) at least two amino acid changes in the heavy chain sequence when compared to the heavy chain amino acid sequence of Fsn503h, or (iii) at least one amino acid change in the light chain sequence when compared to the light chain amino acid sequence of Fsn503h and at least one amino acid change in the heavy chain sequence when compared to the heavy chain amino acid sequence of Fsn503h; wherein each of said amino acid changes are at amino acid residues independently encoded from a DNA segment of the variant DNA sequence, wherein said DNA segment of the variant differs from that of the corresponding DNA sequence encoding the reference antibody by a point mutation in a DNA motif susceptible to deamination by a somatic hypermutation inducing enzyme.

In one embodiment of the sixth aspect of the invention, said amino acid changes are selected from the group consisting of lc12A, lc12S, lc12T, lc19V, lc28R, lc32T, lc32I, lc45A, lc45S, lc45T, lc50H, lc51V, lc51F, lc51I, lc56L, lc56F, lc56I, lc58K, lc66S, lc69A, lc69V, lc81T, lc81I, lc81N, lc85P, lc85S, lc85T, lc90L, lc90F, lc96I, lc96S, lc96I, lc96N, lc108N, hc3H, hc4V, hc4M, hc10A, hc10V, hc14A, hc14S, hc24G, hc24V, hc30T, hc30I, hc31R, hc31T, hc37L, hc37F, hc40P, hc40S, hc52S, hc52I, hc53S, hc53I, hc84T, hc84I, hc92G, and hc92V.

In one embodiment of the sixth aspect of the invention, said amino acid changes are selected from the group consisting of group consisting of lc12A, lc12S, lc12T, lc19V, lc45S, lc45T, lc50H, lc51V, lc56I, lc81I, lc96I, lc96S, lc96I, lc96N, lc108N, hc10A, hc10V, hc14S, hc30I, hc31R, hc37L, hc37F, hc40P, hc40S, hc52I, and hc92G.

In one embodiment of the sixth aspect of the invention, the variant light chain and heavy chain sequences do not differ from that of the reference antibody at any residue other than by the amino acid changes recited above in relation to the sixth aspect.

In one embodiment of the fifth aspect of the invention, said variant antibody molecule has the combination of amino acid mutations as shown for any of the antibodies listed in Tables 2 to 7. In another embodiment of the fourth aspect, said variant antibody molecule has the combination of amino acid mutations as shown for any of the antibodies listed in Table 8. In one such embodiment, said variant antibody has the combination of amino acid mutations as shown for any one of the antibodies listed in Table 8 and does not have any amino acid mutations relative to the Trastuzumab light chain and heavy chain sequences other than those shown for said antibody listed in Table 8.

In one embodiment of the fifth aspect of the invention, said variant antibody has the mutation lc43F.

In one embodiment of the fifth aspect of the invention, said variant antibody has the combination of amino acid mutations as shown for any of variant antibodies 19, 5 or 6 in Table 8. In one such embodiment, said variant does not have any amino acid mutations relative to the Trastuzumab light chain and heavy chain sequences other than those shown for said variant antibody in Table 8.

In one embodiment of the fifth aspect of the invention, the variant antibody is a variant of a trastuzumab antibody comprising relative to trastuzumab, the following amino acid changes: lc9K, lc43F, and hc106V. In one embodiment, the variant antibody is variant antibody 19 as listed in Table 8.

In another embodiment of the fifth aspect of the invention, the variant antibody is a variant of a trastuzumab antibody comprising relative to trastuzumab, the following amino acid changes: lc9R, lc43F, and hc114S. In one embodiment, the variant antibody is variant antibody 5 as listed in Table 8.

In another embodiment of the fifth aspect of the invention, the variant antibody is a variant of a trastuzumab antibody comprising relative to trastuzumab, the following amino acid changes: lc9I, lc43F, lc101D, and hc79V. In one embodiment, the variant antibody is variant antibody 6 as listed in Table 8.

In one embodiment of the sixth aspect of the invention, said variant antibody molecule has the combination of amino acid mutations as shown for any of the antibodies listed in Table 1.

In certain embodiments of the fifth or sixth aspects of the invention, said variant light chain and heavy chain sequences comprise in total at least three, for example at least 4, at least 5 or at least 6 amino acid changes compared to the amino acid sequence of the reference antibody.

In certain embodiments of the fifth or sixth aspects of the invention, one or more of said amino acid changes are in framework regions of said variant antibody. In certain embodiments of the fifth or sixth aspects of the invention, all of said amino acid changes are in framework regions of said variant antibody.

In certain embodiments of the fifth or sixth aspects of the invention, one or more of said amino acid changes are in CDRs of said variant antibody.

In certain embodiments of the fifth or sixth aspects of the invention, the change of affinity of said variant antibody molecule relative to the reference antibody is greater than −2 and the change of stability of said variant antibody molecule relative to reference antibody is greater than −2. In certain embodiments of the fifth or sixth aspects of the invention, the change of affinity of said variant antibody molecule relative to the reference antibody is greater than −10, for example greater than −15, for example, greater than −20, such as greater than −25.

In certain embodiments of the fifth or sixth aspects of the invention, the change of stability of said variant antibody molecule relative to the reference antibody is greater than −10, for example greater than −30, for example, greater than −50, such as greater than −60. Suitably, the aggregation characteristic, melting point characteristic or expression level may be at least 2 fold, three fold, 10 fold different to the reference antibody.

For the avoidance of doubt, the greater the negative affinity value, the greater the affinity. Thus an antibody with an affinity value of −10 is considered to have a greater affinity value of an antibody with an affinity value of −5. Likewise, the greater the negative stability value, the greater the stability. Thus an antibody with a stability value of −10 is considered to have a greater stability value of an antibody with a stability value of −5.

Affinity and stability may be assessed by any suitable method. In the examples, the inventors used the residue scanning affinity maturation tool as part of Schrodinger's Biologics tool Maestro. Values were relative to the parental antibody with the minimum value for improved affinity taken to be ~2 kcal/mol for both affinity and stability.

Definitions

Unless otherwise defined, all technical and scientific terms used herein have the meaning commonly understood by a person who is skilled in the art in the field of the present invention.

Throughout the specification, unless the context demands otherwise, the terms "comprise" or "include", or variations such as "comprises" or "comprising", "includes" or "including" will be understood to imply the inclusion of a stated integer or group of integers, but not the exclusion of any other integer or group of integers.

As used herein, terms such as "a", "an" and "the" include singular and plural referents unless the context clearly demands otherwise. Thus, for example, reference to "an active agent" or "a pharmacologically active agent" includes a single active agent as well as two or more different active agents in combination, while references to "a carrier" includes mixtures of two or more carriers as well as a single carrier, and the like.

The term "DNA segment" refers to a section of a DNA sequence. In the context of the present invention, the DNA segment may be a section of DNA residues, said section being part of a longer DNA sequence which encodes an antibody molecule. The DNA segment may consist of the DNA residues which form a DNA motif, said DNA motif being a sequence-specific binding site for a somatic hypermutation inducing enzyme The term "consisting essentially of" as used herein means that the invention necessarily includes the listed items and is open to including unlisted items that do not materially affect the basic and novel properties of the invention.

As herein defined, an "epitope" refers to a plurality of amino acid residues which are capable of being recognised by, and bound to by, an antibody molecule. Epitopes are generally comprised of chemically active surface groups and have specific three-dimensional structural characteristics, as well as specific charge characteristics which contribute to the three-dimensional structure of the epitope.

Antibody molecules of or for use in the invention may bind to a non-contiguous epitope. A "non-contiguous epitope" is an epitope that is comprised of a series of amino acid residues that are non-linear in alignment, such that the residues are spaced or grouped in a non-continuous manner along the length of a polypeptide sequence.

The terms "peptide", "polypeptide" and "protein" are used herein interchangeably to describe a series of at least two amino acids covalently linked by peptide bonds or modified peptide bonds such as isosteres. No limitation is placed on the maximum number of amino acids which may comprise a peptide or protein. Furthermore, the term polypeptide extends to fragments, analogues and derivatives of a peptide, wherein said fragment, analogue or derivative retains the same biological functional activity as the peptide from which the fragment, derivative or analogue is derived.

The nomenclature used to describe the polypeptide constituents herein follows the conventional practice wherein the amino group (N) is presented to the left and the carboxyl group to the right of each amino acid residue.

Antibodies and Antibody Molecules

An "antibody" is an immunoglobulin, whether natural or partly or wholly synthetically produced. The term also covers any polypeptide, protein or peptide having a binding domain that is, or is homologous to, an antibody binding domain. These can be derived from natural sources, or they may be partly or wholly synthetically produced. Examples of antibodies are the immunoglobulin isotypes and their isotypic subclasses and fragments which comprise an antigen binding domain such as Fab, scFv, Fv, dAb or Fd, and a bi-specific antibody.

As antibodies can be modified in a number of ways, the term "antibody" and "antibody molecule" should be construed as covering any binding member or substance having a binding domain with the required specificity. An antibody molecule of and for use in the invention may be a monoclonal antibody, or a fragment, derivative, functional equivalent or homologue thereof. The term includes any polypeptide comprising an immunoglobulin binding domain, whether natural or wholly or partially synthetic. Chimeric molecules comprising an immunoglobulin binding domain, or equivalent, fused to another polypeptide are therefore included.

The constant region of the antibody may be of any suitable immunoglobulin subtype. In certain embodiments the subtype of the antibody may be of the class IgA, IgM, IgD and IgE where a human immunoglobulin molecule is used. Such an antibody may further belong to any subclass, e.g. IgG1, IgG2a, IgG2b, IgG3 and IgG4.

Fragments of a whole antibody can perform the function of antigen binding. Examples of such binding fragments are a Fab fragment comprising or consisting of the VL, VH, CL and CH1 antibody domains; an Fv fragment consisting of the VL and VH domains of a single antibody; a F(ab')2 fragment; a bivalent fragment comprising two linked Fab fragments; a single chain Fv molecule (scFv), wherein a VH domain and a VL domain are linked by a peptide linker which allows the two domains to associate to form an antigen binding site; and a bi-specific antibody, which may be multivalent or multispecific fragments constructed by gene fusion.

In certain embodiments humanized antibodies may be used. A humanised antibody may be a modified antibody having the hypervariable region of non-human antibody and the constant region of a human antibody. Thus the binding member may comprise a human constant region. The variable region other than the hypervariable region may also be derived from the variable region of a human antibody and/or may also be derived from a non-human antibody. In other cases, the entire variable region may be derived from a non-human antibody and the antibody is said to be chimerised.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. A hybridoma or other cell producing an antibody may be subject to genetic mutation or other changes, which may or may not alter the binding specificity of antibodies produced.

An antibody may be selected from the group consisting of a human antibody, a humanised antibody, a chimeric antibody, a monoclonal antibody, a polyclonal antibody, a synthetic antibody, a camelid antibody, a shark antibody and an in-vitro antibody. In certain embodiments an antigen binding fragment may be used. The antigen binding fragment may be derived from any of the aforementioned antibodies. In certain embodiments the antigen binding fragment is selected from the group consisting of a Fab fragment, a scFv fragment, a Fv fragment and a dAb fragment. In certain embodiments the antibody comprises two complete heavy chains and two complete light chains, or an antigen binding fragment thereof. In certain embodiments the antibody is of the isotype IgG, IgA, IgE or IgM, or an antigen binding fragment thereof. In certain embodiments where the antibody is of the isotype IgG, the antibody may be of the subtype IgG1, IgG2 or IgG3, or an antigen binding fragment thereof. In certain embodiments the antibody is of the subtype IgG4, or an antigen binding fragment thereof.

Production of Antibodies

Antibodies may be provided by a number of techniques. For example, a combinatorial screening technique such as a phage display-based biopanning assay may be used in order to identify amino acid sequences which have binding specificity to an antigen. Such phage display biopanning techniques involve the use of phage display libraries, which are utilised in methods which identify suitable epitope binding ligands in a procedure which mimics immune selection, through the display of antibody binding fragments on the surface of filamentous bacteria. Phage with specific binding activity are selected. The selected phage can thereafter be used in the production of chimeric, CDR-grafted, humanised or human antibodies. Antibodies can be tested for their ability to bind to an antigen using methods known in the art.

Antibodies or antigen fragments for use in the present invention may also be generated wholly or partly by chemical synthesis. The antibodies can be readily prepared according to well-established, standard liquid or, preferably, solid-phase peptide synthesis methods, general descriptions of which are broadly available and are well known by the person skilled in the art. Further, they may be prepared in solution, by the liquid phase method or by any combination of solid-phase, liquid phase and solution chemistry.

Another convenient way of producing antibodies or antibody fragments suitable for use in the present invention is to express nucleic acid encoding them by use of nucleic acid in an expression system.

Antibodies may be generated by mutagenesis of antibody genes to produce artificial repertoires of antibodies. This technique allows the preparation of antibody libraries. Artificial repertoires of immunoglobulins, such as artificial scFv repertoires, may be employed as an immunoglobulin source in order to identify binding molecules which have specificity for a specific epitope.

Methods for generating repertoires are well characterised in the art.

Any suitable means of generating antibody libraries may be used in conjunction with the present invention. Selection protocols for isolating desired members of large libraries are known in the art, as typified by phage display techniques. Such systems, in which diverse peptide sequences are displayed on the surface of filamentous bacteriophage, have proven useful for creating libraries of antibody fragments (and the nucleotide sequences that encode them) for the in-vitro selection and amplification of specific antibody fragments that bind a target antigen. The nucleotide sequences encoding the VH and VL regions are linked to gene fragments which encode leader signals that direct them to the periplasmic space of *E. coli* and as a result the resultant antibody fragments are displayed on the surface of the bacteriophage, typically as fusions to bacteriophage coat proteins (for example pIII or pVIII). Alternatively, antibody fragments are displayed externally on lambda phage capsids (phage bodies). An advantage of phage-based display systems is that, because they are biological systems, selected library members can be amplified simply by growing the phage containing the selected library member in bacterial cells. Furthermore, since the nucleotide sequence that encodes the polypeptide library member is contained on a phage or phagemid vector, sequencing, expression and subsequent genetic manipulation is relatively straight forward.

Methods for the construction of bacteriophage antibody display libraries and lambda phage expression libraries are well known in the art.

A method for producing polypeptides may comprise culturing host cells transformed with a recombinant expression vector encoding a polypeptide under conditions that promote expression of the polypeptide, then recovering the expressed polypeptides from the culture. The person skilled in the art will recognise that the procedure for purifying the expressed polypeptides will vary according to such factors as the type of host cells employed, and whether the polypeptide is intracellular, membrane-bound or a soluble form that is secreted from the host cell.

Any suitable expression system may be employed. Vectors may include a DNA encoding a polypeptide or fragment of the invention, operably linked to suitable transcriptional or translational regulatory nucleotide sequences, such as those derived from a mammalian, avian, microbial, viral, bacterial, or insect gene. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide during translation, but allows secretion of polypeptide from the cell.

Suitable host cells for expression of polypeptides include higher eukaryotic cells and yeast. Prokaryotic systems are also suitable.

Mammalian cells, and in particular CHO cells are particularly preferred for use as host cells. CHO cells are used widely in the production of proteins due to their ease of culture and transfectability. ExpiCHO-S cells are a suspension cell line that can grow to very high densities and allows for high expression of proteins. The plasmid DNA of interest can be transfected into ExpiCHO cells by complexing with ExpiFectamine (a cationic lipid-based transfection reagent) to allow the DNA to condense. This condensed DNA then enters the ExpiCHO cells by endocytosis and is expressed in the nucleus. The expressed proteins are present in the cell culture supernatant and harvested after an appropriate number of days have passed.

Nucleic Acid

Nucleic acid for use in accordance with the present invention may comprise DNA or RNA and may be wholly or partially synthetic. In a preferred aspect, nucleic acid for use in the invention codes for antibodies or antibody fragments of the invention as defined above. The skilled person will be able to determine substitutions, deletions and/or additions to such nucleic acids which will still provide an antibody molecule of or for use in the present invention.

Nucleic acid sequences encoding antibodies or antibody fragments for use with the present invention can be readily prepared by the skilled person. These techniques include (i) the use of the polymerase chain reaction (PCR) to amplify samples of such nucleic acid, e.g. from genomic sources, (ii) chemical synthesis, or (iii) preparing cDNA sequences. DNA encoding antibody fragments may be generated and used in any suitable way known to those of skill in the art, including by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Modifications to the sequences can be made, e.g. using site directed mutagenesis, to lead to the expression of modified peptide or to take account of codon preferences in the host cells used to express the nucleic acid.

The nucleic acid may be comprised as constructs in the form of a plasmid, vector, transcription or expression cassette which comprises at least one nucleic acid as described above. The construct may be comprised within a recombinant host cell which comprises one or more constructs as above. Expression may conveniently be achieved by culturing under appropriate conditions recombinant host cells containing the nucleic acid. Following production by expression the antibody or antibody fragments may be isolated and/or purified using any suitable technique, then used as appropriate.

Systems for cloning and expression of a polypeptide in a variety of different host cells are well known. Suitable host cells include bacteria, mammalian cells, yeast, insect and baculovirus systems. Mammalian cell lines available in the art for expression of a heterologous polypeptide include Chinese hamster ovary (CHO) cells, HeLa cells, baby hamster kidney cells, NS0 mouse myeloma cells. A common, preferred bacterial host is *E. coli*. The expression of antibodies and antibody fragments in prokaryotic cells such as *E. coli* is well established in the art. Expression in eukaryotic cells in culture is also available to those skilled in the art as an option for production of a binding member. General techniques for the production of antibodies are well known to the person skilled in the field.

In certain embodiments of the invention, recombinant nucleic acids comprising an insert coding for a heavy chain variable domain and/or for a light chain variable domain of antibodies are provided. By definition such nucleic acids comprise coding single stranded nucleic acids, double stranded nucleic acids consisting of said coding nucleic acids and of complementary nucleic acids thereto, or these complementary (single stranded) nucleic acids themselves.

Furthermore, nucleic acids encoding a heavy chain variable domain and/or a light chain variable domain of antibodies can be enzymatically or chemically synthesised nucleic acids having the authentic sequence coding for a naturally-occurring heavy chain variable domain and/or for the light chain variable domain, or a mutant thereof.

BRIEF DESCRIPTION OF THE FIGURES

Embodiments of the present invention will now be described, by way of example only, with reference to the accompanying figures in which:

FIG. 1 shows amino acid sequences of the Fsn0503h antibody light chain and heavy chain showing potential mutations above each chain (SEQ ID Nos 1 & 2). Doubly circled amino acids were not permitted in the library due to their uncommon usage at that position. Doubly circled asterisks (*)represent STOP codons that also were not permitted. Singly circled amino acid regions are CDRs.

FIG. 3 shows Table 1 which lists affinity and stability predictions of amino acid mutations in a combinatorial fashion for 1 to 6 mutations. Groups of mutations highlighted in blue represent variants with both improved stability and affinity where the change is greater than −2.

FIG. 5 shows affinity (KD) measurements of each variant alongside the parental Fsn0503h antibody, as measured by BLI with an Octet instrument (Pall).

FIG. 7 shows amino acid sequences of the trastuzumab antibody light chain (SEQ ID NO: 3) showing in bold the amino acid residue at each position of the wild type antibody light chain and, where applicable, in the boxes to the right of each residue, potential mutations. Amino acids shown with two lines were not permitted in the library due to their uncommon usage at that position. Asterisks (*) in two lines represent STOP codons that also were not permitted. Complementarity determining regions CDRs and framework regions (FR) are indicated.

FIG. 8 shows amino acid sequences of the trastuzumab antibody heavy chain (SEQ ID NO: 4) showing in bold the amino acid residue at each position of the wild type antibody antibody chain and, where applicable, in the boxes to the right of each residue, potential mutations. Amino acids shown with two lines were not permitted in the library due to their uncommon usage at that position. Asterisks (*) in two lines represent STOP codons that also were not permitted. Complementarity determining regions CDRs and framework regions (FR) are indicated.

FIG. 11*a* shows Table 2 which lists trastuzumab variants having one mutation relative to the reference trastuzumab antibody. In column 2, L indicates light chain, while H indicates heavy chain. A Affinity is predicted free energy change (ΔΔG) in kcal/mol relative to trastuzumab affinity. A Stability is predicted free energy change (ΔΔG) relative to trastuzumab stability. Negative Δ Affinity and negative Δ Stability values are considered to represent improved affinity and improved stability relative to trastuzumab.

FIG. 11*b* shows Table 3 which lists trastuzumab variants having two mutations relative to the reference trastuzumab antibody. In column 2, L indicates light chain, while H indicates heavy chain.

FIG. 11*c* shows Table 4 which lists trastuzumab variants having three mutations relative to the reference trastuzumab antibody. In column 2, L indicates light chain, while H indicates heavy chain.

FIG. 11*d* shows Table 5 which lists trastuzumab variants having four mutations relative to the reference trastuzumab antibody. In column 2, L indicates light chain, while H indicates heavy chain.

FIG. 11*e* shows Table 6 which lists trastuzumab variants having five mutations relative to the reference trastuzumab antibody. In column 2, L indicates light chain, while H indicates heavy chain.

FIG. 11*f* shows Table 7 which lists trastuzumab variants having six mutations relative to the reference trastuzumab antibody. In column 2, L indicates light chain, while H indicates heavy chain.

FIG. 12 shows Table 8 which lists the 100 trastuzumab variants from tables 1 to 7 having both improved affinity and improved stability, ranked according to improved affinity.

EXAMPLES

Figure 2:
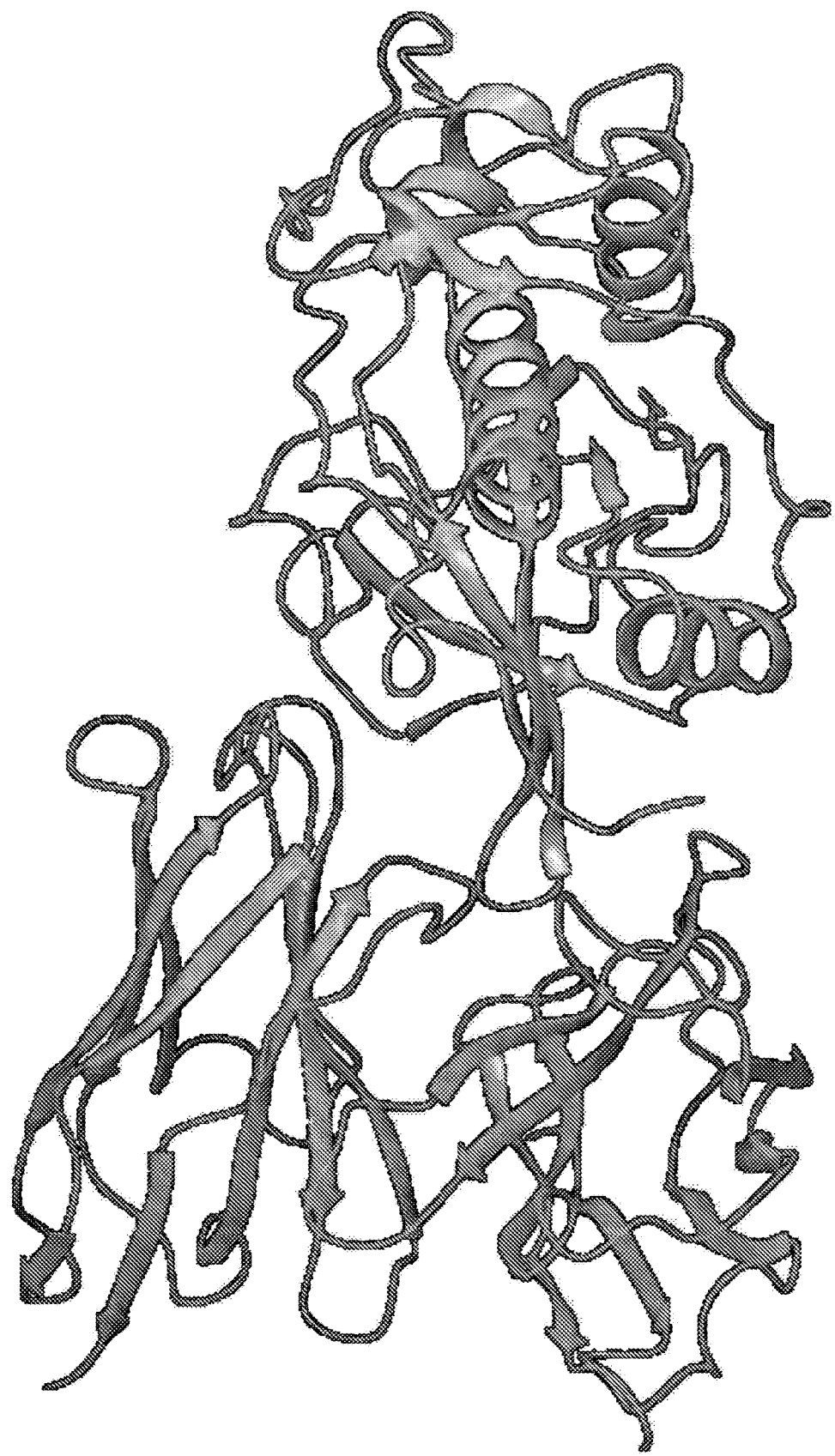
FIG. 2 is a schematic model showing predicted protein-protein interaction between Fsn0503h and Cathepsin S.

Materials and Methods
Library Design

An antibody library was generated for each of (i) a humanised anti-Cathepsin S antibody, Fsn0503h (Fusion Antibodies, Belfast) (Kwok et al. Molecular Cancer 2011, 10:147) and (ii) trastuzumab (Roche) by mimicking the natural somatic hypermutation in humans, searching for specific DNA sequence motifs RGYW in the 3' to 5' strand and WRCY in the 5' to 3' strand, recognised by the AID enzyme, responsible for making mutations within antibodies in the human body.

The DNA sequence has a point mutation introduced at the guanine in position 2 of the DNA sequence motif RGYW or the cytosine in position 3 of the DNA sequence motif WRCY, where the nucleotide is mutated to be any other nucleotide. The AID enzyme in humans introduces natural mutations at these positions. This can cause a possible change to the amino acid at a single point. All these possible mutations were identified throughout the antibody DNA sequence in both directions in the 3' to 5' and 5' to 3' strands to generate all the amino acids that would be possible naturally throughout the antibody sequence to form the initial library.

Each library's size was then curated by removing any recognised sequence liabilities, such as deamidation sites, isomerization sites, n-linked glycosylation sites and oxidation sites from the newly generated amino acid sequences.

Molecular Docking

For each library, the antibody prediction tool in Maestro 11.7 (Schrödinger) was used to perform homology modelling, to generate an antibody model based on the amino acid sequences for the heavy and light variable chain regions. The antigen was imported from PDB. In the case of Fsn0503h, the inventors imported the crystal structure of human Cathepsin S (Cat S) with a C25S mutation with a bound drug (PDB Code: 3MPE). In the case of the library for trastuzumab variants, the extracellular domain of human epidermal growth factor receptor 2 (HER2) (PDB Code: 1N8Z) was used.

The protein preparation wizard (Bioluminate, Schrodinger) was used to assign bond orders (using Chemical Component Dictionary (CCD) database), add hydrogens, create zero-order bonds to metals, create disulphide bonds, convert selenomethionines to methionines, fill in missing side chains and loops using Prime, and generating het states using Epik, for both the antibody and antigen models. The structures were further refined using ProtAssign (Bioluminate, Schrodinger) to define hydroxyl, asparagine, glutamine and histidine states. Waters with less than three bonds to non-waters were removed. Finally, the structures were minimized using the OPLS3e forcefield. (Bioluminate, Schrodinger).

Cathepsin S was docked to the surface of the antibody model using the protein-protein docking tool, Prime. Only the CDR regions of the antibody were considered for molecular docking. Non-CDR regions were masked. Using in vitro information about the epitope of Cat S, a suitable docked pose was selected based on rank and from inspection of shape complementarity and surface interactions (using the protein interaction analysis tool).

Likewise, for the trastuzumab variants, the extracellular domain of human epidermal growth factor receptor 2 (HER2) (PDB Code: 1N8Z) was docked to the surface of the antibody model using the protein-protein docking tool, Prime. Only the CDR regions of the antibody were considered for molecular docking. Non-CDR regions were masked. A suitable docked pose was selected based on rank and from our inspection of shape complementarity and surface interactions (using the protein interaction analysis tool).

Combinatorial Mutation Analysis

Residue scanning was performed on the docked pose of the antibody-antigen complex. Informed mutations were made to the antibody, avoiding highly conserved residues, to increase the affinity of the antibody for the antigen and to enhance stability.

Residue scanning was first done by generating models with a single amino acid variation from the original structure, and repeated (with the same mutations) for up to 6 simultaneous variations from the wild type Ab. The residue mutation tool calculated the stability and affinity of the mutants relative to the original wild type antibody-antigen complex.

The variants were then sorted by difference in affinity and difference in stability relative to the wild type. Results that scored below a threshold of −2 for difference in stability and difference in affinity were selected and ranked based on the combination of the two scores (prioritising difference in affinity).

The best variants of the Fsn503h antibody and of the trastuzumab antibody were synthesised and analysed in vitro.

Antibody Synthesis
Transient Transfection:

Suspension adapted ExpiCHO cells were routinely cultivated at 4–6×10$^6$ cells/ml at 130 rpm, 37° C., 8% $CO_2$, in ExpiCHO Expression Medium in 500 ml vented Erlenmeyer flasks. For each of the Fsn0503h variants, 1 µg/ml of DNA was diluted in 4% (v/v) OptiPRO SFM in a centrifuge tube. In a separate tube, 0.32% (v/v) ExpiFectamine was diluted in 3.7% OptiPRO SFM. The ExpiFectamine/OptiPRO mix was then added to the DNA/OptiPRO mix and incubated at room temperature for 3 minutes before adding to 25 ml ExpiCHO cells at a final density of 6×10$^6$ cells/ml in 125 ml vented Erlenmeyer flasks. Each transfected culture was cultivated at 37° C., 8% $CO_2$ and 130 rpm overnight. Twenty hours post transfection, cells were supplemented with 0.6% (v/v) ExpiCHO enhancer and 24% (v/v) ExpiCHO feed. Cultures were then transferred to incubators at 32° C., 5%

$CO_2$ and 130 rpm. Cultures were harvested by centrifugation at 4000 rpm for 40 minutes at 18° C.

Purification:

Two-step Fsn0503h WT and variant antibody purifications were performed using a Tricorn 5/50 column (GE) packed with 1 ml of MabSelect™ PrismA (GE) followed by a 10 ml (2×5 ml) Hitrap Desalting (Desalt) column (GE). The MabSelect™ PrismA affinity medium was chosen for its high mAb binding and specificity properties and its alkali tolerance for efficient Cleaning-in-place (CIP). All steps were performed at room temperature, using a flow-rate of 4 ml/min, unless otherwise stated. After loading (performed using the AKTA sample pump), the protein A column was washed (in reverse flow mode) with 10 column volumes (CV) of PBS followed by a one-step elution (in reverse flow mode) with 100 mM glycine, pH 3.0. The protein A eluate was collected in a 2 ml loop when the absorbance was above 120 mAU at 280 nm (AKTA equipped with a 10 mm flow cell) and injected immediately onto the pre-equilibrated Desalt column. The Desalt peak elution was collected in a 96-well-2 ml block at 2-8° C. when the eluate had an absorbance above 100 mAU. To avoid any cross-contamination, the automated process also included a CIP of both the affinity and desalt columns. CIP was performed between each sample, for all contact pathways, using 0.2M NaOH (reverse flow mode was used for column cleaning).

The level of expression was determined as the total yield of material, following purification per ml of culture media.

Trastuzumab variants were synthesised using similar techniques.

Affinity Ranking

Enzyme-Linked Immunosorbent Assay:

MaxiSorp 96 well plates were coated with the sixty six 0503 variants at 1 g/ml in PBS for 24 hrs at 4° C. To obtain the EC50 results, the variants were serially diluted from 1000 ng/ml to T1 ng/ml with PBS and coated in duplicate. The standard curve was prepared with the parental 0503 antibody coated at 1 µg/ml in PBS for 24 hrs at 4° C. After 24 hrs, the MaxiSorp plates were washed three times with PBS-T. 200 µl of SuperBlock was added to each well, removed and replaced three times. 100 µl of Cat S antigen at 200 ng/ml was added to each well and left shaking at RT, 150 rpm for 1 hr 30 mins. The plates were washed with PBS-T three times and dried. 100 µl of anti-his-HRP at 5 µg/ml was added to each well and left for 1 hr 30 mins shaking at 150 rpm, RT. The plates were washed three time PBS-T, once with PBS and dried. 100 µl of TMB was added to each well and incubated at 37° C. for 10 mins, which was followed by 50 µl of 1M HCL and the absorbance of the plates was measured at 450 nm.

Affinity Ranking Using the Octet RED96 System (Fsn503h Variants):

Affinity ranking assays were performed by first capturing IgG using anti-human Octet biosensors (ForteBio part no. 18-5060) followed by a baseline step of 2 minutes in HBS-EBT buffer (10 mM HEPES, 150 mM NaCl, 3 mM EDTA, 1 mg/ml BSA, and 0.05% Tween-20, pH 7.4). The mAb capture biosensors were then submerged in wells containing 200 ng/ml of recombinant Cathepsin S antigen for 10 minutes (association step), followed by a 10 min dissociation step in running buffer. To allow for double reference correction, IgG-captured sensors were dipped into wells containing only buffer and blank sensors were also dipped into wells containing the antigen. This referencing provided a means of compensating for both the natural dissociation of the capture IgG and also non-specific binding of the antigen to the sensor surface. All steps were performed at 25° C. in HBS-EBT buffer at a constant flow-rate of 1000 rpm. New sensors were used for each sample. Dissociation rate constants (koff) were calculated using the ForteBio Data Analysis software. All consumables used were those recommended by ForteBio.

Antibody Quantification Using Biolayer Interferometry (the Octet RED96 System):

To measure IgG content, 200 µL aliquots of antibody standards (spanning 0.06 to 512 µg/ml) and IgG containing cell supernatants (diluted within the measurable range of calibration curve) were prepared in duplicate using 1× HBS-EBT buffer (10 mM HEPES, 150 mM NaCl, 3 mM EDTA, 1 mg/ml BSA, and 0.05% Tween-20, pH 7.4) and placed in the wells of a 96-well black microtiter plate (Greiner Bio-One part no. 655209). All samples and standards were measured in duplicate using protein A Biosensors (Fortebio PN 18-5010). The plate was placed in the Octet and allowed to equilibrate to 25° C. in the thermostatted chamber. The run was initiated by placing the sensors in the wells and measuring the change in layer thick-ness (in nanometers, nm) with time, all under computer control. Data were taken for each set of eight samples at a time (one plate column is measured simultaneously) for 180-600 sec at a flow rate of 400-1000 rpm (orbital flow). Data were processed automatically using the Octet User Software version 3.1. The measurement time and flow rate were altered according to the sensitivity required.

Affinity Ranking Using Biolayer Interferometry (the Octet RED96 System) (Trastuzumab Variants):

Affinity ranking assays were performed by first capturing *IgG using anti-human Octet biosensors (ForteBio part no. 18-5060) followed by a baseline step of 2 minutes in HBS-P+ buffer (10 mM HEPES, 150 mM NaCl, 1 mg/ml BSA, and 0.05% Tween-20, pH 7.4). The mAb capture biosensors were then submerged in wells containing 5 nM of recombinant HER2 (Acro Biosystems; P/N. H5225) antigen for 15 minutes (association step), followed by a 20 min dissociation step in running buffer. To allow for double reference correction, IgG-captured sensors were dipped into wells containing only buffer and blank sensors were also dipped into wells containing the antigen. This referencing provided a means of compensating for both the natural dissociation of the capture IgG and also non-specific binding of the antigen to the sensor surface. Steps were performed at either 25° C. or 37° C. in HBS-EBT buffer at a constant flow-rate of 1000 rpm. New sensors were used for each sample. Dissociation rate constants (koff) were calculated using the ForteBio Data Analysis software. All consumables used were those recommended by ForteBio.

*To allow for similar loading levels the quantified (as described above) IgG containing cell supernatants were diluted to an identical concentration.

$K_D$ Determination Using Biolayer Interferometry (the Octet RED96 System):

Kinetic assays were performed by first capturing IgG using anti-human Fc Octet biosensors followed by two baseline steps of 2 minutes each in in HBS-P+ buffer running buffer. The mAb capture biosensors were then submerged in wells containing various concentrations of HER2 for 15 mins followed by 20 mins of dissociation time in running buffer. To allow for double reference correction, IgG-captured sensors were dipped into wells containing only buffer and blank sensors were also dipped into wells containing the antigen concentration series. This referencing providing a means of compensating for both the natural dissociation of the capture IgG and also non-specific binding of the antigen to the sensor surface. All steps were performed at 37° C. in kinetics buffer at a constant flow-rate of 1000 rpm.

Melting Point Determination

Antibodies commonly display 2 measurable melting points in analysis, designated TM1 and TM2 as a result of thermal denaturing of different parts of the assembled molecule. These values were determined by Thermal Shift Assay. Solutions containing 5 µl of Sypro Orange (diluted 1/200 in PBS, pH 7.4); Molecular Probes) and 45 µl of 0.3 mg ml$^{-1}$ antibody were added to low profile PCR tubes (Bio-Rad; TLS0851). Tubes were sealed with optical ultra-clear sealing caps (Bio-Rad; TCS0803) and heated in an i-Cycler iQ5 real-time PCR detection system (Bio-Rad) from 20 to 90° C. in increments of 1° C. Fluorescence changes in the wells of the plate were monitored simultaneously with a charge-coupled (CCD) camera. The wavelengths for excitation and emission were 485 and 575 nm, respectively. The temperature midpoint for the protein unfolding transition, $T_m$, was calculated using the Bio-Rad iQ5 software.

Determination of Monodispersity

The level of monodispersity, defined as free individual molecules of immunoglobulin within an antibody preparation, of each variant was also shown to differ from the wild type molecule. This measurement is commonly used as an indicator of aggregation propensity for antibody molecules. Aggregation is the tendency of protein molecules to associate into multimeric complexes, diminishing the solubility and activity of an antibody preparation over time and is a key attribute contributing to the stability of an antibody molecule in solution.

This was determined on the purified antibody solutions using size-exclusion chromatography. All samples were diluted to a final concentration of 0.1 mg/ml using phosphate buffered saline. Highly purified samples of antibodies were loaded independently onto a Superdex 200 increase 10/300 GL gel-filtration column. 50 µl samples were injected and the column flow rate was maintained at 0.75 µl min$^{-1}$. Separations and equilibration steps were performed in phosphate buffered saline at 22° C. Protein peaks were monitored using absorbance at 280 & 214 nm and spectra were analysed using the Unicorn emulation software package (GE healthcare). Results are reported in $V_r$ (ml) and relative peak area (%) of each peak.

Results

Example 1 Cathepsin S antibody Variants

Library Design

Figure 1B:
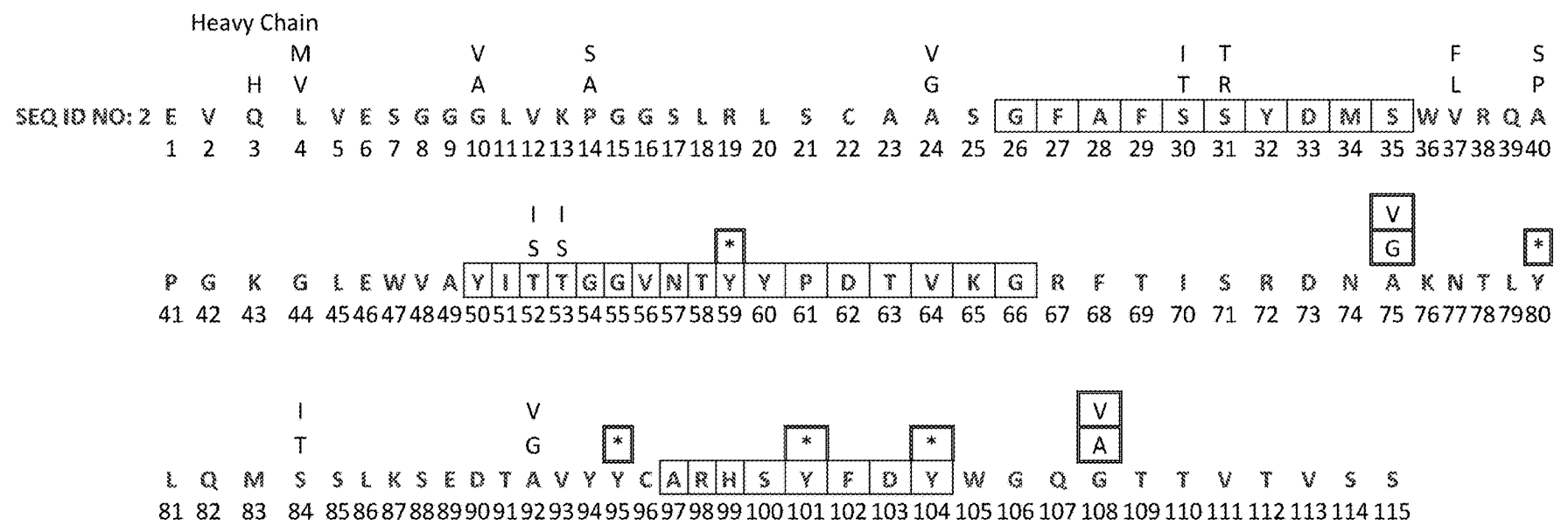

The DNA sequences of the variable domains of the Fsn0503h antibody light and heavy light chains were analysed for motifs susceptible to mutation during somatic hypermutation, and the corresponding potential amino acid results of these mutation plotted above the parental sequence, as shown in FIG. 1. Any undesirable amino acids or STOP codons generated as a result of the DNA mutations were identified.

It was a surprising discovery that there are more mutations within the framework regions than the CDRs, and in particular that CDR-H3 has no functional mutations.

Molecular Docking

The parental Fsn0503h antibody variable domains (Kwok et al. Molecular Cancer 2011, 10:147) were docked with the Cathepsin S protein using Schrödinger molecular docking software as described in the Methods. The outcome of the docking procedure is shown in FIG. 2.

Combinatorial Mutagenesis

Within the docked structures amino acid residue mutations were introduced and the relative difference in both affinity and stability predicted. The mutations were introduced in increasing numbers until no further benefits to stability or affinity were predicted. The results of the combinatorial mutagenesis are shown in FIG. 3. The inventors identified 66 variants that had a predicted improvement in both affinity and stability. The DNA coding for these variants was then synthesised and the antibodies expressed and purified as described in the Methods.

ELISA

Figure 4:
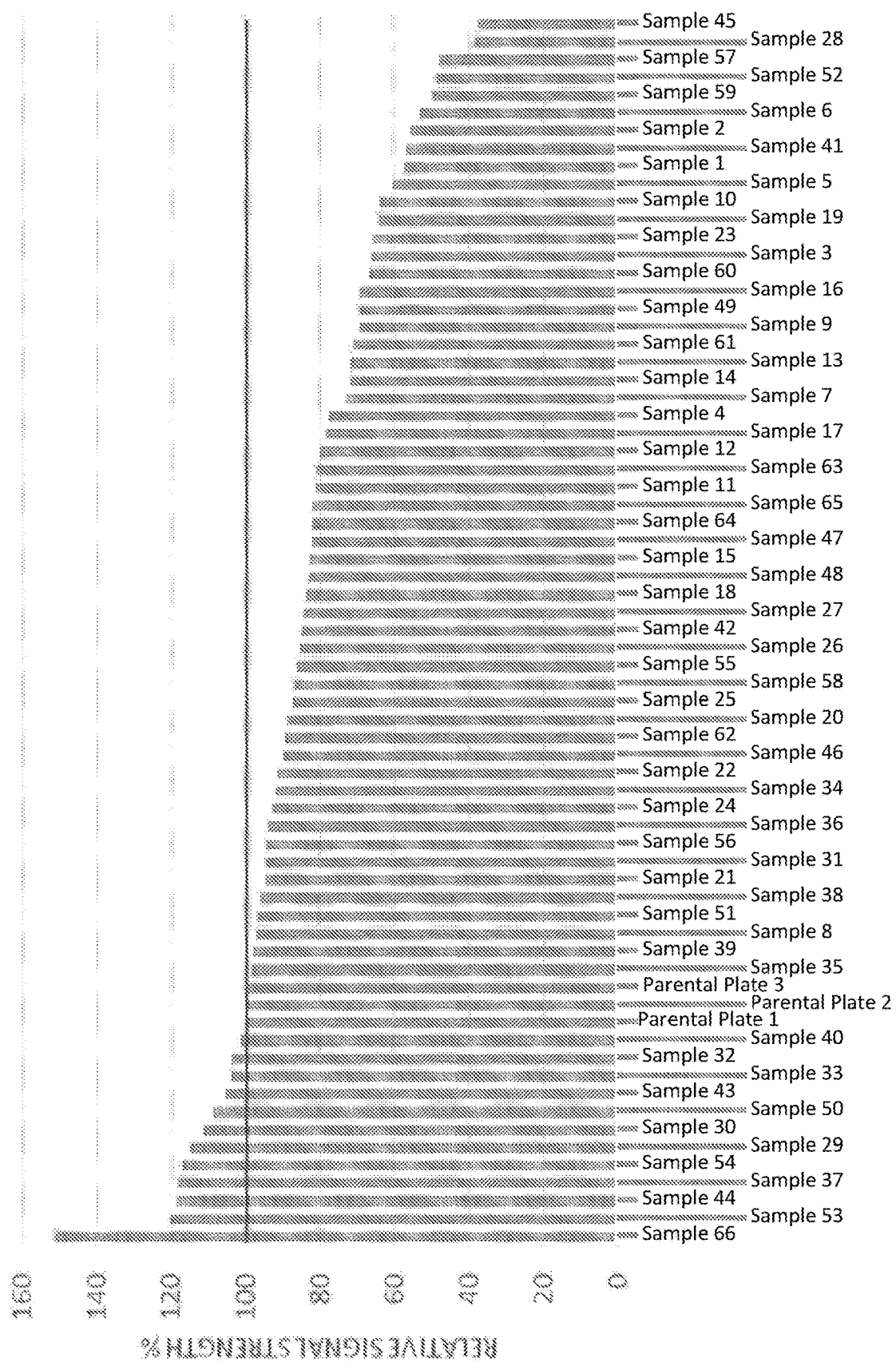
FIG. 4 illustrates an ELISA comparison of each of the expressed variants with the parental Fsn0503h antibody.

Each of the purified variants was analysed by ELISA for binding to recombinant Cathepsin S protein. The results (FIG. 4) show that 12 of the variants have a higher relative OD than the parental Fsn0503h, potentially indicating a higher affinity for the Cathepsin S target.

Affinity Ranking

In order to determine an accurate affinity comparison of each of the variants with the parental Fsn0503h antibody the interactions with Cathepsin S were measured by BLI using an Octet instrument as described in the Methods.

Figure 6:
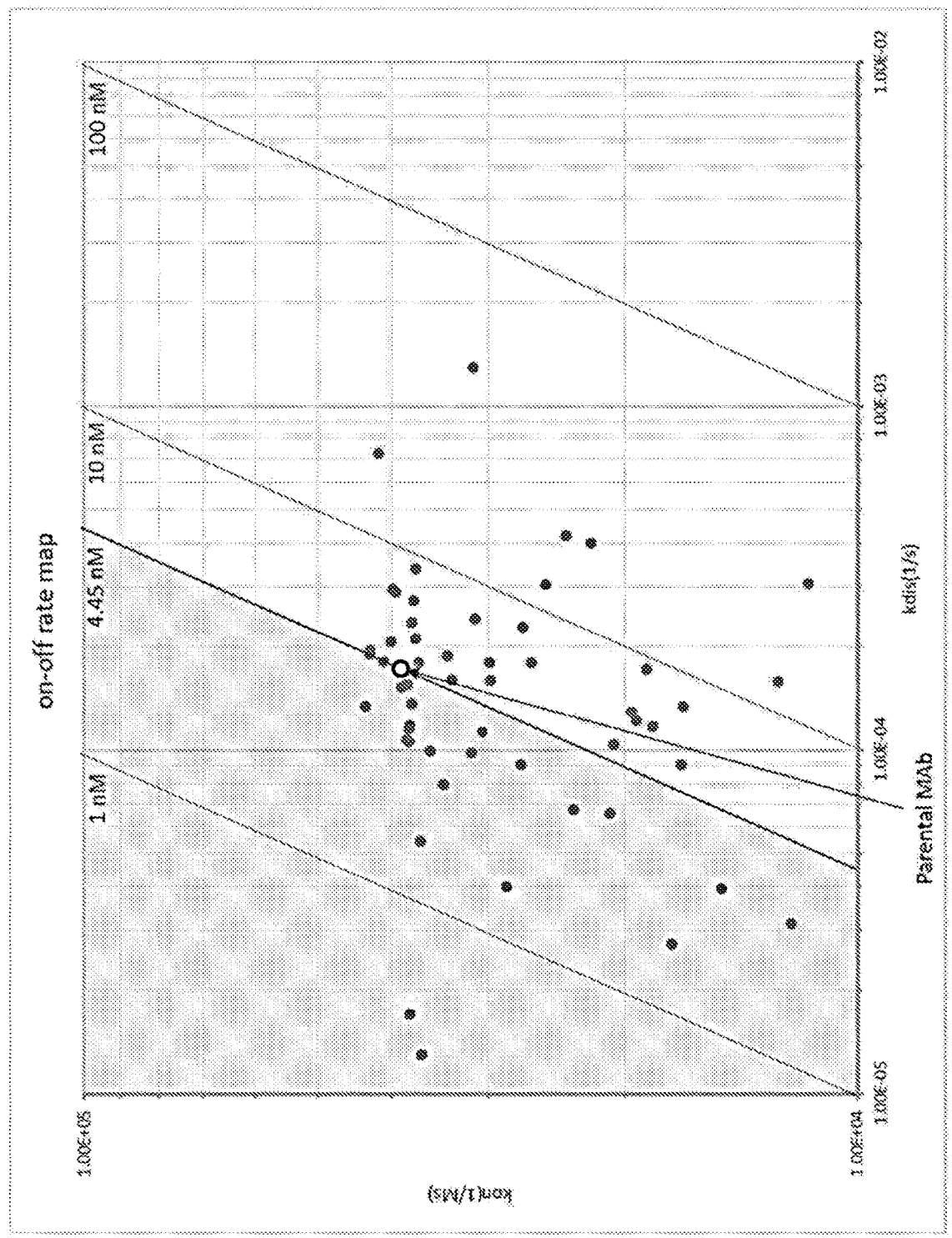
FIG. 6 illustrates an affinity on-off rate map of the variants of Fsn0503h. The parental antibody is shown as the hollow dot. The 4.45 nM line represents equal affinity to the parental antibody, and any variants with an increased affinity (<4.45 nM) are within the area to the left of the 4.45 nM line.

The results show that approximately 50% of the variants have improved affinity when measured against the average reading for the Fsn0503h antibody (FIG. 6). The association (Kon) and dissociation (Kdis) rates are given in FIG. 5.

Influence on Expression

The 66 variants expressed in CHO as described above also demonstrated a range of level of expression relative to the wild type. IgG level was determined by a quantitative human IgG immunoassay on the BLI Octet instrument following purification and expressed the total amount relative to the supernatant volume purified.

Modulation of Melting Point

Figure 22:
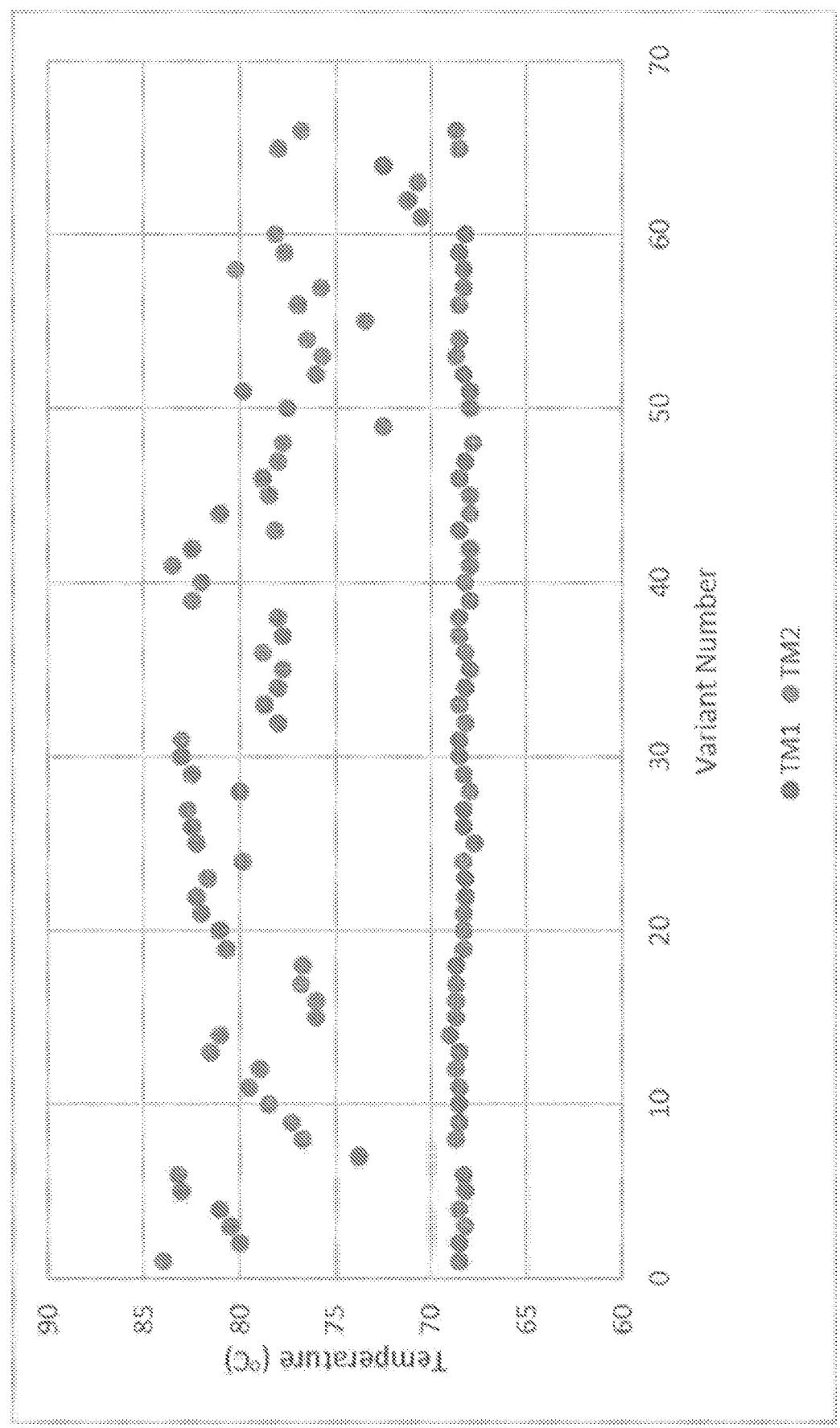
FIG. 22 displays the melting point determination values (TM1 and TM2) of Fsn0503 variants in degrees centigrade. Wild-Type is in position 1.

The 66 variants also demonstrated a range of variation in stability characteristics associated with antibody molecules. This included changes in melting temperature profile at 2 melting points commonly observable in immunoglobulin molecules. The results of melting point determination are shown in FIG. 22. It is noteable that some variants such as Mut 6 and Mut 49 appear to have lost their distinct 2-phase melting pattern, with only a single melting temperature being observable.

Modulation of Monodispersity

Figure 23:
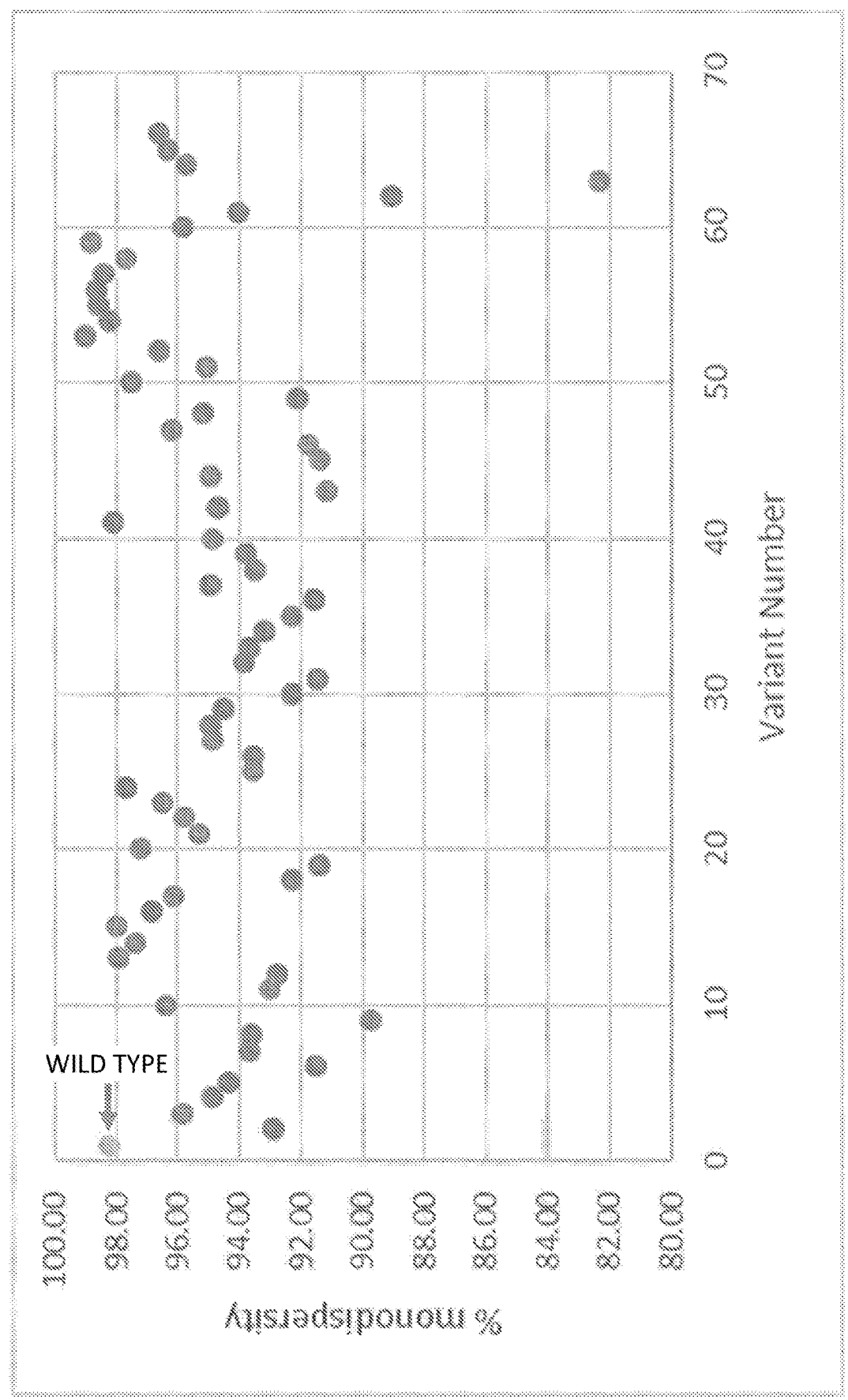
FIG. 23 Shows the measurement of proportion of monodisperse (non-aggregated) molecule of Fsn0503 variants by size-exclusion chromatography. Wild-Type shown in orange.

This characteristic was analysed by analytical size exclusion chromatography of the 66 variants and show a range of values amongst the analysed variants as presented in FIG. 23.

Example 2—Trastuzumab Variants

Library Design

Figure 9:
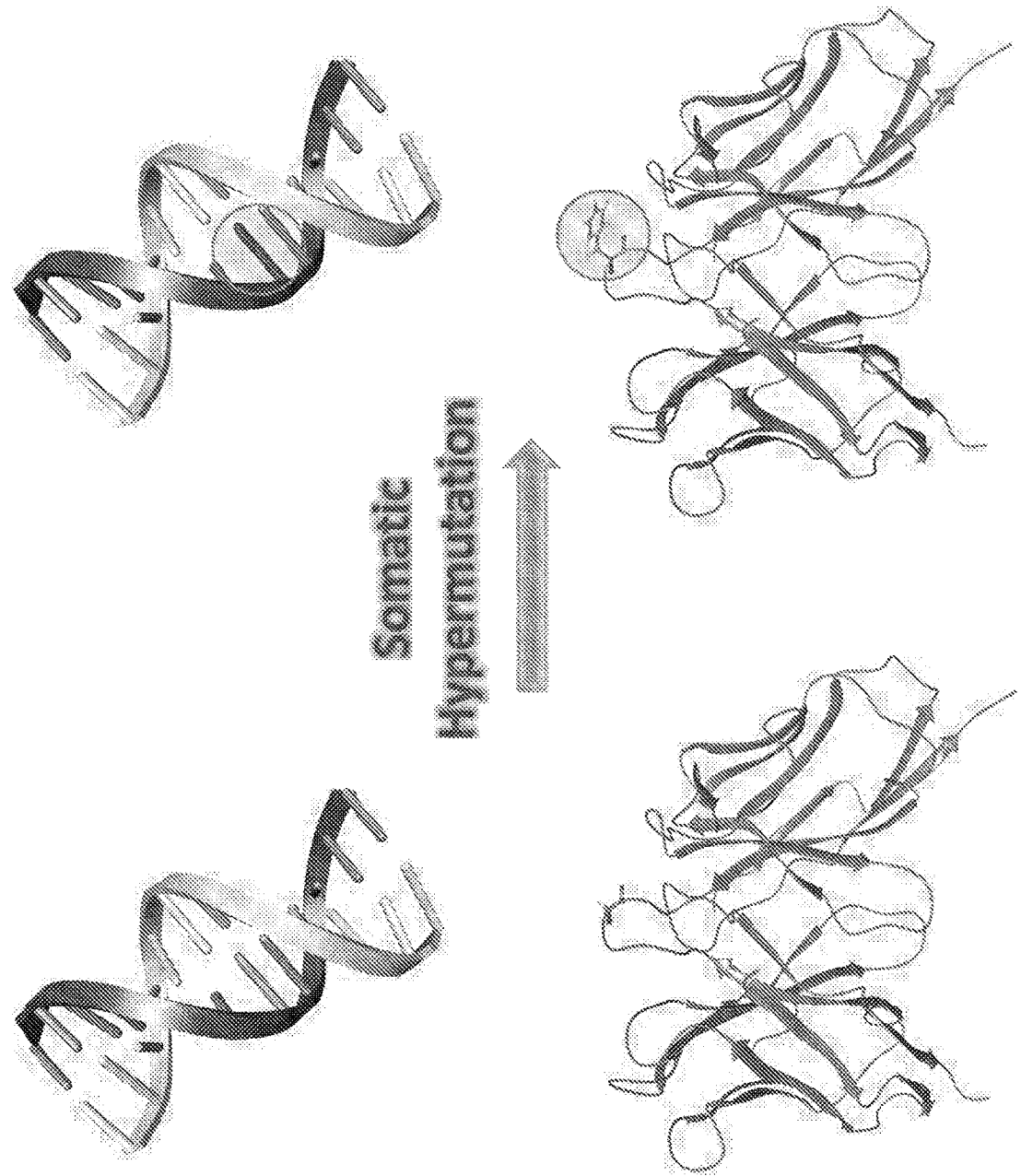
FIG. 9 schematically illustrates how somatic hypermutations may be used to cause alterations to the DNA sequence of antibodies which results in amino acid changes in the protein structure of the antibody leading to enhanced affinity.

A library of antibody variants was produced for trastuzumab based on naturally occurring somatic hypermutation in humans. Using the method described above somatic hypermutation was replicated, producing naturally occurring mutations in the DNA sequence of trastuzumab and subsequently translated to their respective amino acid mutations, as illustrated in FIG. 9. These mutations were compiled into a library of potential mutations at specific sites in both the complementary determining regions (CDRs) as well as in the framework regions (FIGS. 7 and 8), in which potential amino acid results of the method are detailed next to the parental sequence. Any undesirable amino acids or STOP codons generated as a result of the DNA mutations were identified.

Figure 10:
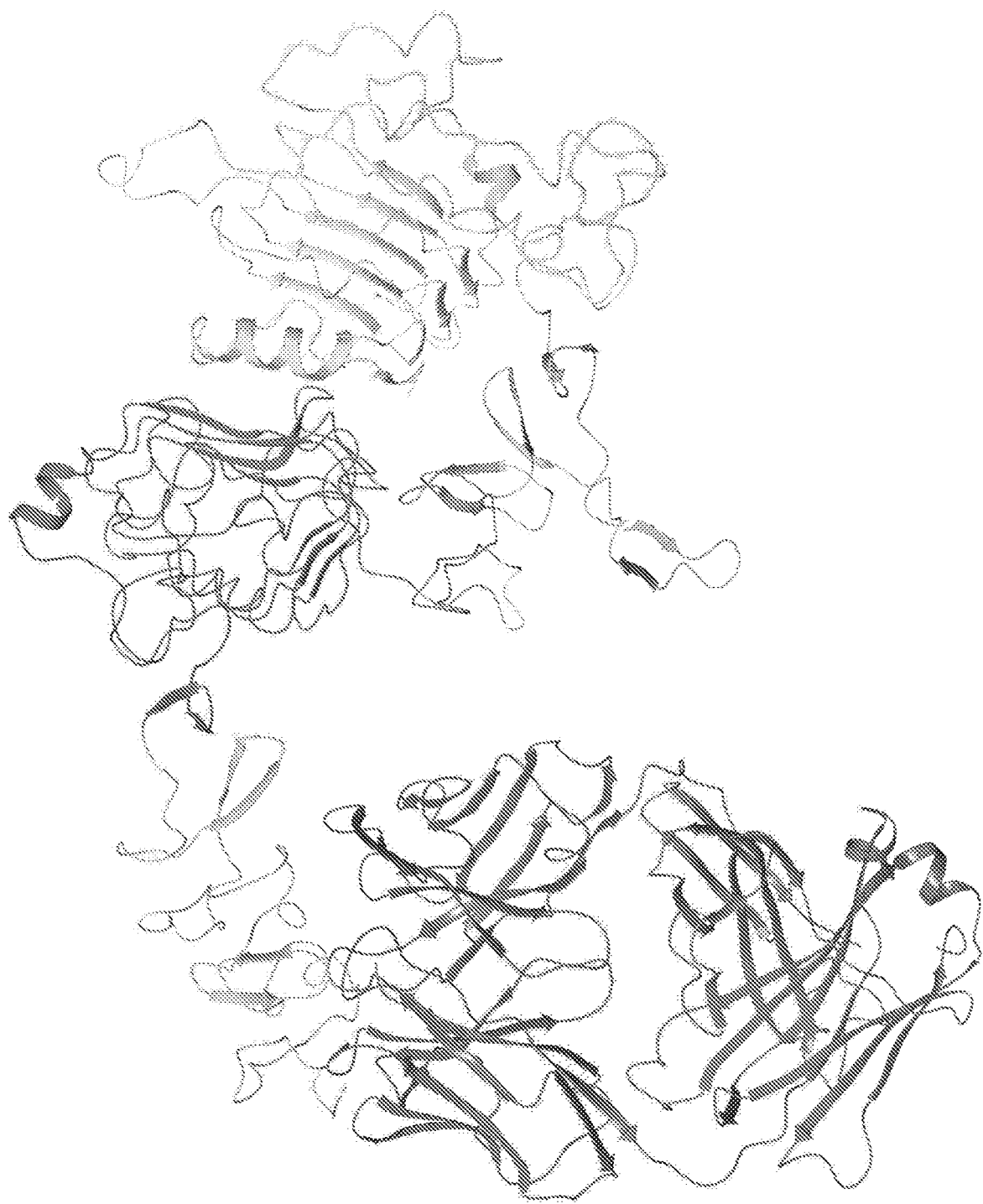
FIG. 10 illustrates the fully resolved crystal structure of trastuzumab in complex with human HER2 which was used to perform residue scanning. Domain IV of the extracellular domain of HER2 was found to bind to trastuzumab.

The fully resolved crystal structure of trastuzumab in complex with the extracellular domain of human epidermal growth factor receptor 2 (HER2) (PDB Code: 1N8Z) is illustrated in FIG. 10. The library of trastuzumab mutations illustrated in FIGS. 7 and 8 was used for mutant scanning. Mutants were scanned consecutively whereby a single amino acid mutation was first analysed, followed by two mutations up until six total mutations in the heavy and light chains and subsequently variants were ranked based on affinity and stability. As with the Fsn503h library, the Schrödinger molecular docking software was used as described in the Methods.

Figure 13C:
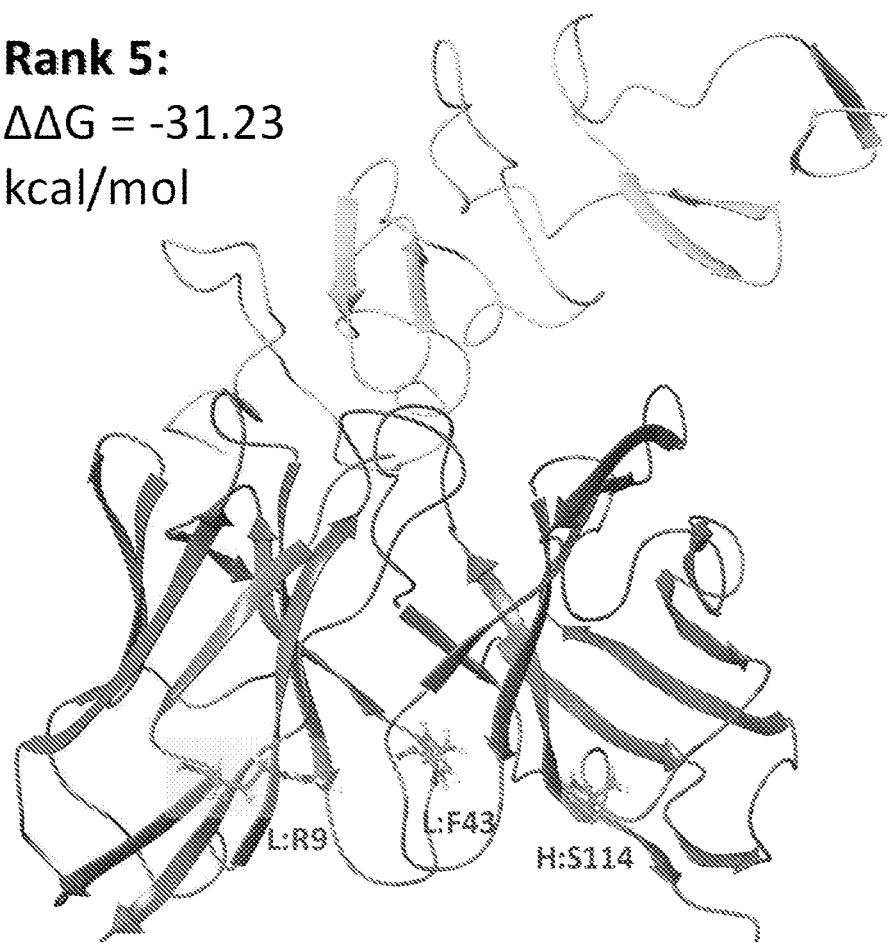
FIG. 13 schematically illustrates the top 5 trastuzumab variants scored based on affinity using the predicted free energy change (MG) in kcal/mol. In the first and third ranked variants there are a total of five mutations, while rank 2 and 4 have four mutations and finally rank 5 contains three amino acid mutations. Domain IV of HER2 where trastuzumab binds is coloured cyan, while the scFv is coloured green and CDRs coloured red. Mutations are highlighted in yellow.

Within the docked structures amino acid residue mutations were introduced and the relative difference in both affinity and stability predicted. The mutations were introduced in increasing numbers until no further benefits to stability or affinity were predicted. The results of the combinatorial mutagenesis are detailed in the tables of FIGS. 11 and 12. A total of 558 potential variants for trastuzumab were found to have both improved affinity and improved stability. The top five ranked affinities for variants are illustrated in FIG. 13. Among these variants, a total of 5 mutations across the heavy and light chains were found to be the most common. The variants were scored relative to the parental antibody affinity using the predicted free energy change ($\Delta\Delta G$).

Off-Rate Ranking

Figure 14:
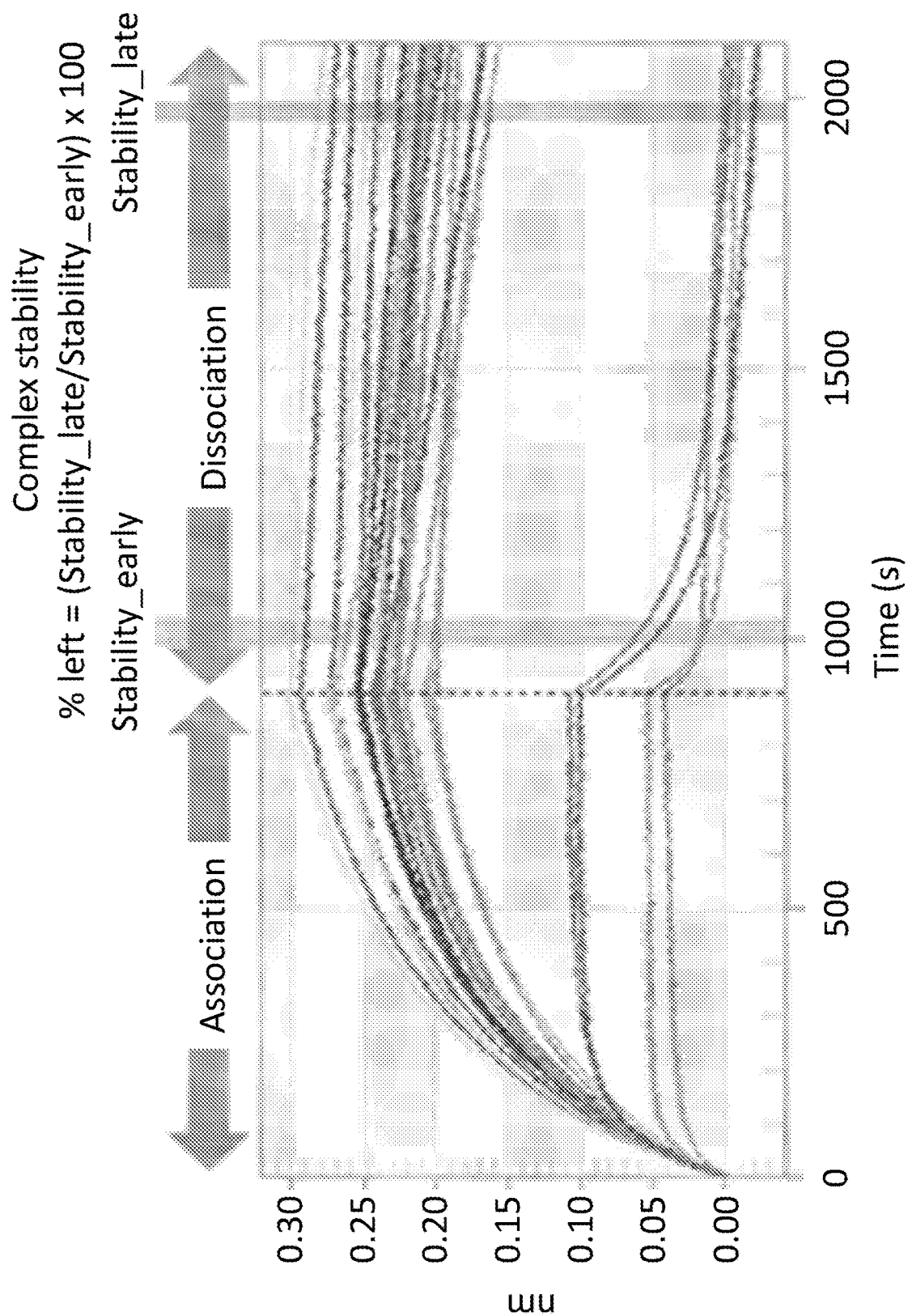
FIG. 14 illustrates sensorgrams from 20 samples showing report points used for ranking. Assay performed at 25° C.
Figure 15:
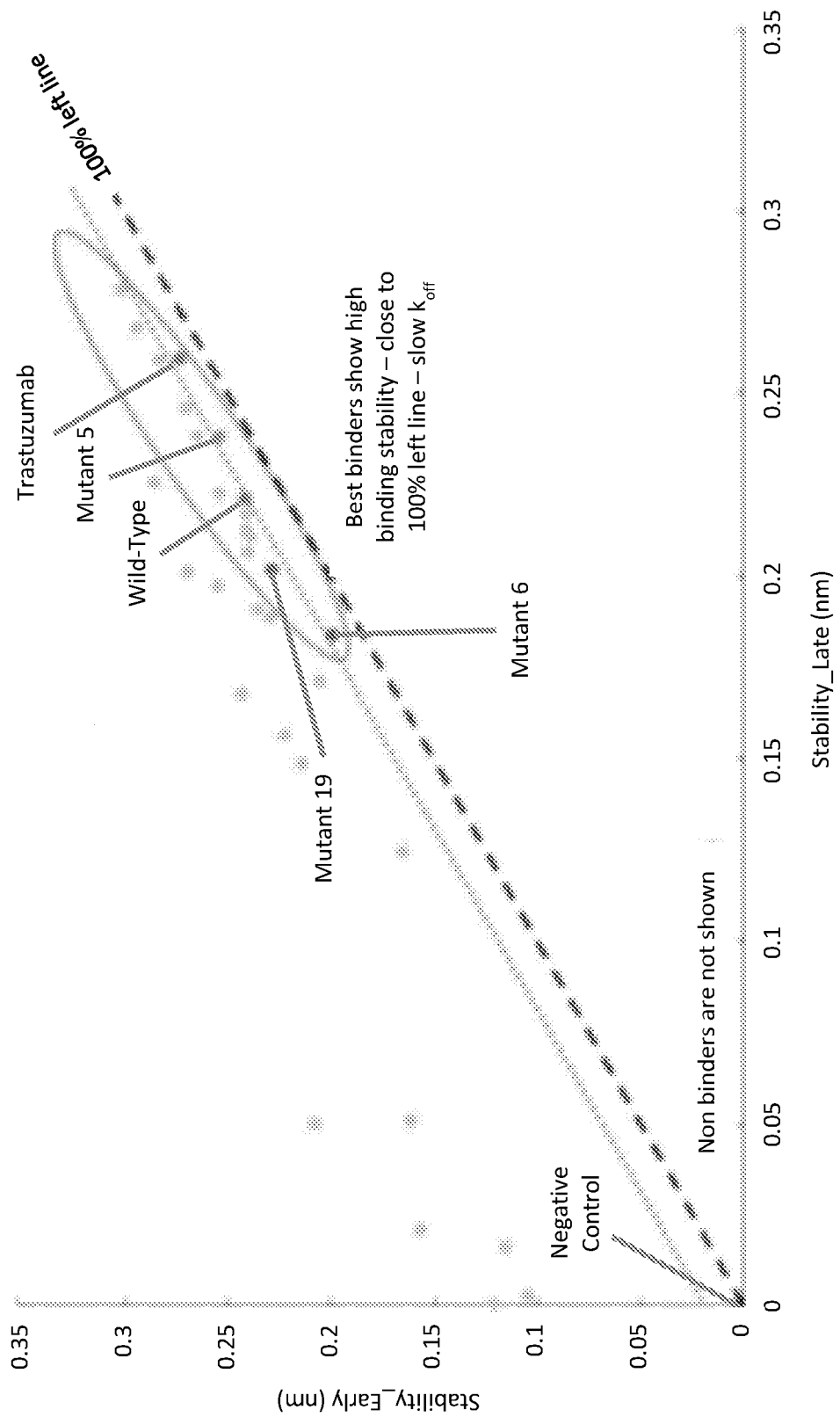
FIG. 15 shows a graph illustrating off-rate ranking of Trastuzumab variants binding to HER2 and shows stability_early vs stability_late for identification of stable binder (best binders circled in blue). In total, 89 samples were analyzed and ranked with respect to binding stability, however for clarity only 29 are shown. Trastuzumab is commercially available antibody material. Wild-Type is antibody having sequence of trastuzumab and transiently expressed in parallel with all Trastuzumab variants/mutants. Mutant is a Trastuzumab variant. Mutants 5, 6 and 19 are trastuzumab variants listed as numbers 5, 6 and 19 in Table 8. Assay performed at 25° C.
Figure 16:
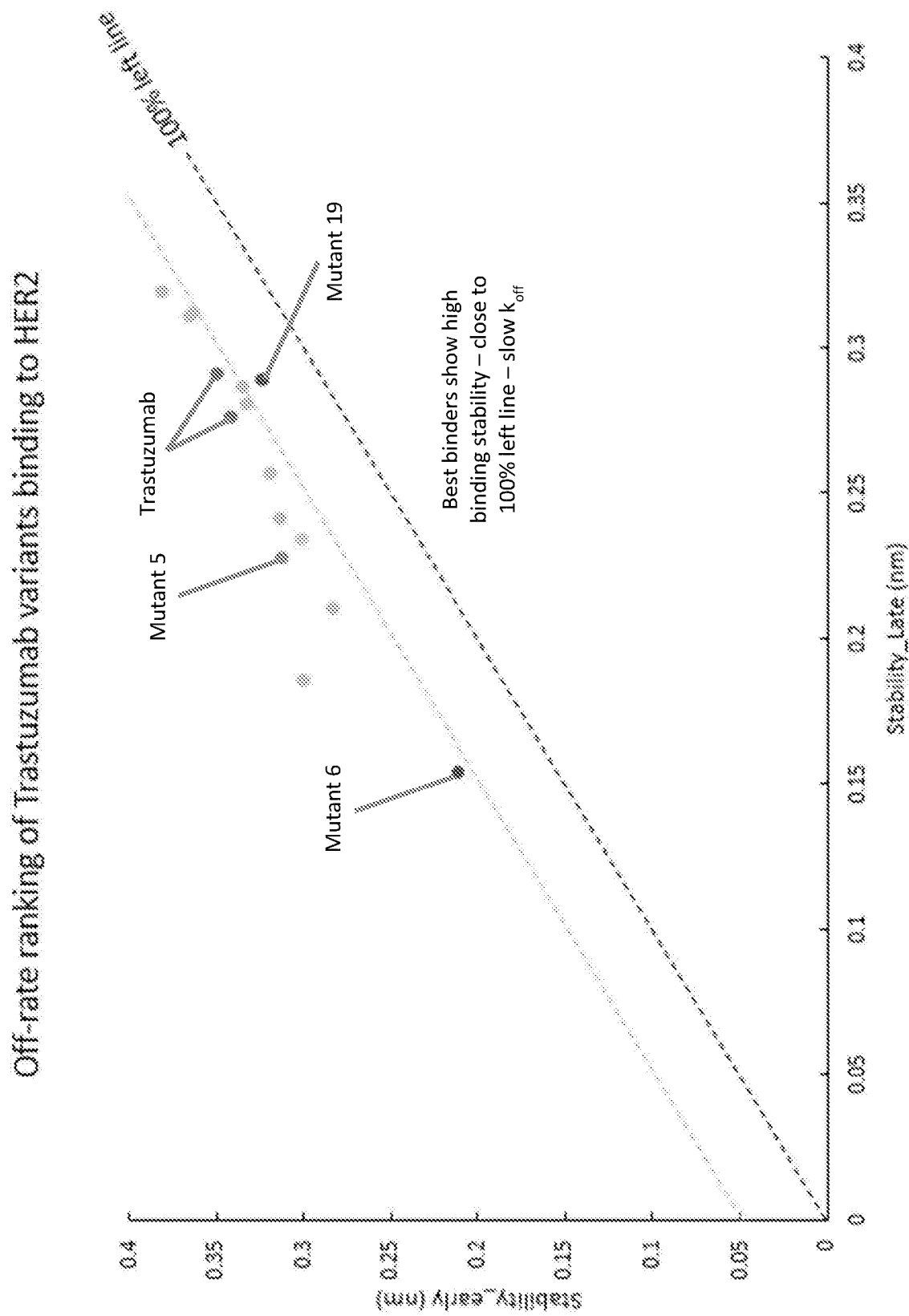
FIG. 16. shows a graph illustrating off-rate ranking of Trastuzumab variants binding to HER2 and shows Stability_early vs stability_late for identification of stable binders from a small sub-set of the top binders shown in FIG. 15 (those binders closest the 100% left line). In total, 14 Trastuzumab variants were analyzed and ranked with respect to binding stability. Trastuzumab is commercially available antibody. Wild-Type is material transiently expressed in parallel with all Trastuzumab variants/mutants. Mutant; is a Trastuzumab variant. Mutants 5, 6 and 19 are trastuzumab variants listed as numbers 5, 6 and 19 in Table 8. Assay performed at 37° C.

A panel of 89 Trastuzuamb variants were screened for binding to the HER2 antigen using biolayer interferometry (see materials and methods for details). Sensorgrams from 20 samples with the report points indicated as colour bars are shown in FIG. 14. FIG. 15 shows a scatterplot of the report points stability_early plotted against stability_late. The best binders (14 in total), with a high binding stability and slow dissociation, are highlighted with a blue circle. The off-rate ranking experiments were repeated for these mutants at 37° C., to provide more biologically relevant data (FIG. 16). Mutant 19 appeared to have enhanced stability compared to that of WT Trastuzumab and was taken forward for kinetic analysis.

KD Determination

Figure 17:
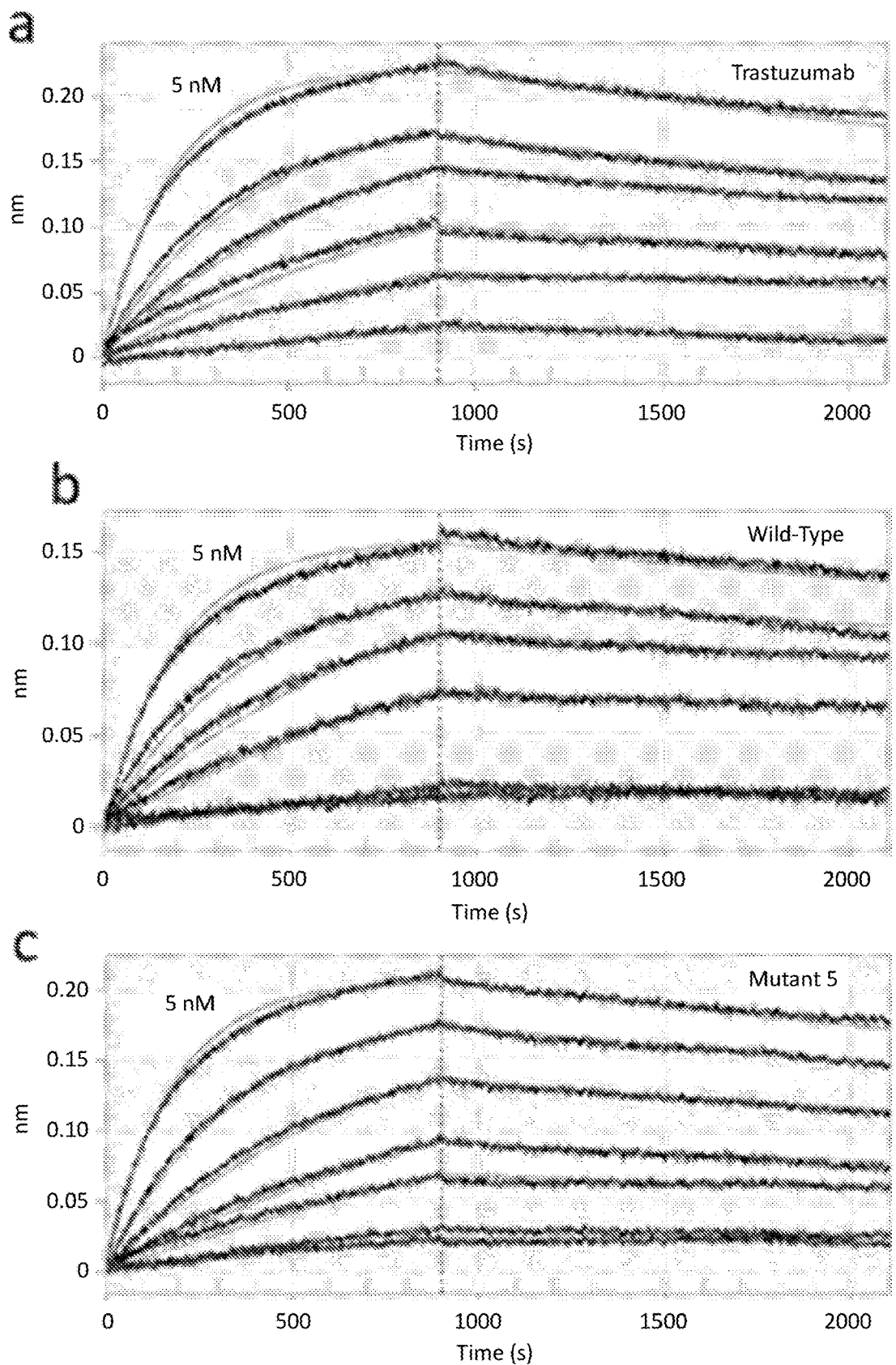
FIG. 17 shows reference corrected BLI binding curves (black), monitored on a surface of non-covalently immobilised Trastuzumab (a), wild-type (b), mutant 5 (c) and (d) mutant 19 antibodies, for various HER2 concentrations (serial diluted two-fold; highest concentration shown on curve) at 37° C. in running buffer. The apparent dissociation rate constant (kd) and association rate ($k_a$) constants were determined by globally fitting (red) a simple 1:1 interaction model, A+B=AB, to the sensorgrams using the software supplied with the instrument. Global fitting results are summarised in table 9.
Figure 17:
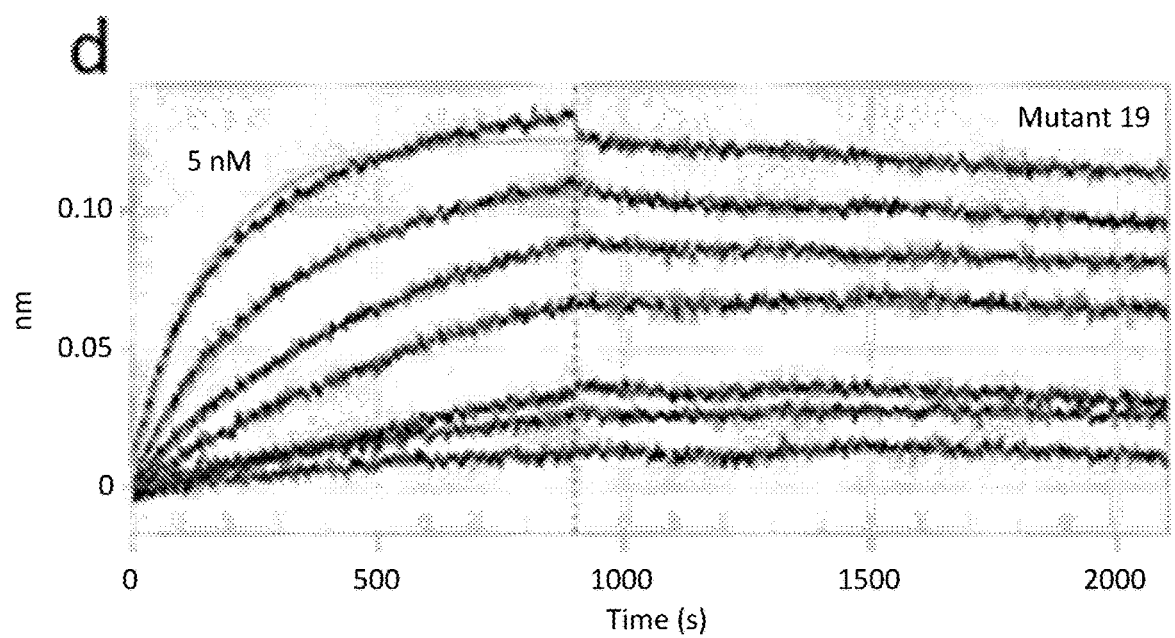
Figure 18:
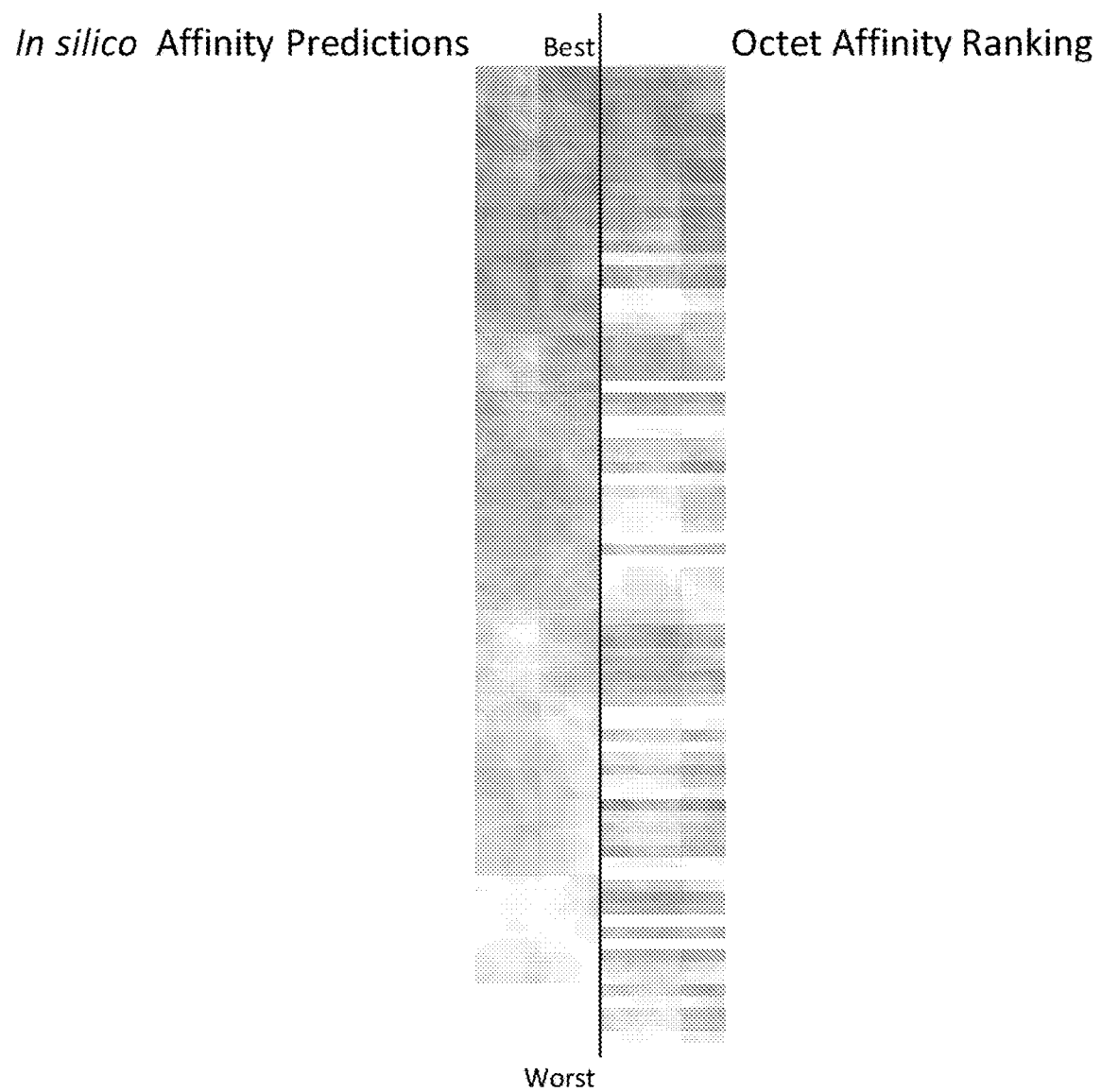
FIG. 18 illustrates schematically the correlation between affinity prediction and measurement for trastuzumab variants.

All samples were diluted in freshly prepared running buffer. Either Trastuzumab or a variant (Mutant) were immobilised onto the surface of a series of biosensors using the capture methods described (see materials and methods). HER2 was passed over the surface to generate a binding response. Binding data for the HER2 interactions were collected at 37° C. on the biosensors. A dilution series of the HER2 antigen (5 nM-0.078 nM) was used in the association step, in order to fit results globally and get the best values for $k_a$, $k_d$, and $K_D$. The response data for the binding of antigen to the surface immobilised IgG were fitted to a 1:1 binding model, yielding the data traces (red—see FIG. 17). The experiments were performed in duplicate and the average kinetic parameters are summarised in Table 9. For example, the data shows that Mutant 19 exhibits an apparent ~2-fold affinity increase compared with that of the wild-type control and commercial Trastuzumab. The increase in affinity is primarily due to the slower Kd, 6.04E-05 compared to 1.20E-04 for the wild-type antibody. FIG. 18 schematically shows a comparison of actual versus predicted affinity for tratuzumab variants selected by in silico predictions of improved affinity and stability. Actual Octet affinity ranking correlates reasonably well for the top 20 predictions

TABLE 9

Kinetic parameters (fit to 1:1 interaction model) for Trastuzumab variants and HER2 interaction

| Name | $K_D$ (pM) | $k_a$ ($m^{-1}s^{-1}$) | $k_d$ ($s^{-1}$) | $R^2$ | $X^2$ | Mean Rmax |
|---|---|---|---|---|---|---|
| Trastuzumab | 192 ± 21 | 1.10E+06 ± 4.50E+04 | 2.12E-04 ± 3.15E-05 | 0.9960 | 0.2185 | 0.2112 |
| HER2 WT | 126 ± 6 | 1.01E+06 ± 1.85E+04 | 1.28E-04 ± 7.50E-06 | 0.9946 | 0.1283 | 0.1693 |
| MUT 5 | 139 ± 5 | 1.05E+06 ± 5.00E+04 | 1.46E-04 ± 1.50E-06 | 0.9977 | 0.1395 | 0.2553 |
| MUT 19 | 52 ± 16 | 1.12E+06 ± 1.30E+05 | 6.04E-05 ± 2.47E-05 | 0.9958 | 0.0984 | 0.1405 |

$R^2$ values indicate how well the fit and experimental data correlate and above 0.95 are considered a good fit; $X^2$ is the sum of the squared deviation should be generally below 3 $X^2$ is the measure of error between the experimental data and the fitted line. The smaller the $X^2$ indicates a better fit.

Monomeric KD Determination

In order to further verify the affinity of the top variants and to understand the contribution of avidity to the measurement of affinity within the top 2 variants (MUT 5 and MUT 19), these molecules were prepared by enzymatic cleavage as Fragment Antigen Binding (Fab) fragments, consisting of the variable domain and CH1 constant domain of the heavy and light chain, in a monomeric form, with a single antigen binding domain per molecule.

Figure 19:
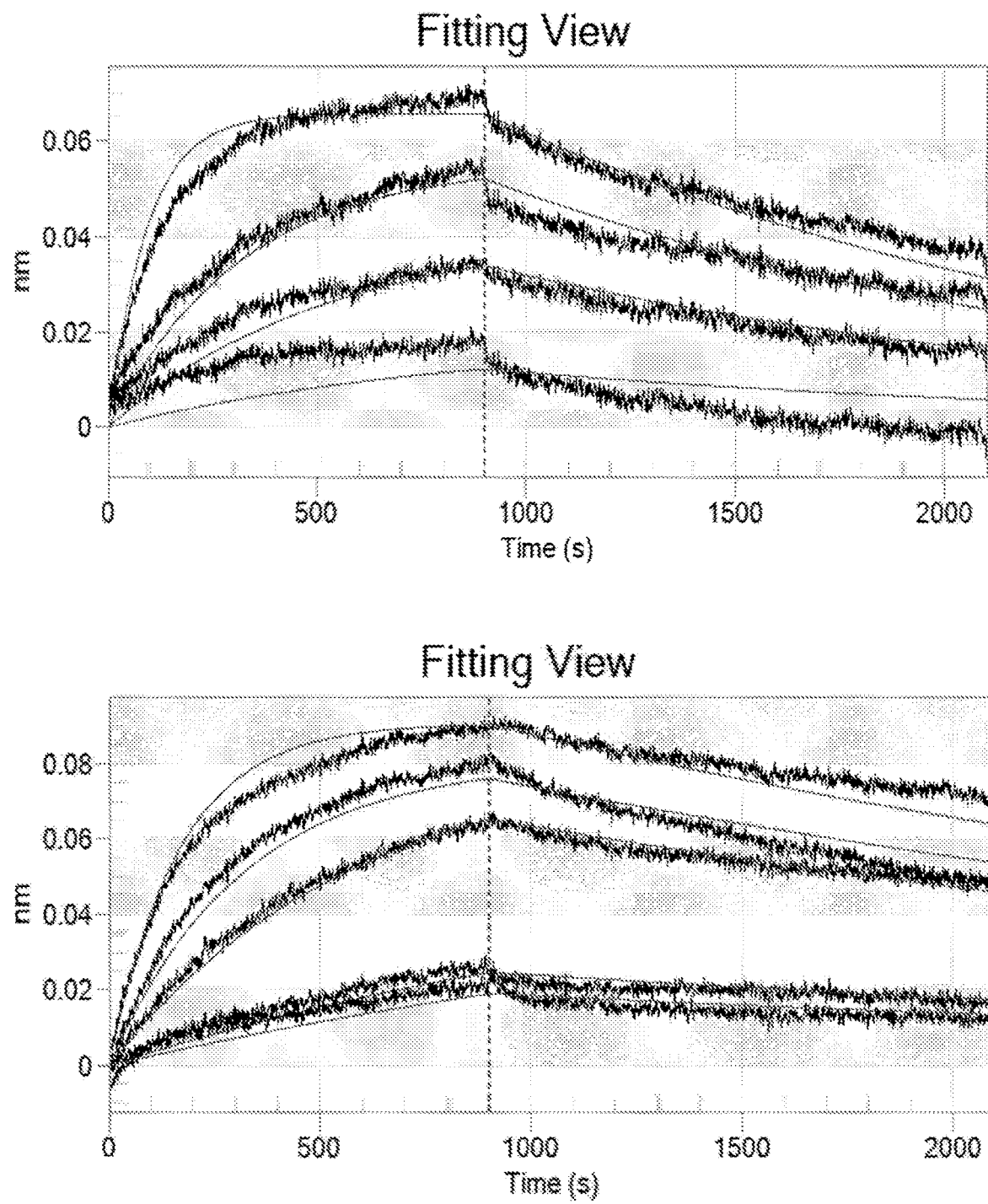
FIG. 19 shows blank corrected BLI binding curves (black), monitored on a surface of non-covalently immobilised HER2 at a range of concentrations of wild-type (a), mutant 5 (b) and (c) mutant 19 antibodies, at 37° C. in running buffer. The apparent dissociation rate constant (kd) and association rate ($k_a$) constants were determined by globally fitting (red) a simple 1:1 interaction model, A+B=AB, to the sensorgrams using the software supplied with the instrument. Global fitting results are summarised in table 10.
Figure 19:
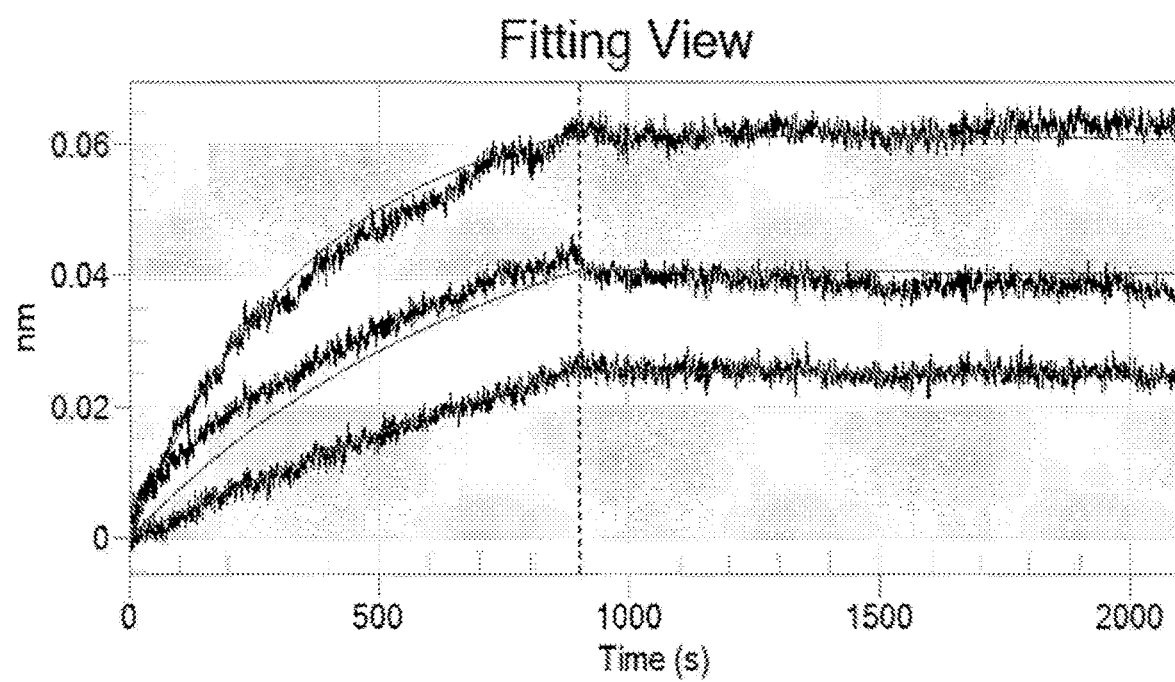

An initial measurement was made after coating the probes with 2.5 µg/ml biotinylated Her2-recombinant Fc fusion protein. A range of concentrations of each of the 3 monomeric antibodies were assessed for binding to the Her2 surface. In this case double-referencing was not applied. The sensorgram data is shown in FIG. 19 and resulting kinetic calculations (on a 1:1 model) are listed in Table 10.

TABLE 10

Kinetic parameters (fit to 1:1 interaction model) for Trastuzumab variants as monomeric Fab and HER2 interaction at a HER2 coating concentration of 2.5 µg/ml

| Antibody | Capture level (nm) | $k_a$ ($m^{-1}s^{-1}$) | $k_d$ ($s^{-1}$) | $K_D$ (M) | $K_D$ (pM) | $K_D$ Steady State | $R^2$ | $X^2$ | Mean $R_{max}$ |
|---|---|---|---|---|---|---|---|---|---|
| WT (4) | 0.719 | 2.05E+06 | 6.17E-04 | 3.01E-10 | 300 | 6.40E-10 | 0.9513 | 0.141 | 0.059 |
| Mut 5 (5) | 0.853 | 1.14E+06 | 2.90E-04 | 2.56E-10 | 256 | 1.20E-10 | 0.9856 | 0.107 | 0.106 |
| Mut 19 (3) | 0.676 | 2.17E+06 | 1.13E-05 | 5.20E-12 | 5.2 | 1.00E-10 | 0.9848 | 0.0289 | 0.061 |

Figure 20:
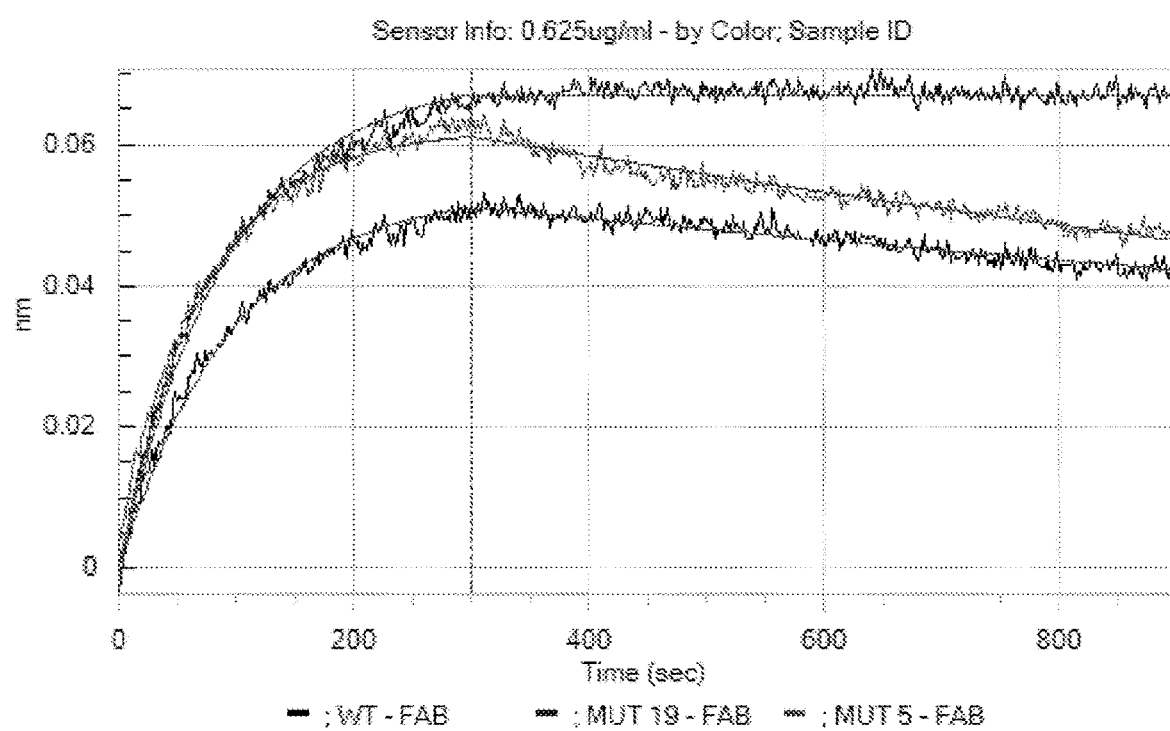
FIG. 20 shows double-reference corrected BLI binding curves (black), monitored on a surface of non-covalently immobilised HER2 at coated at a range of concentrations, presented to a concentration of wild-type (a), mutant 5 (b) and (c) mutant 19 antibodies, at 37° C. in running buffer. The apparent dissociation rate constant ($k_d$) and association rate ($k_a$) constants were determined by globally fitting (red) a simple 1:1 interaction model, A+B=AB, to the sensorgrams using the software supplied with the instrument. Global fitting results are summarised in tables 11, 12 and 13.
Figure 21:
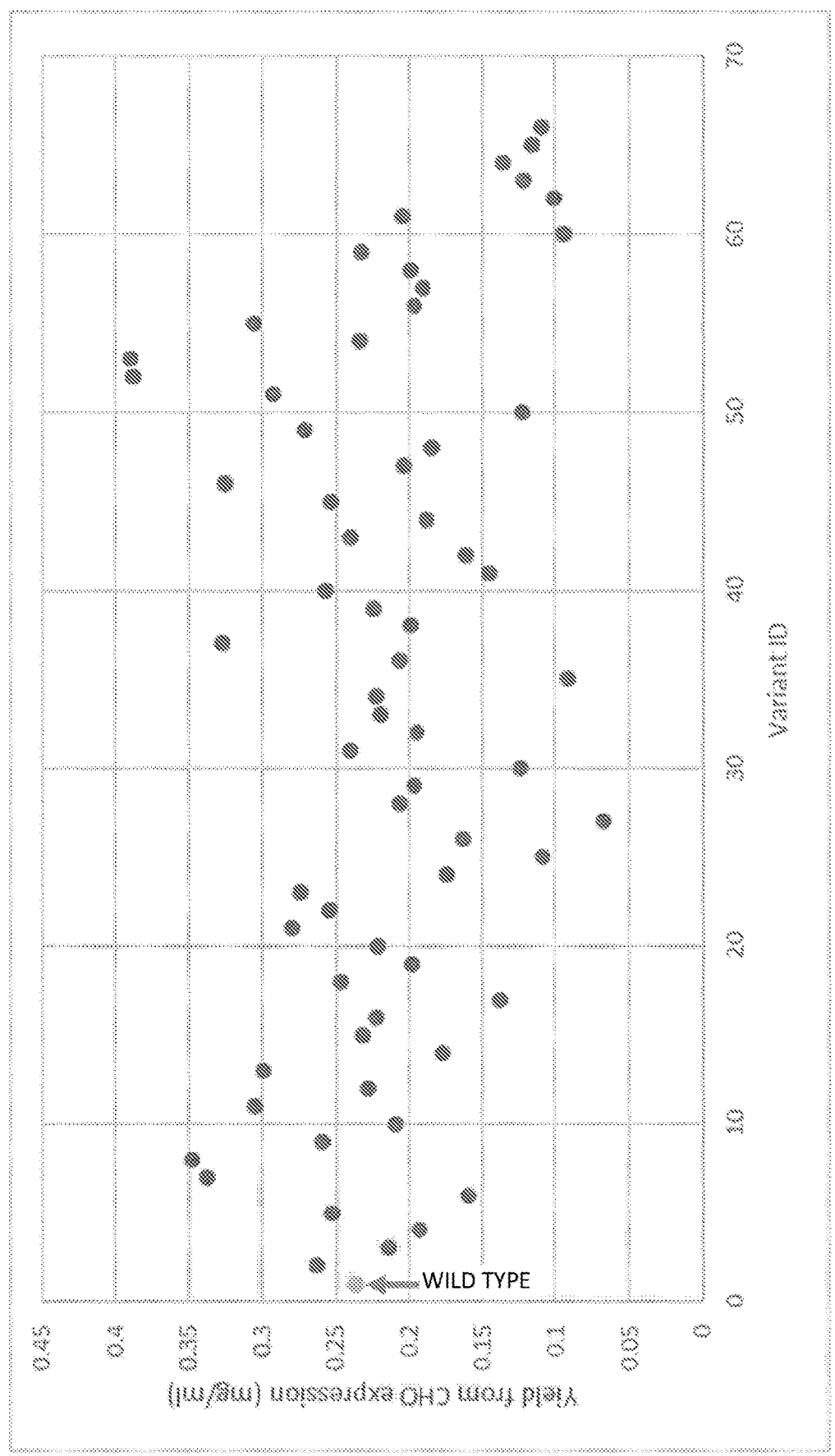
FIG. 21 displays the Expression yield of Fsn0503 variants expressed as mg of purified IgG by Octet immunoassay obtained per ml of transfected CHO supernatant. Wild-Type shown in orange.

Sensors were then prepared by coating with 0.625, 1.25 or 2.5 μg/ml of biotinylated Her2-recombinant Fc fusion protein. The purified Fab fragments were then tested for their binding to these probes. The sensorgram traces are shown in FIG. 20 for these measurements, with details shown in Tables 11, 12 and 13. This data was double-referenced to exclude any drift due to non-specific interactions at the probe surface, unlike the previous experiment.

TABLE 11

Kinetic parameters (fit to 1:1 interaction model) for Trastuzumab variants as monomeric Fab and HER2 interaction at a HER2 coating concentration of 2.5 μg/ml (double-referenced)

| Sample | $K_D$ | $K_D$ Error | $K_{ON}$ | $K_{ON}$ Error | $K_{OFF}$ | $K_{OFF}$ Error | $R^2$ | $X^2$ | $R_{MAX}$ |
|---|---|---|---|---|---|---|---|---|---|
| WT | 2.86E−10 | <1.0E−12 | 1.18E 06 | 5.34E−65 | 3.37E−04 | <1.0E−07 | 0.9938 | 0.0012 | 0.0921 |
| MUT 19 | 1.88E−10 | 2.74E+56 | 1.19E+06 | 3.24E+68 | 2.22E−04 | 3.24E+62 | 0.9959 | 0.0014 | 0.1157 |
| MUT 5 | 3.55E−10 | <1.0E−12 | 1.29E+06 | 2.94E−65 | 4.59E−04 | <1.0E−07 | 0.9872 | 0.0035 | 0.1138 |

TABLE 12

Kinetic parameters (fit to 1:1 interaction model) for Trastuzumab variants as monomeric Fab and HER2 interaction at a HER2 coating concentration of 1.25 μg/ml (double-referenced)

| Sample | $K_D$ | $K_D$ Error | $K_{ON}$ | $K_{ON}$ Error | $K_{OFF}$ | $K_{OFF}$ Error | $R^2$ | $X^2$ | $R_{MAX}$ |
|---|---|---|---|---|---|---|---|---|---|
| WT | 3.12E−10 | <1.0E−12 | 1.10E+06 | 1.73E−65 | 3.43E−04 | <1.0E−07 | 0.9908 | 0.0012 | 0.0717 |
| MUT 19 | 1.68E−10 | 3.79E+56 | 1.03E+06 | 3.91E+68 | 1.73E−04 | 3.91E+62 | 0.9914 | 0.0021 | 0.0917 |
| MUT 5 | 4.50E−10 | <1.0E−12 | 1.26E+06 | 2.24E−65 | 5.67E−04 | <1.0E−07 | 0.9883 | 0.0021 | 0.0904 |

TABLE 13

Kinetic parameters (fit to 1:1 interaction model) for Trastuzumab variants as monomeric Fab and HER2 interaction at a HER2 coating concentration of 0.625 μg/ml (double-referenced)

| Sample | $K_D$ | $K_D$ Error | $K_{ON}$ | $K_{ON}$ Error | $K_{OFF}$ | $K_{OFF}$ Error | $R^2$ | $X^2$ | $R_{MAX}$ |
|---|---|---|---|---|---|---|---|---|---|
| WT | 3.15E−10 | <1.0E−12 | 1.00E+06 | 1.79E−65 | 3.16E−04 | <1.0E−07 | 0.9831 | 0.0013 | 0.0552 |
| MUT 19 | <1.0E−12 | <1.0E−12 | 1.08E+06 | 1.94E−62 | <1.0E−07 | N/A | 0.9894 | 0.0017 | 0.0698 |
| MUT 5 | 3.40E−10 | <1.0E−12 | 1.34E+06 | 2.10E−65 | 4.57E−04 | <1.0E−07 | 0.9787 | 0.0018 | 0.0642 |

The affinity value appears to vary as a result of coating concentration so it is difficult to assign a definitive value for the increase in affinity for MUT 5 and MUT 19 compared to the WT Trastuzemab molecule from these monomeric analysis. Without wishing to be bound by theory, this is thought to be due to the problem of working at the limits of sensitivity of the FortéBio Octet Biosensor instrument.

Conclusion

Using the methods of the present invention, the inventors have successfully demonstrated that the affinity of an antibody for its target can be improved without the need to generate a very large physical library of antibody variants and subsequent selection/screening process. In addition, a pool of variants are generated which, upon expression, display a range of attributes of interest including affinity, expression level and physiochemical characteristics, which are all of interest to the potential developability of an antibody molecule.

Although the invention has been particularly shown and described with reference to particular examples, it will be understood by those skilled in the art that various changes in the form and details may be made therein without departing from the scope of the present invention.

The invention claimed is:

1. A method of generating/producing a library of variant antibody molecules, wherein said variant antibody molecules are variants of a reference antibody, said method comprising the steps:
   a) providing a nucleotide sequence encoding the reference antibody,
   b) in said nucleotide sequence, identifying one or more DNA motifs susceptible to deamination by Activation-Induced Deaminase (AID), wherein said one or more DNA motifs is DGYW or WRCH, wherein D is adenine, guanine, or thymine, R is adenine or guanine G is guanine C is cytosine H is adenine cytosine, or thymine, W is adenine or thymine, and Y is cytosine or thymine;
   c) for one or more of said DNA motifs of which at least one is in a nucleotide sequence encoding a framework region, selecting at least one variant nucleotide residue to substitute for a residue of said DNA motif, wherein said substitution will result in a variant nucleotide sequence which encodes a variant antibody molecule having, relative to the reference antibody, a change in the amino acid sequence being encoded by said DNA motif, and wherein at least one of said residues substituted with at least one variant nucleotide residue is in a codon which encodes an amino acid of a framework region; and
   d) repeating steps (b) and (c);
   such that a library containing a plurality of variants of said reference antibody is generated.

2. The method according to claim 1, wherein said method further comprises screening said library of variants to determine binding to an epitope to which the reference antibody binds, and using those variants determined to bind to said epitope with at least one of an affinity or a stability greater than a predetermined value relative to the reference antibody to generate an optimized library of variant antibody molecules.

3. The method according to claim 1, wherein said method is a computer implemented method.

4. The method according to claim 1, further comprising synthesizing the variant antibody molecules.

5. The method according to claim 1, wherein the reference antibody is trastuzumab or the anti Cathepsin S antibody Fsn0503h.

6. The method according to claim 1, wherein, in step (c), said selecting step is performed for at least two of said DNA motifs, of which each of the at least two is independently in a nucleotide sequence encoding a framework region, which may be the same or a different framework region of the variant antibody molecule.

7. The method according to claim 1, wherein all of said DNA motifs are in DNA sequences which encode framework regions of said antibody molecule.

8. The method according to claim 1 wherein one or more of said DNA motifs are in DNA sequences which encode CDRs of said antibody molecule.

* * * * *

SEQUENCE LISTING

<160> NUMBER OF SEQ ID NOS: 4

<210> SEQ ID NO 1

```
<211> LENGTH: 112
<212> TYPE: PRT
<213> ORGANISM: Artificial Sequence
<220> FEATURE:
<223> OTHER INFORMATION: Fsn0503h antibody light chain
<220> FEATURE:
<221> NAME/KEY: MISC_FEATURE
<222> LOCATION: (12)..(12)
<223> OTHER INFORMATION: Xaa is Thr, Ser, Ala or Pro
<220> FEATURE:
<221> NAME/KEY: MISC_FEATURE
<222> LOCATION: (18)..(18)
<223> OTHER INFORMATION: Xaa is Thr, Ser, Ala or Pro
<220> FEATURE:
<221> NAME/KEY: MISC_FEATURE
<222> LOCATION: (19)..(19)
<223> OTHER INFORMATION: Xaa is Asp, Val, Gly or Ala
<220> FEATURE:
<221> NAME/KEY: MISC_FEATURE
<222> LOCATION: (28)..(28)
<223> OTHER INFORMATION: Xaa is Arg or Ser
<220> FEATURE:
<221> NAME/KEY: MISC_FEATURE
<222> LOCATION: (32)..(32)
<223> OTHER INFORMATION: Xaa is Asn, Ile, Thr or Ser
<220> FEATURE:
<221> NAME/KEY: MISC_FEATURE
<222> LOCATION: (40)..(40)
<223> OTHER INFORMATION: Xaa is Cys or Trp
<220> FEATURE:
<221> NAME/KEY: MISC_FEATURE
<222> LOCATION: (45)..(45)
<223> OTHER INFORMATION: Xaa is Thr, Ser, Ala or Pro
<220> FEATURE:
<221> NAME/KEY: MISC_FEATURE
<222> LOCATION: (50)..(50)
<223> OTHER INFORMATION: Xaa is His or Gln
<220> FEATURE:
<221> NAME/KEY: MISC_FEATURE
<222> LOCATION: (51)..(51)
<223> OTHER INFORMATION: Xaa is Ile, Phe, Val or Leu
<220> FEATURE:
<221> NAME/KEY: MISC_FEATURE
<222> LOCATION: (56)..(56)
<223> OTHER INFORMATION: Xaa is Ile, Phe, Leu or Val
<220> FEATURE:
<221> NAME/KEY: MISC_FEATURE
<222> LOCATION: (58)..(58)
<223> OTHER INFORMATION: Xaa is Lys or Asn
<220> FEATURE:
<221> NAME/KEY: MISC_FEATURE
<222> LOCATION: (66)..(66)
<223> OTHER INFORMATION: Xaa is Ser or Arg
<220> FEATURE:
<221> NAME/KEY: MISC_FEATURE
<222> LOCATION: (69)..(69)
<223> OTHER INFORMATION: Xaa is Asp, Val, Ala or Gly
<220> FEATURE:
<221> NAME/KEY: MISC_FEATURE
<222> LOCATION: (81)..(81)
<223> OTHER INFORMATION: Xaa is Asn, Ile, Thr or Ser
<220> FEATURE:
<221> NAME/KEY: MISC_FEATURE
<222> LOCATION: (85)..(85)
<223> OTHER INFORMATION: Xaa is Thr, Ser, Pro or Ala
<220> FEATURE:
<221> NAME/KEY: MISC_FEATURE
<222> LOCATION: (90)..(90)
<223> OTHER INFORMATION: Xaa is Ile, Phe, Leu or Val
<220> FEATURE:
<221> NAME/KEY: MISC_FEATURE
<222> LOCATION: (93)..(93)
<223> OTHER INFORMATION: Xaa is Trp or Cys
<220> FEATURE:
<221> NAME/KEY: MISC_FEATURE
<222> LOCATION: (96)..(96)
<223> OTHER INFORMATION: Xaa is Asn, Ile, Ser or Thr
<220> FEATURE:
<221> NAME/KEY: MISC_FEATURE
```

<222> LOCATION: (108)..(108)
<223> OTHER INFORMATION: Xaa is Asn or Lys

<400> SEQUENCE: 1

Asp Val Val Met Thr Gln Ser Pro Leu Ser Leu Xaa Val Thr Leu Gly
1               5                   10                  15

Gln Xaa Xaa Ser Ile Ser Cys Arg Ser Ser Gln Xaa Leu Val His Xaa
            20                  25                  30

Asn Gly Asn Thr Tyr Leu His Xaa Tyr Leu Gln Lys Xaa Gly Gln Ser
        35                  40                  45

Pro Xaa Xaa Leu Ile Tyr Lys Xaa Ser Xaa Arg Phe Ser Gly Val Pro
    50                  55                  60

Asp Xaa Phe Ser Xaa Ser Gly Ser Gly Thr Asp Phe Thr Leu Lys Ile
65                  70                  75                  80

Xaa Arg Val Glu Xaa Glu Asp Val Gly Xaa Tyr Tyr Xaa Ser Gln Xaa
                85                  90                  95

Thr His Val Pro Pro Thr Phe Gly Gln Gly Thr Xaa Leu Glu Ile Lys
            100                 105                 110

<210> SEQ ID NO 2
<211> LENGTH: 115
<212> TYPE: PRT
<213> ORGANISM: Artificial Sequence
<220> FEATURE:
<223> OTHER INFORMATION: Fsn0503h antibody heavy chain
<220> FEATURE:
<221> NAME/KEY: MISC_FEATURE
<222> LOCATION: (3)..(3)
<223> OTHER INFORMATION: Xaa is His or Gln
<220> FEATURE:
<221> NAME/KEY: MISC_FEATURE
<222> LOCATION: (4)..(4)
<223> OTHER INFORMATION: Xaa is Met, Val or Leu
<220> FEATURE:
<221> NAME/KEY: MISC_FEATURE
<222> LOCATION: (10)..(10)
<223> OTHER INFORMATION: Xaa is Val, Ala or Gly
<220> FEATURE:
<221> NAME/KEY: MISC_FEATURE
<222> LOCATION: (14)..(14)
<223> OTHER INFORMATION: Xaa is Ser, Ala or Pro
<220> FEATURE:
<221> NAME/KEY: MISC_FEATURE
<222> LOCATION: (24)..(24)
<223> OTHER INFORMATION: Xaa is Val, Gly or Ala
<220> FEATURE:
<221> NAME/KEY: MISC_FEATURE
<222> LOCATION: (30)..(30)
<223> OTHER INFORMATION: Xaa is Ile, Thr or Ser
<220> FEATURE:
<221> NAME/KEY: MISC_FEATURE
<222> LOCATION: (31)..(31)
<223> OTHER INFORMATION: Xaa is Thr, Arg or Ser
<220> FEATURE:
<221> NAME/KEY: MISC_FEATURE
<222> LOCATION: (37)..(37)
<223> OTHER INFORMATION: Xaa is Phe, Leu or Val
<220> FEATURE:
<221> NAME/KEY: MISC_FEATURE
<222> LOCATION: (40)..(40)
<223> OTHER INFORMATION: Xaa is Ser, Pro or Ala
<220> FEATURE:
<221> NAME/KEY: MISC_FEATURE
<222> LOCATION: (52)..(52)
<223> OTHER INFORMATION: Xaa is Ile, Ser or Thr
<220> FEATURE:
<221> NAME/KEY: MISC_FEATURE
<222> LOCATION: (53)..(53)
<223> OTHER INFORMATION: Xaa is Ile, Ser or Thr
<220> FEATURE:
<221> NAME/KEY: MISC_FEATURE

```
<222> LOCATION: (75)..(75)
<223> OTHER INFORMATION: Xaa is Val, Gly or Ala
<220> FEATURE:
<221> NAME/KEY: MISC_FEATURE
<222> LOCATION: (84)..(84)
<223> OTHER INFORMATION: Xaa is Ile, Thr or Ser
<220> FEATURE:
<221> NAME/KEY: MISC_FEATURE
<222> LOCATION: (92)..(92)
<223> OTHER INFORMATION: Xaa is Val, Gly or Ala
<220> FEATURE:
<221> NAME/KEY: MISC_FEATURE
<222> LOCATION: (108)..(108)
<223> OTHER INFORMATION: Xaa is Val, Ala or Gly

<400> SEQUENCE: 2

Glu Val Xaa Xaa Val Glu Ser Gly Gly Xaa Leu Val Lys Xaa Gly Gly
1               5                   10                  15

Ser Leu Arg Leu Ser Cys Ala Xaa Ser Gly Phe Ala Phe Xaa Xaa Tyr
            20                  25                  30

Asp Met Ser Trp Xaa Arg Gln Xaa Pro Gly Lys Gly Leu Glu Trp Val
        35                  40                  45

Ala Tyr Ile Xaa Xaa Gly Gly Val Asn Thr Tyr Tyr Pro Asp Thr Val
    50                  55                  60

Lys Gly Arg Phe Thr Ile Ser Arg Asp Asn Xaa Lys Asn Thr Leu Tyr
65                  70                  75                  80

Leu Gln Met Xaa Ser Leu Lys Ser Glu Asp Thr Xaa Val Tyr Tyr Cys
                85                  90                  95

Ala Arg His Ser Tyr Phe Asp Tyr Trp Gly Gln Xaa Thr Thr Val Thr
            100                 105                 110

Val Ser Ser
        115

<210> SEQ ID NO 3
<211> LENGTH: 107
<212> TYPE: PRT
<213> ORGANISM: Artificial Sequence
<220> FEATURE:
<223> OTHER INFORMATION: Trastuzumab antibody light chain
<220> FEATURE:
<221> NAME/KEY: MISC_FEATURE
<222> LOCATION: (9)..(9)
<223> OTHER INFORMATION: Xaa is Ser, Asn, Thr, Ile, Arg or Lys
<220> FEATURE:
<221> NAME/KEY: MISC_FEATURE
<222> LOCATION: (23)..(23)
<223> OTHER INFORMATION: Xaa is Cys or Trp
<220> FEATURE:
<221> NAME/KEY: misc_feature
<222> LOCATION: (25)..(25)
<223> OTHER INFORMATION: Xaa is Ala, Gly, Val or Asp
<220> FEATURE:
<221> NAME/KEY: MISC_FEATURE
<222> LOCATION: (31)..(31)
<223> OTHER INFORMATION: Xaa is Thr, Ser, Asn or Ile
<220> FEATURE:
<221> NAME/KEY: MISC_FEATURE
<222> LOCATION: (32)..(32)
<223> OTHER INFORMATION: Xaa is Ala, Asp, Gly, Val, Thr, Asn, Ser, Ile,
      Pro, Leu or Phe
<220> FEATURE:
<221> NAME/KEY: MISC_FEATURE
<222> LOCATION: (33)..(33)
<223> OTHER INFORMATION: Xaa is Val, Leu or Ile
<220> FEATURE:
<221> NAME/KEY: MISC_FEATURE
<222> LOCATION: (34)..(34)
<223> OTHER INFORMATION: Xaa is Ala, Gly, Val or Asp
<220> FEATURE:
<221> NAME/KEY: MISC_FEATURE
```

```
<222> LOCATION: (35)..(35)
<223> OTHER INFORMATION: Xaa is Trp or Cys
<220> FEATURE:
<221> NAME/KEY: MISC_FEATURE
<222> LOCATION: (38)..(38)
<223> OTHER INFORMATION: Xaa is Gln, Glu or Lys
<220> FEATURE:
<221> NAME/KEY: misc_feature
<222> LOCATION: (40)..(40)
<223> OTHER INFORMATION: Xaa is Pro, Ala, Ser or Thr
<220> FEATURE:
<221> NAME/KEY: MISC_FEATURE
<222> LOCATION: (43)..(43)
<223> OTHER INFORMATION: Xaa is Ala, Asp, Gly, Val, Thr, Asn, Ser, Ile,
      Pro, Leu or Phe
<220> FEATURE:
<221> NAME/KEY: MISC_FEATURE
<222> LOCATION: (46)..(46)
<223> OTHER INFORMATION: Xaa is Leu, Val or Ile
<220> FEATURE:
<221> NAME/KEY: MISC_FEATURE
<222> LOCATION: (47)..(47)
<223> OTHER INFORMATION: Xaa is Leu, Val or Met
<220> FEATURE:
<221> NAME/KEY: misc_feature
<222> LOCATION: (51)..(51)
<223> OTHER INFORMATION: Xaa Ala, Ser, Pro or Thr
<220> FEATURE:
<221> NAME/KEY: MISC_FEATURE
<222> LOCATION: (76)..(76)
<223> OTHER INFORMATION: Xaa is Ser, Arg, Asn, Thr, Lys or Ile
<220> FEATURE:
<221> NAME/KEY: MISC_FEATURE
<222> LOCATION: (79)..(79)
<223> OTHER INFORMATION: Xaa is Gln, Lys or Glu
<220> FEATURE:
<221> NAME/KEY: MISC_FEATURE
<222> LOCATION: (80)..(80)
<223> OTHER INFORMATION: Xaa is Pro, Thr, Ser or Ala
<220> FEATURE:
<221> NAME/KEY: MISC_FEATURE
<222> LOCATION: (85)..(85)
<223> OTHER INFORMATION: Xaa is Thr, Ser, Asn or Ile
<220> FEATURE:
<221> NAME/KEY: MISC_FEATURE
<222> LOCATION: (89)..(89)
<223> OTHER INFORMATION: Xaa is Gln or His
<220> FEATURE:
<221> NAME/KEY: MISC_FEATURE
<222> LOCATION: (90)..(90)
<223> OTHER INFORMATION: Xaa is Gln, Glu or Ala
<220> FEATURE:
<221> NAME/KEY: MISC_FEATURE
<222> LOCATION: (91)..(91)
<223> OTHER INFORMATION: Xaa is His, Asn, Asp or Tyr
<220> FEATURE:
<221> NAME/KEY: MISC_FEATURE
<222> LOCATION: (93)..(93)
<223> OTHER INFORMATION: Xaa is Thr, Ser, Asn or Ile
<220> FEATURE:
<221> NAME/KEY: MISC_FEATURE
<222> LOCATION: (94)..(94)
<223> OTHER INFORMATION: Xaa is Thr, Ser, Asn or Ile
<220> FEATURE:
<221> NAME/KEY: MISC_FEATURE
<222> LOCATION: (101)..(101)
<223> OTHER INFORMATION: Xaa is Gly, Ala, Val or Asp
<220> FEATURE:
<221> NAME/KEY: MISC_FEATURE
<222> LOCATION: (102)..(102)
<223> OTHER INFORMATION: Xaa is Thr, Ser, Asn or Ile

<400> SEQUENCE: 3

Asp Ile Gln Met Thr Gln Ser Pro Xaa Ser Leu Ser Ala Ser Val Gly
1               5                   10                  15

Asp Arg Val Thr Ile Thr Xaa Arg Xaa Ser Gln Asp Val Asn Xaa Xaa
            20                  25                  30
```

```
Xaa Xaa Xaa Tyr Gln Xaa Lys Xaa Gly Lys Xaa Pro Lys Xaa Xaa Ile
        35                  40                  45

Tyr Ser Xaa Ser Phe Leu Tyr Ser Gly Val Pro Ser Arg Phe Ser Gly
 50                  55                  60

Ser Arg Ser Gly Thr Asp Phe Thr Leu Thr Ile Xaa Ser Leu Xaa Xaa
 65                  70                  75                  80

Glu Asp Phe Ala Xaa Tyr Tyr Cys Xaa Xaa Xaa Tyr Xaa Xaa Pro Pro
                 85                  90                  95

Thr Phe Gly Gln Xaa Xaa Lys Val Glu Ile Lys
            100                 105

<210> SEQ ID NO 4
<211> LENGTH: 120
<212> TYPE: PRT
<213> ORGANISM: Artificial Sequence
<220> FEATURE:
<223> OTHER INFORMATION: Trastuzumab antibody heavy chain
<220> FEATURE:
<221> NAME/KEY: MISC_FEATURE
<222> LOCATION: (2)..(2)
<223> OTHER INFORMATION: Xaa is Val, Leu, Ile or Phe
<220> FEATURE:
<221> NAME/KEY: MISC_FEATURE
<222> LOCATION: (3)..(3)
<223> OTHER INFORMATION: Xaa is Gln or His
<220> FEATURE:
<221> NAME/KEY: MISC_FEATURE
<222> LOCATION: (4)..(4)
<223> OTHER INFORMATION: Xaa is Leu, Met or Val
<220> FEATURE:
<221> NAME/KEY: MISC_FEATURE
<222> LOCATION: (13)..(13)
<223> OTHER INFORMATION: Xaa is Gln, Lys or Glu
<220> FEATURE:
<221> NAME/KEY: MISC_FEATURE
<222> LOCATION: (14)..(14)
<223> OTHER INFORMATION: Xaa is Pro, Ala, Thr or Ser
<220> FEATURE:
<221> NAME/KEY: MISC_FEATURE
<222> LOCATION: (16)..(16)
<223> OTHER INFORMATION: Xaa is Gly, Ala, Val or Asp
<220> FEATURE:
<221> NAME/KEY: MISC_FEATURE
<222> LOCATION: (23)..(23)
<223> OTHER INFORMATION: Xaa is Ala, Glu, Gly, Val, Thr, Lys, Arg, Ile,
      Pro, Leu or Ser
<220> FEATURE:
<221> NAME/KEY: MISC_FEATURE
<222> LOCATION: (24)..(24)
<223> OTHER INFORMATION: Xaa is Ala, Asp, Gly, Val, Thr, Asn, Ser, Ile,
      Pro, Leu or Phe
<220> FEATURE:
<221> NAME/KEY: MISC_FEATURE
<222> LOCATION: (26)..(26)
<223> OTHER INFORMATION: Xaa is Gly, Ala, Val or Asp
<220> FEATURE:
<221> NAME/KEY: MISC_FEATURE
<222> LOCATION: (28)..(28)
<223> OTHER INFORMATION: Xaa is Asn or Lys
<220> FEATURE:
<221> NAME/KEY: MISC_FEATURE
<222> LOCATION: (35)..(35)
<223> OTHER INFORMATION: Xaa is His, Asn, Asp or Tyr
<220> FEATURE:
<221> NAME/KEY: MISC_FEATURE
<222> LOCATION: (42)..(42)
<223> OTHER INFORMATION: Xaa is Gly, Ala, Val or Asp
<220> FEATURE:
<221> NAME/KEY: MISC_FEATURE
<222> LOCATION: (48)..(48)
<223> OTHER INFORMATION: Xaa is Val, Phe, Leu or Ile
<220> FEATURE:
<221> NAME/KEY: MISC_FEATURE
```

```
<222> LOCATION: (49)..(49)
<223> OTHER INFORMATION: Xaa is Ala, Glu, Gly, Val, Thr, Lys, Arg, Ile,
      Pro, Leu or Ser
<220> FEATURE:
<221> NAME/KEY: MISC_FEATURE
<222> LOCATION: (56)..(56)
<223> OTHER INFORMATION: Xaa is Gly, Ala, Val or Asp
<220> FEATURE:
<221> NAME/KEY: MISC_FEATURE
<222> LOCATION: (58)..(58)
<223> OTHER INFORMATION: Xaa is Thr, Ser, Asn or Ile
<220> FEATURE:
<221> NAME/KEY: MISC_FEATURE
<222> LOCATION: (61)..(61)
<223> OTHER INFORMATION: Xaa is Ala, Gly, Val or Asp
<220> FEATURE:
<221> NAME/KEY: MISC_FEATURE
<222> LOCATION: (77)..(77)
<223> OTHER INFORMATION: Xaa is Asn or Lys
<220> FEATURE:
<221> NAME/KEY: MISC_FEATURE
<222> LOCATION: (79)..(79)
<223> OTHER INFORMATION: Xaa is Ala, Gly, Val or Asp
<220> FEATURE:
<221> NAME/KEY: MISC_FEATURE
<222> LOCATION: (82)..(82)
<223> OTHER INFORMATION: Xaa is Gln, Glu or Lys
<220> FEATURE:
<221> NAME/KEY: MISC_FEATURE
<222> LOCATION: (84)..(84)
<223> OTHER INFORMATION: Xaa is Asn or Lys
<220> FEATURE:
<221> NAME/KEY: MISC_FEATURE
<222> LOCATION: (85)..(85)
<223> OTHER INFORMATION: Xaa is Ser or Arg
<220> FEATURE:
<221> NAME/KEY: MISC_FEATURE
<222> LOCATION: (88)..(88)
<223> OTHER INFORMATION: Xaa is Ala, Asp, Gly, Val, Thr, Asn, Ser, Ile,
      Pro, Leu or Phe
<220> FEATURE:
<221> NAME/KEY: MISC_FEATURE
<222> LOCATION: (92)..(92)
<223> OTHER INFORMATION: Xaa is Ala, Gly, Val or Asp
<220> FEATURE:
<221> NAME/KEY: MISC_FEATURE
<222> LOCATION: (96)..(96)
<223> OTHER INFORMATION: Xaa is Cys, Phe, Ser or Tyr
<220> FEATURE:
<221> NAME/KEY: MISC_FEATURE
<222> LOCATION: (103)..(103)
<223> OTHER INFORMATION: Xaa is Gly, Ala, Val or Asp
<220> FEATURE:
<221> NAME/KEY: MISC_FEATURE
<222> LOCATION: (106)..(106)
<223> OTHER INFORMATION: Xaa is Ala, Asp, Gly, Val, Thr, Asn, Ser, Ile,
      Pro, Leu or Phe
<220> FEATURE:
<221> NAME/KEY: MISC_FEATURE
<222> LOCATION: (114)..(114)
<223> OTHER INFORMATION: Xaa is Thr, Ser, Asn or Ile

<400> SEQUENCE: 4

Glu Xaa Xaa Xaa Val Glu Ser Gly Gly Gly Leu Val Xaa Xaa Gly Xaa
1               5                   10                  15

Ser Leu Arg Leu Ser Cys Xaa Xaa Ser Xaa Phe Xaa Ile Lys Asp Thr
            20                  25                  30

Tyr Ile Xaa Trp Val Arg Gln Ala Pro Xaa Lys Gly Leu Glu Trp Xaa
        35                  40                  45

Xaa Arg Ile Tyr Pro Thr Asn Xaa Tyr Xaa Arg Tyr Xaa Asp Ser Val
    50                  55                  60

Lys Gly Arg Phe Thr Ile Ser Ala Asp Thr Ser Lys Xaa Thr Xaa Tyr
65                  70                  75                  80
```

-continued

```
Leu Xaa Met Xaa Xaa Leu Arg Xaa Glu Asp Thr Xaa Val Tyr Tyr Xaa
            85              90                  95

Ser Arg Trp Gly Gly Asp Xaa Phe Tyr Xaa Met Asp Tyr Trp Gly Gln
            100             105             110

Gly Xaa Leu Val Thr Val Ser Ser
        115             120
```